(12) United States Patent
Ali et al.

(10) Patent No.: US 7,915,271 B2
(45) Date of Patent: Mar. 29, 2011

(54) 1,3-OXAZOLIDIN-2-ONE DERIVATIVES USEFUL AS CETP INHIBITORS

(75) Inventors: Amjad Ali, Freehold, NJ (US); Zhijian Lu, Clinton, NJ (US); Peter J. Sinclair, Scotch Plains, NJ (US); Yi-Heng Chen, Whippany, NJ (US); Cameron J. Smith, Lawrenceville, NJ (US); Hong Li, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 129 days.

(21) Appl. No.: 12/087,290

(22) PCT Filed: Dec. 29, 2006

(86) PCT No.: PCT/US2006/049494
§ 371 (c)(1),
(2), (4) Date: Jun. 26, 2008

(87) PCT Pub. No.: WO2007/079186
PCT Pub. Date: Jul. 12, 2007

(65) Prior Publication Data
US 2009/0137548 A1    May 28, 2009

Related U.S. Application Data

(60) Provisional application No. 60/755,284, filed on Dec. 30, 2005.

(51) Int. Cl.
*A61K 31/4166*   (2006.01)
*A61K 31/44*     (2006.01)
*A61K 31/506*    (2006.01)
*C07D 239/34*    (2006.01)
*C07D 413/10*    (2006.01)
*C07D 263/06*    (2006.01)

(52) U.S. Cl. ........ 514/274; 514/326; 514/376; 544/315; 546/209; 546/271.4; 548/229

(58) Field of Classification Search .................. 548/229
See application file for complete search history.

(56) References Cited

FOREIGN PATENT DOCUMENTS
EP   0 294 995     12/1988
EP   0 605 729     7/1994
WO   WO 2006/014413   2/2006

*Primary Examiner* — Shawquia Young
(74) *Attorney, Agent, or Firm* — Mark R. Daniel; James L. McGinnis

(57) ABSTRACT

Compounds having the structure of Formula I, including pharmaceutically acceptable salts of the compounds, are CETP inhibitors, and are useful for raising HDL-cholesterol, reducing LDL-cholesterol, and for treating or preventing atherosclerosis. The compounds have 3 cyclic groups connected by single bonds, as for example triphenyl, which are attached directly to the ring of formula I or attached at the position B.

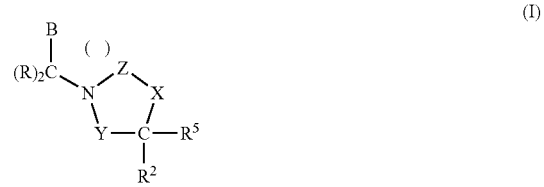

(I)

21 Claims, No Drawings

1,3-OXAZOLIDIN-2-ONE DERIVATIVES USEFUL AS CETP INHIBITORS

CROSS REFERENCE TO RELATED APPLICATIONS

This application is a U.S. National Phase application under 35 U.S.C. §371 of PCT Application No. PCT/US2006/049494, filed Dec. 29, 2006, which claims priority under 35 U.S.C. §119(e) from US Application No. 60/755,284, filed Dec. 30, 2005.

FIELD OF THE INVENTION

This invention relates to a class of chemical compounds that inhibit cholesterol ester transfer protein (CETP) and therefore have utility in raising HDL-cholesterol, lowering LDL -cholesterol, and in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoBliprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S, and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies or are in clinical trials. No CETP inhibitors are currently being marketed. Clinical trials of Pfizer's CETP inhibitor torcetrapib were recently terminated because of increased mortality in patients who were using the drug during outcomes studies. New compounds are needed so that one or more pharmaceutical compounds can be found that are safe and effective. The novel compounds described herein are very potent CETP inhibitors.

SUMMARY OF THE INVENTION

Compounds having Formula I, including pharmaceutically acceptable salts of the compounds, are CETP inhibitors, having the utilities described below, wherein:

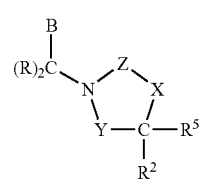

(I)

Y is selected from the group consisting of —C(=O)— and —(CRR$^1$)—;

X is selected from the group consisting of —O—, —NH—, —N(C$_1$-C$_5$alkyl)-, and —(CRR$^6$)—;

Z is selected from the group consisting of —C(=O)—, —S(O)$_2$—, and —C(—N—R$^9$)—, wherein R$^9$ is selected from the group consisting of H, —CN, and C$_1$-C$_5$alkyl optionally substituted with 1-11 halogens;

Each R is independently selected from the group consisting of H, —C$_1$-C$_5$ alkyl, and halogen, wherein —C$_1$-C$_5$ alkyl is optionally substituted with 1-11 halogens;

B is selected from the group consisting of $A^1$ and $A^2$, wherein $A^1$ has the structure:

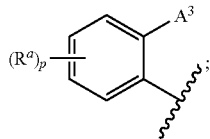

$R^1$ and $R^6$ are each selected from the group consisting of H, —$C_1$-$C_5$ alkyl, halogen, and —$(C(R)_2)_n A^2$, wherein —$C_1$-$C_5$ alkyl is optionally substituted with 1-11 halogens;

$R^2$ is selected from the group consisting of H, —$C_1$-$C_5$ alkyl, halogen, $A^1$, and —$(C(R)_2)_n A^2$, wherein —$C_1$-$C_5$ alkyl is optionally substituted with 1-11 halogens;

Wherein one of B and $R^2$ is $A^1$; and one of B, $R^1$, $R^2$, and $R^6$ is $A^2$ or —$(C(R)_2)_n A^2$; so that the compound of Formula I includes one group $A^1$ and one group $A^2$;

$A^3$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group, wherein the point of attachment of $A^3$ to the phenyl ring to which $A^3$ is attached is a carbon atom; and
(d) a benzoheterocyclic ring comprising a phenyl ring fused to a 5-6-membered heterocyclic ring having 1-2 heteroatoms independently selected from O, N, and —$S(O)_x$— and optionally 1-2 double bonds, wherein the point of attachment of $A^3$ to the phenyl ring to which $A^3$ is attached is a carbon atom;
wherein $A^3$ is substituted with one group $A^4$ and is optionally substituted with 1-4 groups $R^a$;

$A^2$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group;
(d) a benzoheterocyclic ring comprising a phenyl ring fused to a 5-6-membered heterocyclic ring having 1-2 heteroatoms independently selected from O, N, and S and optionally 1-2 double bonds; and
(e) a —$C_3$-$C_8$ cycloalkyl ring optionally having 1-3 double bonds;
wherein $A^2$ is optionally substituted with 1-5 substituent groups independently selected from $R^a$;

$A^4$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group; and
(d) a benzoheterocyclic ring comprising a phenyl ring fused to a 5-6-membered heterocyclic ring having 1-2 heteroatoms independently selected from O, N, and —$S(O)_x$— and optionally 1-2 double bonds;
wherein when $A^4$ is (a) an aromatic ring selected from phenyl and naphthyl; (b) a phenyl ring fused to a 5-7 membered non-aromatic cycloalkyl ring, which optionally comprises 1-2 double bonds; (c) a 5-6-membered heterocyclic ring having 1-4 heteroatoms independently selected from N, S, O, and —N(O)—, and optionally also comprising 1-3 double bonds and a carbonyl group, wherein the point of attachment of the heterocyclic ring to $A^3$ is a N atom of $A^4$; or (d) a benzoheterocyclic ring comprising a phenyl ring fused to a 5-6-membered heterocyclic ring having 1-2 heteroatoms independently selected from O, N, and —$S(O)_x$— and optionally 1-2 double bonds; then $A^4$ is optionally substituted with 1-5 groups $R^a$;

and when $A^4$ is a 5-6-membered heterocyclic ring having 1-4 heteroatoms independently selected from N, S, O, and —N(O)—, and optionally also comprising 1-3 double bonds and a carbonyl group, wherein the point of attachment of the heterocyclic ring to $A^3$ is a carbon atom of $A^4$, then $A^4$ is substituted with one group $R^e$ and is optionally also substituted with 1-4 groups independently selected from $R^a$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)$SC_1$-$C_6$alkyl, —OH, —$NR^3R^4$, —C(=O)$NR^3R^4$, —$NR^3$C(=O)$OC_1$-$C_6$ alkyl, —$NR^3$C(=O)$NR^3R^4$, —$S(O)_xC_1$-$C_6$ alkyl, —$S(O)_yNR^3R^4$, —$NR^3S(O)_yNR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —$CO_2C_1$-$C_6$alkyl, —C(=O)$SC_1$-$C_6$alkyl, —$NR^3$C(=O)$OC_1$-$C_6$ alkyl, and —$S(O)_xC_1$-$C_6$ alkyl, $R^a$ is optionally substituted with 1-15 halogens and is optionally substituted with 1-3 substituent groups independently selected from (a) —H, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally substituted with 1-2 substituent groups independently selected from —$OC_1$-$C_2$ alkyl and phenyl, (f) —$OC_3$-$C_8$ cycloalkyl optionally having 1-3 double bonds and optionally substituted with 1-15 halogens, (g) —$CO_2$H, (h) —C(=O)$CH_3$, (i) —$CO_2C_1$-$C_4$alkyl which is optionally substituted with 1-9 halogens, and (j) phenyl which is optionally substituted with 1-3 groups independently selected from halogen, —CH$_3$, —CF$_3$, —OCH$_3$, and —OCF$_3$;

Each R$^e$ is independently selected from the group consisting of —C$_2$-C$_6$ alkenyl, —C$_2$-C$_6$ alkynyl, —C$_3$-C$_8$ cycloalkyl optionally having 1-3 double bonds, —OC$_2$-C$_6$ alkenyl, —OC$_2$-C$_6$ alkynyl, —OC$_3$-C$_8$ cycloalkyl optionally having 1-3 double bonds, —C(=O)C$_1$-C$_6$alkyl, —C(=O)C$_3$-C$_8$ cycloalkyl, —C(=O)H, —CO$_2$H, —CO$_2$C$_1$-C$_6$alkyl, —C(=O)SC$_1$-C$_6$alkyl, —OH, —NR$^3$R$^4$, —C(=O)NR$^3$R$^4$, —NR$^3$C(=O)OC$_1$-C$_6$ alkyl, —NR$^3$C(=O)NR$^3$R$^4$, —S(O)$_x$C$_1$-C$_6$ alkyl, —S(O)$_y$NR$^3$R$^4$, —NR$^3$S(O)$_y$NR$^3$R$^4$, —CN, —NO$_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which R$^e$ is attached is a carbon atom, wherein said heterocyclic ring is optionally substituted with 1-5 substituent groups independently selected from halogen, —C$_1$-C$_3$ alkyl, and —OC$_1$-C$_3$ alkyl, wherein —C$_1$-C$_3$ alkyl and —OC$_1$-C$_3$ alkyl are optionally substituted with 1-7 halogens;

wherein for compounds in which R$^e$ is selected from the group consisting of —C$_2$-C$_6$ alkenyl, —C$_2$-C$_6$ alkynyl, —C$_3$-C$_8$ cycloalkyl optionally having 1-3 double bonds, —OC$_2$-C$_6$ alkenyl, —OC$_2$-C$_6$ alkynyl, —OC$_3$-C$_8$ cycloalkyl optionally having 1-3 double bonds, —C(=O)C$_1$-C$_6$alkyl, —C(=O)C$_3$-C$_8$ cycloalkyl, —CO$_2$C$_1$-C$_6$alkyl, —C(=O)SC$_1$-C$_6$alkyl, —NR$^3$C(=O)OC$_1$-C$_6$ alkyl, and —S(O)$_x$C$_1$-C$_6$ alkyl, R$^e$ is optionally substituted with 1-15 halogens and is optionally substituted with 1-3 substituent groups independently selected from (a) —OH, (b) —CN, (c) —NR$^3$R$^4$, (d) —C$_3$-C$_8$ cycloalkyl optionally having 1-3 double bonds and optionally substituted with 1-15 halogens, (e) —OC$_1$-C$_4$alkyl optionally substituted with 1-9 halogens and optionally also substituted with 1-2 substituent groups independently selected from —OC$_1$-C$_2$ alkyl and phenyl, (f) —OC$_3$-C$_8$ cycloalkyl optionally having 1-3 double bonds and optionally substituted with 1-15 halogens, (g) —CO$_2$H, (h) —C(=O)CH$_3$, (i) —CO$_2$C$_1$-C$_4$alkyl which is optionally substituted with 1-9 halogens, and G) phenyl which is optionally substituted with 1-3 groups independently selected from halogen, —CH$_3$, —CF$_3$, —OCH$_3$, and —OCF$_3$;

n is 0 or 1;

p is an integer from 0-4;

x is 0, 1, or 2;

y is 1 or 2;

R$^3$ and R$^4$ are each independently selected from H, —C$_1$-C$_5$ alkyl, —C(=O)C$_1$-C$_5$ alkyl and —S(O)$_y$C$_1$-C$_5$ alkyl, wherein —C$_1$-C$_5$ alkyl in all instances is optionally substituted with 1-11 halogens; and R$^5$ is selected from the group consisting of H, —OH, —C$_1$-C$_{58}$ alkyl, and halogen, wherein —C$_1$-C$_5$ alkyl is optionally substituted with 1-11 halogens.

In the compounds of formula I and in compounds described subsequently, alkyl, alkenyl and alkynyl groups can be linear or branched, unless otherwise stated.

DETAILED DESCRIPTION OF THE INVENTION

In embodiments of the invention, the compound has Formula Ia, Ib, or Id, including pharmaceutically acceptable salts.

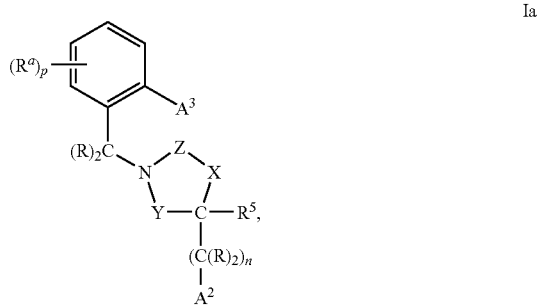

Ia

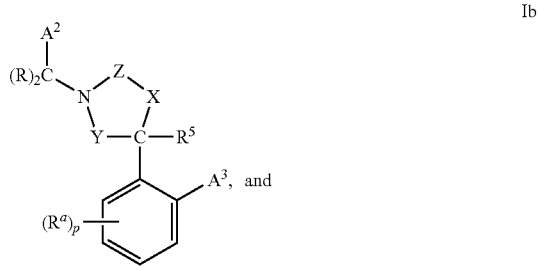

Ib, and

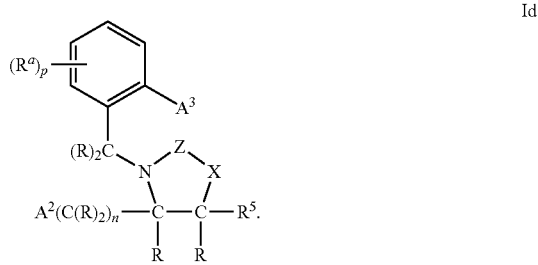

Id

In embodiments of the invention, the groups in the structures are as follows, independent of one another:

Y is —(CRR$^1$)—.

R and R$^6$ are each independently selected from the group consisting of H and —C$_1$-C$_5$ alkyl, wherein —C$_1$-C$_5$ alkyl is optionally substituted with 1-11 halogens.

R$^1$ is selected from the group consisting of H, —C$_1$-C$_5$ alkyl, and —(C(R)$_2$)$_n$A$^2$, wherein —C$_1$-C$_5$ alkyl is optionally substituted with 1-11 halogens, wherein one of B and R$^2$ is A$^1$; and one of B, R$^1$, and R$^2$ is A$^2$ or —(C(R)$_2$)$_n$A$^2$; so that the compound of Formula I includes one group A$^1$ and one group A$^2$.

A$^3$ is selected from the group consisting of:

(a) an aromatic ring selected from phenyl and naphthyl;

(b) a 5-6-membered heterocyclic ring having 1-4 heteroatoms independently selected from N, S, O, and —N(O)—, and optionally also comprising 1-3 double bonds and a carbonyl group, wherein the point of attachment of A$^3$ to the phenyl ring to which A$^3$ is attached is a carbon atom; and (c) a benzoheterocyclic ring comprising a phenyl ring fused to a 5-6-membered heterocyclic ring having 1-2 heteroatoms independently selected from O, N, and —S(O)$_x$— and optionally 1-2 double bonds, wherein the point of attachment of A$^3$ to the phenyl ring to which A$^3$ is attached is a carbon atom;

wherein $A^3$ is substituted with one group $A^4$ and is optionally substituted with 1-4 groups $R^a$.

$A^2$ is selected from the group consisting of:
(a) an aromatic ring selected from phenyl and naphthyl;
(b) a 5-6-membered heterocyclic ring having 1-4 heteroatoms independently selected from N, S, O, and —N(O)—, and optionally also comprising 1-3 double bonds and a carbonyl group;
(c) a benzoheterocyclic ring comprising a phenyl ring fused to a 5-6-membered heterocyclic ring having 1-2 heteroatoms independently selected from O, N, and S and optionally 1-2 double bonds; and
(d) a —$C_3$-$C_8$ cycloalkyl ring optionally having 1-3 double bonds;
wherein $A^2$ is optionally substituted with 1-5 substituent groups independently selected from $R^a$.

Each $R^a$ is independently selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —C(=O)H, —$CO_2$H, —$CO_2C_1$-$C_6$alkyl, —OH, —$NR^3R^4$, —$NR^3$C(=O)$OC_1$-$C_6$ alkyl, —S(O)$_x C_1$-$C_6$ alkyl, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —$CO_2C_1$-$C_6$alkyl, —$NR^3$C(=O)$OC_1$-$C_6$alkyl, and —S(O)$_x C_1$-$C_6$ alkyl, $R^a$ is optionally substituted with 1-15 halogens and is optionally substituted with one substituent group selected from (a) —OH, (b) —$NR^3R^4$, (c) —$OC_1$-$C_4$alkyl optionally substituted with 1-9 halogens and optionally substituted with 1-2 substituent groups independently selected from $OC_1$-$C_2$ alkyl and phenyl, and (d) phenyl which is optionally substituted with 1-3 groups independently selected from halogen, —$CH_3$, —$CF_3$, —$OCH_3$, and —$OCF_3$.

Each $R^e$ is independently selected from the group consisting of —$C_2$-$C_6$ alkenyl, —$C_3$-$C_8$ cycloalkyl optionally having 1-3 double bonds, —C(=O)$C_1$-$C_6$alkyl, —C(=O)H, —$CO_2$H, —$CO_2C_1$-$C_6$alkyl, —OH, —$NR^3R^4$, —$NR^3$C(=O)$OC_1$-$C_6$alkyl, —S(O)$_x C_1$-$C_6$ alkyl, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^e$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^e$ is selected from the group consisting of —$C_2$-$C_6$ alkenyl, —$C_3$-$C_8$ cycloalkyl optionally having 1-3 double bonds, —C(=O)$C_1$-$C_6$alkyl, —$CO_2C_1$-$C_6$alkyl, —$NR^3$C(=O)$OC_1$-$C_6$ alkyl, and —S(O)$_x C_1$-$C_6$ alkyl, $R^e$ is optionally substituted with 1-15 halogens and is optionally substituted with one substituent group selected from (a) —OH, (b) —$NR^3R^4$, (c) —$OC_1$-$C_4$alkyl optionally substituted with 1-9 halogens and optionally also substituted with 1-2 substituent groups independently selected from $OC_1$-$C_2$ alkyl and phenyl, and (d) phenyl which is optionally substituted with 1-3 groups independently selected from halogen, —$CH_3$, —$CF_3$, —$OCH_3$, and —$OCF_3$.

p is an integer from 0-2.

$R^3$ and $R^4$ are each independently selected from H and —$C_1$-$C_5$ alkyl, wherein —$C_1$-$C_5$ alkyl in all instances is optionally substituted with 1-11 halogens.

$R^5$ is selected from the group consisting of H, —OH, and —$C_1$-$C_5$ alkyl, wherein —$C_1$-$C_5$ alkyl is optionally substituted with 1-11 halogens.

Z is selected from the group consisting of —C(=O)—, —S(O)$_2$—, and —C(=N—$R^9$)—, wherein $R^9$ is selected from the group consisting of H, —CN, and $CH_3$ Each R is independently selected from the group consisting of H and $C_1$-$C_2$ alkyl.

$R^6$ is selected from the group consisting of H and —$C_1$-$C_3$ alkyl, wherein $C_1$-$C_3$ alkyl is optionally substituted with 1-5 halogens.

$R^1$ is selected from the group consisting of H, —$C_1$-$C_3$ alkyl, and —$(C(R)_2)_n A^2$, wherein —$C_1$-$C_3$ alkyl is optionally substituted with 1-5 halogens.

$R^2$ is selected from the group consisting of H, —$C_1$-$C_3$ alkyl, $A^1$, and —$(C(R)_2)_n A^2$, wherein —$C_1$-$C_3$ alkyl is optionally substituted with 1-5 halogens, wherein one of B and $R^2$ is $A^1$; and one of B, $R^1$, and $R^2$ is $A^2$ or —$(C(R)_2)_n A^2$; so that the compound of Formula I includes one group $A^1$ and one group $A^2$.

$A^3$ is selected from the group consisting of:
(a) phenyl;
(b) a 5-6-membered aromatic heterocyclic ring having 1-2 heteroatoms independently selected from N, S, O, and —N(O)—, wherein the point of attachment of $A^3$ to the phenyl ring to which $A^3$ is attached is a carbon atom; and
(c) a benzoheterocyclic ring comprising a phenyl ring fused to a 5-membered aromatic heterocyclic ring having 1-2 heteroatoms independently selected from O, N, and —S(O)$_x$,
wherein the point of attachment of $A^3$ to the phenyl ring to which $A^3$ is attached is a carbon atom;
wherein $A^3$ is substituted with one group $A^4$ and is optionally substituted with 1-4 groups $R^a$.

$A^2$ is selected from the group consisting of:
(a) phenyl;
(b) a 5-6-membered heterocyclic ring having 1-4 heteroatoms independently selected from N, S, O, and —N(O)—, and optionally also comprising 1-3 double bonds;
(c) a benzoheterocyclic ring comprising a phenyl ring fused to a 5-membered heterocyclic ring having 1-2 heteroatoms independently selected from O, N, and S; and
(d) a —$C_5$-$C_6$ cycloalkyl ring;
wherein $A^2$ is optionally substituted with 1-5 substituent groups independently selected from $R^a$.

Each $R^a$ is independently selected from the group consisting of —$C_1$-$C_4$ alkyl, —$C_2$-$C_4$ alkenyl, cyclopropyl, —$OC_1$-$C_2$alkyl, —C(=O)$C_1$-$C_2$alkyl, —C(=O)H, —$CO_2$H, —$CO_2C_1$-$C_4$alkyl, —OH, —$NR^3R^4$, —$NR^3$C(=O)$OC_1$-$C_4$alkyl, —S(O)$_x C_1$-$C_2$ alkyl, halogen, —CN, —$NO_2$, and a 5-6-membered heterocyclic ring having 1-2 heteroatoms independently selected from N, S, and O, wherein the point of attachment of said heterocyclic ring to the ring to which $R^a$ is attached ring is a carbon atom, wherein said heterocyclic ring is optionally substituted with 1-5 substituent groups independently selected from halogen;

wherein for compounds in which $R^a$ is selected from the group consisting of —$C_1$-$C_4$ alkyl, —$C_2$-$C_4$ alkenyl, —$OC_1$-$C_2$alkyl, —C(=O)$C_1$-$C_2$alkyl, —$CO_2C_1$-$C_4$alkyl, —$NR^3C$(=O)$OC_1$-$C_4$ alkyl, and —S(O)$_x$$C_1$-$C_2$ alkyl, the alkyl group of $R^a$ is optionally substituted with 1-5 halogens and is optionally substituted with one substituent group selected from (a) —H, (b) —$NR^3R^4$, (c) —$OCH_3$ optionally substituted with 1-3 fluorine atoms and optionally also substituted with one phenyl group, and (d) phenyl which is optionally substituted with 1-3 groups independently selected from halogen, —$CH_3$, —$CF_3$, —$OCH_3$, and —$OCF_3$.

Each $R^e$ is independently selected from the group consisting of —$C_2$-$C_4$ alkenyl, cyclopropyl, —C(=O)$C_1$-$C_2$alkyl, —C(=O)H, —$CO_2$H, —$CO_2C_1$-$C_4$alkyl, —OH, —$NR^3R^4$, —$NR^3C$(=O)$OC_1$-$C_4$alkyl, —S(O)$_x$$C_1$-$C_2$ alkyl, —CN, —$NO_2$, and a 5-6-membered heterocyclic ring having 1-2 heteroatoms independently selected from N, S, and O, wherein the point of attachment of said heterocyclic ring to the ring to which $R^e$ is attached is a carbon atom, wherein said heterocyclic ring is optionally substituted with 1-5 substituent groups independently selected from halogen;

wherein for compounds in which $R^e$ is selected from the group consisting of —$C_2$-$C_4$ alkenyl, —C(=O)$C_1$-$C_2$alkyl, —$CO_2C_1$-$C_4$alkyl, —$NR^3C$(=O)$OC_1$-$C_4$alkyl, and —S(O)$_x$$C_1$-$C_2$ alkyl, the alkyl group of $R^e$ is optionally substituted with 1-5 halogens and is optionally also substituted with one substituent group selected from (a) —OH, (b) —$NR^3R^4$, (c) —$OCH_3$ optionally substituted with 1-3 fluorine atoms and optionally substituted with one phenyl group, and (d) phenyl which is optionally substituted with 1-3 groups independently selected from halogen, —$CH_3$, —$CF_3$, —$OCH_3$, and —$OCF_3$.

p is an integer from 0-2.

$R^3$, $R^4$, and $R^5$ are each independently selected from H and —$C_1$-$C_3$ alkyl.

In many embodiments: the following definitions apply:

X is —O—;

Z is —C(=O)—;

Y is —CHR$^1$, where R$^1$ is selected from H and $C_1$-$C_2$alkyl;

R and $R^5$ are H;

$R^2$ and B are each selected from $A^1$ and $A^2$, wherein one of $R^2$ and B is $A^1$ and the other of $R^2$ and B is $A^2$;

$A^2$ is selected from the group consisting of phenyl, pyridyl, pyrazolyl, thienyl, 1,2,4-triazolyl, and imidazolyl;

$A^3$ is selected from the group consisting of phenyl, thiazolyl, and pyrazolyl;

$A^4$ is selected from the group consisting of phenyl, pyridyl, thiazolyl, pyrazolyl, 1,2,4-triazolyl, pyrimidinyl, piperidinyl, pyrrolidinyl, and azetidinyl;

$A^2$ is optionally substituted with 1-3 substituents independently selected from halogen, —$OCH_3$, —$OCF_3$, and $C_1$-$C_3$alkyl optionally substituted with 1-3 halogens;

$A^3$ is substituted with one group $A^4$ and is optionally substituted with 1-2 substituents independently selected from halogen, —OH, —$OCH_3$, —$OCF_3$, and $C_1$-$C_3$alkyl optionally substituted with 1-3 halogens;

$A^4$ is optionally substituted with 1-3 substituents independently selected from the group consisting of (a) —$C_1$-$C_5$ alkyl optionally substituted with 1-3 halogens and optionally substituted with —OH, (b) —$C_2$-$C_4$ alkenyl optionally substituted with 1-3 halogens, (c) —C(=O)$C_1$-$C_2$alkyl optionally substituted with 1-3 halogens and optionally substituted with one group selected from —OH, —$CO_2CH_3$, —C(=O)$CH_3$, —$NR^3R^4$, and —$OC_1$-$C_2$alkyleneOC$_1$-$C_2$alkyl, (d) —C(=O)H, (e) —$CO_2$H, (f) —$CO_2C_1$-$C_4$alkyl optionally substituted with one group selected from —C(=O)$C_1$-$C_2$alkyl, —OH, —$CO_2CH_3$, —$CO_2$H, —$NR^3R^4$, and —$OC_1$-$C_2$alkyleneOC$_1$-$C_2$alkyl, (g) —OH, (h) —S(O)$_x$$C_1$-$C_2$ alkyl, (i) halogen, (j) —CN, (k) —$NO_2$, (l) —C(=O)$NR^3R^4$, (m) —$OC_1$-$C_2$alkyleneOC$_1$-$C_2$alkyl, (n) —$OC_1$-$C_3$ alkyl optionally substituted with 1-3 halogens, (o) —C(=O)$OC_1$-$C_2$alkyl optionally substituted with 1-3 halogens and optionally substituted with one group selected from —OH, —$CO_2CH_3$, —$NR^3R^4$, and —$OC_1$-$C_2$alkyleneOC$_1$-$C_2$alkyl, (p) —$NR^3C$(=O)$C_1$-$C_2$alkyl, (q) —$NR^3R^4$, and (r) —S(O)$_x$$NR^3R^4$, provided that if $A^4$ is a heterocyclic group connected to $A^3$ through a ring carbon atom of $A^4$, then at least one substituent on $A^4$ must be selected from $R^e$, where $R^e$ is selected from the group consisting of (a) —$C_1$-$C_5$ alkyl substituted with —OH and optionally substituted with 1-3 halogens, (b) —$C_2$-$C_4$ alkenyl optionally substituted with 1-3 halogens, (c) —C(=O)$C_1$-$C_2$alkyl optionally substituted with 1-3 halogens and optionally substituted with one group selected from —OH, —$CO_2CH_3$, —C(=O)$CH_3$, —$NR^3R^4$, and —$OC_1$-$C_2$alkyleneOC$_1$-$C_2$alkyl, (d) —C(=O)H, (e) —$CO_2$H, (f) —$CO_2C_1$-$C_4$alkyl optionally substituted with one group selected from —C(=O)$C_1$-$C_2$alkyl, —OH, —$CO_2CH_3$, —$CO^2$H, —$NR^3R^4$, and —$OC_1$-$C_2$alkyleneOC$_1$-$C_2$alkyl, (g) —OH, (h) —S(O)$_x$$C_1$-$C_2$ alkyl, (i) —CN, (j) —$NO_2$, (k) —C(=O)$NR^3R^4$, (l) —$OC_1$-$C_2$alkyleneOC$_1$-$C_2$alkyl, (m) —C(=O)$OC_1$-$C_2$alkyl optionally substituted with 1-3 halogens and optionally substituted with one group selected from —OH, —$CO_2CH_3$, —$NR^3R^4$, and —$OC_1$-$C_2$alkyleneOC$_1$-$C_2$alkyl, (n) —$NR^3C$(=O)$C_1$-$C_2$alkyl, (o) —$NR^3R^4$; and (p) —S(O)$_x$$NR^3R^4$;

$R^a$ is selected from halogen, —$CH_3$, —$CF_3$, —$OCH_3$, and —$OCF_3$;

$R^3$ and $R^4$ are each independently selected from H and $CH_3$; and x is 0, 1 or 2.

In embodiments, B is $A^1$ and $R^2$ is $A^2$.

In embodiments, B is $A^2$ and $R^2$ is $A^1$.

In embodiments, $A^2$, $A^3$, and $A^4$ are phenyl.

In embodiments, each $R^a$ is selected from the group consisting of (a) —$C_1$-$C_4$ alkyl which is optionally substituted with 1-5 fluorine atoms and is optionally substituted with one group selected from —H, —$OCH_3$, and —$NR^3R^4$; (b) —$OC_1$-$C_2$alkyl, which is optionally substituted with 1-3 fluorine atoms; (c) —$C_2$-$C_4$ alkenyl; (d) —$C_1$-$C_2$ alkyl-O—$C_1$-$C_2$ alkyl-phenyl; (e) cyclopropyl; (f) —C(=O)H; (g) —$CO_2$H; (h) —$CO_2C_1$-$C_4$ alkyl; (i) —OH; (j) —$NR^3R^4$; (k) —S(O)$_x$$C_1$-$C_2$ alkyl; (l) halogen; (m) —CN; (n) —$NO_2$; and (o) a 5-6-membered heterocyclic ring comprising 1-2 oxygen atoms which is optionally substituted with $C_1$-$C_2$alkyl.

In other embodiments, the compound has Formula Ic, including pharmaceutically acceptable salts thereof, wherein

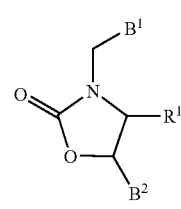

Ic wherein one of $B^1$ and $B^2$ is

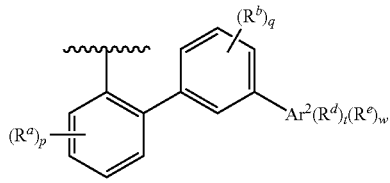

and the other of $B^1$ and $B^2$ is $Ar^1(R^c)_u$;
$Ar^1$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group;
(d) a benzoheterocyclic ring comprising a phenyl ring fused to a 5-6-membered heterocyclic ring having 1-2 heteroatoms independently selected from O, N, and S and optionally 1-2 double bonds; and
(e) a —$C_3$-$C_8$ cycloalkyl ring optionally having 1-3 double bonds;

$Ar^2$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a benzoheterocyclic ring comprising a phenyl ring fused to a 5-6-membered heterocyclic ring having 1-2 heteroatoms independently selected from O, N, and S and optionally 1-2 double bonds; and
(d) a 5-6-membered heterocyclic ring having 1-4 heteroatoms independently selected from N, S, O, and —N(O)—, and optionally also comprising 1-3 double bonds and a carbonyl group;

$R^1$ is selected from the group consisting of H, —$C_1$-$C_5$ alkyl, and halogen, wherein —$C_1$-$C_5$ alkyl is optionally substituted with 1-11 halogens;

$R^3$ and $R^4$ are each independently selected from H, —$C_1$-$C_5$ alkyl, —C(═O)$C_1$-$C_5$ alkyl and —S(O)$_y$$C_1$-$C_5$ alkyl, wherein —$C_1$-$C_5$ alkyl in all instances is optionally substituted with 1-11 halogens;

Each $R^a$, $R^b$, $R^c$, and $R^d$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —O$C_1$-$C_6$alkyl, —O$C_2$-$C_6$ alkenyl, —O$C_2$-$C_6$ alkynyl, —O$C_3$-$C_8$ cycloalkyl optionally having 1-3 double bonds, —C(═O)$C_1$-$C_6$alkyl, —C(═O)$C_3$-$C_8$ cycloalkyl, —C(═O)H, —$CO_2$H, —$CO_2$$C_1$-$C_6$alkyl, —C(═O)S$C_1$-$C_6$alkyl; —OH, —$NR^3R^4$, —C(═O)$NR^3R^4$, —$NR^3$C(═O)O$C_1$-$C_6$alkyl, —$NR^3$C(═O)$NR^3R^4$, —S(O)$_x$$C_1$-$C_6$ alkyl, —S(O)$_y$$NR^3R^4$, —$NR^3$S(O)$_y$$NR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$, $R^b$, $R^c$, or $R^d$ is attached is a carbon atom, wherein said heterocyclic ring is optionally substituted with 1-5 substituent groups independently selected from halogen, —$C_1$-$C_3$ alkyl, and —O$C_1$-$C_3$ alkyl, wherein —$C_1$-$C_3$ alkyl and —O$C_1$-$C_3$ alkyl are optionally substituted with 1-7 halogens;

wherein when $R^a$, $R^b$, $R^c$, and $R^d$ are selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —O$C_1$-$C_6$alkyl, —O$C_2$-$C_6$ alkenyl, —O$C_2$-$C_6$ alkynyl, —O$C_3$-$C_8$ cycloalkyl optionally having 1-3 double bonds, —C(═O)$C_1$-$C_6$alkyl, —C(═O)$C_3$-$C_8$ cycloalkyl, —$CO_2$$C_1$-$C_6$alkyl, —C(═O)S$C_1$-$C_6$alkyl, —$NR^3$C(═O)O$C_1$-$C_6$ alkyl, and —S(O)$_x$$C_1$-$C_6$ alkyl, then $R^a$, $R^b$, $R^c$, and $R^d$ are optionally substituted with 1-15 halogens and are optionally substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —O$C_1$-$C_4$alkyl optionally substituted with 1-9 halogens and optionally substituted with 1-2 substituent groups independently selected from O$C_1$-$C_2$ alkyl and phenyl, (f) —O$C_3$-$C_8$ cycloalkyl optionally having 1-3 double bonds and optionally substituted with 1-15 halogens, (g) —$CO_2$H, (h) —C(═O)$CH_3$, (i) —$CO_2$$C_1$-$C_4$alkyl which is optionally substituted with 1-9 halogens, and (j) phenyl which is optionally substituted with 1-3 groups independently selected from halogen, —$CH_3$, —$CF_3$, —$OCH_3$, and —$OCF_3$;

$R^e$ is selected from the group consisting of —$C_2$-$C_6$ alkenyl, —$C_2$-$C_6$ alkynyl, —$C_3$-$C_8$ cycloalkyl optionally having 1-3 double bonds, —O$C_2$-$C_6$ alkenyl, —O$C_2$-$C_6$ alkynyl, —O$C_3$-$C_8$ cycloalkyl optionally having 1-3 double bonds, —C(═O)$C_1$-$C_6$alkyl, —C(═O)$C_3$-$C_8$ cycloalkyl, —C(═O)H, —$CO_2$H, —$CO_2$$C_1$-$C_6$alkyl, —C(═O)S$C_1$-$C_6$alkyl, —OH, —$NR^3R^4$, —C(═O)$NR^3R^4$, —$NR^3$C(═O)O$C_1$-$C_6$ alkyl, —$NR^3$C(═O)$NR^3R^4$, —S(O)$_x$$C_1$-$C_6$ alkyl, —S(O)$_y$$NR^3R^4$, —$NR^3$S(O)$_y$$NR^3R^4$, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^e$ is attached is a carbon atom, wherein said heterocyclic ring is optionally substituted with 1-5 substituent groups independently selected from halogen, —$C_1$-$C_3$ alkyl, and —O$C_1$-$C_3$ alkyl, wherein —$C_1$-$C_3$ alkyl and —O$C_1$-$C_3$ alkyl are optionally substituted with 1-7 halogens;

wherein when $R^e$ is selected from the group consisting of —$C_2$-$C_6$ alkenyl, $C_2$-$C_6$ alkynyl, —$C_3$-$C_8$ cycloalkyl optionally having 1-3 double bonds, —O$C_2$-$C_6$ alkenyl, —O$C_2$-$C_6$ alkynyl, —O$C_3$-$C_8$ cycloalkyl optionally having 1-3 double bonds, —C(═O)$C_1$-$C_6$alkyl, —C(═O)$C_3$-$C_8$ cycloalkyl, —$CO_2$$C_1$-$C_6$alkyl, —C(═O)S$C_1$-$C_6$alkyl, —$NR^3$C(═O)O$C_1$-$C_6$alkyl, and —S(O)$_x$$C_1$-$C_6$ alkyl, then $R^e$ is optionally substituted with 1-15 halogens and is optionally substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —O$C_1$-$C_4$alkyl optionally substituted with 1-9 halogens and optionally substituted with 1-2 substituent groups independently selected from —O$C_1$-$C_2$ alkyl and phenyl, (f) —O$C_3$-$C_8$ cycloalkyl optionally having 1-3 double bonds and optionally substituted with 1-15 halogens, (g) —$CO_2$H, (h) —C(═O)$CH_3$, (i) —$CO_2$$C_1$-$C_4$alkyl which is optionally substituted with 1-9 halogens, and (j) phenyl which is optionally substituted with 1-3 groups independently selected from halogen, —$CH_3$, —$CF_3$, —$OCH_3$, and —$OCF_3$;

p is an integer from 0-4;

q is an integer from 0-4;

u is an integer from 0-5;

x is 0, 1 or 2; and y is 1 or 2;

wherein when $Ar^2$ is selected from the group consisting of:

(a) an aromatic ring selected from phenyl and naphthyl;

(b) a phenyl ring fused to a 5-7 membered non-aromatic cycloalkyl ring, which optionally comprises 1-2 double bonds;

(c) a benzoheterocyclic ring comprising a phenyl ring fused to a 5-6-membered, heterocyclic ring having 1-2 heteroatoms independently selected from O, N, and S and optionally 1-2 double bonds; and (d) a 5-6-membered heterocyclic ring having 1-4 heteroatoms independently selected from N, S, O, and —N(O)—, and optionally also comprising 1-3 double bonds and a carbonyl group, wherein the point of attachment of the heterocyclic ring to the phenyl group to which the heterocyclic ring is attached is a heteroatom of the heterocyclic ring;

then t is an integer from 0-5, and w is 0;

and when $Ar^2$ is a 5-6-membered heterocyclic ring having 1-4 heteroatoms independently selected from N, S, O, and —N(O)—, and optionally also comprising 1-3 double bonds and a carbonyl group, wherein the point of attachment of the heterocyclic ring to the phenyl group to which the heterocyclic ring is attached is a carbon atom of the heterocyclic ring, then t is an integer from 0-4, and w is 1.

Embodiments of the compound have Formula Ie, including pharmaceutically acceptable salts thereof:

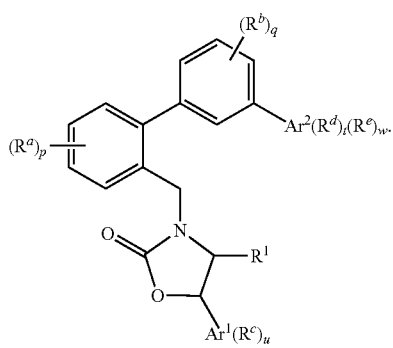

Ie

In embodiments, the compound has Formula If, including pharmaceutically acceptable salts thereof:

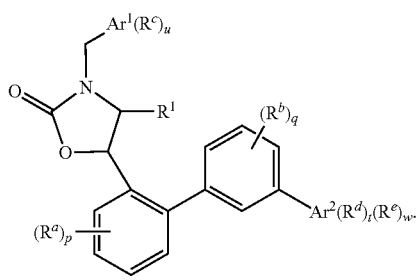

If

In embodiments, the compound has Formula Ig, including pharmaceutically acceptable salts thereof:

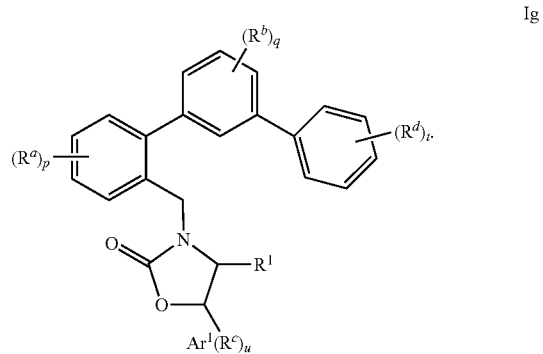

Ig

In embodiments, each $R^d$ is independently selected from the group consisting of —$C_1$-$C_4$ alkyl, —$C_2$-$C_4$ alkenyl, cyclopropyl, —$OC_1$-$C_4$alkyl, —$C(\!=\!O)C_1$-$C_4$alkyl, —$C(\!=\!O)H$, —$CO_2H$, —$CO_2C_1$-$C_4$alkyl, —OH, —$NR^3R^4$, —$NR^3C(\!=\!O)OC_1$-$C_4$alkyl, —$S(O)_xC_1$-$C_2$ alkyl, halogen, —CN, —$NO_2$, and a 5-6-membered heterocyclic ring having 1-2 heteroatoms independently selected from N, S, and O, wherein the point of attachment of said heterocyclic ring to the ring to which $R^d$ is attached is a carbon atom, wherein said heterocyclic ring is optionally substituted with 1-5 substituent groups independently selected from halogen;

wherein when $R^d$ is selected from the group consisting of —$C_1$-$C_4$ alkyl, —$C_2$-$C_4$ alkenyl, cyclopropyl, —$OC_1$-$C_4$alkyl, —$C(\!=\!O)C_1$-$C_4$alkyl, —$CO_2C_1$-$C_4$alkyl, —$NR^3C(\!=\!O)OC_1$-$C_4$alkyl, and —$S(O)_xC_1$-$C_2$ alkyl, then the alkyl, alkenyl and cyclopropyl group of $R^d$ is optionally substituted with 1-5 halogens and is optionally substituted with one substituent group selected from (a) —OH, (b) —$NR^3R^4$, (c) —$OCH_3$ optionally substituted with 1-3 fluorine atoms and optionally substituted with one phenyl group, and (d) phenyl which is optionally substituted with 1-3 groups independently selected from halogen, —$CH_3$, —$CF_3$, —$OCH_3$, and —$OCF_3$; and t is an integer from 0-5.

Embodiments may have Formula Ih, or a pharmaceutically acceptable salt thereof:

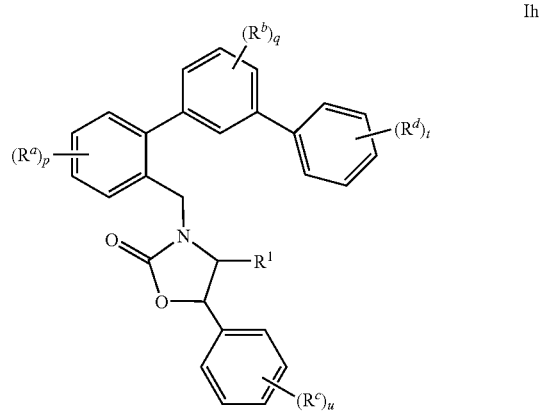

Ih

In independent embodiments, including pharmaceutically acceptable salts:

$R^1$ is selected from the group consisting of H, and —$C_1$-$C_5$ alkyl, wherein —$C_1$-$C_5$ alkyl is optionally substituted with 1-11 halogens.

$R^3$ and $R^4$ are each independently selected from H and —$C_1$-$C_5$ alkyl, wherein —$C_1$-$C_5$ alkyl in all instances is optionally substituted with 1-11 halogens.

Each $R^a$, $R^b$, and $R^c$ is independently selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —C(=O)H, —$CO_2$H, —$CO_2C_1$-$C_6$alkyl, —OH, —$NR^3R^4$, —$NR^3$C(=O)$OC_1$-$C_6$ alkyl, —S(O)$_x$$C_1$-$C_6$ alkyl, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein when $R^a$, $R^b$, and $R^c$ are selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —$CO_2C_1$-$C_6$alkyl, —$NR^3$C(=O)$OC_1$-$C_6$ alkyl, and —S(O)$_x$$C_1$-$C_6$ alkyl, then $R^a$, $R^b$ and $R^d$ are optionally substituted with 1-15 halogens and are optionally substituted with one substituent group selected from (a) —H, (b) —$NR^3R^4$, (c) —$OC_1$-$C_4$alkyl optionally substituted with 1-9 halogens and optionally substituted with 1-2 groups independently selected from —$OC_1$-$C_2$ alkyl and phenyl, and (d) phenyl which is optionally substituted with 1-3 groups independently selected from halogen, —$CH_3$, —$CF_3$, —$OCH_3$, and —$OCF_3$.

Each $R^d$ is independently selected from the group consisting of —$C_1$-$C_4$ alkyl, —$C_2$-$C_4$ alkenyl, —$OC_1$-$C_2$alkyl, —C(=O)$C_1$-$C_2$alkyl, —C(=O)H, —$CO_2$H, —$CO_2C_1$-$C_4$alkyl, —OH, —$NR^3R^4$, —$NR^3$C(=O)$OC_1$-$C_4$ alkyl, —S(O)$_x$$C_1$-$C_2$ alkyl, halogen, —CN, —$NO_2$, and a 5-6-membered heterocyclic ring having 1-2 heteroatoms independently selected from N, S, and O, wherein the point of attachment of said heterocyclic ring to the ring to which $R^a$ is attached is a carbon atom, wherein said heterocyclic ring is optionally substituted with 1-5 substituent groups independently selected from halogen;

wherein when $R^d$ is selected from the group consisting of —$C_1$-$C_4$ alkyl, —$C_2$-$C_4$ alkenyl, —$OC_1$-$C_2$alkyl, —C(=O)$C_1$-$C_2$alkyl, —$CO_2C_1$-$C_4$alkyl, —$NR^3$C(=O)$OC_1$-$C_4$ alkyl, and —S(O)$_x$$C_1$-$C_2$ alkyl, then the alkyl or alkenyl group of $R^d$ is optionally substituted with 1-5 halogens and is optionally substituted with one group selected from (a) —H, (b) —$NR^3R^4$, (c) —$OCH_3$ optionally substituted with 1-3 fluorine atoms and optionally substituted with one phenyl group, and (d) phenyl which is optionally substituted with 1-3 groups independently selected from halogen, —$CH_3$, —$CF_3$, —$OCH_3$, and —$OCF_3$.

In embodiments:
p is an integer from 0-2.
q is an integer from 0-2.
t is an integer from 0-3.
u is an integer from 0-2.
x is 0, 1 or 2.
y is 1 or 2.

In independent embodiments, including pharmaceutically acceptable salts:
$R^1$ is selected from H and —$C_1$-$C_2$ alkyl.
$R^3$ and $R^4$ are each independently selected from H and —$C_1$-$C_3$ alkyl.

Each $R^a$, $R^b$, and $R^c$ is independently selected from the group consisting of —$C_1$-$C_4$ alkyl, —$C_2$-$C_4$ alkenyl, —$OC_1$-$C_2$alkyl, —C(=O)$C_1$-$C_2$alkyl, —C(=O)H, —$CO_2$H, —$CO_2C_1$-$C_4$alkyl, —OH, —$NR^3R^4$, —$NR^3$C(=O)$OC_1$-$C_4$ alkyl, —S(O)$_x$$C_1$-$C_2$ alkyl, halogen, —CN, and —$NO_2$;

wherein when $R^a$, $R^b$, and $R^c$ are selected from —$C_1$-$C_4$ alkyl, —$C_2$-$C_4$ alkenyl, —$OC_1$-$C_2$alkyl, —C(=O)$C_1$-$C_2$alkyl, —$CO_2C_1$-$C_4$alkyl, —$NR^3$C(=O)$OC_1$-$C_4$alkyl, and —S(O)$_x$$C_1$-$C_2$ alkyl, then the alkyl and alkenyl groups of $R^a$, $R^b$, and $R^c$ are optionally substituted with 1-5 halogens and are optionally substituted with one group selected from (a) —OH, (b) —$NR^3R^4$, (c) —$OCH_3$ optionally substituted with 1-3 fluorine atoms and optionally substituted with one phenyl group, and (d) phenyl which is optionally substituted with 1-3 groups independently selected from halogen, —$CH_3$, —$CF_3$, —$OCH_3$, and —$OCF_3$.

$R^d$ is selected from the group consisting of —$C_1$-$C_4$ alkyl, —$C_2$-$C_4$ alkenyl, —$NR^3R^4$, —C(=O)H, —$CO_2$H, —$CO_2C_1$-$C_4$alkyl, —OH, halogen, —CN, and —$NO_2$, wherein —$C_1$-$C_4$alkyl and —$C_2$-$C_4$ alkenyl in all uses are optionally substituted with 1-5 fluorine atoms.
p is an integer from 1-2.
q is an integer from 1-2.
t is an integer from 0-3.
u is an integer from 1-2.
x is 0, 1 or 2.

In additional embodiments, including pharmaceutically acceptable salts:
$R^1$, $R^3$ and $R^4$ are each independently selected from H and $CH_3$.
$R^a$, $R^b$, and $R^c$ are each independently selected from the group consisting of —$C_1$-$C_3$ alkyl, —$OC_1$-$C_2$alkyl, halogen and —OH, wherein —$C_1$-$C_3$ alkyl and —$OC_1$-$C_2$alkyl are optionally substituted with 1-3 F.

$R^d$ is selected from the group consisting of —$C_1$-$C_3$ alkyl, —$NR^3R^4$, —$CO_2$H, —$CO_2C_1$-$C_3$alkyl, halogen, and —CN, wherein —$C_1$-$C_3$ alkyl and —$CO_2C_1$-$C_3$alkyl are optionally substituted with 1-3 F.
p is an integer from 1-2.
q is an integer from 1-2.
t is an integer from 0-3.
u is an integer from 1-2.

DEFINITIONS

"Ac" is acetyl, which is $CH_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl; hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated (e.g., cycloalkyl may be defined as having one or more double bonds). The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"EDC" is 1-ethyl-3-(3-dimethylaminopropyl)carbodiimide.

"Heterocyclyl," "heterocycle," and "heterocyclic" means a fully or partially saturated or aromatic 5-6 membered ring containing 1-4 heteroatoms independently selected from N, S and O, unless otherwise stated.

"Benzoheterocycle" represents a phenyl ring fused to a 5-6-membered heterocyclic ring having 1-2 heteroatoms, each of which is O, N, or S, where the heterocyclic ring may be saturated or unsaturated. Examples include indole, benzofuran, 2,3-dihydrobenzofuran and quinoline.

"DIPEA" is diisopropylethylamine.

"Halogen" includes fluorine, chlorine, bromine and iodine.

"HOBT" is 1-Hydroxybenzotriazole.

"IPAC" is isopropyl acetate.

"Me" represents methyl.

"Weinreb amine" is N,O-dimethylhydroxylamine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to include all such isomeric forms of the compounds of Formula I and all mixtures of the compounds. When structures are shown with a stereochemical representation, other stereochemical structures are also included individually and collectively, such as enantiomers, diastereoisomers (where diastereomers are possible), and mixtures of the enantiomers and/or diastereomers, including racemic mixtures.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the biphenyl and biaryl compounds herein are observed as mixtures of atropisomers (rotamers) in the NMR spectra. The individual atropisomers as well as mixtures thereof are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds of this invention are particularly effective in raising HDL-C and/or increasing the ratio of HDL-C to LDL-C. The compounds are also effective in lowering LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier without other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I and Ia-Ij) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations of compounds of this invention with statins other than simvastatin, such as lovastatin, rosuvastatin, pravastatin, fluvastatin, atorvastatin, rivastatin, itavastatin, and ZD4522.

Finally compounds of this invention can be used with compounds that are useful for treating other diseases, such as diabetes, hypertension and obesity, as well as other anti-atherosclerostic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these disease, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including vildagliptin, sitagliptin, and saxagliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

These other active ingredients that may be used in combination with the current invention also include antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and $\beta_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as losartan; (2) angiotensin converting enzyme inhibitors (ACE inhibitors), such as enalapril and captopril; (3) calcium channel blockers such as nifedipine and diltiazam; and (4) endothelian antagonists.

Anti-obesity compounds may be administered in combination with the compounds of this invention, including: (1) growth hormone secretagogues and growth hormone secretagogue receptor agonists/antagonists, such as NN703, hexarelin, and MK-0677; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, aminone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6, beta-Ala11, Phe13, Nle14]Bn(6-14) and [D-Phe6, Phe13]Bn(6-13)propylamide; (32) CNTF (Ciliary neurotrophic factors), such as GI-181771 (Glaxo-SmithKline), SR146131 (Sanofi Synthelabo), butabindide, PD170, 292, and PD 149164 (Pfizer); (33) CNTF derivatives, such as axokine (Regeneron); (34) monoamine reuptake inhibitors, such as sibutramine; (35) UCP-1 (uncoupling protein-1,2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone βagonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) a minorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

CETP Assay

An in vitro continuous assay for determining IC$_{50}$'s to identify compounds that are CETP inhibitors was performed based on a modification of the method described by Epps et al. employing BODIPY®-CE as the cholesteryl ester lipid donor and BODIPY®-TG as the triglyceride lipid donor. See Epps et al. (1995) *Method for measuring the activities of cholesteryl ester transfer protein (lipid transfer protein)*, Chem. Phys. Lipids. 77, 51-63.

Particles used in the assay were created from the following materials by probe sonication essentially as described by Epps et al. Synthetic cholesteryl ester (CE) donor HDL particles contained DOPC (Dioleoyl Phosphatidyl Choline), BODIPY®-CE (Molecular Probes C-3927), triolein (a triglyceride), dabcyl dicetylamide, (a non-diffusable quencher molecule to reduce background fluorescence) and apoHDL. Synthetic triglyceride (TG) donor HDL particles contained DOPC, BODIPY®-TG, and apoHDL. BODIPY®-TG was synthesized at room temperature from diolein and the BODIPY containing fatty acid analog 4,4-difluoro-5-(2-thienyl)-4-bora-3a,4a-diaza-s-indacene-3-dodecanoic acid (Molecular Probes) in methylene chloride in the presence of dicyclohexyl carbodimide. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat #7205). An assay cocktail containing CETP, 1×CETP buffer (50 mM Tris, pH 7.4, 100 mM NaCl, 1 mM EDTA), 3% human serum, and half the final concentration of acceptor particles was prepared, and 100 μL of the assay cocktail was added to each well of the plate. Test compounds in DMSO were added in a volume of 3 μL. The plate was mixed on a plate shaker and then incubated at 25° C. for 1 hour. A second assay cocktail containing donor particles, the remaining acceptor particles and 1×CETP buffer was prepared. 47 μL of the second assay cocktail was added to the reaction wells to start the assay. Assays were performed in a final volume of 150 μL. CE transfer reactions were performed as follows: final concentrations of materials were: 2.5 ng/μL CE donor particles, 7.5 ng/μL acceptor particles (each expressed by protein content), 1×CETP buffer, 14-30 nM recombinant human CETP (expressed in CHO cells and partially purified), and up to 2% DMSO when testing compounds; reactions were followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well. TG transfer reactions were performed as described above with the exception that 2.5 ng/uL TG donor particles were used. TG transfer was measured at an excitation wavelength of 538 nm while reading emission at 568 nm every 45 sec for 45 min at 37° C. with a cutoff filter at 550 nm.

Data were evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate IC$_{50}$.

EXAMPLES

The following schemes and examples are provided so that the invention will be more fully appreciated and understood. Starting materials are made using known procedures or as shown below.

The examples should not be construed as limiting the invention in any way. The scope of the invention is defined by the appended claims. Compounds of this invention have an IC$_{50}$ value as measured for the CE transfer reaction, the TG transfer reaction, or both as described above of less than or equal to 50 μM. IC$_{50}$ values of one or both reactions are generally in the range of 5 nM-15 μM, and are preferably in the range of 5 nM-5 μM, more preferably in the range of 5 nM-1 μM, still more preferably in the range of 5 nM-200 nM, and even more preferably in the range of 5 nM-100 nM.

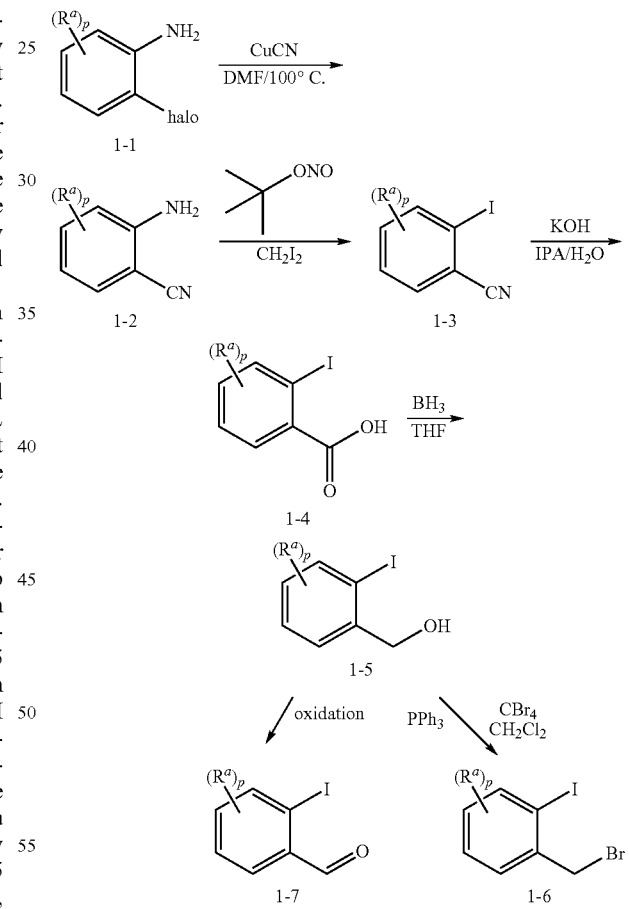

Intermediates 1-2, 1-3, 14, 1-5, 1-6 and 1-7 utilized in the present invention wherein R$^a$ is as defined in the claims can be purchased or prepared as shown in Scheme 1. An appropriately substituted 2-haloaniline 1-1 where the halogen is preferably iodo or bromo is treated with CuCN in DMF at elevated temperature to afford the corresponding 2-cyanoaniline 1-2. Alternatively, the nitrile can be prepared by treatment of 1-1 with KCN and CuI in the presence of a palladium (II) salt or in the presence of certain copper or nickel complexes (See: Smith, M. B. and March, J. "March's Advanced Organic Chemistry", 5th Ed., John Wiley and Sons, New York, pp. 867 (2001) and references therein). Iodides 1-3 are prepared by treatment of 1-2 with isoamylnitrite, n-pentylnitrite, t-butyl nitrite or the like in diiodomethane (see for example: Smith et al., *J. Org. Chem.* 55, 2543, (1990) and references cited therein). Alternatively, the iodide can be prepared first by diazonium formation using isoamylnitrite, n-pentylnitrite, t-butyl nitrite, sodium nitrite, nitrous acid or the like followed by heating in the presence of an iodide salt such as copper iodide, sodium iodide, potassium iodide, tetrabutylammonium iodide or the like. Hydrolysis of iodo-nitrile 1-3 is carried out using potassium hydroxide in isopropanol and water to afford the iodoacid 14. Further reduction with borane, lithium aluminum hydride, lithium borohydride or the like in ether, tetrahydrofuran, dimethoxyethane or the like affords the 2-iodo alcohols 1-5. Intermediates 1-5 can be transformed into benzyl bromides 1-6 using reagents such as triphenylphosphine and carbon tetrabromide in solvents such as dichloromethane or the like (see Smith, M. B. and March, J. "March's Advanced Organic Chemistry", 5th Ed., John Wiley and Sons, New York, pp. 518-199 (2001) and references therein). Intermediates 1-6 can also be transformed into aldehydes 1-7 by treatment with Dess-Martin periodinane in dichloromethane or by Swern oxidation conditions, tetrapropylammonium perruthenate, pyridinium chlorochromate, sulfur trioxide-pyridine, or the like (see Smith, M. B. and March, J. "March's Advanced Organic Chemistry", 5th Ed., John Wiley and Sons, New York, pp. 1167-1171 (2001) and references cited therein).

SCHEME 2

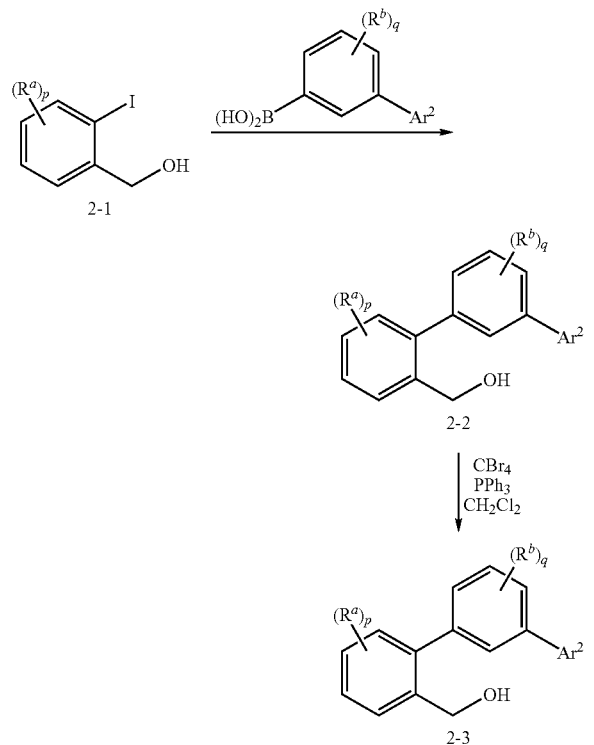

Intermediates 2-2 and 2-3 utilized in the present invention wherein $R^a$, $R^b$ and $Ar^2$ are as defined in the claims can be prepared as shown in Scheme 2. Benzyl alcohols 2-1 can be purchased or prepared according to the procedure outlined in Scheme 1. Intermediates 2-2 can be prepared via Suzuki reaction wherein 2-1 is coupled with an appropriately substituted aryl boronic acid or aryl boronate ester in the presence of a palladium catalyst. The coupling reaction may be carried out using Pd(II)acetate and potassium carbonate in aqueous acetone at reflux. Alternatively the reaction may employ tetrakis(triphenylphosphine)palladium in an ethanol/toluene mix in the presence of sodium carbonate. Alternatively, as practiced by those skilled in the art the reaction can employ a number of Palladium (0) compounds and Palladium (II) salts in a number of solvents and in the presence of a variety of ligands, bases, and promoters, generally but not exclusively, with heating and/or microwave irradiation. Some appropriate reaction condition as can be found described in Miyaua et al., *Chem. Rev.* 95, 2457 (1995) and references cited within and as described in Smith, M. B. and March, J. "March's Advanced Organic Chemistry", 5th Ed., John Wiley and Sons, New York, pp. 868-869 (2001) and references cited therein. Compounds 2-3 are prepared from intermediates 2-2 as described in Scheme 1.

SCHEME 3

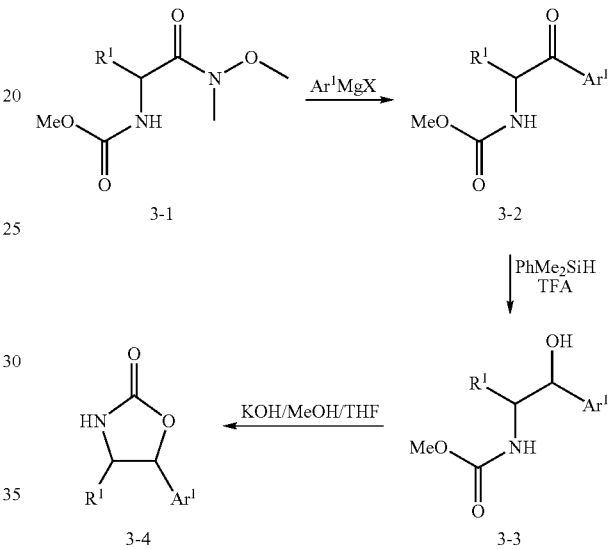

Intermediates 34 of the present invention wherein $R^1$ and $Ar^1$ are as defined in the claims can be prepared as shown in scheme 3. Treatment of an N-carbamoyl-N-methoxy-N-methyl)amide of an amino acid 3-1 which can be purchased or prepared by known methods with a Grignard or other organometallic reagent such as an organolithium affords the corresponding ketone 3-2. Reduction of the ketone with sodium borohydride or zinc borohydride in alcoholic solvents or THF or the like or with other reducing agents such as phenyldimethyl silane in THF affords alcohol 3-3 which can be cyclized to oxazolidinone 34 upon treatment with base such as KOH in solvents such as MeOH, EtOH or the like and THF, dioxane, dimethoxyethane or the like.

SCHEME 4

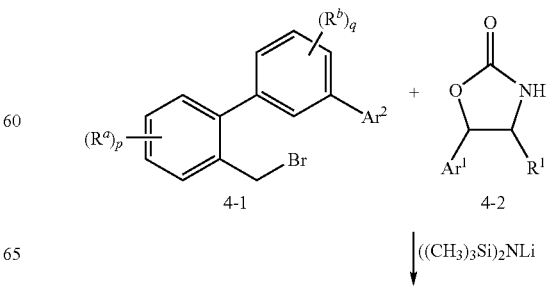

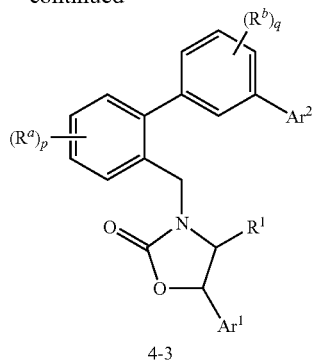

4-3

Compounds of the present invention 4-3 wherein $R^1$, $R^a$, $R^b$, $Ar^1$ and $Ar^2$ are as defined in the claims can be prepared as shown in Scheme 4. Oxazolidinones 4-2, prepared as shown in Schemes 3 can be alkylated with benzyl bromides 4-1 which is prepared as shown in Scheme I using bases such as sodium hexamethyldisiliazide or sodium hydride in solvents like tetrahydrofuran, dimethoxyethane, diethyl ether or the like to afford products 4-3.

Compounds of the present invention 5-4 wherein $R^1$, $R^a$, $R^b$, $Ar^1$, and $Ar^2$ are as defined in the claims can be prepared as shown in Scheme 5. Oxazolidinones 5-2, prepared as shown in Schemes 10 and 11 can be alkylated with benzyl bromides 5-1 which is prepared as shown in Scheme 1 using bases such as sodium hexamethyldisiliazide or sodium hydride in solvents like tetrahydrofuran, dimethoxyethane, diethyl ether or the like to afford products 5-3. Compounds 5-5 are then prepared via a Suzuki or Stille reaction or variation thereof employing palladium catalyzed cross coupling of iodide 5-3 with an appropriately substituted aryl- or heteroaryl-boronic acid, -boronate ester or -trialkyl tin as described in Miyaua et al., *Chem. Rev.* 95, 2457 (1995) and references cited within and as described in de Meijere, A. and Diedrich, F. "Metal-Catalyzed Cross Coupling Reactions", $2^{nd}$ Ed., WILEY-VCH Verlag GmbH & Co. KgaA, Weinheim (2004) and references cited therein. Alternatively, aryl boronic acids or arylboronate esters can be prepared by treatment of aryl halide 5-3 with a suitable reagent such as a diborane silyl borane or stannyl borane or the like in the presence of a palladium or platinum catalys or by metal halogen exchange and treatment with a suitable boron electrophile as described in de Meijere, A. and Diedrich, F. "Metal-Catalyzed Cross Coupling Reactions", $2^{nd}$ Ed., WILEY-VCH Verlag GmbH & Co. KgaA, Weinheim (2004), chapter 2. Aryl boron reagent 54 can then be treated with an appropriately substituted aryl halide in the presence of a suitable palladium catalyst to afford compounds 5-5.

SCHEME 5

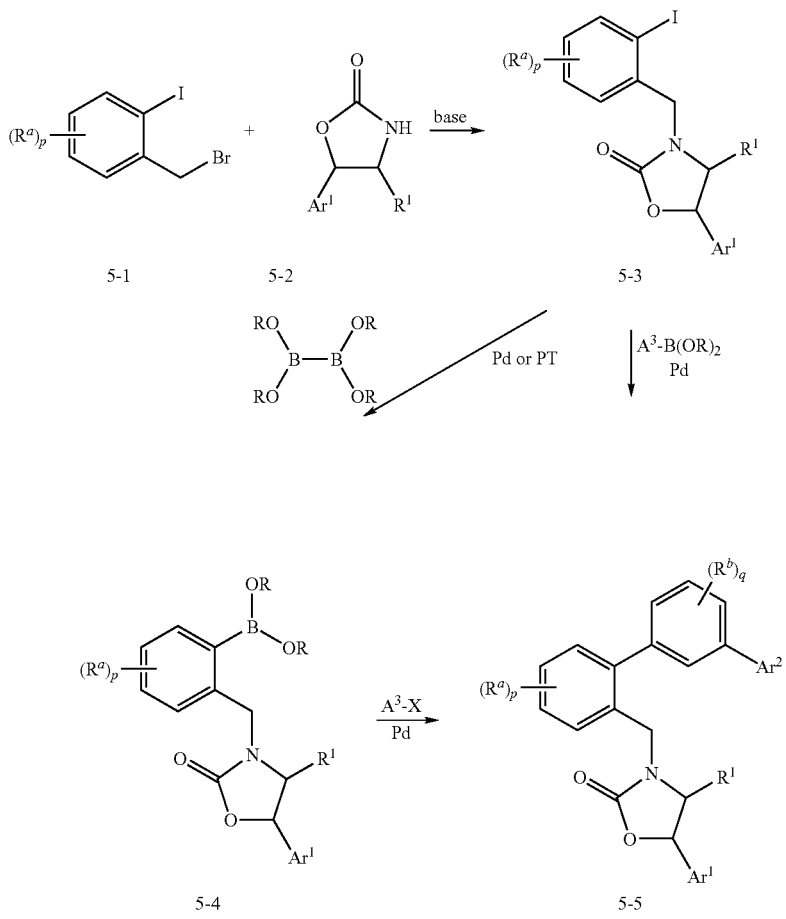

SCHEME 6

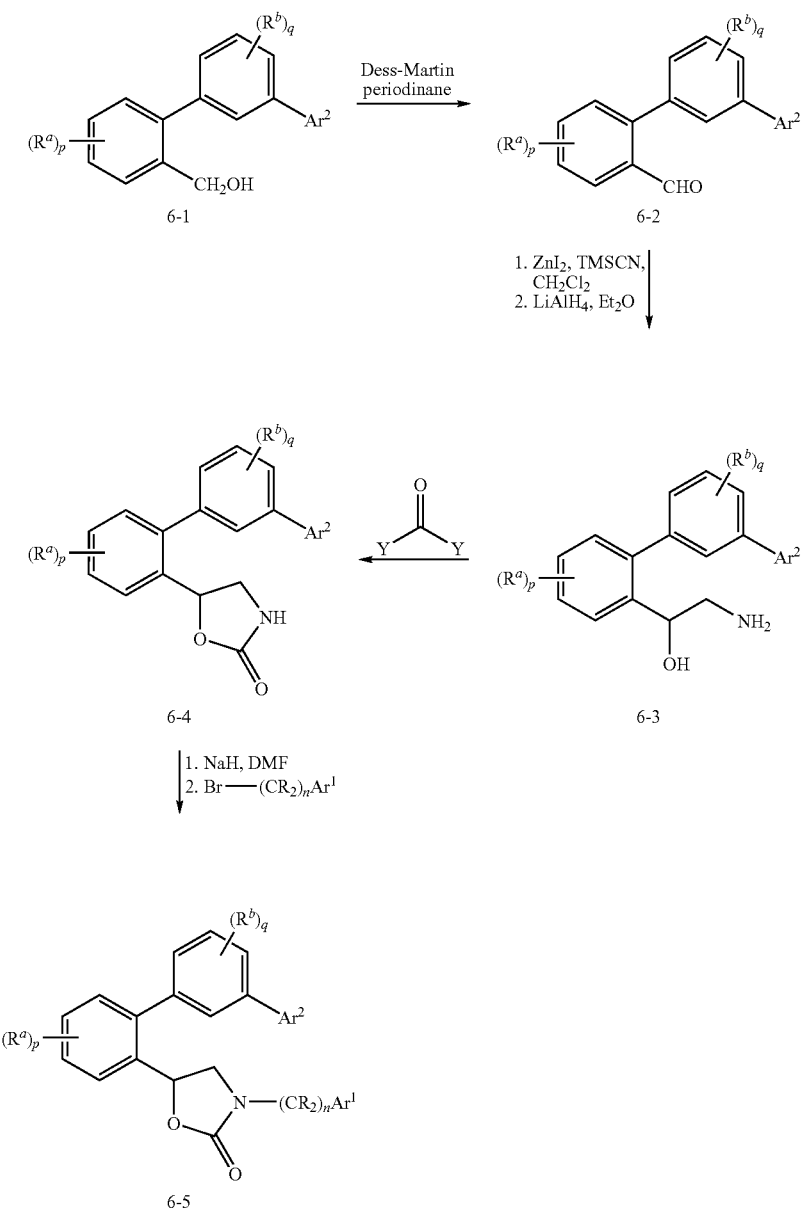

Compounds 6-5 of the present invention wherein $R^1$, $R^a$, $R^b$, $Ar^1$, and $Ar^2$ are as defined in the claims can be prepared as shown in Scheme 6. Benzyl alcohols 6-1 can be purchased or prepared according to the procedure outline in Scheme 2. Reaction of 6-1 with the Dess-Martin periodinane affords the corresponding benzylaldehydes 6-2. Other methods for oxidizing a primary hydroxyl group to an aldehyde can also be used, for example, Swern oxidation conditions, tetrapropylammonium perruthenate, pyridinium chlorochromate, sulfur trioxide-pyridine, or the like (see Smith, M. B. and March, J. "March's Advanced Organic Chemistry", 5$^{th}$ Ed., John Wiley and Sons, New York, pp. 1167-1171 (2001) and references cited therein). 2-Amino-1-phenylethanols 6-3 can be prepared from 6-2 via the corresponding silylated cyanohydrin by treatment with trimethylsilyl cyanide and catalytic zinc iodide followed by reduction with lithium aluminum hydride or the like reducing agent. Alternatively, 2-amino-1-phenylethanols 6-3 can be prepared from 6-2 via the corresponding cyanohydrin by treatment with potassium cyanide followed by reduction. 2-Amino-1-phenylethanols 6-3 can be cyclized to oxazolidinones 64 using reagents such as phosgene (Y=Cl), triphosgene (Y=OCCl$_3$) or carbonyl diimidazole (Y=imidazole) with bases such as triethylamine, diisopropylethyl amine or the like in solvents like dichloromethane, dichloroethane, tetrahydrofuran, dimethoxyethane or the like. Oxazolidinones 64 can be alkylated with alkyl, heteroalkyl, aryl, or heteroaryl bromides using bases such as sodium hexamethyldisiliazide or sodium hydride in solvents like tetrahydrofuran, dimethoxyethane, diethyl ether or the like to afford products 6-5. Enantiopure products may be obtained via chiral chromatography.

SCHEME 7

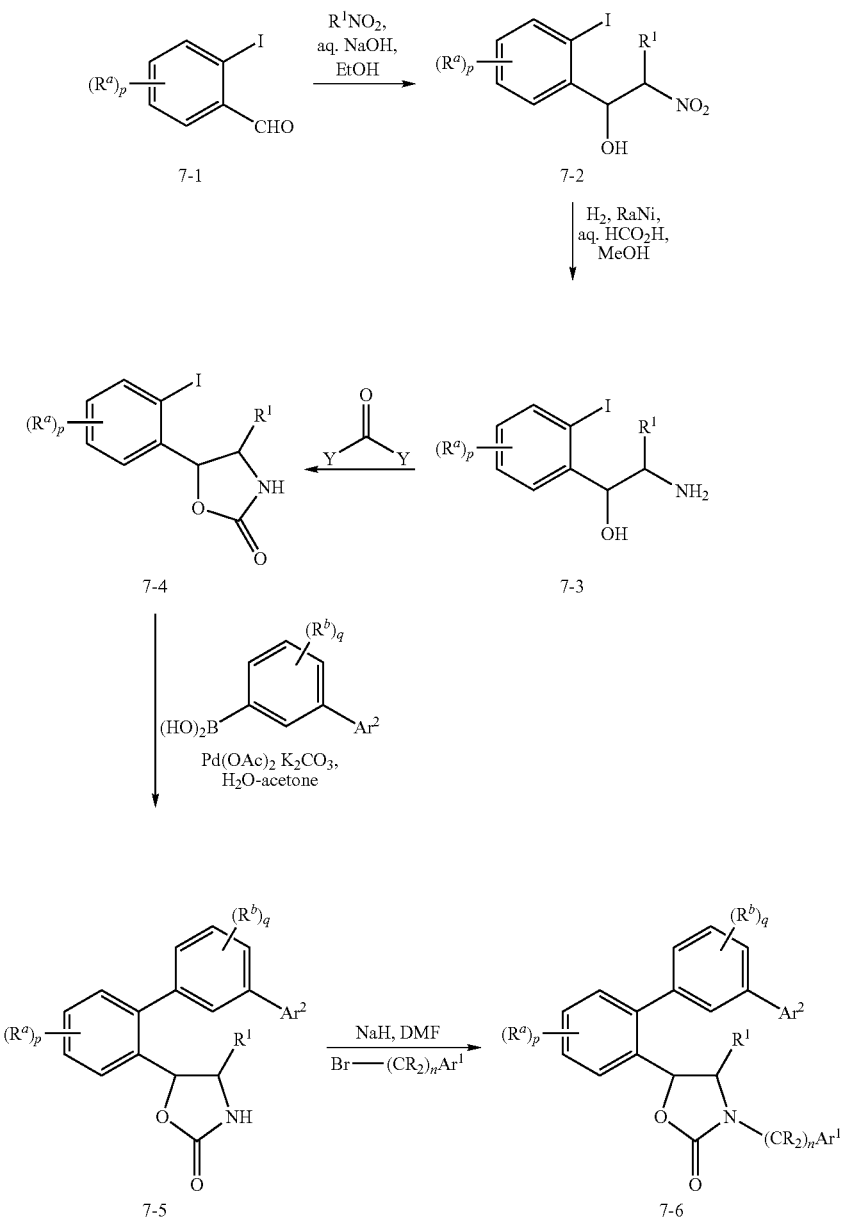

Compounds 7-6 of the present invention wherein $R^1$, $R^a$, $R^b$, $Ar^1$, and $Ar^2$ are as defined in the claims can be prepared as shown in Scheme 7. Aldehydes 7-1 can be purchased or prepared as outlined in Scheme 1. Condensation of 7-1 with a nitroalkane affords the substituted nitroalcohols 7-2. This reaction may be catalyzed by aqueous bases such as sodium hydroxide or the like in solvents such as ethanol, methanol, or the like. Nitroalcohols 7-2 can be reduced to aminoalcohols 7-3 with reductants such as Raney nickel, palladium on activated carbon, or platinum oxide in the presence of hydrogen gas and aqueous acid in alcoholic solvents such as methanol, ethanol or the like (See: Langer, O., et al., *Bioorg. Med. Chem.*, 2001, 9, 677-694). Aminoalcohols 7-3 can be cyclized to oxazolidinones 7-4 using reagents such as phosgene (Y=Cl), triphosgene (Y=OCCl₃) or carbonyl diimidazole (Y=imidazole) with bases such as triethylamine, diisopropylethylamine or the like in solvents like dichloromethane, dichloroethane, tetrahydrofuran, dimethoxyethane or the like. Oxazolidinones 7-5 are prepared via a Suzuki or Stille reaction or variation thereof employing palladium catalyzed cross coupling of iodides 7-4 with appropriately substituted aryl- or heteroaryl-boronic acids, -boronate esters or -trialkyl tin compounds, as described in Miyaura et al., *Chem. Rev.* 95, 2457 (1995) and references cited within, and as described in Smith, M. B. and March, J. "March's Advanced Organic Chemistry", 5th Ed., John Wiley and Sons, New York, pp. 868-869 (2001) and references cited therein. Oxazolidinones 7-5 can be alkylated with alkyl, heteroalkyl, aryl, or heteroaryl bromides using bases such as sodium hexamethyldisiliazide or sodium hydride in solvents like tetrahydrofuran, dimethoxyethane, diethyl ether or the like to afford products 7-6. Enantiopure products may be obtained via chiral chromatography.

SCHEME 8

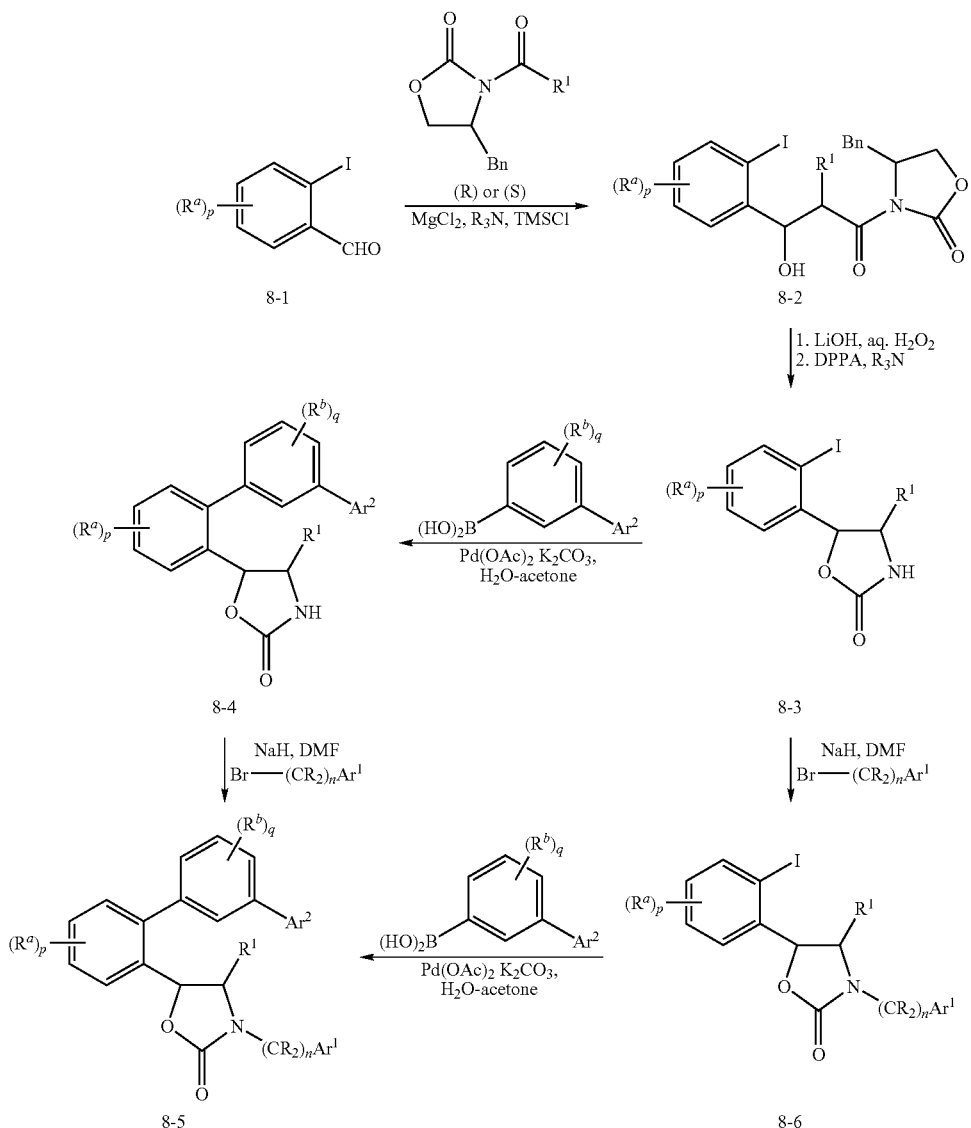

Compounds 8-5 of the present invention wherein R, R¹, A², A³ and n are as defined in the claims can be prepared as shown in Scheme 8. Aldehydes 8-1 can be purchased or prepared according to the procedure outline in Scheme 1. Condensation of 8-1 with chiral N-acyloxazolidinones affords the aldol adducts 8-2, as described in Evans, D. A. et al., *J. Am. Chem. Soc.*, 2002, 124, 392-3. The chiral N-acyloxazolidinones can be purchased or prepared as described in Ager, D. J.; Allen, D. A.; Schaad, D. R. *Synthesis* 1996, 1283-5. Compounds 8-2 can be hydrolyzed to the corresponding acids and then treated with diphenylphosphorazidate and a trialkylamine base to effect a Curtius rearrangement, affording chiral oxazolidinones 8-3. Oxazolidinones 8-4 are prepared via a Suzuki or Stille reaction or variation thereof employing palladium catalyzed cross coupling of iodides 8-3 with appropriately substituted aryl- or heteroaryl-boronic acids, -boronate esters or -triallyl tin compounds, as described in Miyaura et al., *Chem. Rev.* 95, 2457 (1995) and references cited within, and as described in Smith, M. B. and March, J. "March's Advanced Organic Chemistry", 5th Ed., John Wiley and Sons, New York, pp. 868-869 (2001) and references cited therein. Oxazolidinones 84 can be alkylated with alkyl, heteroalkyl, aryl, or heteroaryl bromides using bases such as sodium hexamethyldisiliazide or sodium hydride in solvents like tetrahydrofuran, dimethoxyethane, diethyl ether or the like to afford products 8-5. Alternatively, oxazolidinones 8-3 are alkylated with the appropriate bromides to afford compounds 8-6, which are subjected to a Suzuki or Stille reaction or variation thereof with appropriately substituted aryl- or heteroaryl-boronic acids, -boronate esters or -trialkyl tin compounds to afford products 8-5.

INTERMEDIATE 1

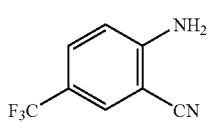

2-Amino-5-(trifluoromethyl)benzonitrile

A 2-liter flask was charged with 100 g (0.348 mol) of 4-amino-3-iodobenzotrifluoride, 40 g of CuCN and 750 mL of DMF. The mixture was heated to and then maintained at reflux for 1 hour. The reaction was cooled and poured into 3 L of water containing 300 mL of concentrated ammonium hydroxide. To the mixture was added 1 L CH₂Cl₂. The mixture was then filtered through Celite. The layers were separated and the aqueous layer was back extracted with CH₂Cl₂. The organic extracts were combined and the solvent removed under reduced pressure. The residue was dissolved in 1.5 L of ether and the resulting solution was washed with 1N ammonium hydroxide, aqueous sodium bisulfite, 1N aqueous HCl and brine. The solution was dried over anhydrous MgSO₄ and filtered through a silica gel plug containing a layer of MgSO₄ on top. The plug was washed with 0.5 L ether. The ether solutions were combined and concentrated to 750 mL and let stand at room temperature. After 2 days the resulting solids were collected, washed with hexanes and dried under reduced pressure to afford 2-amino-5-(trifluoromethyl)benzonitrile. ¹H NMR (CDCl₃, 500 MHz) δ 7.68 (s, 1H), 7.58 (d, J=8.5 Hz, 1H), 6.81 (d, J=8.5 Hz, 1H), 4.80 (br s, 2H).

INTERMEDIATE 2

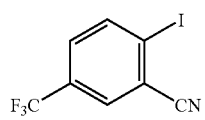

2-Iodo-5-(trifluoromethyl)benzonitrile

To a solution of 2-amino-5-(trifluoromethyl)benzonitrile (Intermediate 7, 15.1 g) and diiodomethane (24 mL) in acetonitrile (150 mL) at 35° C. was added t-butyl nitrite (21 mL) dropwise. The reaction was maintained at approximately 35° C. during the addition. The reaction was aged for 30 min and then heated to 60° C. for 30 minutes. The reaction mixture was cooled, diluted with ether and washed twice with water, twice with aqueous sodium bisulfite, water and then brine. The solution was dried over anhydrous MgSO₄, filtered through a silica gel plug and then concentrated giving afford a red oil. The product was purified by silica gel chromatography eluting sequentially with hexanes, 3:1 hexanes/CH₂Cl₂ and 1:1 hexanes/CH₂Cl₂ to afford 2-iodo-5-(trifluoromethyl) benzonitrile. ¹H NMR (CDCl₃, 500 MHz) δ 8.10 (d, J=8.5 Hz, 1H), 7.85 (d, J=1.8 Hz, 1H), 7.52 (dd, J=8.5, 1.8 Hz, 1H).

INTERMEDIATE 3

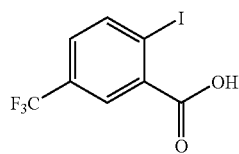

2-Iodo-5-(trifluoromethyl)benzoic Acid

Potassium hydroxide (3.78 g; 0.0673 mol) was added to a stirred solution of 2-iodo-5-(trifluoromethyl)benzonitrile (Intermediate 8; 4 g; 0.0135 mol) in a 1:1 isopropanol:H₂O solution (60 mL). The reaction was heated at reflux for 14 h and then partitioned between H₂O (50 mL) and EtOAc (50 mL). The aqueous layer was extracted with EtOAc (50 mL) and acidified to pH 5 with 6N HCl. The aqueous layer was further extracted with EtOAc (4×50 mL) and the combined extracts were washed with brine (50 mL), dried over MgSO₄, filtered, and concentrated in vacuo to afford 2-iodo-5-(trifluoromethyl)benzoic acid as a yellow solid. LCMS=317.0 (M+1)⁺. ¹H NMR (CDCl₃, 500 MHz): δ 8.27 (d, J=1.6 Hz, 1H), 8.25 (d, J=8.2 Hz, 1H), 7.47 (dd, J=8.2, 1.8 Hz, 1H).

INTERMEDIATE 4

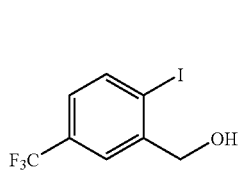

[2-Iodo-5-(trifluoromethyl)phenyl]methanol

Borane-THF (1.0M solution in THF; 94 mL; 94 mmol) was added to a stirred solution of 2-iodo-5-(trifluoromethyl)benzoic acid (Intermediate 3, 2.97 g; 9.4 mmol) in THF (300 mL) at 0° C. under N₂. The reaction was heated at reflux for 90 min and then carefully quenched with 6N HCl until no further gas evolution. The reaction was diluted with H₂O (250 mL) and extracted with EtOAc (3×250 mL). The combined extracts were washed with brine (300 mL), dried over MgSO₄, filtered, and concentrated in vacuo. The crude material was purified by flash chromatography on silica gel (0-25% EtOAc/hexanes gradient) to afford [2-iodo-5-(trifluoromethyl)phenyl]methanol as a white solid. LCMS=285.0 (M−17)⁺. ¹H NMR (CDCl₃, 500 MHz): δ 7.97 (d, J=8.3 Hz, 1H), 7.79 (s, 1H), 7.28 (d, J=8.4 Hz, 1H), 4.75 (s, 2H).

INTERMEDIATE 5

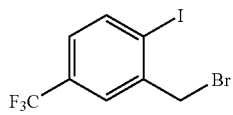

2-(Bromomethyl)-1-iodo-4-(trifluoromethyl)benzene

Carbon tetrabromide (1.86 g; 5.6 mmol) and triphenylphosphine (1.47 g; 5.6 mmol) were added successively to a stirred solution of [2-iodo-5-(trifluoromethyl)phenyl] methanol (Intermediate 10, 1.13 g; 3.74 mmol) in CH₂Cl₂ (25 mL) at 0° C. under N₂. The reaction was stirred at room temperature for 48 h. A second equivalent of carbon tetrabromide (1.2 g; 3.74 mmol) and triphenylphosphine (0.98 g; 3.74 mmol) was added and the reaction was stirred an additional 14 h. The solvent was removed in vacuo and the residue was purified by flash chromatography on silica gel (0-25% EtOAc/hexanes gradient) to afford 2-(bromomethyl)-1-iodo-4-(trifluoromethyl)benzene as a clear oil. ¹H NMR (CDCl₃, 500 MHz): δ 8.02 (d, J=8.2 Hz, 1H), 7.73 (d, J=1.8 Hz, 1H), 7.26 (dd, J=8.3, 1.8 Hz, 1H), 4.64 (s, 2H).

INTERMEDIATE 6

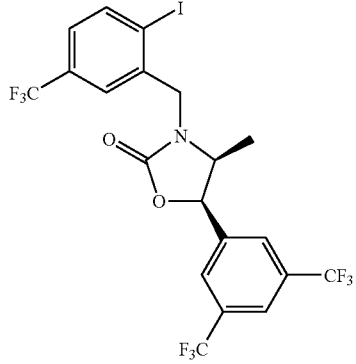

(4S,5R)-5-[3,5-bis(trifluoromethyl)phenyl]-3-[2-iodo-5-(trifluoromethyl)benzyl]-4-methyl-1,3-oxazolidin-2-one (4S,5R)-5-[3,5-bis(trifluoromethyl)phenyl]-4-methyl-1,3-oxazolidin-2-one (400 mg, 1.28 mmol) was treated with NaH (60% in oil, 128 mg, 3.2 mmol) and 2-(bromomethyl)-1-iodo-4-(trifluoromethyl)benzene (Example 70, 466 mg, 1.28 mmol) as described in Example 66 to afford (4S,5R)-5-[3,5-bis(trifluoromethyl)phenyl]-3-[2-iodo-5-(trifluoromethyl)benzyl]-4-methyl-1,3-oxazolidin-2-one as a white solid. LCMS=598.0 (M+1)$^+$. $^1$H NMR (CDCl$_3$, 500 MHz): δ 8.06 (d, J=8.2 Hz, 1H), 7.93 (s, 1H), 7.82 (s, 2H), 7.61 (s, 1H), 7.33 (dd, J=8.2, 1.4 Hz, 1H), 5.79 (d, J=7.8 hz, 1H), 4.91 (d, J=16 Hz, 1H), 4.40 (d, J=16 Hz, 1H), 4.16-4.06 (m, 1H), 0.83 (d, J=6.4 Hz, 3H).

INTERMEDIATE 7

(4S,5R)-5-[3,5-Bis(trifluoromethyl)phenyl]-4-methyl-1,3-oxazolidin-2-one

This intermediate is made directly from the chiral starting material CBZ-L-alanine by the 3-step route shown below. The compound (4R,5S)-5-[3,5-bis(trifluoromethyl)phenyl]-4-methyl-1,3-oxazolidin-2-one can be made by an analogous route starting from CBZ-D-alanine.

Step 1

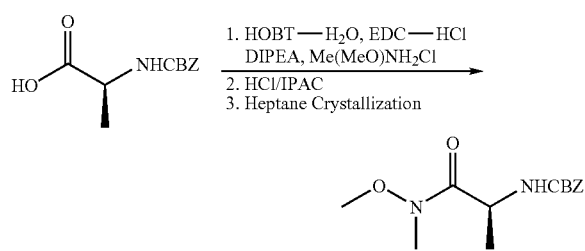

CBZ-L-Alanine (6.5 kg, 28.5 mol), HOBT-hydrate (4.8 kg, 34.8 mol), Weinreb amine-HCl salt (3.4 kg, 36.2 mol) and THF (32 L) are charged to a clean flask under nitrogen. (Weinreb amine is N,O-dimethylhydroxylamine.) The mixture is cooled to 0-10° C. and then DIPEA (12.4 L) is slowly added at a temperature less than 25° C. EDC-HCl (7 Kg, 36.2 mol) is then added slowly with cooling at 15'-25° C. The slurry is aged overnight at 20°-25° C. The mixture is then cooled to 0°-10° C. and 3 N HCl (12 L) is added slowly. Then IPAC (32 L) is added and the layers are separated. The organic layer is washed once with HCl (13 L) and twice with 8% NaHCO3 (13 L) (CAUTION: FOAMING). The organic layer is then concentrated under vacuum to about 15 L at 50° C. The clear solution is cooled slowly to room temperature, allowing the product to crystallize. Heptane (~70 L) is then added slowly. The slurry is filtered, washed with heptane (18 L), and dried at room temperature on the filter pot. Product is obtained with >99.9% ee measured by chiral HPLC.

Step 2

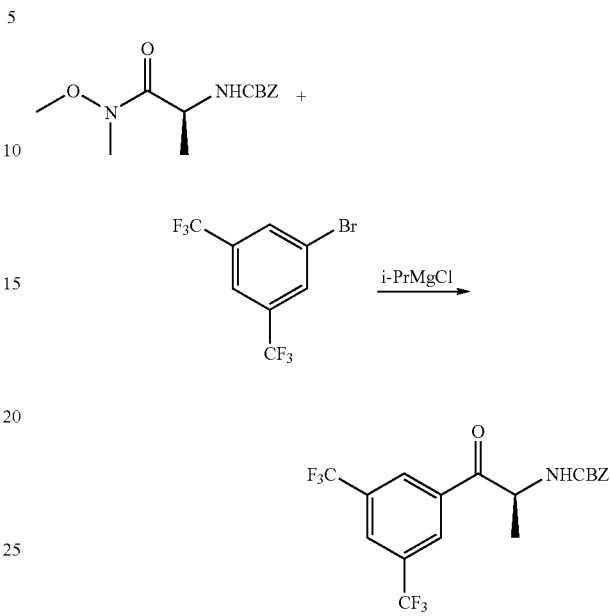

The Weinreb amide from Step 1 (6 kg, 22.5 mol) and 3,5-bis(trifluoromethyl)bromobenzene (4.85 L, 28.1 mol) are dissolved in anhydrous THF (24 L). The solution is purged with nitrogen to remove oxygen. The water content should be <500 ppm at this point. Atmospheric distillation can be carried out to azeotropically remove water if necessary. The solution is cooled to −10° C. and iso-PrMgCl in THF (56.4 mol) is slowly added (2 hours) to the reaction via addition funnel, maintaining a reaction temperature ≦−5° C. The solution is allowed to warm to 20° C. and aged overnight at 20° C., until the amide is <0.5 LCAP. The reaction is then cooled to −10° C. under nitrogen and is quenched slowly over 2 hours into 5N HCl (14 L) that is maintained at 0-5° C. MTBE (12 L) is added and the biphasic mixture is agitated for 5 min. After warming to 20°-25° C., it is allowed to settle for 30 min, and then the layers are separated. The organic layer is washed with water twice (12 L).

The organic layer is vacuum transferred through a 1-micron in-line PTFE filter into a distillation flask and is then concentrated to ~12 L under vacuum (internal temperature <40° C.) to a minimum agitated volume. The solution is then azeotropically dried with toluene and taken to a minimum agitated volume again. The solution is used directly in the next step.

Step 3: Reduction of Ketone (Step 2) to Chiral Oxazolidinone:

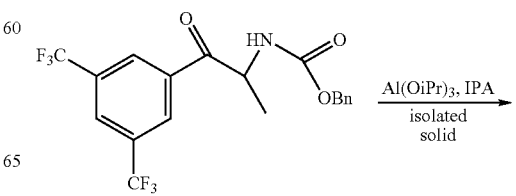

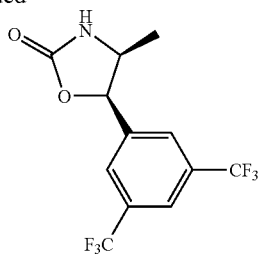

The ketone from the previous step (6 kg) is heated at 50° C. with 0.3 eq of Al(O-i-Pr)$_3$ (790 g) in 12 L IPA and 18 L of toluene for 15.5 hours. The solution is cooled to ambient temperature, and solid KOH pellets (1.35 kg) are added slowly with vigorous stirring, while keeping the temperature at <25° C. After about 2 hours, when HPLC shows >99.5% cyclization, 33 L of 1N HCl solution is added to quench the reaction, which is kept at <25° C. If a rag layer of solids forms, it should be filtered off. The rag layer is racemic oxazolidinone, and removal increases the enantiomeric excess. The organic layer is then washed first with 36 L of 0.5N HCl, then with 6 L IPA combined with 45 L water, and finally with 6 L IPA combined with 36 L water. The organic layer is transferred via an inline filter. The solvent is switched to heptane (target volume is ~42 L) at −40° C. until <2 v % toluene is left. Aging at room temperature for 2 h gives solid Intermediate 7.

INTERMEDIATE 8

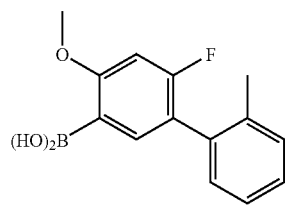

2-methoxy-4-fluoro-5-(2'-methylphenyl) Boronic Acid

Step A: 2-fluoro-2'-methylbiphenyl-4-yl Methyl Ether

A mixture of 4-bromo-3-fluoroanisole, 2-methylphenyl boronic acid, tetrakis(triphenylphosphine) palladium (5% mol) and sodium carbonate (0.23 g, 2.1 mmol) in 20 ml of water/EtOH/toluene (1:2:4) was heated to reflux for 5 h. TLC (EtOAc:hexane/2:98) showed that the reaction was over. The solvents was removed. Water (10 ml) was added. The organic was extracted with methylene chloride (3×50 ml). The combined methylene chloride layers were washed with brine, and dried over sodium sulfate. The title compound was obtained after purification with preparative TLC using 2% EtOAc in hexane as the eluant.

Step B: 2-fluoro-5-iodo-2'-methylbiphenyl-4-yl Methyl Ether

To a mixture of silver sulfate (0.34 g, 1.11 mmol), iodine (0.28 g, 1.11 mmol) in MeOH (10 ml) at room temperature, a solution of 2-fluoro-2'-methylbiphenyl-4-yl methyl ether from above (0.24 g, 1.11 mmol) in MeOH (5 ml) was added dropwise. The mixture was stirred at room temperature for 4 h until the color turned to light yellow. The solid was filtered off and the filtrate was concentrated. The residue was purified via flash column using hexane as the eluant to give the title compound.

Step C: 2-methoxy-4-fluoro-5-(2'-methylphenyl) Boronic Acid

To a solution of 2-fluoro-5-iodo-2'-methylbiphenyl-4-yl methyl ether (0.32 g, 0.93 mmol) in THF at −78° C., n-BuLi (0.48 ml, 1.22 mmol, 2.5M in hexane) was added dropwise by syringe. The solution was stirred at −78° C. for 30 min. Trimethyl borate (0.31 ml, 2.8 mmol) was added. The whole was stirred at −78° C. for 3 h. The reaction was quenched with a saturated solution of ammonium chloride. The mixture was extracted with EtOAc (3×15 ml). The combined EtOAc layers were dried over sodium sulfate. The title compound was used upon removal of solvent.

INTERMEDIATE 9

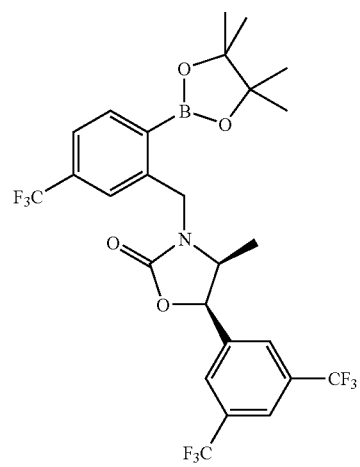

(4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (4S,5R)-5-[3,5-bis(trifluoromethyl)phenyl]-3-[2-iodo-5-(trifluoromethyl)benzyl]-4-methyl-1,3-oxazolidin-2-one (INTERMEDIATE 6, 0.75 g, 1.25 mmol), bis(pinacolato) diboron (339 mg, 1.5 mmol), 1,1'-bis(diphenylphosphino) ferrocene-palladium dichloride dichloromethane adduct (214 mg, 0.262 mmol), potassium acetate (257 mg, 2.616 mmol) and 1,4-dioxane (2.5 mL) were sealed in a microwave vessel. The reaction mixture was irradiated by microwave at 140° C. for 20 minutes then at 130° C. for 30 minutes. The reaction crude was treated with brine followed by ethyl acetate extractions. The combined extracts were dried over Na$_2$SO$_4$ followed by filtration and concentration in vacuo to afford a dark oil. The mixture was used for next step without purification.

INTERMEDIATE 10

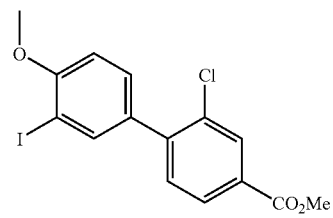

Methyl 2-chloro-3'-iodo-4'-methoxybiphenyl-4-carboxylate

Step A Methyl 4-iodo-3-chlorobenzoate

A mixture of methyl 4-amino-3-chlorobenzoate (1.0 g, 5.4 mmol), n-pentyl nitrite (0.95 g, 8.1 mmol) and iodine (1.78 g, 7.0 mmol) was stirred under refluxing for 1 h. The mixture was diluted with methylene chloride (30 ml). The purple solution was washed with saturated sodium thiosulfate solution, brine, and dried over sodium sulfate. The title compound was obtained after flash column using EtOAc:hexane/2:98 as the eluant.

Step B Methyl 2-chloro-4'-methoxybiphenyl-4-carboxylate

A mixture of methyl 4-iodo-3-chlorobenzoate (1.20 g, 4.05 mmol) from Step A, 4-methoxy phenyl boronic acid (1.23 g, 8.1 mmol), tetrakis(triphenylphosphine) palladium (0.23 g, 5% mol) and sodium carbonate (0.94 g, 8.9 mmol) in 50 ml of water/EtOH/toluene (1:2:4) was heated to reflux overnight. TLC (EtOAc:hexane/1:9) showed that the reaction was over. The solvents were removed. Water (30 ml) was added. The organic was extracted with methylene chloride (3×50 ml). The combined methylene chloride layers were washed with brine, and dried over sodium sulfate. The title compound was obtained after flash column using EtOAc:hexane/1:9 as the eluant. $^1$H NMR (CDCl$_3$, 500 MHz): δ 8.16 (d, J=1.5 Hz, 1H), 7.97 (dd, J=8, 1.5 Hz, 1H), 7.43 (m, 3H), 7.01 (d, J=6.5 Hz, 2H), 4.00 (s, 3H), 3.91 (s, 3H).

Step C Methyl 2-chloro-3'-iodo-4'-methoxybiphenyl-4-carboxylate

To a mixture of silver sulfate (0.97 g, 3.11 mmol) and iodine (0.79 g, 3.11 mmol) in MeOH (20 ml) at room temperature, a solution of methyl 2-chloro-4'-methoxybiphenyl-4-carboxylate (0.86 g, 3.11 mmol) in 1:1 mixture of MeOH/EtOAc (10 ml) was added. The mixture was stirred at room temperature for 6 h until color of the reaction turned to pale. The solid was filtered off and the filtrate was concentrated. The title compound was obtained after flash column using EtOAc:hexane/5:95 as the eluant. $^1$H NMR (CDCl$_3$, 500 MHz): δ 8.15 (d, J=1.5 Hz, 1H), 7.97 (dd, J=8, 2 Hz, 1H), 7.89 (d, J=2 Hz, 1H), 7.46 (dd, J=8.5, 2 Hz, 1H), 7.40 (d, J=8 Hz, 1H), 6.91 (d, J=8 Hz, 1H), 3.98 (s, 6H).

INTERMEDIATE 11

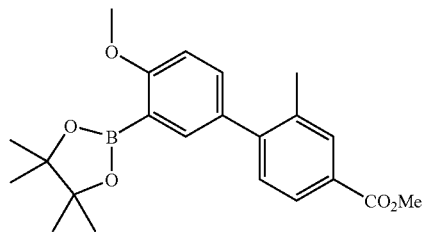

Methyl 4'-methoxy-2-methyl-3'-(4,4,5,5-tetramethyl-1,3,2-dioxaborolan-2-yl)biphenyl-4-carboxylate 3'-iodo-4'-methoxy-2-methylbiphenyl-4-carboxylate (500 mg, 1.308 mmol), bis(pinacolato)diboron (353 mg, 1.57 mmol), 1,1'-bis(diphenylphosphino)ferrocene-palladium dichloride dichloromethane adduct (214 mg, 0.262 mmol), potassium acetate (257 mg, 2.616 mmol) and 1,4-dioxane (2.5 mL) were placed in a sealed tube and subjected to microwave irradiation at 140° C. for 20 minutes then at 130° C. for 30 minutes. The crude reaction was treated with brine followed by ethyl acetate extractions. The combined extracts were dried over Na$_2$SO$_4$ followed by filtration and concentration in vacuo to afford methyl 4'-methoxy-2-methyl-3'-(4,4,5,5-tetramethyl-1,3,2-dioxaborolan-2-yl)biphenyl-4-carboxylate as a dark oil which was used in the next step without further purification. LCMS calc.=382.20; found=383.41 (M+1)$^+$.

INTERMEDIATE 12

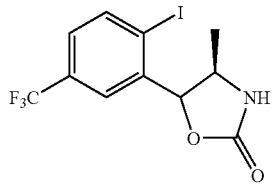

(4R,5R)-5-[2-iodo-5-(trifluoromethyl)phenyl]-4-methyl-1,3-oxazolidin-2-one

Step A: 2-iodo-5-(trifluoromethyl)benzaldehyde

To a solution of 2-iodo-5-(trifluoromethyl)benzonitrile (INTERMEDIATE 2, 42 g) in CH$_2$Cl$_2$ (300 mL) at −78° C. was added a solution of DIBAL in CH$_2$Cl$_2$ (175 mL, 1M) over 30 minutes. A precipitate formed. The reaction was warmed to 0° C. An additional 25 mL of the DIBAL solution was added dropwise over 30 minutes. The reaction was poured into 200 mL 2N aqueous HCl, diluted with ether and stirred 1 hour. TLC analysis indicates imine still present and an additional 100 mL 2N aqueous was added and the reaction stirred overnight. Imine was still present by TLC analysis and 200 mL 2N aqueous HCl was added and the mixture stirred 2 hours. The layers were separated and the aqueous layer back extracted with ether. The ether extracts were combined, washed with brine, dried over anhydrous MgSO$_4$, filtered and concentrated. The product was purified by silica gel chromatography eluting with 95:5 hexanes/EtOAc to give 2-Iodo-5-(trifluoromethyl)benzaldehyde as a white solid. $^1$H NMR (500 MHz, CDCl$_3$): (10.00 (s, 1H), 8.12 (s, 1H), 8.11 (d, J=8 Hz, 1H), 7.53 (dd, J=2 Hz, 8 Hz, 1H).

Step B: (4S)-4-benzyl-3-{(2R,3S)-3-hydroxy-3-[2-iodo-5-(trifluoromethyl)phenyl]-2-methylpropanoyl}-1,3-oxazolidin-2-one

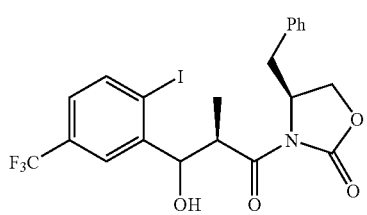

A mixture of 1.8 g of 5'-isopropyl-2'-methoxy-4-(trifluoromethyl)biphenyl-2-carbaldehyde (Step A), 1.16 g of (4S)-

4-benzyl-3-propionyl-1,3-oxazolidin-2-one, 0.048 g of magnesium chloride, 1.40 mL of triethylamine, and 0.91 mL of chlorotrimethylsilane in 10 mL of EtOAc was stirred at r.t. for 24 h, then filtered through a 10×10 cm plug of silica gel, eluting with 400 mL of Et$_2$O. The filtrate was concentrated, and 10 mL of MeOH was added along with 2 drops of trifluoroacetic acid. This solution was stirred at r.t. for 30 min and concentrated to a pale yellow oil. The residue was purified by flash chromatography on a Biotage Horizon, 65i column, eluting with 15 CV of 10% acetone in hexanes to provide 1.42 g (53%) of the title compound. Mass spectrum (ESI) 516.2 (M-OH). $^1$H NMR (500 MHz, CDCl$_3$): δ 8.00 (d, J=8.5 Hz, 1H), 7.76 (d, J=2 Hz, 1H), 7.22-7.32 (m. 4H), 7.07 (br d, J=6.5 Hz, 2H), 5.18 (dd, J=6.5 Hz, 7.5 Hz, 1H), 4.67 (m, 1H), 4.46 (dq, J=6.5 Hz, 7.5 Hz, 1H), 4.17 (t, J=9 Hz, 1H), 4.11 (dd, J=3 Hz, 9 Hz, 1H), 3.97 (d, J=8 Hz, 1H), 3.19 (dd, J=7 Hz, 13.5 Hz, 1H), 2.57 (dd, J=9.5 Hz, 13.5 Hz, 1H), 1.34 (d, J=7.5 Hz, 3H).

Step C: (4R,5R)-5-[2-iodo-5-(trifluoromethyl)phenyl]-4-methyl-1,3-oxazolidin-2-one To a 0° C. solution of 0.65 g of (4S)-4-benzyl-3-{(2R,3S)-3-hydroxy-3-[2-iodo-5-(trifluoromethyl)phenyl]-2-methylpropanoyl}-1,3-oxazolidin-2-one in 6 mL of 3:1 tetrahydrofuran-water was added 0.102 g of lithium hydroxide in 1.5 mL of water, then 0.554 mL of a 30% aqueous solution of hydrogen peroxide. The solution was stirred 1 h at 0° C., at which point LC/MS analysis showed no starting material. A 1.5 M solution of sodium sulfate (3.7 mL) was added to the cold solution, which was then poured into a separatory funnel and extracted with 2×10 mL of CH$_2$Cl$_2$. The combined CH$_2$Cl$_2$ extracts were back-extracted with 20 mL of 3:1 water-saturated aqueous NaHCO$_3$. The combined aqueous layers were acidified (pH <1) with 6 N HCl and extracted with 4×10 mL of EtOAc. The combined EtOAc extracts were washed with 10 mL of brined, dried over Na$_2$SO$_4$, and concentrated. The residue was dissolved in 10 mL of toluene. Diphenylphosphoryl azide (0.315 mL) and 0.24 mL of triethylamine were added and the mixture was stirred overnight at 100° C., then cooled and concentrated. The residue was purified by flash chromatography on a Biotage Horizon, 40S column, eluting with 1 CV of 5% EtOAc in hexanes, followed by a linear gradient of EtOAc in hexanes from 5 to 100% over 10 CV to provide 0.302 g (67%) of the title compound. Mass spectrum (ESI) 372.1 (M+1). $^1$H NMR (500 MHz, CDCl$_3$): δ 8.02 (d, J=8 Hz, 1H), 7.61 (d, J=1.5 Hz, 1H), 7.32 (dd, J=2 Hz, 8 Hz, 1H), 6.16 (s, 1H), 5.39 (d, J=4 Hz, 1H), 3.76 (dq, J=6 Hz, 4.5 Hz, 1H), 1.62 (d, J=6 Hz, 3H). Analytical HPLC on Chiralpak AD 4.6×250 min, eluting with 4% ethanol in heptane at 0.75 mL/min (t$_R$=21.56 min for R,R; t$_R$=18.00 min for S,S) showed 98% e.e.

INTERMEDIATE 13

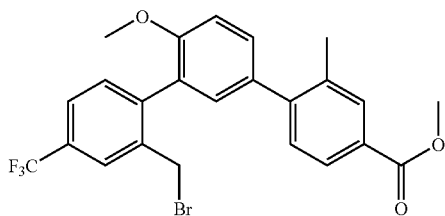

Methyl 2"-(bromomethyl)-4'-methoxy-2-methyl-4"-(trifluoromethyl)-1,1':3',1"-terphenyl-4-carboxylate Step A: methyl 4'-methoxy-2-methylbiphenyl-4-carboxylate To methyl 4-bromo-3-methyl benzoate (92 g, 0.402 mol), (4-methoxyphenyl)boronic acid (61.1 g, 0.402 mol), Na$_2$CO$_3$ (85.2 g, 0.804 mol), and PdCl$_2$(PPh$_3$)$_2$ (1410 mg, 2.01 mmol) was added EtOH (1.23 L) and water (0.61 L). The reaction was then heated to 80° C. for 1 hour. The reaction was cooled to room temperature, 550 ml of water was added, and the mixture was left standing for 1 hour. The resulting solids were filtered and washed with a solution of EtOH and H$_2$O (1:1, 750 mL). The solids were ground using a mortar and pestle and then slurried in 250 mL H$_2$O at room temperature for 1 h, then filtered and washed with water (2×125 mL) and dried to give methyl 4'-methoxy-2-methylbiphenyl-4-carboxylate. $^1$H NMR (CDCl$_3$, 400 MHz) δ 7.95 (s, 1H), 7.89 (d, J=7.9 Hz, 1H), 7.29 (d, J=7.9 Hz, 1H), 7.27 (d, J=8.7 Hz, 2H), 6.98 (d, J=8.7 Hz, 2H), 3.94 (s, 3H), 3.87 (s, 3H), 2.33 (s, 3H).

Step B: methyl 3'-bromo-4'-methoxy-2-methylbiphenyl-4-carboxylate

To a solution of methyl 4'-methoxy-2-methylbiphenyl-4-carboxylate (71.5 g, 0.279 mol) in acetonitrile (1.43 L) and water (572 mL) was added oxone (180.1 g, 0.293 mol). Then a solution of KBr (38.2 g, 0.321 mol) in water (143 mL) was slowly added over 30 minutes. The reaction was stirred for 2.5 hours, then water (715 mL) was added and the mixture was left standing for 1 hour. The solids were filtered and washed as follows: with a solution of MeCN/water (1:1, 350 mL, twice), water (700 mL, twice, then 350 mL) and dried to afford methyl 3'-bromo-4'-methoxy-2-methylbiphenyl-4-carboxylate. $^1$H NMR (CDCl$_3$, 400 MHz) δ 7.94 (s, 1H), 7.89 (d, J=8.1 Hz, 1H), 7.53 (d, J=2.2 Hz, 1H), 7.3-7.2 (m, 2H), 6.97 (d, J=8.4 Hz, 1H), 3.96 (s, 3H), 3.94 (s, 3H), 2.32 (s, 3H).

Step C: methyl 2"-(hydroxymethyl)-4'-methoxy-2-methyl-4"-(trifluoromethyl)-1,1':3',1"-terphenyl-4-carboxylate To methyl 3'-bromo-4'-methoxy-2-methylbiphenyl-4-carboxylate (80.0 g, 0.239 mol), pinacole borane (72.8 g, 0.287 mol), Pd(dba)$_2$ (4120 mg, 7.17 mmol), P(Cy)$_3$ (2140 mg, 7.65 mmol), and KOAc (70.3 g, 0.717 mol) was added dioxane (1.2 L). The reaction was heated to 80° C. and stirred for 3 hours. The reaction was then cooled to room temperature and filtered. The solids were dissolved with EtOAc (800 mL), washed with brine (400 mL, twice), and concentrated. The residue was dissolved in THF (300 mL), and [2-chloro-5-(trifluoromethyl)phenyl]methanol (47.1 g, 0.223 mol) and (t-Bu$_2$P)$_2$ferrocene PdCl$_2$ were added. A solution of K$_2$CO$_3$ (83.7 g, 0.606 mol in water (214 mL) was added and the mixture was heated to 45° C. and stirred for 9 hours. The reaction was cooled to room temperature and diluted with EtOAc (428 mL), and washed with water (428 mL) and brine (428 mL). To the organic material was added 21.5 g charcoal (Darco KB –100 mesh) and the mixture was stirred for 1 hour. The mixture was filtered, and the solid material was washed with EtOAc (428 mL). The filtrate was concentrated and then re-dissolved in MeOH (677 mL) and left to stand for 1 hour. To the mixture was added water (169 mL) over 2 hours, and then the mixture was left to stand for 1 hour. The resulting solids were washed with a solution of MeOH and water (4:1, 170 mL, three times) and dried to afford methyl 2"-(hydroxymethyl)-4'-methoxy-2-methyl-4"-(trifluoromethyl)-1, 1':3',1"-terphenyl-4-carboxylate.

Step D: methyl 2"-(bromomethyl)-4'-methoxy-2-methyl-4"-(trifluoromethyl)-1,1':3',1"-terphenyl-4-carboxylate To a 0° C. solution of methyl 2"-(hydroxymethyl)-4'-methoxy-2-methyl-4"-(trifluoromethyl)-1,1':3',1"-terphenyl-4-carboxylate (1.500 g, 3.49 mmol) in CH$_2$Cl$_2$ (14 mL) was added CBr$_4$ (2.429 g, 7.33 mmol), and then a solution of triphenyl phosphine (1.830 g, 6.98 mmol) in CH$_2$Cl$_2$ (15 mL). The solution was warmed to room temperature and stirred for twelve hours. The reaction was concentrated, and the residue was purified by flash chromatography on silica gel (0 to 25% EtOAc/hexanes) to afford methyl 2"-(bromomethyl)-4'-methoxy-2-methyl-4"-(trifluoromethyl)-1,1':3',1"-terphenyl-4-carboxylate. R$_f$=0.59 (50% EtOAc/hexanes). LCMS=494.8 (M+1)$^+$. $^1$H NMR (CDCl$_3$, 500 MHz) δ 7.95 (s, 1H), 7.89 (d, J=8.0 Hz, 1H), 7.80 (s, 1H), 7.59 (d, J=7.6 Hz, 1H), 7.40-7.33 (m, 3H), 7.21 (d, J=2.3 Hz, 1H), 7.06 (d, J=8.5 Hz, 1H), 4.44-4.39 (m, 2H), 3.93 (s, 3H), 3.82 (s, 3H), 2.37 (s, 3H).

INTERMEDIATE 14

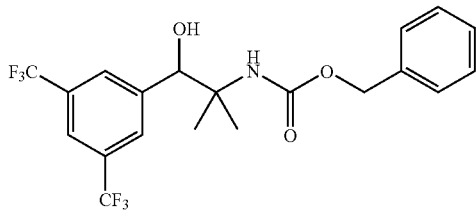

(5R)-5-[3,5-bis(trifluoromethyl)phenyl]-3-{[4'-fluoro-5'-isopropyl-2'-methoxy-4-(trifluoromethyl)biphenyl-2-yl]methyl}-4,4-dimethyl-1,3-oxazolidin-2-one Step A: Benzyl {2-[methoxy(methyl)amino]-1,1-dimethyl-2-oxoethyl}carbamate N-Methylmorpholine (682 mg, 741 µL, 6.74 mmol) and isobutylchloroformate (460 mg, 441 µL, 3.37 mmol) were added successively to a stirred solution of N-carbobenzyloxy-2-methylalanine (0.64 g, 2.69 mmol) in dry CH$_2$Cl$_2$ at 0° C. under N$_2$. The resulting cloudy mixture was stirred at 0° C. for 90 min. N,O-Dimethylhydroxylamine hydrochloride (316 mg, 3.24 mmol) was added portionwise and the mixture was warmed to room temperature and stirred for 3 h. The mixture was poured into 1N HCl (30 mL) and extracted with CH$_2$Cl$_2$ (3×40 mL). The combined extracts were washed with 1N HCl (30 mL), dried (Na$_2$SO$_4$) and concentrated in vacuo to give the crude product. This was purified by flash chromatography (Si, 40×160 mm, 0-80% EtOAc in hexanes gradient) to afford benzyl {2-[methoxy(methyl)amino]-1,1-dimethyl-2-oxoethyl}carbamate. R$_f$=0.47 (50% EtOAc in hexanes). LCMS calc.=303.1; found=303.2 (M+Na)$^+$. $^1$H NMR (500 MHz, CDCl$_3$) δ 7.37-7.29 (m, 5H), 5.82 (s, 1H), 5.09 (s, 2H), 3.60 (s, 3H), 3.18 (s, 3H), 1.60 (s, 6H).

Step B: Benzyl (1,1-dimethyl-2-oxoethyl)carbamate

Diisobutylaluminum hydride (1.77 mL, 1M solution in toluene, 0.708 mmol) was added to a stirred solution of benzyl {2-[methoxy(methyl)amino]-1,1-dimethyl-2-oxoethyl}carbamate (198.5 mg, 0.708 mmol) in dry THF (7.1 mL) at −78° C. under N$_2$. The reaction was stirred at −78° C. for 4 h. MeOH (100 µL) and 1N HCl (250 µL) were added and the reaction was allowed to warm to room temperature. The mixture was diluted with Et$_2$O (50 mL) and washed with 1N HCl (2×50 mL), 50% saturated NaHCO$_3$ (50 mL) and water (50 mL), then dried (MgSO$_4$) and concentrated in vacuo to give benzyl (1,1-dimethyl-2-oxoethyl)carbamate. R$_f$=0.40 (20% EtOAc in hexanes). LCMS calc.=244.1; found=244.1 (M+Na)$^+$. $^1$H NMR (500 MHz, CDCl$_3$) δ 9.43 (s, 1H), 7.38-7.30 (m, 5H), 5.34 (s, 1H), 5.09 (s, 2H), 1.37 (s, 6H).

Step C: Benzyl {2-[3,5-bis(trifluoromethyl)phenyl]-2-hydroxy-1,1-dimethylethyl}carbamate Ethylmagnesium bromide (1.63 mL, 1M in THF, 1.63 mmol) was added dropwise to a stirred solution of 1-iodo-3,5-bis(trifluoromethyl)benzene (608 mg, 317 µL, 1.79 mmol) in dry THF (1 mL) at room temperature under N$_2$ and the reaction was stirred for 30 min. The resulting solution was added to a stirred solution of benzyl (1,1-dimethyl-2-oxoethyl)carbamate (163.5 mg, 0.739 mmol) in dry THF (1 mL) at −20° C. and reaction was allowed to warm to room temperature over 3 h. Saturated NH$_4$Cl (10 mL) and water (10 mL) were added and the mixture was extracted with EtOAc (3×20 mL). The combined extracts were dried (Na$_2$SO$_4$) and concentrated in vacuo to give the crude product. This was purified by flash chromatography (Si, 25×160 mm, 0-40% EtOAc in hexanes gradient) to afford benzyl {2-[3,5-bis(trifluoromethyl)phenyl]-2-hydroxy-1,1-dimethylethyl}carbamate. R$_f$=0.40 (20% EtOAc in hexanes). LCMS calc.=436.1; found=436.0 (M+1)$^+$. $^1$H NMR (600 MHz, CDCl$_3$) δ 7.80 (s, 1H), 7.77 (s, 2H), 7.39-7.33 (m, 5H), 5.12-5.08 (m, 2H), 1.36 (s, 1H), 4.90 (d, J=4.4 Hz, 1H), 4.81 (s, 1H), 1.36 (s, 3H), 1.23 (s, 3H).

INTERMEDIATE 15

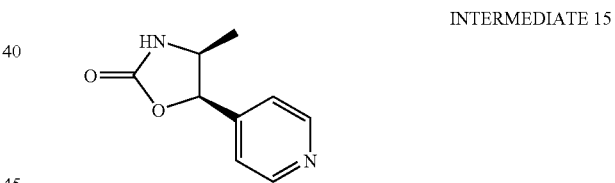

(4S,5R)-4-Methyl-5-pyridin-4-yl-1,3-oxazolidin-2-one

Step A: Benzyl {(1S)-2-[methoxy(methyl)amino]-1-methyl-2-oxoethyl}carbamate

CBZ-L-Alanine (6.5 kg, 28.5 mol), HOBT-hydrate (4.8 kg, 34.8 mol), Me(MeO)NH$_2$Cl (3.4 kg, 36.2 mol) and THF (32 L) were charged to a clean flask under nitrogen. The mixture was cooled to 0°-10° C. and diisopropylethylamine (12.4 L) was slowly added at a temperature less than 20° C. EDC-HCl (7 kg, 36.2 mol) was added slowly with slight cooling at 15°-25° C. The slurry was aged overnight at 20°-25° C. The mixture was cooled to 0°-10° C. and 3N HCl (13 L) is added slowly. Isopropyl acetate (45.5 L) was added and the layers were separated. The organic layer was washed once with HCl (13 L) and twice with 8% NaHCO$_3$ (13 L). The organic layer was concentrated under vacuum to <20 L at 50° C. The clear solution was cooled slowly to room temperature, allowing the product to crystallize. Heptane (~70 L) was added slowly. The slurry was filtered, washed with heptane (18 L), and dried at room temperature on the filter pot. Benzyl {(1S)-2-[methoxy (methyl)amino]-1-methyl-2-oxoethyl}carbamate was obtained with >99.9% ee measured by chiral HPLC.

Step B: Benzyl [(1S)-1-methyl-2-oxo-2-pyridin-4-ylethyl]carbamate

A solution of isopropylmagnesium chloride (1.6 mL, 1M in THF, 3.23 mmol) was added dropwise to a stirred solution of benzyl {(1S)-2-[methoxy(methyl)amino]-1-methyl-2-oxoethyl}carbamate (879 mg, 3.30 mmol) in dry THF (4.2 mL) at −15° C. under $N_2$. The reaction was stirred at −15° C. for 30 min then a suspension of 4-pyridylmagnesium bromide in dry THF (prepared by adding ethyl magnesium bromide (6 mL, 2M in THF, 6.00 mmol) to a stirred solution of 4-iodopyridine (1.35 g, 6.60 mmol) in dry THF (45 mL) at room temperature under $N_2$ and stirring for 30 min) was added dropwise by cannula. The reaction was allowed to warm to room temperature and was stirred for 5 h. 1N HCl (15 mL) was added to quench the reaction and the mixture was adjusted to basic pH with saturated $NaHCO_3$. The mixture was extracted with EtOAc (2×50 mL) and $CH_2Cl_2$ (3×50 mL). The EtOAc and $CH_2Cl_2$ extracted were washed with brine separately, dried ($Na_2SO_4$), combined and concentrated in vacuo to give the crude product. This was purified by flash chromatography (Si, 40×160 mm, 0-100% EtOAc in hexanes gradient) to afford benzyl [(2R)-1-methyl-2-oxo-2-pyridin-4-ylethyl]carbamate, as a colorless solid. $R_f$=0.33 (50% EtOAc/hexanes). LCMS calc.=285.1; found=285.3 $(M+1)^+$. $^1$H NMR (500 MHz, $CDCl_3$) δ 8.85 (d, J=3.3 Hz, 2H), 7.76 (d, J=5.5 Hz, 2H), 7.36-7.32 (m, 5H), 5.70 (d, J=6.8 Hz, 1H), 5.31-5.25 (m, 1H), 5.13 (s, 2H), 1.43 (s, 3H).

Step C: Benzyl [(1S,2R)-2-hydroxy-1-methyl-2-pyridin-4-ylethyl]carbamate

Lithium tri-tert-butoxyaluminum hydride (964 mg, 3.79 mmol) was added to a solution of benzyl [(2R)-1-methyl-2-oxo-2-pyridin-4-ylethyl]carbamate (539.1 mg, 1.90 mmol) in dry EtOH (40 mL) at −78° C. under $N_2$. The reaction was stirred at −78° C. for 2 h. 2% Aqueous acetic acid was added to quench the reaction and the mixture was adjusted to basic pH with saturated $NaHCO_3$ (~50 mL). The mixture was extracted with EtOAc (3×100 mL) and the combined extracts were washed with brine (50 mL), dried ($Na_2SO_4$) and concentrated in vacuo to give the crude product. This was purified by flash chromatography (Si, 40×160 mm, 0-100% EtOAc in hexanes gradient) to afford benzyl [(1S,2R)-2-hydroxy-1-methyl-2-pyridin-4-ylethyl]carbamate, as a colorless solid. $R_f$=0.49 (EtOAc). LCMS calc.=287.1; found=287.3 $(M+1)^+$. $^1$H NMR (500 MHz, $CDCl_3$) δ 8.41 (d, J=5.7 Hz, 2H), 7.36-7.32 (m, 7H), 5.27 (d, J=7.4 Hz, 1H), 5.10 (s, 2H), 4.89 (s, 1H), 4.02 (br s, 1H), 0.96 (d, J=6.7 Hz, 3H).

Step D: (4S,5R)-4-Methyl-5-pyridin-4-yl-1,3-oxazolidin-2-one

A solution of benzyl [(1S,2R)-2-hydroxy-1-methyl-2-pyridin-4-ylethyl]carbamate in 7.5N aq. KOH/MeOH/THF (1:2:4, 7 mL) was stirred at room temperature overnight. The reaction was diluted with water (20 mL) and extracted with EtOAc (3×20 mL). The combined organic layers were dried ($Na_2SO_4$) and concentrated in vacuo to afford (4S,5R)-4-methyl-5-phenyl-1,3-oxazolidin-2-one. LCMS calc.=179.1; found=179.2 $(M+1)^+$.

INTERMEDIATE 16

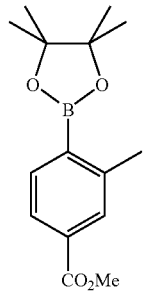

Methyl 3-methyl-4-(4,4,5,5-tetramethyl-1,3,2-dioxaborolan-2-yl)benzoate

A roundbottom flask was charged with methyl 4-bromo-3-methylbenzoate (200 mg, 0.878 mmol), bis(pinacolato)diboron (277 mg, 1.089 mmol), $PdCl_2(dppf)CH_2Cl_2$ (70 mg, 0.0873 mmol), KOAc (171 mg, 1.75 mmol), and DMSO (10 mL). The reaction was degassed with $N_2$ and heated at 40° C. for 1 hour, 60° C. for 1 hour, and then 80° C. for 12 hours. The reaction was diluted with EtOAc (25 mL) and hexanes (75 mL) and the organics were washed with water (2×25 mL) and brine (50 mL). The organic layer was dried over $Na_2SO_4$, filtered, and concentrated. Purification of the residue by flash chromoatography on silica gel (0 to 15% EtOAc/hexanes) afforded methyl 3-methyl-4-(4,4,5,5-tetramethyl-1,3,2-dioxaborolan-2-yl)benzoate. $^1$H NMR ($CDCl_3$, 500 MHz) δ 7.82 (s, 1H), 7.80 (s, 2H), 3.91 (s, 3H), 2.57 (s, 3H), 1.35 (s, 12H).

INTERMEDIATE 17

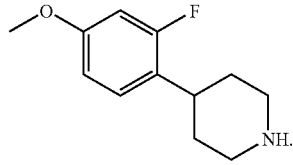

4-(2-fluoro-4-methoxyphenyl)piperidine

Step A: 1-benzyl-4-(2-fluoro-4-methoxyphenyl)piperidin-4-ol

To a stirred and cooled (0° C.) solution of 4-bromo-3-fluoroanisole (1 g; 4.88 mmol) in anhydrous THF (7 mL) was added isopropyl magnesium chloride (2.0M in THF; 2.22 mL; 4.43 mmol) dropwise. The reaction was stirred at room temperature for 30 min and then cooled to 0° C. 1-benzyl-4-piperidone (0.72 mL; 4.03 mmol) was added dropwise and the reaction was stirred at room temperature for 14 h. The reaction was quenched with saturated $NH_4Cl$ and partitioned between EtOAc (50 mL) and $H_2O$ (30 mL). The aqueous layer was extracted with EtOAc (3×50 mL) and the combined extracts were washed with brine (50 mL), dried ($MgSO_4$), filtered and concentrated in vacuo. The residue was purified by flash silica gel chromatography (0-50% EtOAc/hexanes gradient) to afford 1-benzyl-4-(2-fluoro-4-methoxyphenyl) piperidin-4-ol as a light orange solid. LCMS=315.9 $(M+1)^+$. $^1$H NMR ($CDCl_3$, 500 MHz) δ 7.38-7.31 (m, 5H), 7.28-7.24 (m, 1H), 6.66 (dd, J=8.7, 2.5 Hz, 1H), 6.61 (dd, J=14.4, 2.5

Hz, 1H), 3.79 (s, 3H), 3.56 (s, 2H), 2.77 (br d, J=10.6 Hz, 2H), 2.54-2.48 (m, 2H), 2.31-2.24 (m, 2H), 1.84 (d, J=12.3 Hz, 2H).

Step B: 1-benzyl-4-(2-fluoro-4-methoxyphenyl)-1,2,3,6-tetrahydropyridine

A stirred mixture of 1-benzyl-4-(2-fluoro-4-methoxyphenyl)piperidin-4-ol (Step A; 300 mg; 0.952 mmol) and p-toluenesulfonic acid monohydrate (18 mg; 0.0952 mmol) in benzene (20 mL) was heated at 80° C. for 14 h. An additional 100 mg of p-toluenesulfonic acid monohydrate was added and the reaction heated at 80° C. for 1 h. The reaction was partitioned between EtOAc (50 mL) and H$_2$O (50 mL). The aqueous layer was extracted with EtOAc (3×50 mL) and the combined extracts were washed with H$_2$O (3×50 mL) and brine (50 mL), dried (MgSO$_4$), filtered and concentrated in vacuo. The residue was purified by flash silica gel chromatography (0-10% EtOAc/hexanes gradient) to afford 1-benzyl-4-(2-fluoro-4-methoxyphenyl)1,2,3,6-tetrahydropyridine as a yellow oil. LCMS=297.9 (M+1)$^+$. $^1$H NMR (CDCl$_3$, 500 MHz) δ 9.56 (br s, 1H), 7.42-7.38 (m, 2H), 7.34 (t, J=7.3 Hz, 2H), 7.28 (d, J=7.3 Hz, 2H), 7.17 (t, J=8.7 Hz, 1H), 6.64 (dd, J=8.7, 2.5 Hz, 1H), 6.59 (dd, J=13.0, 2.5 Hz, 1H), 5.91-5.89 (m, 1H), 3.78 (s, 3H), 3.66 (br s, 2H), 3.18 (br s, 2H), 2.71 (br s, 2H), 2.54 (br s, 2H).

Step C: 4-(2-fluoro-4-methoxyphenyl)piperidine

A solution of 1-benzyl-4-(2-fluoro-4-methoxyphenyl)1,2,3,6-tetrahydropyridine (Step B; 117 mg; 0.393 mmol) in MeOH (10 mL) was treated with a catalytic amount of 10% Pd/C and the reaction was placed under an atmosphere of H$_2$ (Parr Shaker; 45 PSI) for 48 h. The reaction was filtered through Celite and the filtrate was concentrated in vacuo. The residue was purified by flash silica gel chromatography (0-100% EtOAc/hexanes gradient) to afford 4-(2-fluoro-4-methoxyphenyl)piperidine as a tan solid. LCMS 210.1 (M+1)$^+$. $^1$H NMR (CDCl$_3$, 500 MHz) δ 7.16 (t, J=8.7 Hz, 1H), 6.68 (dd, J=8.7, 2.5 Hz, 1H), 6.60 (dd, J=12.3, 2.5 Hz, 1H), 3.78 (s, 3H), 3.63 (d, J=12.6 Hz, 2H), 3.09-2.98 (m, 2H), 2.18 (q, J=12.1 Hz, 2H), 2.02 (d, J=13.3 Hz, 2H).

INTERMEDIATE 18

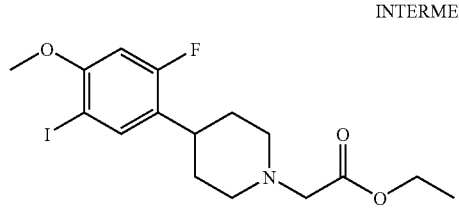

Ethyl [4-(2-fluoro-5-iodo-4-methoxyphenyl)piperidin-1-yl]acetate

Step A: Ethyl [4-(2-fluoro-4-methoxyphenyl)piperidin-1-ly]acetate

To a stirred solution of 4-(2-fluoro-4-methoxyphenyl)piperidine (40 mg; 0.19 mmol) in DMF (1 mL) under an atmosphere of N$_2$ was added N,N-diisopropylethylamine (33 μL; 0.19 mmol), followed by ethyl bromoacetate (21 μL; 0.19 mmol). The resultant solution was stirred at room temperature for 2.5 h. The reaction was partitioned between EtOAc (10 mL) and H$_2$O (10 mL). The aqueous layer was extracted with EtOAc (3×10 mL) and the combined extracts were washed with brine (10 mL), dried (Na$_2$SO$_4$), filtered and concentrated in vacuo. The residue was purified by flash silica gel chromatography (0-25% EtOAc/hexanes gradient) to afford ethyl [4-(2-fluoro-4-methoxyphenyl)piperidin-1-yl] acetate as a colorless oil. LCMS=295.9 (M+1)$^+$. $^1$H NMR (CDCl$_3$, 500 MHz) δ 7.14 (t, J=8.7 Hz, 1H), 6.65 (dd, J=8.5, 2.5 Hz, 1H), 6.58 (dd, J=12.43, 2.5 Hz, 1H), 4.20 (q, J=7.1 Hz, 2H), 3.77 (s, 3H), 3.26 (s, 2H), 3.06 (d, J=11.4 Hz, 2H), 2.80 (tt, J=12.1, 3.7 Hz, 1H), 2.32 (t, J=11.2 Hz, 2H), 1.87 (qd, J=12.3, 3.3 Hz, 2H), 1.78 (d, J=12.1 Hz, 2H), 1.29 (t, J=7.1 Hz, 3H).

Step B: Ethyl [4-(2-fluoro-5-iodo-4-methoxyphenyl)piperidin-1-yl]acetate

A mixture of ethyl [4-(2-fluoro-4-methoxyphenyl)piperidin-1-yl]acetate (Step A; 21.6 mg; 0.073 mmol), iodine (45.6 mg; 0.146 mmol) and silver sulfate (37 mg; 0.146 mmol) in MeOH (1.5 mL) was stirred at room temperature for 2 h. The reaction was filtered through Celite and the filtrate was concentrated in vacuo. The residue was redissolved in ether (25 mL) and washed with H$_2$O (25 mL). The aqueous layer was extracted with ether (3×25 mL) and the combined extracts were washed with brine (25 mL), dried (MgSO$_4$), filtered and concentrated in vacuo. The residue was purified by flash silica gel chromatography (0-10% EtOAc/hexanes gradient) to afford ethyl [4-(2-fluoro-5-iodo-4-methoxyphenyl)piperidin-1-yl]acetate as a yellow oil. LCMS=421.8 (M+1)$^+$. $^1$H NMR (CDCl$_3$, 500 MHz) δ 7.61 (d, J=8.3 Hz, 1H), 6.45 (d, J=11.9 Hz, 1H), 4.21 (q, J=7.1 Hz, 2H), 3.84 (s, 3H), 3.26 (s, 2H), 3.05 (d, J=11.2 Hz, 2H), 2.80 (tt, J=12.0, 3.9 Hz, 1H), 2.33 (t, J=10.6 Hz, 2H), 1.87 (qd, J=12.3, 3.2 Hz, 2H), 1.78 (d, J=12.1 Hz, 2H), 1.29 (t, J=7.1 Hz, 3H).

INTERMEDIATE 19

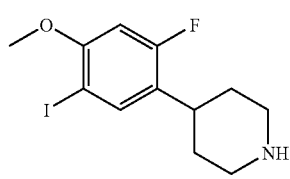

4-(2-fluoro-5-iodo-4-methoxyphenyl)piperidine

Step A: Tert-Butyl 4-(2-fluoro-4-methoxyphenyl)piperidine-1-carboxylate

A mixture of 4-(2-fluoro-4-methoxyphenyl)piperidine (200 mg; 0.957 mmol) and N,N-diisopropylethylamine (183 μL; 1.053 mmol) was treated with di-tert-butyldicarbonate (230 mg; 1.053 mmol) as described earlier to afford tert-butyl 4-(2-fluoro-4-methoxyphenyl)piperidine-1-carboxylate as a colorless oil. LCMS=254.0 (M+1−100+44)$^+$. $^1$H NMR (CDCl$_3$, 500 MHz) δ 7.07 (t, J=8.7 Hz, 1H), 6.65 (dd, J=8.5, 2.3 Hz, 1H), 6.59 (dd, J=12.3, 2.3 Hz, 1H), 4.23 (br s, 2H), 3.78 (s, 3H), 2.91 (tt, J=12.2, 3.2 Hz, 1H), 2.84-2.76 (m, 2H), 1.79-1.75 (m, 2H), 1.65-1.56 (m, 2×), 1.48 (s, 9H).

Step B: 4-(2-fluoro-5-iodo-4-methoxyphenyl)piperidine and Tert-Butyl 4-(2-fluoro-5-iodo-4-methoxyphenyl)piperidine-1-carboxylate A stirred mixture of tert-butyl 4-(2-fluoro-4-methoxyphenyl)piperidine-1-carboxylate (Step A; 255 mg; 0.825 mmol)

in MeOH. (15 mL) was treated with iodine (345 mg; 1.107 mmol) and silver sulfate (281 mg; 1.107 mmol). The reaction was stirred at room temperature for 2 h. The reaction was filtered through Celite and the filtrate was concentrated in vacuo. The residue was redissolved in ether (50 mL) and washed with $H_2O$ (50 mL). The aqueous layer was extracted with ether (3×50 mL) and the combined extracts were washed with brine (50 mL), dried ($MgSO_4$), filtered and concentrated in vacuo. The residue was purified by flash silica gel chromatography (0-10% EtOAc/hexanes gradient) to afford tert-butyl 4-(2-fluoro-5-iodo-4-methoxyphenyl)piperidine-1-carboxylate as a colorless glass. The aqueous layer was then re-extracted with EtOAc (3×100 mL) and the combined extracts were dried ($MgSO_4$), filtered, and the solvent was removed under reduced pressure until a precipitate formed. This solid was collected by filtration and dried in a vacuum oven to afford 4-(2-fluoro-5-iodo-4-methoxyphenyl)piperidine as a off-white solid.

tert-butyl 4-(2-fluoro-5-iodo-4-methoxyphenyl)piperidine-1-carboxylate: LCMS=379.7 (M+1−100+44)$^+$. $^1$H NMR (CDCl$_3$, 500 MHz) δ 7.54 (d, J=8.3 Hz, 1H), 6.55 (d, J=12.2 Hz, 1H), 4.23 (br s, 2H), 3.85 (s, 3H), 2.91 (tt, J=12.3, 3.5 Hz, 1H), 2.79 (t, J=12.1 Hz, 2H), 1.78-1.74 (m, 2H), 1.59 (qd, J=12.6, 4.1 Hz, 2H), 1.48 (s, 9H).

4-(2-fluoro-5-iodo-4-methoxyphenyl)piperidine: LCMS=335.7 (M+1)$^+$. $^1$H NMR (CDCl$_3$, 500 MHz) δ 9.62 (br s, 1H), 7.59 (d, J=8.3 Hz, 1H), 6.56 (d, J=12.2 Hz, 1H), 3.85 (s, 3H), 3.64 (d, J=12.1 Hz, 2H), 3.06-3.97 (m, 3H), 2.21-2.12 (m, 2H), 2.05-2.00 (m, 2H).

INTERMEDIATE 20

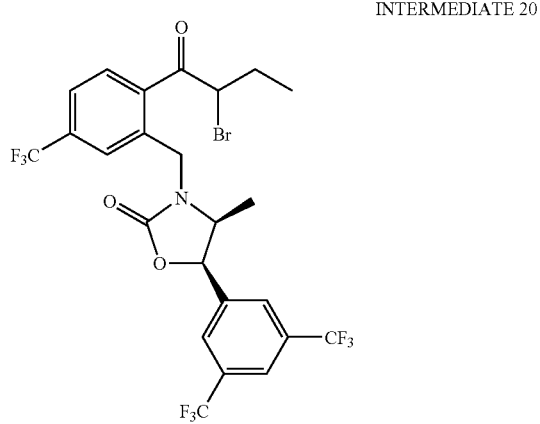

(4S,5R)-5-[3,5-Bis(trifluoromethyl)phenyl]-3-[2-(2-bromobutanoyl)-5-(trifluoromethyl)benzyl]-4-methyl-1,3-oxazolidin-2-one Step A: Methyl 2-({(4S,5R)-5-[3,5-bis(trifluoromethyl)phenyl]-4-methyl-2-oxo-1,3-oxazolidin-3-yl}methyl)-4-(trifluoromethyl)benzoate Palladium(II) acetate (0.109 g, 0.486 mmol), DPPF (0.269 g, 0.486 mmol), K$_2$CO$_3$ (2.013 g, 14.57 mmol) and Et$_3$N (0.677 mL, 4.86 mmol) were added to a solution of (4S,5R)-5-[3,5-bis(trifluoromethyl)phenyl]-3-[2-iodo-5-(trifluoromethyl)benzyl]-4-methyl-1,3-oxazolidin-2-one (2.9 g, 4.86 mmol) in MeCN (30 mL) and MeOH (10 mL). The reaction mixture was purged with N$_2$, the flask was capped and a CO balloon was attached to it. After bubbling CO gas into the solution through a needle attached to the balloon for 5 min, the mixture was heated under a CO balloon at 70° C. overnight. The mixture was diluted with EtOAc (300 mL), filtered through the Celite, then washed with water (3×50 mL), brine (1×), dried (Na$_2$SO$_4$), filtered and the solvent was evaporated in vacuo. The residue was purified by flash chromatography on silica gel to give methyl 2-({(4S,5R)-5-[3,5-bis(trifluoromethyl)phenyl]-4-methyl-2-oxo-1,3-oxazolidin-3-yl}methyl)-4-(trifluoromethyl)benzoate. LCMS calc.=530.1; found=529.9 (M+1)$^+$. $^1$H NMR (500 MHz, CDCl$_3$) L 8.09 (d, J=8.1 Hz, 1H); 7.92 (s, 1H); 7.82 (s, 2H); 7.79 (s, 1H); 7.69 (d, J=8.1 Hz, 1H); 5.75 (d, J=7.8 Hz, 1H); 5.10 (d, J=16.2 Hz, 1H); 4.81 (d, J=16.2 Hz, 1H); 4.19-4.11 (m, 1H); 3.99 (s, 3H); 0.81 (d, J=6.5 Hz, 3H).

Step B: (4S,5R)-5-[3,5-Bis(trifluoromethyl)phenyl]-3-[2-(hydroxymethyl)-5-(trifluoromethyl)benzyl]-4-methyl-1,3-oxazolidin-2-one To a solution of methyl 2-({(4S,5R)-5-[3,5-bis(trifluoromethyl)phenyl]-4-methyl-2-oxo-1,3-oxazolidin-3-yl}methyl)-4-(trifluoromethyl)benzoate (1.55 g, 2.93 mmol) in THF (65 mL) at 0° C. under N$_2$, was added dropwise 1N Super hydride in THF (5.86 mL, 5.86 mmol). The reaction was stirred at 0° C. for 1 h. More Super hydride was added to push the reaction to completion.

The reaction was carefully quenched with water and the aqueous layer was extracted with EtOAc (3×). The combined organic layers were washed with brine, dried (Na$_2$SO$_4$), filtered and the solvent was evaporated in vacuo. The residue was purified by flash chromatography on silica gel to give (4S,5R)-5-[3,5-bis(trifluoromethyl)phenyl]-3-[2-(hydroxymethyl)-5-(trifluoromethyl)benzyl]-4-methyl-1,3-oxazolidin-2-one. LCMS calc.=502.1; found=502.0 (M+1)$^+$. $^1$H NMR (500 MHz, CDCl$_3$) δ 7.91 (s, 1H); 7.78 (s, 2H); 7.65 (t, J=9.5 Hz, 2H); 7.55 (s, 1H); 5.72 (d, J=8.1 Hz, 1H); 5.09 (d, J=15.5 Hz, 1H); 4.86 (d, J=3.7 Hz, 2H); 4.29 (d, J=15.5 Hz, 1H); 4.06-4.00 (m, 1H); 2.59 (s, 1H); 0.82 (d, J=6.6 Hz, 3H).

Step, C: 2-({(4S,5R)-5-[3,5-Bis(trifluoromethyl)phenyl]-4-methyl-2-oxo-1,3-oxazolidin-3-yl}methyl)-4-(trifluoromethyl)benzaldehyde To a solution of (4S,5R)-5-[3,5-bis(trifluoromethyl)phenyl]-3-[2-(hydroxymethyl)-5-(trifluoromethyl)benzyl]-4-methyl-1,3-oxazolidin-2-one (510 mg, 1.017 mmol) in CH$_2$Cl$_2$ (20 mL) at 0° C. under N$_2$, was added Dess-Martin periodinane (647 mg, 1.526 mmol) portionwise. The reaction was stirred at 0° C. for 1 h. The reaction was carefully quenched with saturated NaHCO$_3$ and the aqueous layer was extracted with CH$_2$Cl$_2$. The combined organic layers were washed with brine, dried (Na$_2$SO$_4$), filtered and the solvent was evaporated in vacuo. The residue was purified by flash chromatography on silica gel to give 2-({(4S,5R)-5-[3,5-bis(trifluoromethyl)phenyl]-4-methyl-2-oxo-1,3-oxazolidin-3-yl}methyl)-4-(trifluoromethyl)benzaldehyde as a white solid. LCMS calc.=500.1; found=500.0 (M+1)$^+$. $^1$H NMR (500 MHz, CDCl$_3$) δ 10.29 (s, 1H); 8.04 (d, J=7.8 Hz, 1H); 7.93 (s, 1H); 7.85 (d, J=8.0 Hz, 1H); 7.83 (s, 1H); 7.82 (s, 2H); 5.77 (d, J=7.9 Hz, 1H); 5.11 (d, J=16.5 Hz, 1H); 4.94 (d, J=16.5 Hz, 1H); 4.23-4.18 (m, 1H); 0.84 (d, J=6.5 Hz, 3H).

Step D: (4S,5R)-5-[3,5-Bis(trifluoromethyl)phenyl]-3-[2-butyryl-5-(trifluoromethyl)benzyl]-4-methyl-1,3-oxazolidin-2-one To a solution of 2-({(4S,5R)-5-[3,5-bis(trifluoromethyl)phenyl]-4-methyl-2-oxo-1,3-oxazolidin-3-yl}methyl)-4-(trifluoromethyl)benzaldehyde (654 mg, 1.310 mmol) in toluene (25 mL) at −78° C. under N₂, was added dropwise 2M n-propyl magnesium chloride (0.655 mL, 1.310 mmol). The reaction was stirred at −78° C. for 4 h. The reaction was carefully quenched with water and the aqueous layer was extracted with EtOAc. The combined organic layers were washed with brine, dried (Na₂SO₄), filtered and the solvent was evaporated in vacuo to give a mixture of products (4S,5R)-5-[3,5-bis(trifluoromethyl)phenyl]-3-[2-butyryl-5-(trifluoromethyl)benzyl]-4-methyl-1,3-oxazolidin-2-one and by product (4S,5R)-5-[3,5-bis(trifluoromethyl)phenyl]-3-[2-(hydroxymethyl)-5-(trifluoromethyl)benzyl]-4-methyl-1,3-oxazolidin-2-one with the ratio of 3 to 1. The mixture obtained above was dissolved in CH₂Cl₂ (50 mL) at 0° C. under N₂ and Dess-Martin periodinane (834 mg, 1.965 mmol) was added portionwise. The reaction was stirred at 0° C. for 1 h. The reaction was carefully quenched with satd NaHCO₃ and was extracted with CH₂Cl₂ (3×). The combined organic layers were washed with brine, dried (Na₂SO₄), filtered and the solvent was evaporated in vacuo. The residue was purified by flash chromatography on silica gel to give (4S,5R)-5-[3,5-bis(trifluoromethyl)phenyl]-3-[2-butyryl-5-(trifluoromethyl)benzyl]-4-methyl-1,3-oxazolidin-2-one. LCMS calc.=542.1; found=542.0 (M+1)⁺. ¹H NMR (500 MHz, CDCl₃) δ 7.91 (s, 1H); 7.81 (s, 2H); 7.79 (d, J=8.2 Hz, 2H); 7.69 (d, J=8.0 Hz, 1H); 5.74 (d, J=7.8 Hz, 1H); 4.91 (d, J=16.1 Hz, 1H); 4.57 (d, J=16.1 Hz, 1H); 4.24-4.19 (m, 1H); 3.01-2.89 (m, 2H); 1.82-1.72 (m, 2H); 1.03 (t, J=7.4 Hz, 3H); 0.80 (d, J=6.5 Hz, 3H).

Step E: (4S,5R)-5-[3,5-Bis(trifluoromethyl)phenyl]-3-[2-(2-bromobutanoyl)-5-(trifluoromethyl)benzyl]-4-methyl-1,3-oxazolidin-2-one To a solution of (4S,5R)-5-[3,5-bis(trifluoromethyl)phenyl]-3-[2-butyryl-5-(trifluoromethyl)benzyl]-4-methyl-1,3-oxazolidin-2-one (300 mg, 0.554 mmol) in CHCl₃ (3 mL) at 0° C. under N₂, was added dropwise a solution of bromine (0.030 mL, 0.582 mmol) in CHCl₃ (2 mL). The reaction was stirred at 0° C. for 1 h. The reaction mixture was evaporated in vacuo. The residue was purified by flash chromatography on silica gel to give (4S,5R)-5-[3,5-bis(trifluoromethyl)phenyl]-3-[2-(2-bromobutanoyl)-5-(trifluoromethyl)benzyl]-4-methyl-1,3-oxazolidin-2-one as a white solid. LCMS calc.=622.0; found=621.7 (M+1)⁺. ¹H NMR (500 MHz, CDCl₃, 1:1 mixture of atropisomers) δ 7.91 (s, 1H); 7.85 (d, J=5.1 Hz, 1H); 7.83-7.77 (m, 2.5H); 7.74-7.69 (m, 1.5H); 5.79 (d, J=7.8 Hz, 0.5H); 5.74 (d, J=7.9 Hz, 0.5H); 5.06-4.92 (m, 2H); 4.57 (d, J=16.4 Hz, 0.5H); 4.47 (d, J=16.0 Hz, 0.5H); 4.24-4.16 (m, 1H); 2.35-2.25 (m, 1H); 2.19-2.09 (m, 1H); 1.18-1.16 (m, 3H); 0.80 (d, J=6.6 Hz, 1.5H); 0.78 (d, J=6.6 Hz, 1.5H).

INTERMEDIATE 21

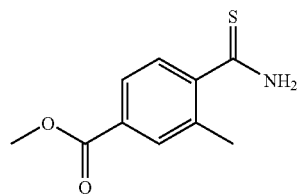

Methyl 4-(aminocarbonothioyl)-3-methylbenzoate

Step A: Methyl 4-cyano-3-methylbenzoate

To a microwave tube, was added methyl 4-bromo-3-methylbenzoate (100 mg, 0.437 mmol), Pd(Ph₃P)₄ (25.2 mg, 0.022 mmol), Zn(CN)₂ (51.3 mg, 0.437 mmol) and DMF (2 mL). The mixture was flushed with N₂ and capped tightly. The reaction mixture was exposed to microwave irradiation at 150° C. for 5 min. The mixture was diluted with EtOAc and washed with water. The organic layer was dried (Na₂SO₄), filtered and the solvent was evaporated in vacuo. The residue was purified by flash chromatography on silica gel to give methyl 4-cyano-3-methylbenzoate. LCMS calc.=176.1; found=176.1 (M+1)⁺. ¹H NMR (500 MHz, CDCl₃) δ 8.02 (s, 1H); 7.95 (d, J=8.1 Hz, 1H); 7.71 (d, J=8.0 Hz, 1H); 7.29 (s, 1H); 3.98 (s, 3H); 2.64 (s, 3H).

Step B: Methyl 4-(aminocarbonothioyl)-3-methylbenzoate

To a solution of methyl 4-cyano-3-methylbenzoate (36 mg, 0.205 mmol) in 1,4-dioxane (0.5 mL) and water (0.500 mL), was added sodium hydrogen sulfide (0.019 mL, 0.616 mmol) and triethylamine hydrochloride (170 mg, 1.233 mmol). The reaction mixture was heated at 55° C. overnight. The reaction was allowed to cool and water was added. The mixture was extracted with EtOAc. The combined organic layers were dried (Na₂SO₄), filtered and the solvent was evaporated in vacuo to give the product as a yellow solid. LCMS calc.=210.1; found=210.2 (M+1)⁺. ¹H NMR (500 MHz, CDCl₃) 7.86 (s, 1H); 7.84 (d, J=8.1 Hz, 1H); 7.42 (d, J=7.9 Hz, 1H); 7.16 (s, 2H); 3.93 (s, 3H); 2.51 (s, 3H).

INTERMEDIATE 22

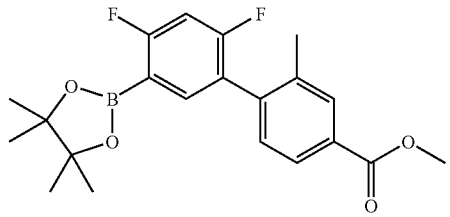

Methyl 2',4'-difluoro-2-methyl-5'-(4,4,5,5-tetramethyl-1,3,2-dioxaborolan-2-yl)biphenyl-4-carboxylate

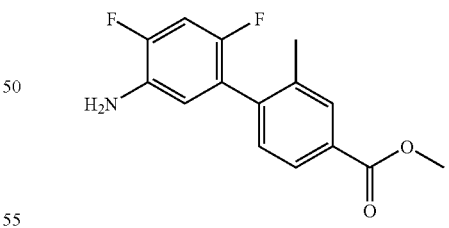

Step A: Methyl 5'-amino-2',4'-difluoro-2-methylbiphenyl-4-carboxylate 5-bromo-2,4-difluoroaniline (500 mg, 2.40 mmol), methyl 3-methyl-4-(4,4,5,5-tetramethyl-1,3,2-dioxaborolan-2-yl)benzoate (INTERMEDIATE 16, 797 mg, 2.88 mmol), sodium carbonate (2.40 mL, aq., 2M, 2.88 mmol), 1,1'-bis(diphenylphosphino) ferrocene-palladium dichloride dichloromethane adduct (196 mg, 0.24 mmol) and ethanol (15 ml) were heated in an 80° C. oil bath for 3 hours then allowed to cool to ambient overnight. Volatiles were removed under reduced pressure. The pot residue was worked up w/DCM/brine/Na$_2$SO$_4$/filtration/concentration to afford a dark oil. The resulting oil was purified by flash chromatography (SiO$_2$, Biotage 40+M cartridge). The column was eluted by a 0% to 40% EtOAc/hexanes gradient mixture. Related fractions were pooled and concentrated invacuo to afford the title compound. LCMS (ESI) calc.=277.09; found=278.03 (M+1)$^+$.

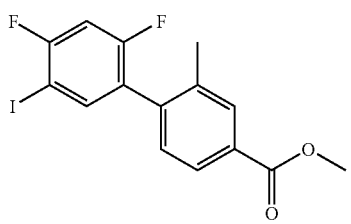

Step B: Methyl 2',4'-difluoro-5'-iodo-2-methylbiphenyl-4-carboxylate

Methyl 5'-amino-2',4'-difluoro-2-methylbiphenyl-4-carboxylate (STEP A, 500 mg, 1.80 mmol), 3-methylbutyl nitrite (317 mg, 2.71 mmol), iodine (549 mg, 2.16 mmol) and chloroform (15 ml) were refluxed in an oil bath for 5 hours then allowed to cooled to ambient overnight. Reaction crude was purified by flash chromatography (SiO$_2$, Biotage 40+M cartridge) eluted with a EtOAc/hexanes gradient mixture. Related fractions were pooled and concentrated in vacuo to afford the title compound. LCMS (ESI) calc.=387.98; found=388.92 (M+1)$^+$.

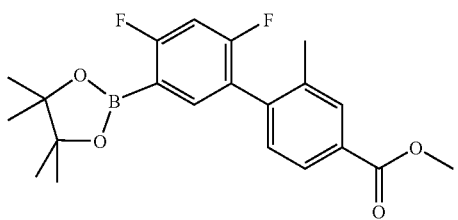

Step C: methyl 2',4'-difluoro-2-methyl-5'-(4,4,5,5-tetramethyl-1,3,2-dioxaborolan-2-yl)biphenyl-4-carboxylate Methyl 2',4'-difluoro-5'-iodo-2-methylbiphenyl-4-carboxylate (STEP B, 1.551 g, 4.55 mmol), bis(pinacolato)diboron (1.385 g, 5.46 mmol), potassium acetate (0.892 g, 9.09 mmol), 1,1'-bis(diphenylphosphino) ferrocene-palladium dichloride dichloromethane adduct (0.743 g, 0.909 mmol) and 1,4-dioxane (10 ml) were placed in a sealed tube and heated in a microwave oven at 140° C. for 30 min. LCMS trace of reaction aliquot indicated formation of the de-brominated by-product and the desired borate/boronic acid. Reaction crude was diluted with ethyl acetate and filtered. The filtrate was worked up with brine, extracted with ethyl acetate, dried over Na$_2$SO$_4$, filtered and evaporated to afford a dark mixture as a crude mixture of the title compound, to be used as it was for next step. LCMS (ESI) calc.=388.17; found=389.11 (M+1)$^+$.

INTERMEDIATE 23

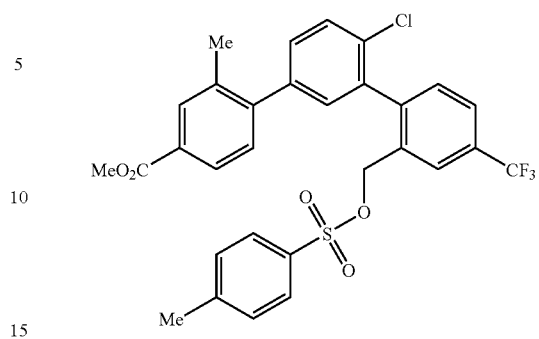

The triaryl tosylate shown above is made by the following multistep process:

Biaryldichlorobenzyl Alcohol 1

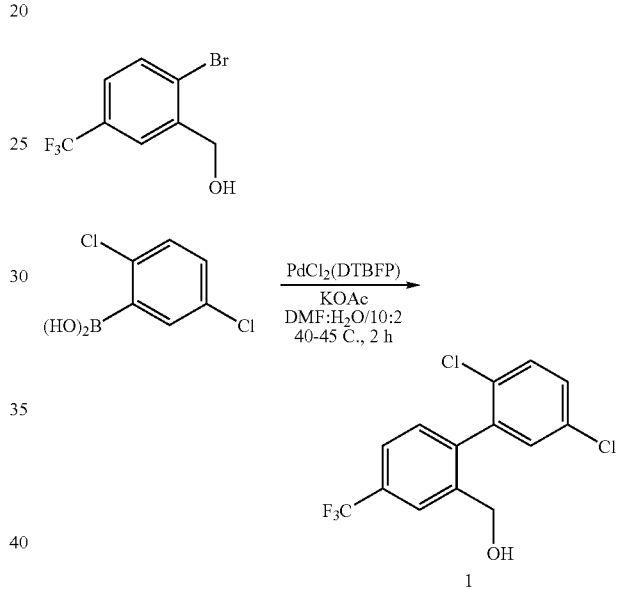

A 100 L flask equipped with an overhead stirrer, thermocouple, nitrogen inlet, dropping funnel and a steam pot was charged with 30 L of DMF, 8 L of GMP water, 5000 g of the benzyl alcohol starting material and 4458 g of potassium acetate. The mixture was degassed by sparging with nitrogen and then was placed under nitrogen. PdCl$_2$(DTBPF) (64.8 g) was charged to the reaction mixture, and the batch was heated to 40-45° C. (DTBPF is 1,1'-bis(di-tert-butylphosphino)ferrocene).

A 20 L flask equipped with an overhead stirrer and nitrogen inlet was charged with 10 L of DMF and 4114 g of dichlorophenyl boronic acid. The solution was degassed by sparging with nitrogen and placed under nitrogen. This solution was transferred slowly to the reaction using a dropping funnel over about 1 h. The reaction is monitored by HPLC and is complete in ca. 2 h. After the reaction reaches completion, toluene (20 L) and 0.2 M acetic acid (20 L) are added to the reaction mixture. The two-phase mixture is transferred to a 170 L cylinder. Toluene (20 L) and 0.2 M acetic acid (20 L) are added to the reaction flask, and this mixture is also transferred to the 170 L cylinder. The layers are separated, and the organic (upper) layer is washed with 10 wt % aqueous sodium chloride (2×40 L) and then with GMP water (40 L). The organic phase is then filtered through a bed of silica gel (3 kg), and the silica gel is rinsed with additional toluene (2×20 L) until all of the product is recovered. The toluene solution is batch concentrated to a volume of 20 L and then is flushed with 2×50 L portions of heptane. The batch volume is adjusted to 60 L, and the batch is warmed to completely dissolve any precipitated product.

The batch was seeded with crystals from earlier batches and was allowed to cool to ambient temperature overnight. The mixture was cooled to 0° C. and filtered. The wet cake was rinsed with cold heptane (0° C., 15 L) and dried under nitrogen and vacuum in the funnel, yielding the desired biarylbenzyl alcohol 1.

Biarylbenzyl Benzoate 2

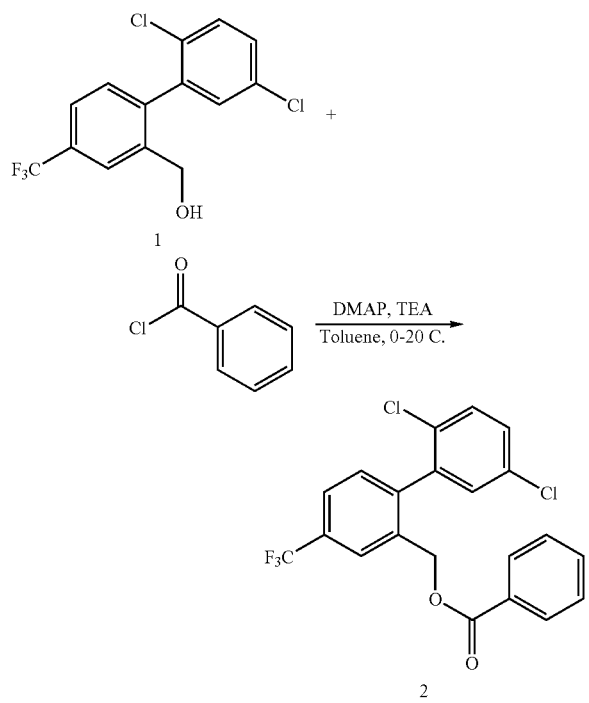

A 100 L flask equipped with an overhead stirrer, thermocouple, nitrogen inlet, dropping funnel and a steam pot was charged with 51 L of toluene, 4869 mL of triethylamine, 5100 g of the biaryl benzyl alcohol 1 from the previous step, and 102 g of 4-dimethylaminopyridine (DMAP). The solution was cooled to 0° C. Benzoyl chloride (2120 mL) was added slowly to the batch from a dropping funnel over ca. 1 h. The addition is exothermic. After the addition was complete, the batch was warmed to ambient temperature. A thick white slurry forms. The reaction is monitored by HPLC and is complete about 2 hours after warming to ambient temperature.

Aqueous HCl (1.0 M, 20 L) was added to the reaction flask, and the batch was transferred to a 100 L extractor. The lower aqueous layer was separated, and the batch was washed sequentially with 2×12 L of 1.0 M HCl and then with 2×12 L of GMP water. The toluene solution was dried over anhydrous sodium sulfate and then filtered through a sintered glass funnel. The toluene solution was batch concentrated to a volume of 10 L, and then 51 L of heptane was added while maintaining the temperature at 40-45° C. The batch was allowed to cool to ambient temperature overnight. The batch was then cooled to −5° C. and filtered. The wet cake was rinsed with cold heptane (−5° C., 16 L) and dried in the funnel under nitrogen and then vacuum, yielding biarylbenzyl benzoate 2.

Boronic Acid 3

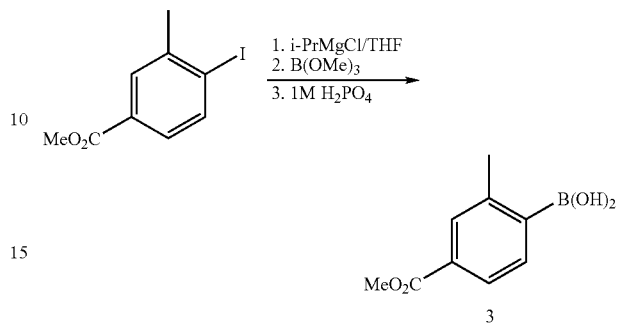

A 3-Liter round bottom flask equipped with a mechanical stirrer, thermocouple, and addition funnel was charged with 100 g of solid 4-iodo-3-methylbenzoic acid methyl ester and 1.0 L of dry THF. The mixture was cooled to −25° C., and 218 mL of i-PrMgCl (2M in THF) was added dropwise over 25 min while the internal temperature was maintained at <−15° C. The batch was kept at <−10° C. for 1 hr after the addition of the Grignard reagent. Analysis of a hydrolyzed aliquot showed greater than 97% deiodination.

The reaction was then cooled to about −20° C. and quenched with trimethyl borate (77 g). The trimethyl borate reaction is exothermic. The temperature increased to about 4° C. during the addition of the trimethyl borate over a time of about 3 min. The resulting solution was aged for 1 h at <0° C. The batch was then cooled to about −20° C. and further quenched with 1.0 L of 1M $H_3PO_4$. This quench was also exothermic, raising the temperature to 3° C. by the end of the quench. The batch was aged at room temperature overnight.

The THF was then removed by distillation at <45° C. under reduced pressure. The product slurry was allowed to cool to room temperature, and then was filtered. The cake was washed with water (3×500 ml) and toluene (2×250 mL) and then was dried under vacuum with nitrogen sweep for 18 h to give the boronic acid 3 as an off-white crystalline solid.

Triaryl benzoate 4

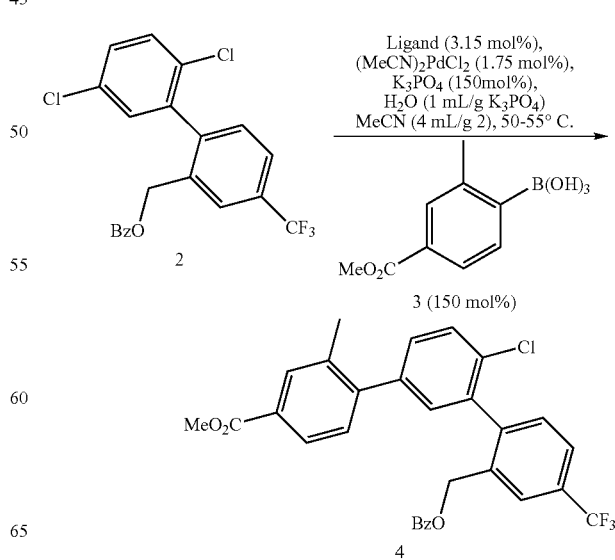

The catalyst was first made in a nitrogen-filled glovebox by charging bis(acetonitrile)palladium dichloride (107 mg) and 1,2-bis(di-tert-butylphosphinomethyl)benzene (292 mg) into a vessel equipped with a stir bar. Acetonitrile (35 mL) was then charged. The resulting suspension was agitated at ambient temperature for ~2 hr prior to use.

A 100 mL Schlenk vessel equipped with a stir bar, nitrogen/vacuum inlet, and septum was charged with boronic acid 3 (6.79 g, 35.3 mmole) and biaryl benzoate 2 (9.45 g). The flask was purged with nitrogen and transferred to a glovebox. The catalyst suspension that was made as described in the previous paragraph was then charged to the Schlenk vessel in the glovebox. The vessel in which the catalyst suspension was made was rinsed with acetonitrile (5 mL); the rinse was also transferred into the Schlenk vessel.

Aqueous $K_3PO_4$ (15.0 g of 50% w/w $K_3PO_4$, 7.5 g of $K_3PO_4$) was charged to the thick slurry in the Schlenk vessel in the glovebox at ambient temperature. The Schlenk vessel was sealed, removed from the glovebox, and attached to a nitrogen bubbler. The resulting biphasic mixture was agitated and warmed for 22 hr in an oil bath which was maintained at 55° C., at which time the amount of unreacted biaryl benzoate remaining was 1.7% relative to triaryl benzoate product by HPLC analysis. Acetonitrile (40 mL) was added at 30° C., and the bottom aqueous layer was separated. The aqueous layer was back-extracted with acetonitrile (3 mL), and this extract was combined with the main organic layer. The reaction mixture was concentrated to ~40% of the original volume while maintaining an external temperature and pressure of 40-42° C. and 190-200 mbar. The batch was cooled to −30° C., and the organic layer was filtered through a sintered glass funnel directly into the crystallization vessel. The reaction vessel was rinsed with $CH_3CN$ (17 mL), and the rinses were filtered into the reaction vessel. Once the batch cooled, it was observed that the triaryl benzoate 4 began crystallizing quickly.

The rapidly crystallizing mixture, which was in a 100 mL, 3-neck round-bottom flask equipped with mechanical stirrer, nitrogen inlet/bubbler, and addition funnel, was diluted with 43 mL of additional $CH_3CN$, giving an assay of ~6 mL $CH_3CN$/g of triaryl benzoate product. Water (25 mL) was added over 60 min at ambient temperature to the thick slurry to give ~27 vol % water (relative to $CH_3CN$). The suspension was agitated at ambient temperature until the concentration of triaryl benzoate in the supernatant reached about 5.5 g/L by HPLC analysis (overnight age). The batch was cooled in an ice bath to ~2° C. and agitated for about 2 hours, at which time the concentration of triaryl benzoate 4 in the supernatant reached ~1.6 g/L. The suspension was filtered on a sintered funnel and the cake was washed with 46 ml of 75:25 v/v of chilled $CH_3CN$:water, which was used as a displacement wash. The triaryl benzoate cake was dried under vacuum and a nitrogen tent at room temp until a constant weight was obtained.

Triaryl Alcohol (5)

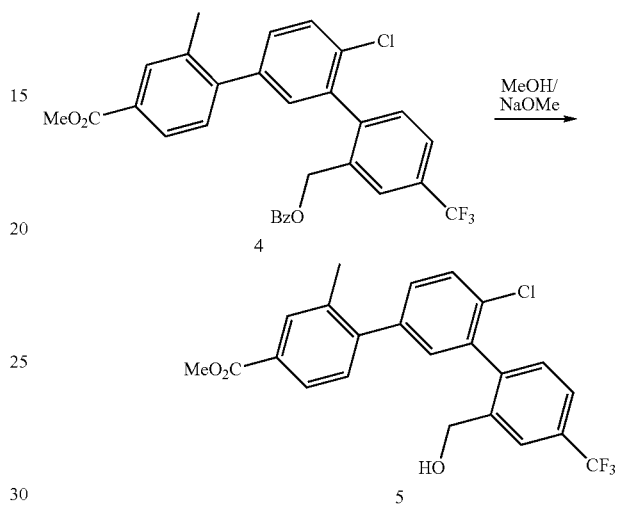

To a 100 L flask with overhead stirrer, nitrogen line and temperature probe was added 2 kg of the solid triaryl benzoate (4) and dry methanol (20 L). A subsurface sparge of the slurry with nitrogen with stirring was carried out for 5 min. Sodium methoxide (30 wt % solution in MeOH, 210 mL) was added to the slurry, and the reaction mixture was aged at RT until <0.15% starting triaryl benzoate remained (approximately 3-4 h). The reaction mixture became homogeneous about 1 hr before the end of reaction. 5M HCl (250 mL) was added, followed by toluene (10 L) and water (15 L). The phases were separated, and the organic layer was washed once with water (10 L). The batch was then concentrated to remove water and residual methanol. The triaryl alcohol 5 was used in the next step without further purification.

Triaryl Tosylate 6

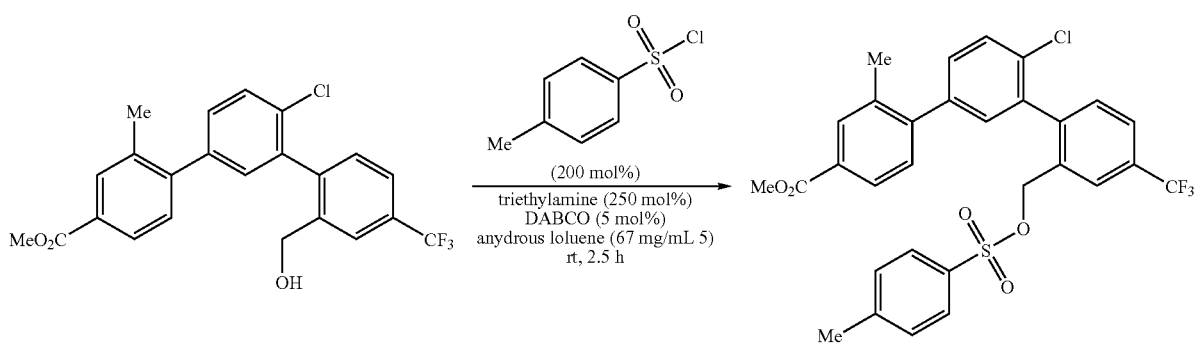

A 75-L round-bottomed flask equipped with an overhead stirrer, nitrogen inlet, thermocouple and dropping funnel was charged with 1490 g of triaryl alcohol 5 in toluene (22.2 L). TsCl (1232 g) was added to the solution and stirred, followed by a solution of triethylamine (1197 mL), DABCO (19.3 g) and toluene (2.5 L) via addition funnel over a period of 3 minutes. The internal temperature rose to 32° C. The reaction was monitored by HPLC, reaching >99.7% conversion within 2 h.

Once the starting triaryl alcohol was consumed, the solution was filtered through a pad of silica gel (1700 g, Merck Grade 9385), so that the cloudy suspension became a clear solution. The filter cake was washed with 5.0 L of toluene, and the combined washes were added to a 100-L reactor/extractor. The stirred solution was mixed with 6.0 L of 10% w/w $NaHSO_4$ (900 g in 9.0 L GMP water) and stirred vigorously. The phases were partitioned, and the aqueous phase was cut (pH=1). The organic (top) layer was washed with GMP water (2×9.0 L), and the aqueous layers were separated. The pH values of the 2 washes were 1 and 4, respectively.

The organic layer was concentrated to an oil and dissolved in 10-14 volumes of 3-7% toluene in heptane. The organics were heated until the solution became clear and homogeneous (between 60-80° C., depending on toluene concentration), and were then slowly cooled to rt. Seeding of the solution (with seeds obtained from earlier batches) was conducted at 50° C., and crystal growth was immediately observed. After overnight cooling to rt, the mother liquor was decanted, and the crystals were washed with 10.0 L of 10% toluene/heptane followed by 6.0 L heptane. The bright white solid was dried for 72 h under vacuum in a nitrogen tent, yielding tosylate 6.

Example 1

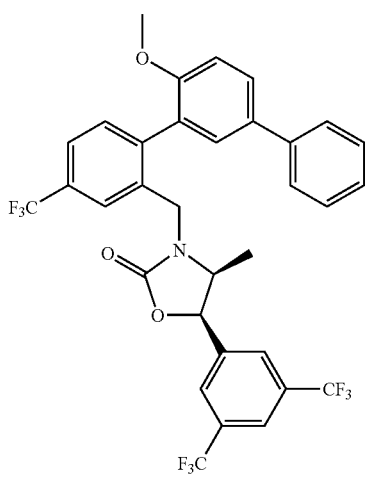

(4S,5R)-5-[3,5-bis(trifluoromethyl)phenyl]-3-{[6'-methoxy-4-(trifluoromethyl)-1,1':3',1"-terphenyl-2-yl]methyl}-4-methyl-1,3-oxazolidin-2-one Step A

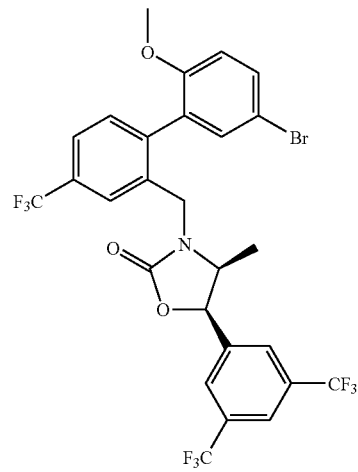

(4S,5R)-5-[3,5-bis(trifluoromethyl)phenyl]-3-{[5'-bromo-2'-methoxy-4-(trifluoromethyl)biphenyl-2-yl]methyl}-4-methyl-1,3-oxazolidin-2-one A mixture of (4S,5R)-5-[3,5-bis(trifluoromethyl)phenyl]-3-[2-iodo-5-(trifluoromethyl)benzyl]-4-methyl-1,3-oxazolidin-2-one (6-80 g, 11.39 mmol), 2-methoxy-5-bromo-phenyl boronic acid (3.00 g, 12.99 mmol), and sodium carbonate (2.65 g, 25.0 mmol) in 200 ml of 1:2:4 mixture of water:EtOH:toluene was stirred at room temperature for 30 min. Catalytic amount of tetrakis(triphenylphosphine) palladium (0.66 g, 5% mol) was added. The mixture was stirred under reflux for 24 h. TLC ($CH_2Cl_2$:hexane/1:1) showed no starting material. The solvents were removed. Water (100 ml) was added. The mixture was extracted with methylene chloride (3×100 ml). The combined methylene chloride layers were washed with brine and dried over sodium sulfate. The title compound was obtained after flash column using $CH_2Cl_2$:hexane/6:4 as the eluant. $^1$H NMR ($CDCl_3$, 500 MHz): δ 1:1 mixture of atropisomers 7.88 (s, 1H), 7.74 (s, 1H), 7.72 (s, 1H), 7.67 (t, J=7 Hz, 1H), 7.62 (s, 1H), 7.54 (m, 1H), 7.37-7.42 (m, 1H), 7.31-7.34 (m, 1H), 6.90-6.93 (m, 1H), 5.63 (d, J=8 Hz, 0.5H), 5.25 (d, J=8 Hz, 0.5H), 4.98 (d, J=15.5 Hz, 0.5H), 4.88 (d, J=16 Hz, 0.5H), 4.12 (d, J=15.5 Hz, 0.5H), 3.88 (d, J=16.5 Hz, 0.5H), 3.84 (s, 3H), 3.81 (s, 3H), 3.73 (m, 1H), 0.59 (d, J=6.5 Hz, 1.5H), 0.45 (d, J=6.5 Hz, 1.5H).

Step B (4S,5R)-5-[3,5-bis(trifluoromethyl)phenyl]-3-{[6'-methoxy-4-(trifluoromethyl)-1,1':3',1"-terphenyl-2-yl]methyl}-4-methyl-1,3-oxazolidin-2-one A mixture of the title compound from Step A (0.05 g, 0.076 mmol), phenyl boronic acid (0.014 g, 0.11 mmol), tetrakis (triphenylphosphine) palladium (5% mol) and sodium carbonate (0.018 g, 0.17 mmol) in 7 ml of water/EtOH/toluene (1:2:4) was heated to reflux for 4 h. TLC($CH_2Cl_2$:hexane/1:1) showed that the reaction was over. The solvents were removed. Water (30 ml) was added. The organic was extracted with methylene chloride (3×40 ml). The combined methylene chloride layers were washed with brine, and dried over sodium sulfate. The title compound was obtained after preparative TLC using CH$_2$Cl$_2$:hexane/6:4 as the eluant. $^1$H NMR (CDCl$_3$, 500 MHz): δ 1:1 mixture of atopoisomers 7.86 (s, 0.5H), 7.84 (s, 0.5H), 7.26-7.71 (m, 10H), 7.10 (dd, J=8.5, 3 Hz, 1H), 6.96 (t, J=7.5 Hz, 1H), 6.86 (d, J=9 Hz, 1H), 5.57 (d, J=8 Hz, 0.5H), 5.10 (d, J=7.5 Hz, 0.5H), 5.05 (d, J=16 Hz, 0.5H), 4.92 (d, J=16 Hz, 0.5H), 4.19 (d, J=15.5 Hz, 0.5H), 3.99 (d, J=16 Hz, 0.5H), 3.90 (s, 1.5H), 3.88 (s, 1.5H), 3.72 (m, 1H), 0.564 (d, J=6.5 Hz, 1.5H), 0.40 (d, J=6.5 Hz, 1.5H). LC-MS (M+1): 654.3.

The following compounds (Table 1) were prepared using the same procedure in Example 1.

TABLE 1

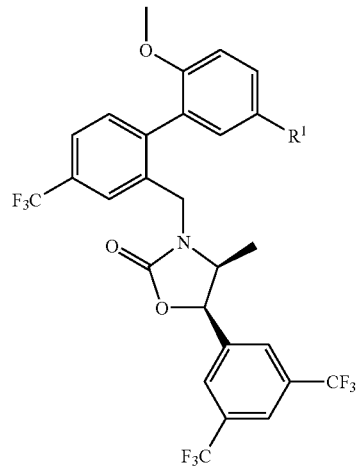

| Example | R$^1$ | LC/MS Data |
|---|---|---|
| 2 | 2-methylphenyl | 668.0 |
| 3 | 2-CF$_3$-phenyl | 722.1 |
| 4 | 2-F, 6-Cl-phenyl | 706.0 |
| 5 | 2-F-phenyl | 672.0 |
| 6 | 2-CN-phenyl | 679.2 |
| 7 | 2-MeO-phenyl | 684.0 |
| 8 | 2-Cl-phenyl | 688.1 |
| 9 | 3-F-phenyl | 672.0 |
| 10 | 2-Et-phenyl | 682.5 |
| 11 | 2-Me, 3-Cl-phenyl | 702.3 |
| 12 | 4-F-phenyl | 671.98 |

TABLE 1-continued
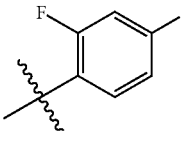
| Example | R¹ | LC/MS Data |
|---|---|---|
| 13 | 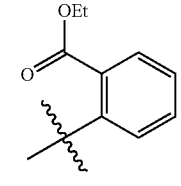 | 689.9 |
| 14 | 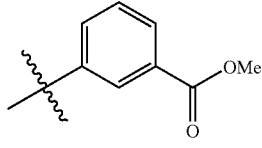 | 726.2 |
| 15 | 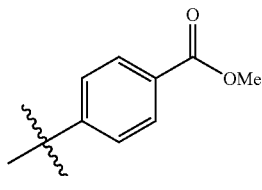 | 711.95 |
| 16 | 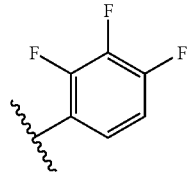 | 712.2 |
| 17 | 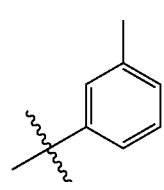 | 708.3 |
| 18 | 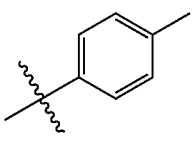 | 668.4 |
| 19 | 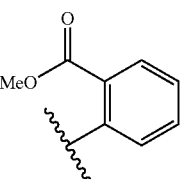 | 668.2 |
| 20 | 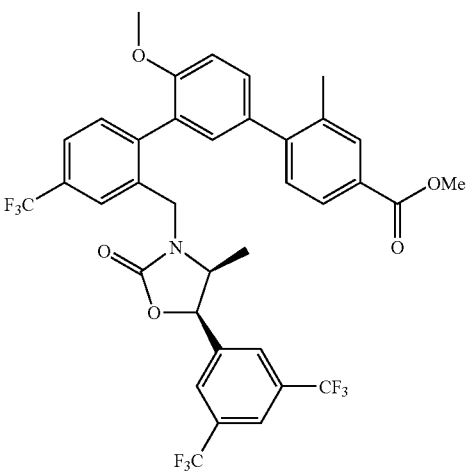 | 712.2 |
Example 21

Step A

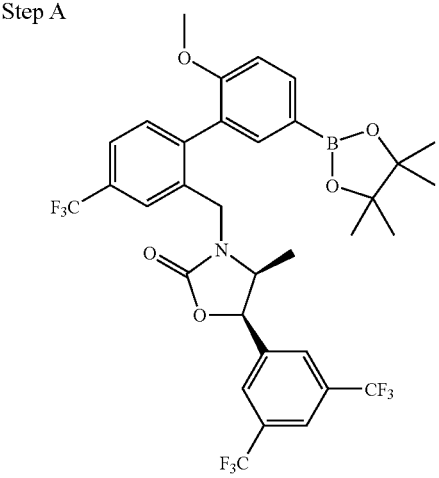

(4S,5R)-5-[3,5-bis(trifluoromethyl)phenyl]-3-{[2'-methoxy-5'-(4,4,5,5-tetramethyl-1,3,2-dioxaborolan-2-yl)-4-(trifluoromethyl)biphenyl-2-yl]methyl}4-methyl-1,3-oxazolidin-2-one (4S,5R)-5-[3,5-bis(trifluoromethyl)phenyl]-3-{[5'-bromo-2'-methoxy-4-(trifluoromethyl) biphenyl-2-yl]methyl}-4-methyl-1,3-oxazolidin-2-one (500 mg, 0.762 mmol), bis(pinacolato)diboron (388 mg, 1.53 mmol), 1,1'-bis(diphenylphosphino)ferrocene-palladium dichloride dichloromethane adduct (150 mg, 0.184 mmol), potassium acetate (150 mg, 1.53 mmol) and 1,4-dioxane (5 mL) were sealed in a microwave vessel. The reaction mixture was irradiated by microwave to 140° C. for 40 minutes. Additional bis(pinacolato)diboron (388 mg, 1.53 mmol) was added followed by microwave irradiation at 140° C. for 20 minutes. Then additional potassium acetate (150 mg, 1.53 mmol) was added followed by microwave irradiation at 140° C. for 20 minutes. The reaction crude was worked up with water. The resulting mixture was extracted with EtOAc. The combined organic extracts were dried over $Na_2SO_4$, filtered, and concentrated to afford a dark solid. The solid was purified by a reverse-phase preparatory HPLC (column: Kromasil 100-5C18, 100×21.1 mm) eluting with a $MeCN/H_2O$ gradient mixture to afford (4S,5R)-5-[3,5-bis(trifluoromethyl)phenyl]-3-{[2'-methoxy-5'-(4,4,5,5-tetramethyl-1,3,2-dioxaborolan-2-yl)-4-(trifluoromethyl)biphenyl-2-yl]methyl}-4-methyl-1,3-oxazolidin-2-one as a dark oil. LCMS calc.=703.22; found=704.47 (M+1)+.

Step B

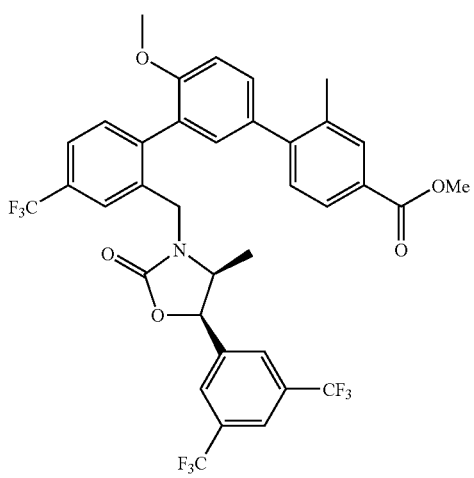

Methyl 2"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-carboxylate A mixture of (4S,5R)-5-[3,5-bis(trifluoromethyl)phenyl]-3-{[2'-methoxy-5'-(4,4,5,5-tetramethyl-1,3,2-dioxaborolan-2-yl)-4-(trifluoromethyl)biphenyl-2-yl]methyl}-4-methyl-1,3-oxazolidin-2-one (60 mg, 0.085 mmol), methyl 4-bromo-3-methylbenzoate (29 mg, 0.128 mmol), 1,1'-bis(diphenylphosphino)ferrocene-palladium dichloride dichloromethane adduct (28 mg, 30%), aqueous potassium hydroxide (57 μL, 3M, 0.171 mmol) and 1,4-dine (1 mL) was placed in a sealed tube and subjected to microwave irradiation at 140° C. for 15 minutes. The crude reaction was purified by preparative TLC on SiO2 (eluted with 30% EtOAc in hexanes) to afford methyl 2"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-carboxylate as a solid foam. LCMS calc.=725.18; found=726.49 (M+1)+. $^1$H NMR signals are doubled because of atropoisomerism. $^1$H NMR (CDCl$_3$, 500 MHz) 7.94 (d, J=8.5 Hz, 1H), 7.88-7.83 (m, 2H), 7.71 (s, 0.5H), 7.69 (s, 0.5H), 7.68-7.60 (m, 2H), 7.45-7.39 (m, 2H), 7.38, 7.37 (d, J=2 Hz, 1H), 7.28 (d, J=8 Hz, 0.5H), 7.24 (d, J=8 Hz, 0.5H), 7.14 (d, J=2 Hz, 1H), 7.07 (t, J=8 Hz, 1H), 5.58 (d, J=8.5 Hz, 0.5H), 5.28 (d, J=8 Hz, 0.5H), 4.96 (d, J=10 Hz, 0.5H), 4.93 (d, J=9.5 Hz, 0.5H), 4.16 (d, J=15.5 Hz, 0.5H), 3.96 (d, J=16 Hz, 0.5H), 3.92 (s, 3H), 3.86 (s, 3H), 3.82-3.93 (m, 1H), 2.37 (s, 1.5H), 2.31 (s, 1.5H), 0.54 (d, J=6.5 Hz, 1.5H), 0.42 (d, J=6.5 Hz, 1.5H).

Example 22

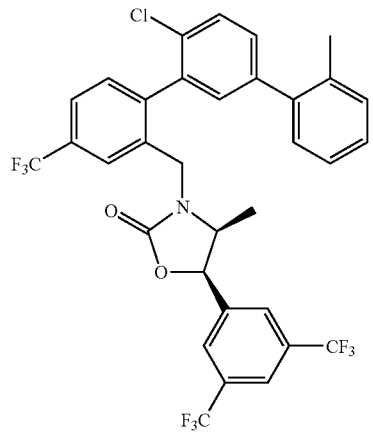

(4S,5R)-5-[3,5-bis(trifluoromethyl)phenyl]-3-{[6'-chloro-2"-methyl-4-(trifluoromethyl)-1,1':3',1"-terphenyl-2-yl]methyl}-4-methyl-1,3-oxazolidin-2-one Step A

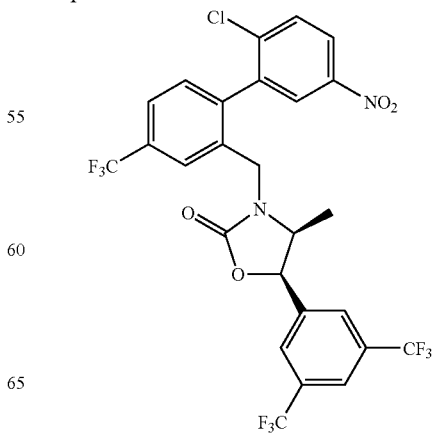

(4S,5R)-5-[3,5-bis(trifluoromethyl)phenyl]-3-{[2'-chloro-5'-nitro-4-(trifluoromethyl)biphenyl-2-yl]methyl}-4-methyl-1,3-oxazolidin-2-one A mixture of (4S,5R)-5-[3,5-bis(trifluoromethyl)phenyl]-3-[2-iodo-5-(trifluoromethyl)-benzyl]-4-methyl-1,3-oxazolidin-2-one (1.0 g, 1.68 mmol), 2-chloro-5-nitro phenyl boronic acid (0.67 g, 3.3 mmol), tetrakis(triphenylphosphine) palladium (97 mg, 5% mol) and sodium carbonate (0.39 g, 3.68 mmol) in 50 ml of water/EtOH/toluene (1:2:4) was heated to reflux for 4 h. TLC(CH$_2$Cl$_2$:hexane/1:1) showed that the reaction was complete. The solvents were removed. Water (30 ml) was added. The organic was extracted with methylene chloride (3×40 ml). The combined methylene chloride layers were washed with brine, and dried over sodium sulfate. The title compound was obtained after flash column using CH$_2$Cl$_2$:hexane/6:4 as the eluant. $^1$H NMR (CDCl$_3$, 500 MHz): δ 1:1 mixture of roamers 8.16-8.31 (m, 1H), 8.21 (d, J=2.5 Hz, ½H), 8.16 (d, J=2.5 Hz, ½H), 7.90 (s, 1H), 7.71-7.78 (m, 5H), 7.42-7.46 (m, 1H), 5.66 (d, J=4.5 Hz, ½H), 5.64 (d, J=4.5 Hz, ½H), 4.93 (d, J=15.5 Hz, ½H), 4.79 (d, J=16 Hz, ½H), 4.03 (d, J=16 Hz, ½H), 3.94 (m, 1H), 3.91 (d, J=15.5 Hz, ½H), 0.70 (d, J=6.5 Hz, 1.5H), 0.64 (d, J=6.5 Hz, 1.5H).

Step B

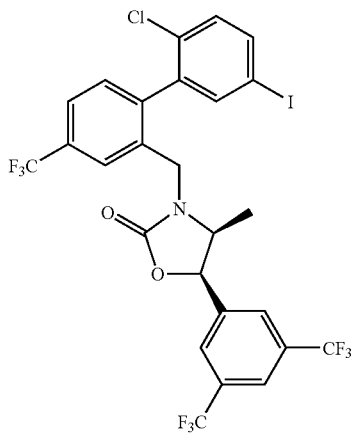

(4S,5R)-5-[3,5-bis(trifluoromethyl)phenyl]-3-{[2'-chloro-5'-iodo-4-(trifluoromethyl)biphenyl-2-yl]methyl}-4-methyl-1,3-oxazolidin-2-one To a solution of the title compound from Step A (1.14 g, 1.82 mmol) in EtOH (20 ml) at room temperature was added SnCl$_2$.H$_2$O (5 eq). The solution was stirred at room temperature for 4 h. TLC (CH$_2$Cl$_2$:hexane/1:1) showed that the reaction was over. EtOAc (50 ml) was added. The mixture was washed with water (2×20 ml), brine, and dried over sodium sulfate. The solvent was removed under reduced pressure and the residue was diluted with chloroform (30 ml). n-Pentyl nitrite (0.36 ml, 2.73 mmol) and iodine (0.55 g, 2.18 mmol) were added. The mixture was stirred under refluxing for 1 h. The mixture was diluted with methylene chloride (30 ml). The purple solution was washed with saturated sodium thiosulfate solution, brine, and dried over sodium sulfate. The title compound was obtained after flash column using EtOAc:hexane/2:98 as the eluant. $^1$H NMR (CDCl$_3$, 500 MHz): δ a mixture of 1:1 atopoisomers 7.90 (s, 1H), 7.77 (s, 1H), 7.70-7.75 (m, 4H), 7.65 (d, J=2.5 Hz, ½H), 7.61 (d, J=2.5 Hz, ½H), 7.40 (m, 1H), 7.28 (m, 1H), 5.66 (d, J=8 Hz, ½H), 5.64 (d, J=8 Hz, ½H), 4.85 (d, J=15.5 Hz, ½H), 4.82 (d, J=14 Hz, ½H), 4.02 (d, J=16 Hz, ½H), 3.96 (m, ½H), 3.95 (d, J=15.5 Hz, ½H), 3.79 (m, ½H), 0.64 (d, J=6.5 Hz, 1.5H), 0.57 (d, J=6.5 Hz, 1.5H).

Step C (4S,5R)-5-[3,5-bis(trifluoromethyl)phenyl]-3-{[6'-chloro-2''-methyl-4-(trifluoromethyl)-1,1':3',1''-terphenyl-2-yl]methyl}-4-methyl-1,3-oxazolidin-2-one A mixture of the title compound from Step B (0.064 g, 0.9 mmol), 2-methyl phenylboronic acid (0.018 g, 0.14 mmol), tetrakis(triphenylphosphine) palladium (10 mg, 5% mol) and sodium carbonate (0.048 g, 0.45 mmol) in 7 ml of water/EtOH/toluene (1:2:4) was heated to reflux for 2 h. TLC (CH$_2$Cl$_2$:hexane/8:2) showed that the reaction was over. The solvents were removed. Water (10 ml) was added. The organic was extracted with methylene chloride (3×20 ml). The combined methylene chloride layers were washed with brine, and dried over sodium sulfate. The title compound was obtained after purification with preparative TLC using 18% EtOAc in hexane as the eluant. $^1$H NMR (CDCl$_3$, 500 MHz): δ 1:1 mixture of atropisomers 7.89 (s, 1H), 7.72 (m, 3H), 7.60 (d, J=1.5 Hz, 0.5H), 7.67.59 (d, J=1.5 Hz, 0.5H), 7.48 (m, 1H), 7.38 (m, 1H), 7.21-7.32 (m, 4H), 7.14 (d, J=7.5 Hz, 0.5H), 7.10 (t, J=7.5 Hz, 0.5H), 6.87 (t, J=7.5 Hz, 0.5H), 6.80 (d, J=7.5 Hz, 0.5H), 5.62 (t, J=8.0 Hz, 1H), 5.00 (d, J=15.5 Hz, 0.5H), 4.83 (d, J=16 Hz, 0.5H), 4.12 (d, J=16 Hz, 0.5H), 4.02 (d, J=15.5 Hz, 0.5H), 3.95 (m, 0.5H), 3.87 (m, 0.5H), 2.33 (s, 1.5H), 2.33 (s, 1.5H), 0.61 (d, J=6.5 Hz, 1.5H), 0.57 (d, J=6.5 Hz, 1.5H). LC-MS (M$^+$): 672.2.

Example 23

The following compound was prepared using the procedures described above (LC/MS 730.4):

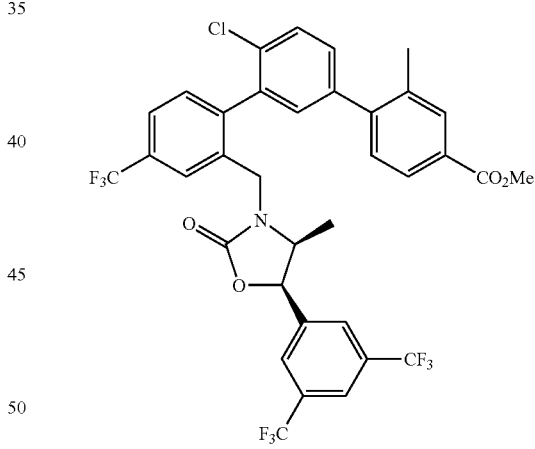

This compound (Example 23) has also been made by the following procedure from INTERMEDIATES 7 and 23:

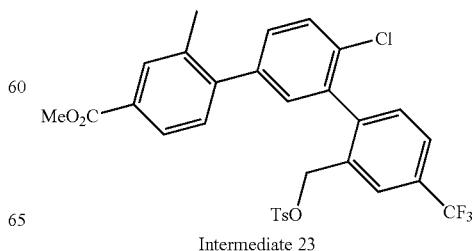

Intermediate 23

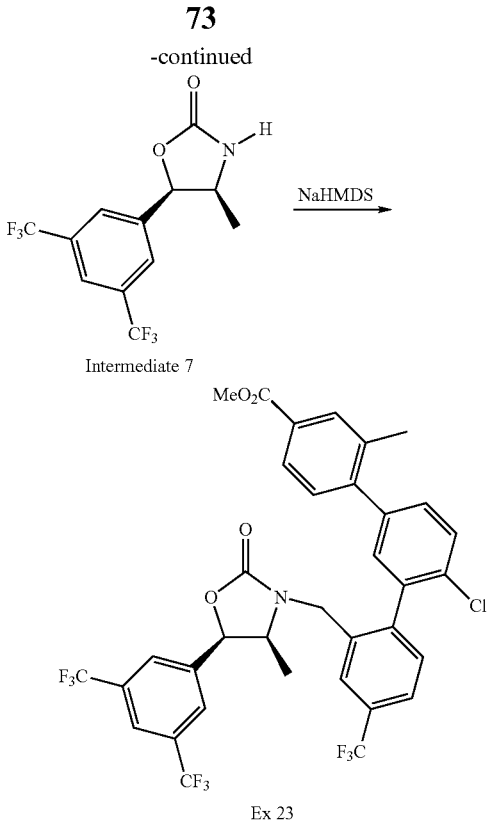

The chiral oxazolidinone (INTERMEDIATE 7) (1.35 kg) and dry DMF (30.8 L) were added to a 100 L flask. After cooling to −15 to −20° C., NaHMDS (1.96 L of 2M solution) was added, and the mixture was aged 15-30 min. The triaryl-tosylate (INTERMEDIATE 23, 2.2 kg) in DMF was added to the resulting sodium salt of the oxazolidinone, and the mixture was allowed to warm to 0 to 5° C. After the triaryl tosylate was consumed, 2.44 L of 5M HCl was added, followed by 22 L of 20% heptane/ethyl acetate. Finally, water (11 L) was added slowly. The layers were separated and then the organic layer was washed with DMF:water twice and then with water twice. The organic layer was assayed for yield and then filtered through a plug of silica gel to remove excess oxazolidinone. The solution was then solvent switched to methanol for subsequent steps.

Example 24

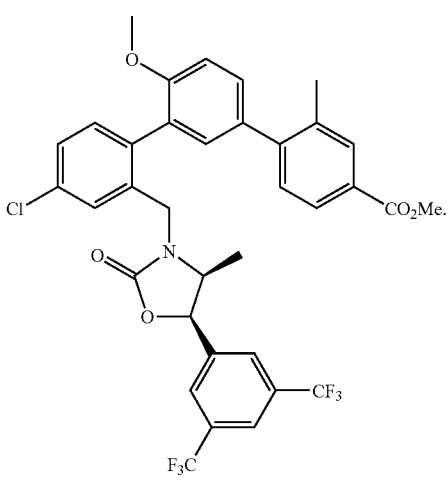

Methyl 2"-({(4S,5R)-5-[3,5-bis(trifluoromethyl) phenyl]-4-methyl-2-oxo-1,3-oxazolidin-3-yl}methyl)-4"-chloro-4'-methoxy-2-methyl-1,1':3', 1"-terphenyl-4-carboxylate Step A 1-bromo-2-(bromomethyl)-4-chlorobenzene A mixture of 2-bromo-5-chloro-toluene (2.00 g, 9.75 mmol), NBS (2.08 g, 11.7 mmol) and catalytic amount of AIBN in carbon tetrachloride (50 ml) was heated to and maintained at reflux for 4 h. TLC (EtOAc:hexane/5:95) showed no starting material. The mixture was filtered and the filtrate was concentrated. The title compound was obtained as a white solid (2.20 g) after flash column using EtOAc:hexane/ 5:95 as the eluant. $^1$H NMR (CDCl$_3$, 500 MHz) δ 7.53 (d, J=9.0 Hz, 1H), 7.47 (d, J=2.5 Hz, 1H), 7.18 (dd, J=8.5, 2.5 Hz, 1H), 4.60 (s, 2H).

Step B (4S,5R)-5-[3,5-bis(trifluoromethyl)phenyl]-3-(2-bromo-5-chlorobenzyl)-4-methyl-1,3-oxazolidin-2-one To a solution of (4S,5R)-5-[3,5-bis(trifluoromethyl)phenyl]-4-methyl-1,3-oxazolidin-2-one (0.050 g, 0.16 mmol) in THF (1 ml) at 0° C. was added NaH (7.6 mg, 0.19 mmol, 60%). The mixture was stirred at 0° C. for 30 min. The title compound from Step A (0.059 g, 0.21 mmol) was added. The whole was stirred at 0° C. for 1 h and warmed to room temperature for 4 h. The reaction was quenched with saturated ammonium chloride. The organic was extracted with ethyl acetate (3×15 ml). The combined ethyl acetate layers were washed with brine and dried over sodium sulfate. The title compound was obtained after preparative TLC purification using EtOAc:hexane/2:8 as the eluant. $^1$H NMR (CDCl$_3$, 500 MHz) δ 7.92 (s, 1H), 7.82 (s, 2H), 7.55 (d, J=8.5 Hz, 1H), 7.43 (d, J=2.5 Hz, 1H), 7.23 (dd, J=8.5, 2.5 Hz, 1H), 5.77 (d, J=8.0 Hz, 1H), 4.86 (d, J=16.0 Hz, 1H), 4.36 (d, J=16.0 Hz, 1H), 4.11 (m, 1H), 0.82 (d, J=6.5 Hz, 3H).

Step C Methyl 2"-({(4S,5R)-5-[3,5-bis(trifluoromethyl)phenyl]-4-methyl-2-oxo-1,3-oxazolidin-3-yl}methyl)-4"-chloro-4'-methoxy-2-methyl-1,1':3', 1"-terphenyl-4-carboxylate A mixture of the title compound from Step B (0.068 g, 0.13 mmol), methyl 4'-methoxy-2-methyl-3'-(4,4,5,5-tetramethyl-1,3,2-dioxaborolan-2-yl)biphenyl-4-carboxylate (INTERMEDIATE 11) (0.075 g, 0.19 mmol), tetrakis(triphenylphosphine) palladium (15 mg, 5% mol) and sodium carbonate (0.07 g, 0.65 mmol) in 7 ml of water/EtOH/toluene (1:2:4) was heated to reflux for 5 h. TLC (EtOAc:hexane/1:3) showed that the reaction was over. The solvents were removed. Water (10 ml) was added. The organic was extracted with methylene chloride (3×20 ml). The combined methylene chloride layers were washed with brine, and dried over sodium sulfate. The title compound was obtained after purification with preparative TLC using 10% EtOAc in hexane as the eluant. $^1$H NMR (CDCl$_3$, 500 MHz): δ 1:1 mixture of atropisomers 7.96 (d, J=9 Hz, 1H), 7.88 (m, 2H), 7.72 (s, 1H), 7.65 (s, 1H), 7.49 (d, J=2 Hz, 0.5H), 7.39 (m, 2H), 7.36 (d, J=2 Hz, 0.5H), 7.24-7.28 (m, 2H), 7.15 (m, 1H), 7.70 (m, 1H), 5.62 (d, J=8 Hz, 0.5H), 5.52 (d, J=8 Hz, 0.5H), 4.91 (t, J=16 Hz, 1H), 4.08 (d, J=15.5 Hz, 0.5H), 3.95 (s, 3H), 3.88 (s, 3H), 3.87 (d, J=16 Hz, 0.5H), 3.84 (m, 1H), 2.39 (s, 1.5H), 2.33 (s, 1.5H), 0.56 (d, J=7 Hz, 1.5H), 0.43 (d, J=6.5 Hz, 1.5H).

Example 25

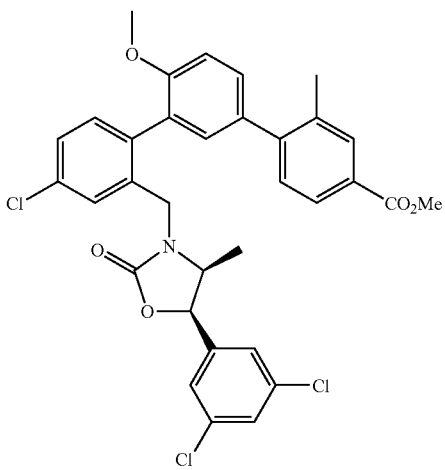

The title compound was obtained according to the procedure outlined in Example 24 starting from (4S,5R)-5-[3,5-bis(chloro) phenyl]-4-methyl-1,3-oxazolidin-2-one. $^1$H NMR (CDCl$_3$, 500 MHz): δ 1:1 mixture of atropisomers 7.96 (d, J=6.5 Hz, 1H), 7.89 (dd, J=8, 1Hz, 1H), 7.45 (m, 2H), 7.34-7.40 (m, 3H), 7.22-7.31 (m, 2H), 7.13 (d, J=2.5 Hz, 0.5H), 7.12 (d, J=2.5 Hz, 0.5H), 7.01-7.07 (m, 2H), 5.45 (d, J=8.5 Hz, 0.5H), 5.20 (d, J=8 Hz, 0.5H), 4.88 (d, J=16 Hz, 0.5H), 4.83 (d, J=15.5 Hz, 0.5H), 4.08 (d, J=15.5 Hz, 0.5H), 3.95 (s, 3H), 3.87 (s, 3H), 3.85 (d, J=16 Hz, 0.5H), 3.75 (m, 1H), 2.38 (s, 1.5H), 2.33 (s, 1.5H), 0.58 (d, J=6.5 Hz, 1.5H), 0.44 (d, J=6 Hz, 1.5H). LC-MS (M+1): 626.38.

Example 26

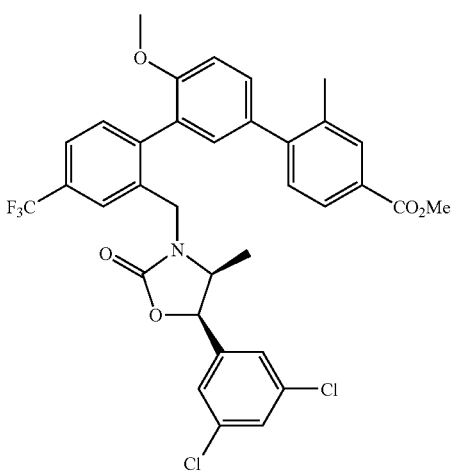

Methyl 2"-{[(4S,5R)-5-(3,5-dichlorophenyl)-4-methyl-2-oxo-1,3-oxazolidin-3-yl]methyl}-4'-methoxy-2-methyl-4"-(trifluoromethyl)-1,1':3',1"-terphenyl-4-carboxylate ((4S,5R)-5-(3,5-dichlorophenyl)-3-[2-iodo-5-(trifluoromethyl)benzyl]-4-methyl-1,3-oxazolidin-2-one (100 mg, 0.1886 mmol), methyl 4'-methoxy-2-methyl-3'-(4,4,5,5-tetramethyl-1,3,2-dioxaborolan-2-yl)biphenyl-4-carboxylate (108 mg, 0.283 mmol), 1,1'-bis(diphenylphosphino)ferrocene-palladium dichloride dichloromethane adduct (46 mg, 0.056 mmol), aqueous sodium carbonate (190 μL, 2M, 0.380 mmol) and 1,4-dioxane (2 mL) were placed in a sealed tube and subjected to microwave irradiation at 130° C. for 30 minutes and then at 135° C. for 15 minutes to complete the reaction. The crude reaction mixture was purified by preparative TLC on SiO$_2$ (eluted sequentially with 30% ethyl acetate in hexanes, 70% dichloromethane in hexanes and then 80% dichloromethane in hexanes) to afford methyl 2"-{[(4S,5R)-5-(3,5-dichlorophenyl)-4-methyl-2-oxo-1,3-oxazolidin-3-yl]methyl}-4'-methoxy-2-methyl-4"-(trifluoromethyl)-1,1': 3',1"-terphenyl-4-carboxylate as a white solid. LCMS calc.=657.13; found=658.46 (M+1)$^+$. $^1$H NMR signals are doubled because of atropisomerism $^1$H NMR (CDCl$_3$, 500 MHz), 7.94 (d, J=7 Hz, 1H), 7.87 (d, J=8.5 Hz, 1H), 7.70 (s, 0.5H), 7.65-7.61 (m, 1.5H), 7.47-7.36 (m, 3H), 7.32 (d, J=2 Hz, 0.5H), 7.29-7.23 (m, 1.5H), 7.11 (dd, J=6.3, 2.0 Hz, 1H), 7.08-7.02 (m, 1.5H), 7.00 (dd, J=8.3, 2.0 Hz, 0.5H), 5.41 (d, J=8.5 Hz, 0.5H), 5.16 (d, J=8.0 Hz, 0.5H), 4.91 (d, J=16 Hz, 0.5H), 4.85 (d, J=16.5 Hz, 0.5H), 4.17 (d, J=16 Hz, 0.5H), 3.98-3.90 (m, 3.5H), 3.856, 3.851 (s, 3H), 3.74-3.66 (m, 1H), 2.36, 2.32 (s, 3H), 0.55 (d, J=7 Hz, 1.5H), 0.43 (d, J=6 Hz, 1.5H).

Example 27

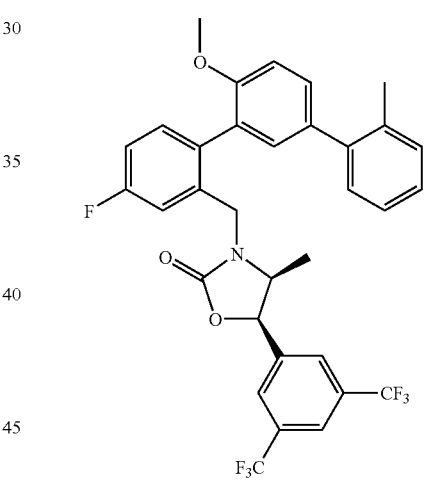

Step A

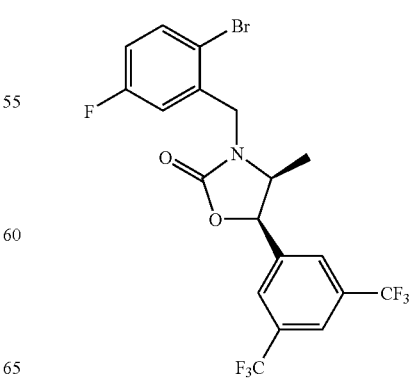

(4S,5R)-5-[3,5-bis(trifluoromethyl)phenyl]-3-(2-bromo-5-fluorobenzyl-4-methyl-1,3-oxazolidin-2-one To a solution of (4S,5R)-5-[3,5-bis(trifluoromethyl)phenyl]-4-methyl-1,3-oxazolidin-2-one (2.0 g, 6.39 mmol) in THF (40 mL) at 0° C. was added NaH (285 mg, 60 w/w % in mineral oil, 7.13 mmol, 1.1 eq.) in one portion. The resulting foaming mixture was stirred in an ice bath. Additional THF (50 mL) was added into the reaction. The mixture was stirred at 0° C. for 30 min. A solution of 2-bromo-5-fluorobenzyl bromide (1.712 g, 6.39 mmol) in THF (20 mL) was added. The resulting mixture was stirred cold for 30 min and then allowed to warm to room temperature. The reaction was completed in 3 hours. The reaction was quenched with $NH_4Cl$ (aq., sat., 80 mL). Volatiles were removed in vacuo. The crude mixture was extracted with EtOAc and dried over $Na_2SO_4$. The residue was purified by flash chromatography on $SiO_2$ (Biotage 40+M cartridge, EtOAc/hexane, gradient). (4S,5R)-5-[3,5-bis(trifluoromethyl)phenyl]-3-(2-bromo-5-fluorobenzyl)-4-methyl-1,3-oxazolidin-2-one was obtained as a clear oil. LC-MS: 500.09 (M+1)$^+$. $^1$H NMR (CDCl$_3$, 500 MHz) δ 7.88 (s, 1H), 7.79 (s, 2H), 7.55 (dd, J=8.8, 5.2 Hz, 1H), 7.17 (dd, J=8.7, 4.5 Hz, 1H), 6.95 (m, 1H), 5.74 (d, J=8.0 Hz, 1H), 4.83 (d, J=15.8, 1H), 4.54 (d, J=16.0 Hz, 1H), 4.11 (m, 1H), 0.80 (d, J=6.6 Hz, 3H).

Step B

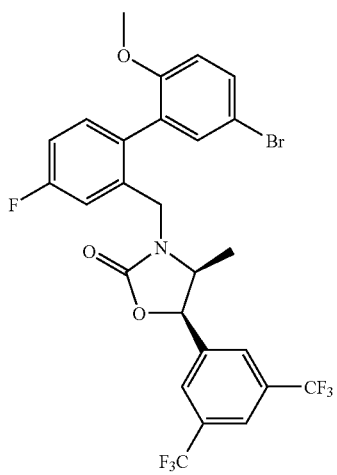

(4S,5R)-5-[3,5-bis(trifluoromethyl)phenyl]-3-[(5'-bromo-4-fluoro-2'-methoxybiphenyl-2-yl)methyl]-4-methyl-1,3-oxazolidin-2-one (4S,5R)-5-[3,5-bis(trifluoromethyl)phenyl]-3-(2-bromo-5-fluorobenzyl)-4-methyl-1,3-oxazolidin-2-one (600 mg, 1.2 mmol), (5-bromo-2-methoxyphenyl)boronic acid (319 mg, 1.38 mmol), sodium carbonate aqueous solution (1.27 mL, 2M, 2.54 mmol), toluene (3.5 mL) and ethanol (400 μL) were mixed and stirred at room temperature for 45 minutes followed by addition of tetrakis(triphenylphosphine)palladium (0) (87 mg, 4.5 mol %). The resulting mixture was heated in a 90° C. oil bath for 24 hours to complete the reaction. The crude reaction was diluted with brine and extracted with ethyl acetate. The combined extracts were dried over $Na_2SO_4$ followed by filtration and concentration in vacuo to afford a dark oil. The crude oil was purified by reverse-phase preparative HPLC (Kromasil 100-5C18, 100×21.1 mm) eluting with a MeCN (0.1% TFA, v/v)/H$_2$O (0.1% TFA, v/v) gradient mixture affording (4S,5R)-5-[3,5-bis(trifluoromethyl)phenyl]-3-[(5'-bromo-4-fluoro-2'-methoxybiphenyl-2-yl)methyl]-4-methyl-1,3-oxazolidin-2-one. LCMS calc.=607.04; found=607.98 (M+1)$^+$.

Step C (4S,5R)-5-[3,5-bis(trifluoromethyl)phenyl]-3-[(4-fluoro-6'-methoxy-2''-methyl-1,1':3',1''-terphenyl-2-yl)methyl]-4-methyl-1,3-oxazolidin-2-one (4S,5R)-5-[3,5-bis(trifluoromethyl)phenyl]-3-[(5'-bromo-4-fluoro-2'-methoxybiphenyl-2-yl)methyl]-4-methyl-1,3-oxazolidin-2-one (50 mg, 0.082 mmol), (2-methylphenyl)boronic acid (22 mg, 0.165 mmol), 1,1'-bis(diphenylphosphino)ferrocene-palladium dichloride dichloromethane adduct (20 mg, 0.024 mmol), aqueous potassium hydroxide (55 μL, 3M, 0.165 mmol) and 1,4-dioxane (1 mL) were placed in a sealed tube and subjected to microwave irradiation at 140° C. for 20 minutes to complete the reaction. The crude reaction mixture was purified by preparative TLC on SiO$_2$ (eluted with 20% Ethyl Acetate in hexanes) to afford (4S,5R)-5-[3,5-bis(trifluoromethyl)phenyl]-3-[(4-fluoro-6'-methoxy-2''-methyl-1,1':3',1''-terphenyl-2-yl)methyl]-4-methyl-1,3-oxazolidin-2-one as a colorless glass. LCMS calc.=617.18; found=618.16 (M+1)$^+$. $^1$H NMR signals are doubled because of atropisomerism $^1$H NMR (CDCl$_3$, 500 MHz) δ 7.84 (s, 1H), 7.68 (s, 1H), 7.62 (s, 1H), 7.36-7.32 (m, 1H), 7.30-7.22 (m, 4H), 7.22-7.18 (m, 1.5H), 7.18-7.14 (m, 0.5H), 7.14-7.11 (m, 1H), 7.11-7.05 (m, 1H), 7.02 (t, J=8.0 Hz, 1H), 5.58 (d, J=8.5 Hz, 0.55H), 5.28 (d, J=8 Hz, 0.45H), 4.90 (d, J=3.5 Hz, 0.45H), 4.09 (d, J=15.5 Hz, 0.45H), 3.88 (d, J=16.5 Hz, 0.55H), 3.844, 3.838 (s, 3H), 3.82-3.75 (m, 1H), 2.32, 2.56 (s, 3H), 0.52 (d, J=6.5 Hz, 1.35H), 0.38 (d, J=6.5 Hz, 1.65H).

Example 28

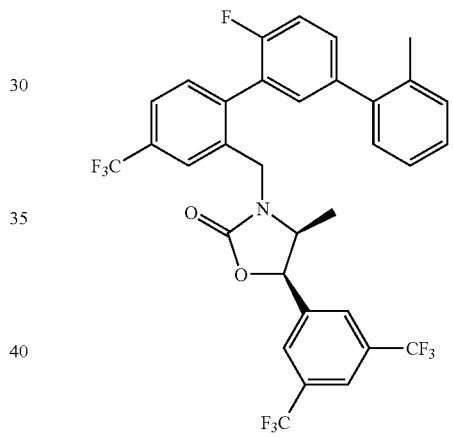

(4S,5R)-5-[3,5-bis(trifluoromethyl)phenyl]-3-{[6'-fluoro-2''-methyl-4-(trifluoromethyl)-1,1':3',1''-terphenyl-2-yl]methyl}-4-methyl-1,3-oxazolidin-2-one Step A

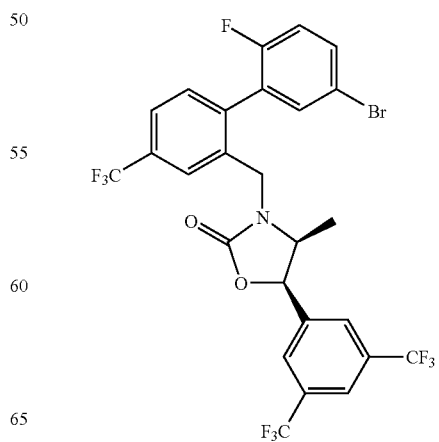

(4S,5R)-5-[3,5-bis(trifluoromethyl)phenyl]-3-{[5'-bromo-2'-fluoro-4-(trifluoromethyl)-biphenyl-2-yl]methyl}-4-methyl-1,3-oxazolidin-2-one (4S,5R)-5-[3,5-bis(trifluoromethyl)phenyl]-3-[2-iodo-5-(trifluoro-ethyl)benzyl]-4-methyl-1,3-oxazolidin-2-one (500 mg, 0.837 mmol) was mixed with (5-bromo-2-fluorophenyl) boronic acid (211 mg, 0.963 mmol), toluene (5 mL), ethanol (278 µL) and sodium carbonate aqueous solution (2M, 0.89 mL, 1.78 mmol). The resulting mixture was stirred at 20° C. for 30 min followed by addition of tetrakis (triphenylphosphine) palladium(0) (43.5 mg, 0.0376 mmol, 4.5 mol %). The reaction mixture was heated in a 90° C. oil bath for 40 hours to complete the reaction. The resulting crude mixture was purified by flash chromatography (SiO₂, Biotage 40+M cartridge). The column was eluted by an Ethyl acetate/hexanes mixture. Related fractions were pooled and concentrated in vacuo to afford (4S,5R)-5-[3,5-bis(trifluoromethyl)phenyl]-3-{[5'-bromo-2'-fluoro-4-(trifluoromethyl)biphenyl-2-yl]methyl}-4-methyl-1,3-oxazolidin-2-one. LCMS calc.=645.02; found=645.94 (M+1)⁺.

Step B (4S,5R)-5-[3,5-bis(trifluoromethyl)phenyl]-3-{[6'-fluoro-2"-methyl-4-(trifluoromethyl)-1,1':3',1"-terphenyl-2-yl]methyl}-4-methyl-1,3-oxazolidin-2-one (4S,5R)-5-[3,5-bis(trifluoromethyl)phenyl]-3-{[5'-bromo-2'-fluoro-4-(trifluoromethyl) biphenyl-2-yl]methyl}-4-methyl-1,3-oxazolidin-2-one (79 mg, 0.123 mmol), (2-methylphenyl) boronic acid (25 mg, 0.182 mmol), 1,1'-bis (diphenylphosphino)ferrocene-palladium dichloride dichloromethane adduct (10 mg, 0.0122 mmol), aqueous potassium hydroxide (82 µL, 3M, 0.246 mmol) and 1,4-dioxane (1 mL) were placed in a sealed tube and subjected to microwave irradiation at 140° C. for 15 minutes to complete the reaction. The crude reaction mixture was purified by preparative TLC on SiO₂ (eluted with 30% Ethyl Acetate in hexanes) to afford (4S,5R)-5-[3,5-bis(trifluoromethyl)phenyl]-3-{[6'-fluoro-2"-methyl-4-(trifluoromethyl)-1,1':3',1"-terphenyl-2-yl]methyl)}-4-methyl-1,3-oxazolidin-2-one as a ckear glass. LCMS calc.=655.16; found=656.11 (M+1)⁺. ¹H NMR signals are doubled because of atropisomerism ¹H NMR (CDCl₃, 500 MHz) δ 7.86 (s, 1H), 7.73 (s, 1H), 7.72-7.66 (m, 2H), 7.48 (d, J=8 Hz, 1H), 7.41-7.36 (m, 1H), 7.29-7.23 (m, 4H), 7.19-7.23 (m, 3H), 5.56 (br s, 1H), 4.96 (br s, 1H), 4.13 (br d, J=46.5 Hz, 1H), 3.83 (br d, J=43.5 Hz, 1H), 2.29 (s, 3H), 0.56, 0.51 (br s, 3H).

Example 29

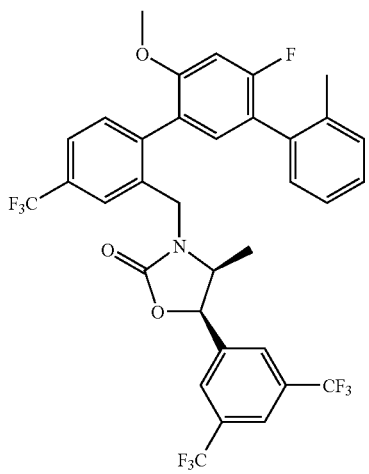

(4S,5R)-5-[3,5-bis(trifluoromethyl)phenyl]-3-{[4'-fluoro-6'-methoxy-2"-methyl-4-(trifluoromethyl-1,1': 3',1"-terphenyl-2-yl]methyl}-4-methyl-1,3-oxazolidin-2-one A mixture of (4S,5R)-5-[3,5-bis(trifluoromethyl)phenyl]-3-[2-iodo-5-(trifluoromethyl)-benzyl]-4-methyl-1,3-oxazolidin-2-one (0.050 g, 0.084 mmol), 2-methoxy-4-fluoro-5-(2'-methylphenyl) boronic acid (excess), tetrakis (triphenylphosphine) palladium (5% mol) and sodium carbonate (19.5 mg, 0.18 mmol) in 7 ml of water/EtOH/toluene (1:2:4) was heated to reflux for 4 h. TLC (CH₂Cl₂: hexane/1:1) showed that the reaction was over. The solvents were removed. Water (10 ml) was added. The organic was extracted with methylene chloride (3×10 ml). The combined methylene chloride layers were washed with brine, and dried over sodium sulfate. The title compound was obtained after flash column using CH₂Cl₂:hexane/6:4 as the eluant. LC-MS (M+1): 686.1.

Example 30

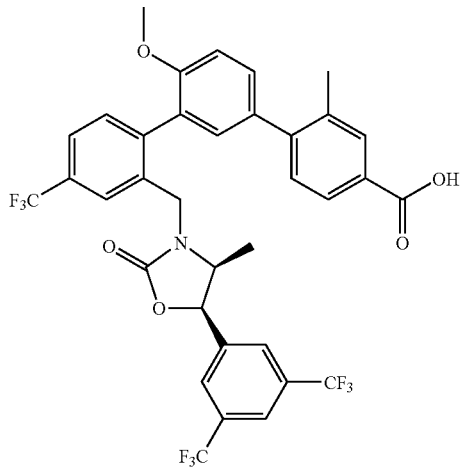

2"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-carboxylic Acid methyl 2"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-carboxylate (20 mg, 0.0276 mmol), aqueous potassium hydroxide (300 µL, 3M, 0.90 mmol) and ethanol (2 mL) were stirred at 20° C. for 2 hours and 20 minutes to complete the hydrolysis. The reaction mixture was acidified by acetic acid. The mixture was purified by preparative TLC on silica gel, (eluted with AcOH/EtOAc/hexanes=5/25/70, v/v) to afford 2"-({(4S,5R)-5-[3,5-bis(trifluoromethyl)phenyl]-4-methyl-2-oxo-1,3-oxazolidin-3-yl}methyl)-4'-methoxy-2-methyl)-4"-(trifluoromethyl)-1,1':3',1"-terphenyl-4-carboxylic acid. LCMS calc.=711.17; found=712.10 (M+1)⁺. ¹H NMR signals are doubled because of atropoisomerism. ¹H NMR (CDCl₃, 500 MHz) δ 7.99 (d, J=8.0 Hz, 1H), 7.92 (d, J=8.5 Hz, 1H), 7.85 (d, J=5 Hz, 1H), 7.72-7.68 (m, 1.5H), 7.67-7.60 (m, 2.5H), 7.47-7.36 (m, 2H), 7.32 (d, J=8.0 Hz, 0.5H), 7.28 (d, J=8.0 Hz, 0.5H), 7.15 (s, 1H), 7.08 (d, J=8.5, 7.0 Hz, 1H), 5.58 (d, J=8.0 Hz, 0.5H), 5.29 (d, J=6.5 Hz, 0.5H), 4.97 (d, J=15.5 Hz, 0.5H), 4.94 (d, J=14 Hz, 0.5H), 4.16 (d, J=16 Hz, 0.5H), 3.96 (d, J=15.5 Hz, 0.5H), 3.87 (s, 3H), 3.83-3.74 (m, 1H), 2.38, 2.33 (s, 3H), 0.55 (d, J=6.5 Hz, 1.5H), 0.42 (d, J=7 Hz, 1.5H).

Example 31

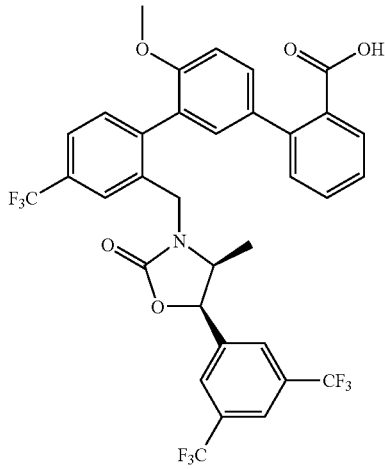

2"-({(4S,5R)-5-[3,5-bis(trifluoromethyl)phenyl]-4-methyl-2-oxo-1,3-oxazolidin-3-yl}methyl)-4'-methoxy-4"-(trifluoromethyl)-1,1':3',1"-terphenyl-2-carboxylic Acid Methyl 2"-({(4S,5R)-5-[3,5-bis(trifluoromethyl)phenyl]-4-methyl-2-oxo-1,3-oxazolidin-3-yl}methyl)-4' methoxy-4"-(trifluoromethyl)-1,1':3',1"-terphenyl-2-carboxylate (50 mg, 0.07 mmol), aqueous potassium hydroxide (1.1 mL, 3M, 3.3 mmol), water (1.5 mL) and ethanol (3.6 mL) were stirred at 20° C. for 23 hours. The reaction mixture was acidified by HCl (aq., 1N). Volatiles were removed under reduced pressure. The resulting mixture was worked up with ethyl acetate, washed with brine. The combined organic extracts were dried over Na₂SO₄, filtered, and concentrated to an oil. This oil was purified by a reverse-phase preparative HPLC (column: Kromasil 100-5C18, 100×21.1 mm) eluting with a MeCN (0.1% v/v TFA buffered)/H₂O (0.1% v/v TFA buffered) gradient mixture to afford 2"-({(4S,5R)-5-[3,5-bis(trifluoromethyl)phenyl]-4-methyl-2-oxo-1,3-oxazolidin-3-yl}methyl)-4'-methoxy-4"-(trifluoromethyl)-1,1':3',1"-terphenyl-2-carboxylic acid. LCMS calc.=697.15; found=698.16 (M+1)⁺. ¹H NMR signals are doubled because of atropisomerism ¹H NMR (CDCl₃, 500 MHz) δ 7.94 (t, J=7.0 Hz, 1H), 7.85 (d, J=7.0 Hz, 1H), 7.68-7.63 (m, 2.5H), 7.63-7.59 (m, 1.5H), 7.59-7.54 (m, 1H), 7.47-7.35 (m, 4H), 7.14 (dd, J=8.0, 2.0 Hz, 1H), 7.04 (d, J=8.5 Hz, 1H), 5.53 (d, J=8.0 Hz, 0.4H), 5.42 (d, J=8.0 Hz, 0.6H), 5.02 (d, J=15.5 Hz, 0.6H), 4.85 (d, J=15.5 Hz, 0.4H), 4.11-4.02 (m, 0.4H), 3.87-3.77 (m, 3.6H), 0.99 (d, J=6.5 Hz, 0.6H), 0.93 (d, J=7.0 Hz, 0.4H), 0.58 (d, J=7.0 Hz, 1.2H), 0.54 (d, J=6.5 Hz, 1.8H).

Example 32

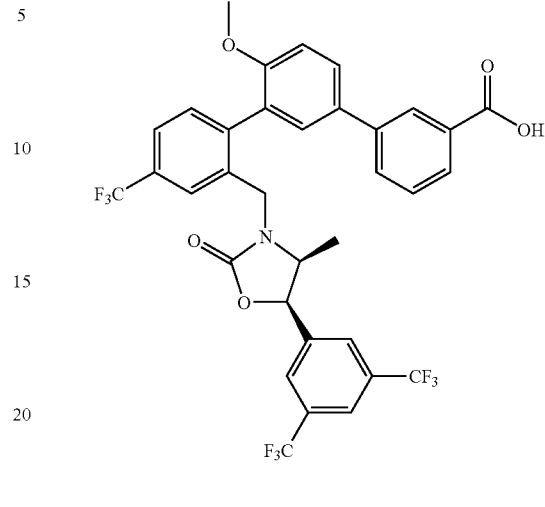

2"-({(4S,5R)-5-[3,5-bis(trifluoromethyl)-phenyl]-4-methyl-2-oxo-1,3-oxazolidin-3-yl}methyl)-4'-methoxy-4"-(trifluoromethyl)-1,1':3',1"-terphenyl-3-carboxylic Acid The title compound from Example 15 was stirred with LiOH (3 eq) in a 2:1 mixture of dioxane and water at room temperature overnight. The solvent was removed and the aqueous solution was acidified with 1N HCl to pH ~4. The mixture was extracted with EtOAc (3×10 ml). The combined EtOAc layers were dried over sodium sulfate. The title compound was obtained after preparative TLC on silica gel using EtOAc:hexane/1:1 as the eluant. ¹H NMR (CDCl₃, 500 MHz): δ 1:1 mixture of atropoisomers 8.32 (s, 0.5H), 8.29 (s, 0.5H), 8.08 (m, 1H), 7.46-7.85 (m, 10H), 5.61 (d, J=8 Hz, 0.5H), 5.20 (d, J=8 Hz, 0.5H), 5.04 (d, J=16 Hz, 0.5H), 4.95 (d, J=15.5 Hz, 0.5H), 4.17 (d, J=16 Hz, 0.5H), 3.97 (d, J=15.5 Hz, 0.5H), 3.91 (s, 1.5H), 3.83 (s, 1.5H), 3.79 (m, 1H), 0.58 (d, J=6.5 Hz, 1.5H), 0.42 (d, J=6.5 Hz, 1.5H). LC-MS (M+1): 698.18.

Example 33

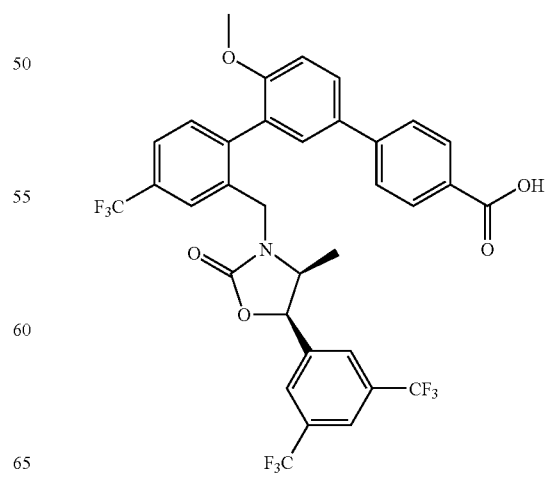

2"-({(4S,5R)-5-[3,5-bis(trifluoromethyl)phenyl]-4-methyl-2-oxo-1,3-oxazolidin-3-yl}methyl)-4'-methoxy-4"-(trifluoromethyl)-1,1':3',1"-terphenyl-4-carboxylic Acid Methyl 2"-({(4S,5R)-5-[3,5-bis(trifluoromethyl)phenyl]-4-methyl-2-oxo-1,3-oxazolidin-3-yl}methyl)-4'-methoxy-4"-(trifluoromethyl)-1,1':3',1"-terphenyl-4-carboxylate (10 mg, 0.014 mmol), aqueous potassium hydroxide (150 µL, 3M, 0.45 mmol) and ethanol (1 mL) were stirred at 20° C. for 2 hours and 30 minutes to complete the hydrolysis. The reaction mixture was acidified by HCl (aq., 1N) and then basified by sodium bicarbonate. Volatiles were removed under reduced pressure. The resulting mixture was worked up with ethyl acetate, washed with brine. The combined organic extracts were dried over $Na_2SO_4$, filtered, and concentrated to an oil. This oil was purified by preparative TLC on $SiO_2$ (eluted with 50% EtOAc in hexanes) to afford 2"-({(4S,5R)-5-[3,5-bis(trifluoromethyl)phenyl]-4-methyl-2-oxo-1,3-oxazolidin-3-yl}methyl)-4'-methoxy-4"-(trifluoromethyl)-1,1':3',1"-terphenyl-4-carboxylic acid. LCMS calc.=697.15; found=698.03 $(M+1)^+$. $^1H$ NMR signals are doubled because of atropisomerism $^1H$ NMR ($CDCl_3$, 500 MHz), 8.16-8.11 (m, 2H), 7.83 (d, J=8.0 Hz, 1H), 7.74-7.69 (m, 2H), 7.69-7.65 (m, 2.5H), 7.65-7.61 (m, 1.5H), 7.57 (s, 1H), 7.48-7.42 (m, 2.0H), 7.11 (dd, J=8.8, 2.5 Hz, 1H), 5.57 (d, J=8.0 Hz, 0.5H), 5.17 (d, J=8.0 Hz, 0.5H), 4.97 (d, J=15.5 Hz, 0.5H), 4.93 (d, J=15.5 Hz, 0.5H), 4.16 (d, J=16 Hz, 0.5H), 3.95 (d, J=16.0 Hz, 0.5H), 3.88, 3.87 (s, 3H), 3.80-3.72 (m, 1H), 0.55 (d, J=6.5 Hz, 1.5H), 0.41 (d, J=6.5 Hz, 1.5H).

Example 34

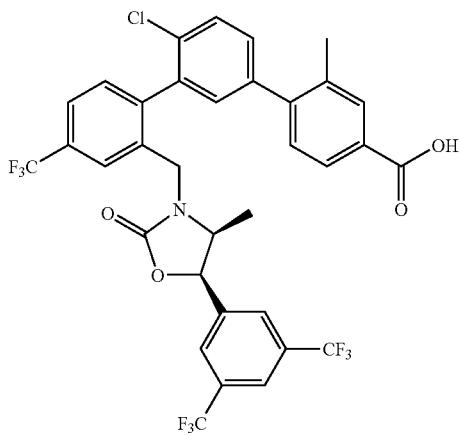

2"-({(4S,5R)-5-[3,5-bis(trifluoromethyl)phenyl]-4-methyl-2-oxo-1,3-oxazolidin-3-yl}methyl)-4'-chloro-2-methyl-4"-(trifluoromethyl)-1,1':3',1"-terphenyl-4-carboxylic Acid methyl 2"-({(4S,5R)-5-[3,5-bis(trifluoromethyl)phenyl]-4-methyl-2-oxo-1,3-oxazolidin-3-yl}methyl)-4'-chloro-2-methyl-4"-(trifluoromethyl)-1,1':3',1"-terphenyl-4-carboxylate (25 mg, 0.034 mmol), aqueous potassium hydroxide (300 µL, 3M, 0.90 mmol) and ethanol (2 mL) were stirred at 20° C. overnight. Volatiles were removed under reduced pressure. The resulting residue was treated with brine followed by extraction with ethyl acetate. The combined extracts were dried over $Na_2SO_4$ followed by filtration and concentration in vacuo to afford an oil. This oil was purified by preparative TLC on $SiO_2$ (eluted with 50% EtOAc in hexanes) to afford a clear glass. The glass was further purified by reverse phase preparative HPLC (Kromasil 100-5C18, 100×21.1 mm) eluting by a MeCN (0.1% TFA, v/v)/$H_2O$ (0.1% TFA, v/v) gradient mixture affording 2"-({(4S,5R)-5-[3,5-bis(trifluoromethyl)phenyl]-4-methyl-2-oxo-1,3-oxazolidin-3-yl}methyl)-4'-chloro-2-methyl-4"-(trifluoromethyl)-1,1':3',1"-terphenyl-4-carboxylic acid. LCMS calc.=715.12; found=716.12 $(M+1)^+$. $^1H$ NMR signals are doubled because of atropisomerism $^1H$ NMR ($CDCl_3$, 500 MHz) δ 7.99 (d, J=8.0 Hz, 1H), 7.92 (d, J=8.5 Hz, 1H), 7.85 (d, J=5 Hz, 1H), 7.72-7.68 (m, 1.5H), 7.67-7.60 (m, 2.5H), 7.47-7.36 (m, 2H), 7.32 (d, J=8.0 Hz, 0.5H), 7.28 (d, J=8.0 Hz, 0.5H), 7.15 (s, 1H), 7.08 (dd, J=8.5, 7.0 Hz, 1H), 5.58 (d, J=8.0 Hz, 0.5H), 5.29 (d, J=6.5 Hz, 0.5H), 4.97 (d, J=15.5 Hz, 0.5H), 4.94 (d, J=14 Hz, 0.5H), 4.16 (d, J=16 Hz, 0.5H), 3.96 (d, J=15.5 Hz, 0.5H), 3.87 (s, 3H), 3.83-3.74 (m, 1H), 2.38, 2.33 (s, 3H), 0.55 (d, J=6.5 Hz, 1.5H), 0.42 (d, J=7 Hz, 1.5H).

The compound above (Example 34) has also been made from its methyl ester (Example 23) using the following procedure:

THF (12 L) was placed in a 75 L flask equipped with an overhead stirrer, thermocouple, nitrogen inlet, dropping funnel and a steam pot that contained ca. 12 L of a methanol solution of the triaryl oxazolidinone methyl ester (Ex. 23, 2190 g, 3 moles). Hydrogen peroxide (1800 mL of a 35 wt % solution) was added. The addition was exothermic, and the batch temperature increased from 16° C. to 23° C.

Lithium hydroxide monohydrate (378 g, 9 moles) was then charged to the reaction vessel, and the reaction was heated to 60° C. The reaction was monitored by HPLC and was complete in 15-16 h. The reaction mixture was cooled to 0-10° C., and aqueous sodium bisulfite (2185 g in ca. 18 L water) was slowly added over 2 hours to quench the hydrogen peroxide. The addition was very exothermic. The absence of peroxide was confirmed using EM Quant Peroxide test strips.

MTBE (22 L) and GMP water (8 L) were then added, and the mixture was transferred to a 100 L extractor. The lower aqueous layer was cut away, and the upper organic layer was washed with 10 wt % brine (2010 g NaCl in ca. 18 L GMP water). The lower layer was cut away and the hazy organic layer was dried over anhydrous sodium sulfate.

The dried organic phase was transferred through an in-line filter (1 µm) to a 100 L flask attached to a batch concentrator. The MTBE was removed and replaced with cyclohexane. The volume was adjusted to 20 L. The batch was heated to 50-65° C. to completely dissolve any precipitated solids, and then was cooled to ca. 60° C. and seeded with crystals obtained from earlier batches. The solution was allowed to cool to ambient temperature overnight, yielding a white solid. The white solid was isolated by filtration, rinsed with 2×2 L of cyclohexane, and dried under a nitrogen bag with vacuum.

The solid carboxylic acid obtained at this point is a mixture of anhydrous product and a cyclohexane solvate (typically 3-5 wt % cyclohexane). The solvate is converted to the anhydrous material by heating in a vacuum oven at a temperature of 110-135° C., with the exact temperature depending on the design and size of the oven that is used.

Example 35

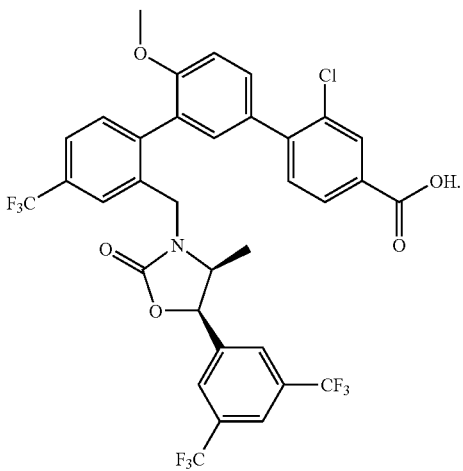

2"-({(4S,5R)-5-[3,5-bis(trifluoromethyl)phenyl]-4-methyl-2-oxo-1,3-oxazolidin-3-yl}methyl)-2-chloro-4'-methoxy-4"-(trifluoromethyl)-1,1':3',1"-terphenyl-4-carboxylic acid Step A: methyl 2"-({(4S,5R)-5-[3,5-bis(trifluoromethyl)phenyl]-4-methyl-2-oxo-1,3-oxazolidin-3-yl}methyl)-2-chloro-4'-methoxy-4"-(trifluoromethyl)-1,1':3',1"-terphenyl-4-carboxylate A mixture of INTERMEDIATE 9 (0.1 g), INTERMEDIATE 10 (0.1 g, 0.25 mmol), tetrakis(triphenylphosphine) palladium (5% mol) and sodium carbonate (58 mg, 0.55 mmol) in 7 ml of water/EtOH/toluene (1:2:4) was heated to reflux for 2 h. TLC (EtOAc:hexane/1:9) showed that the reaction was over. The solvents were removed. Water (10 ml) was added. The organic was extracted with methylene chloride (3×15 ml). The combined methylene chloride layers were washed with brine, and dried over sodium sulfate. The title compound was obtained after flash column using $CH_2Cl_2$:hexane/8:2 as the eluant. $^1$H NMR (CDCl$_3$, 500 MHz) δ 1:1 mixture of atropisomers 7.10-8.20 (m, 12H), 5.60 (d, J=8.5 Hz, 0.5H), 5.29 (d, J=8 Hz, 0.5H), 5.01 (d, J=16.5 Hz, 0.5H), 4.97 (d, J=16.5 Hz, 0.5H), 4.21 (d, J=16 Hz, 0.5H), 4.00 (d, J=16 Hz, 0.5H), 3.97 (s, 3H), 3.91 (s, 1.5H), 3.90 (s, 1.5H), 3.78 (m, 1H), 0.55 (d, J=7 Hz, 1.5H), 0.43 (d, J=6.5 Hz, 1.5H).

Step B: 2"-({(4S,5R)-5-[3,5-bis(trifluoromethyl)phenyl]-4-methyl-2-oxo-1,3-oxazolidin-3-yl}methyl)-2-chloro-4'-methoxy-4"-(trifluoromethyl)-1,1':3',1"-terphenyl-4-carboxylic Acid The title compound from Example 25 was stirred with LiOH (5 eq) in a 2:1 mixture of dioxane and water at room temperature overnight. The solvent was removed and the aqueous solution was acidified with 1N HCl to pH 4. The organic was extracted with EtOAc (3×10 ml). The combined EtOAc layers were dried over sodium sulfate. The title compound was obtained after preparative reverse phase HPLC. $^1$H NMR (CDCl$_3$, 500 MHz): δ 1:1 mixture of atropisomers 8.21 (d, J=12 Hz, 1H), 8.04 (d, J=8 Hz, 1H), 7.87 (d, J=5.5 Hz, 1H), 7.76 (s, 0.5H), 7.72 (s, 1H), 7.69 (s, 0.5H), 7.67 (d, J=3.5 Hz, 1H), 7.65 (s, 1H), 7.44-7.58 (m, 3H), 7.37 (d, J=2 Hz, 0.5H), 7.35 (d, J=0.5 Hz, 0.5H), 7.13 (d, J=4 Hz, 0.5H), 7.12 (d, J=5 Hz, 0.5H), 5.61 (d, J=8 Hz, 0.5H), 5.30 (d, J=12.5 Hz, 0.5H), 5.01 (d, J=12.5 Hz, 0.5H), 4.98 (d, J=13 Hz, 0.5H), 4.21 (d, J=15.5 Hz, 0.5H), 4.00 (d, J=16 Hz, 0.5H), 3.91 (s, 1.5H), 3.90 (s, 1.5H), 3.80 (m, 1H), 0.56 (d, J=6.5 Hz, 1.5H), 0.44 (d, J=6.5 Hz, 1.5H). LC-MS (M+1): 732.1.

Example 36

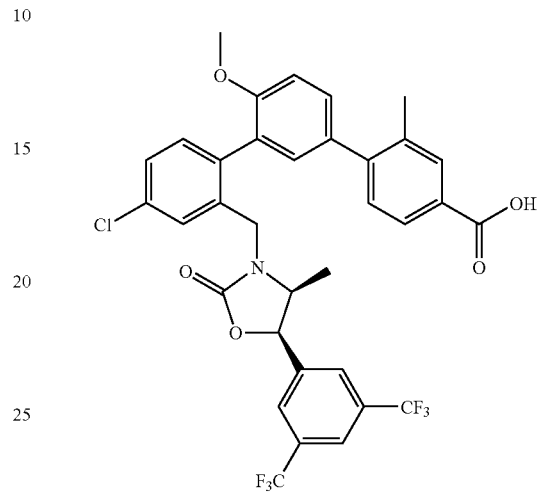

The title compound from Example 24 was stirred with LiOH (3 eq) in a 2:1 mixture of dioxane and water at room temperature overnight. The solvent was removed and the aqueous solution was acidified with 1N HCl to pH ~4. The organic was extracted with EtOAc (3×10 ml). The combined EtOAc layers were dried over sodium sulfate. The title compound was obtained after preparative TLC plate using EtOAc: hexane/1:1 as the eluant. $^1$H NMR (CDCl$_3$, 500 MHz): δ a 1:1 mixture of atropisomers 8.02 (d, J=7.5 Hz, 1H), 7.95 (d, J=7.5 Hz, 1H), 7.87 (s, 1H), 7.72 (s, 1H), 7.66 (s, 1H), 7.49 (s, 1H), 7.24-7.41 (m, 4H), 7.15 (s, 1H), 7.08 (d, J=7 Hz, 0.5H), 7.06 (d, J=8 Hz, 0.5H), 5.62 (d, J=8.5 Hz, 0.5H), 5.35 (d, J=8 Hz, 0.5H), 4.93 (d, J=16 Hz, 0.5H), 4.90 (d, J=15.5 Hz, 0.5H), 4.08 (d, J=15.5 Hz, 0.5H), 3.88 (s, 3H), 3.85 (m, 1.5H), 2.39 (s, 1.5H), 2.34 (s, 1.5H), 0.57 (d, J=6.5 Hz, 1.5H), 0.44 (d, J=6.5 Hz, 1.5H). LC-MS (M): 678.3.

Example 37

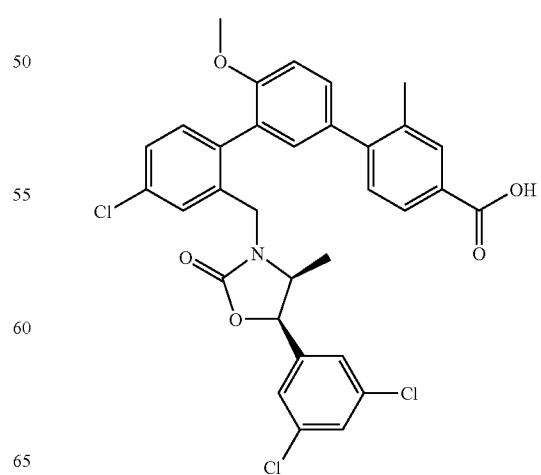

The title compound from Example 25 was stirred with LiOH (3 eq) in a 2:1 mixture of dioxane and water at room temperature overnight. The solvent was removed and the aqueous solution was acidified with 1N HCl to pH ~4. The organic was extracted with EtOAc (3×10 ml). The combined EtOAc layers were dried over sodium sulfate. The title compound was obtained after preparative TLC plate using EtOAc: hexane/1:1 as the eluant. LC-MS (M+1): 612.0.

Example 38

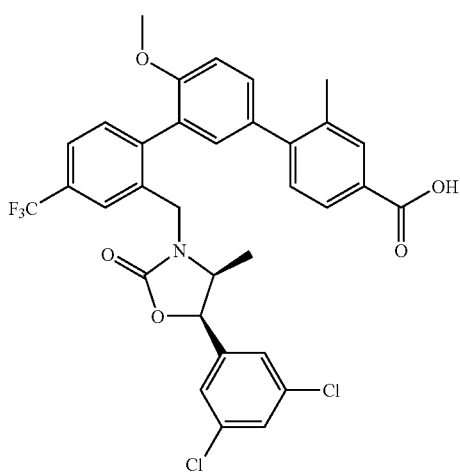

2"-{[(4S,5R)-5-(3,5-dichlorophenyl)-4-methyl-2-oxo-1,3-oxazolidin-3-yl]methyl}-4'-methoxy-2-methyl-4"-(trifluoromethyl)-1,1':3',1"-terphenyl-4-carboxylic Acid Methyl 2"-{[(4S,5R)-5-(3,5-dichlorophenyl)-4-methyl-2-oxo-1,3-oxazolidin-3-yl]methyl}-4'-methoxy-2-methyl-4"-(trifluoromethyl)-1,1':3',1"-terphenyl-4-carboxylate (EXAMPLE 26) (50 mg, 0.076 mmol), aqueous potassium hydroxide (600 μL, 3M, 1.8 mmol) and ethanol (4 mL) were stirred at 20° C. for 6 hours. The reaction mixture was acidified by HCl (aq., 1N) and then basified by sodium bicarbonate. Volatiles were removed under reduced pressure. The resulting mixture was worked up with ethyl acetate, washed with brine. The combined organic extracts were dried over $Na_2SO_4$, filtered, and concentrated to afford an oil. The oil was purified by preparative TLC (eluted with EtOAc/hexanes) to afford 2"-{[(4S,5R)-5-(3,5-dichlorophenyl)-4-methyl-2-oxo-1,3-oxazolidin-3-yl]methyl}-4'-methoxy-2-methyl-4"-(trifluoromethyl)-1,1':3',1"-terphenyl-4-carboxylic acid. LCMS calc.=643.11; found=644.14 (M+1)$^+$. $^1$H NMR signals are doubled because of atropisomerism $^1$H NMR (CDCl$_3$, 500 MHz) δ 8.01 (d, J=5.5 Hz, 1H), 7.94 (d, J=8.0 Hz, 1H), 7.70 (s, 1H), 7.65-7.61 (m, 1.5H), 7.44-7.37 (m, 3H), 7.34-7.31 (m, 1H), 7.29 (d, J=8.0 Hz, 0.5H), 7.29 (d, J=8.0 Hz, 0.5H), 7.27-7.24 (m, 0.5H), 7.14 (dd, J=7.0, 2.5 Hz, 1H), 7.09-7.03 (m, 1.5H), 7.00 (dd, J=8.25, 2.0 Hz, 1H), 5.42 (d, J=8.5 Hz, 0.55H), 5.17 (d, J=8.0 Hz, 0.45H), 4.92 (d, J=16.0 Hz, 0.55H), 4.86 (d, J=16.0 Hz, 0.45H), 4.18 (d, J=15.5 Hz, 0.55H), 3.96 (d, J=15.5 Hz, 0.45H), 3.86 (s, 3H), 3.75-3.66 (m, 1H), 2.38, 2.34 (s, 3H), 0.56 (d, J=6.5 Hz; 1.35H), 0.44 (d, J=6.5 Hz, 1.65H).

Example 39

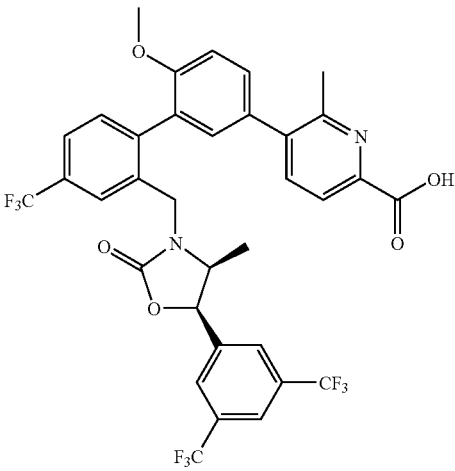

5-[2'-({(4S,5R)-5-[3,5-bis(trifluoromethyl)phenyl]-4-methyl-2-oxo-1,3-oxazolidin-3-yl}methyl)-6-methoxy-4'-(trifluoromethyl)biphenyl-3-yl]-6-methylpyridine-2-carboxylic Acid Step A

5-(4-methoxyphenyl)-6-methylpyridin-2-amine (4-methoxyphenyl)boronic acid (1 g, 6.58 mmol), 5-bromo-6-methylpyridin-2-amine (1.23 g, 6.58 mmol), 1,1'-bis(diphenylphosphino)ferrocene-palladium dichloride dichloromethane adduct (537 mg, 0.658 mmol), potassium acetate (1.29 g, 13.16 mmol) and 1,4-dioxane (5 mL) were placed in a sealed tube and the mixture was subjected to microwave irradiation at 140° C. for 30 minutes. The resulting crude mixture was purified by flash column chromatography on SiO$_2$ (Biotage 40+M cartridge, ethyl acetate) to afford 5-(4-methoxyphenyl)-6-methylpyridin-2-amine as a purple solid. LCMS calc.=214.11; found=215.17 (M+1)$^+$.

Step B

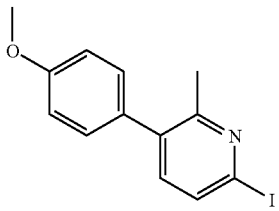

6-iodo-3-(4-methoxyphenyl)-2-methylpyridine 5-(4-methoxyphenyl)-6-methylpyridin-2-amine (500 mg, 2.33 mmol) and iodine (710 mg, 2.8 mmol) were stirred in chloroform (10 mL) at room temperature for 12 minutes followed by addition of n-amyl nitrite (545.9 mg, 4.66 mmol). The resulting mixture was heated in a 82° C. oil bath for 1.5 hours to finish the transformation. The reaction was quenched by addition of saturated $NaS_2O_3$ aqueous solution. The reaction mixture was extracted with dichloromethane. The combined organic extracts were dried over $Na_2SO_4$ followed by filtration and concentration. The resulting crude was purified by flash column chromatography on $SiO_2$ (Biotage 40+M cartridge, dichloromethane/hexanes, gradient) to afford a yellow oil. The oil was further purified by preparative TLC on $SiO_2$ (eluted with 80% dichloromethane in hexanes) to afford 6-iodo-3-(4-methoxyphenyl)-2-methylpyridine. LCMS calc.=325.00; found=326.06 $(M+1)^+$.

Step C

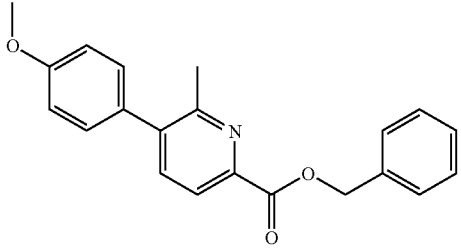

Benzyl 5-(4-methoxyphenyl)-6-methylpyridine-2-carboxylate 6-iodo-3-(4-methoxyphenyl)-2-methylpyridine (100 mg, 0.308 mmol), dichloro bis(triphenylphosphine)palladium(II) (22 mg, 0.031 mmol), triethylamine (46.7 mg, 0.462 mmol), benzyl alcohol (1 mL, 9.66 mmol) were mixed in acetonitrile (3 mL). The resulting mixture was placed under to carbon monoxide at 45 psi at 60° C. for 18 hours. The resulting reaction crude was purified by preparative TLC on $SiO_2$ (eluted with 25% ethyl acetate in hexanes then 10% triethylamine, 20% ethyl acetate in hexanes) to afford benzyl 5-(4-methoxyphenyl)-6-methylpyridine-2-carboxylate. LCMS calc.=333.14; found=334.13 $(M+1)^+$.

Step D

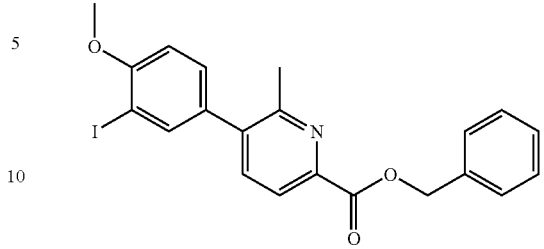

Benzyl 5-(3-iodo-4-methoxyphenyl)-6-methylpyridine-2-carboxylate

Benzyl 5-(4-methoxyphenyl)-6-methylpyridine-2-carboxylate (150 mg, 0.45 mmol), iodine (228 mg, 0.898 mmol), silver sulfate (402 mg, 1.29 mmol) were stirred in methanol (3 mL) at room temperature overnight. More iodine (57 mg, 0.22 mmol) and silver sulfate (100 mg, 0.32 mmol) were added into reaction mixture after 25 hours. Added aqueous $NaHSO_3$ solution (sat., 20 mL) into the reaction mixture after additional 1.5 hours to quench the reaction. The reaction mixture was extracted with ethyl acetate. The combined extracts were dried over $Na_2SO_4$ followed by filtration and concentration to afford a clear oil. The crude oil was purified by preparative TLC on $SiO_2$ (eluted with 30% ethyl acetate in hexanes) to afford benzyl 5-(3-iodo-4-methoxyphenyl)-6-methylpyridine-2-carboxylate. LCMS calc.=459.03; found=460.17 $(M+1)^+$.

Step E

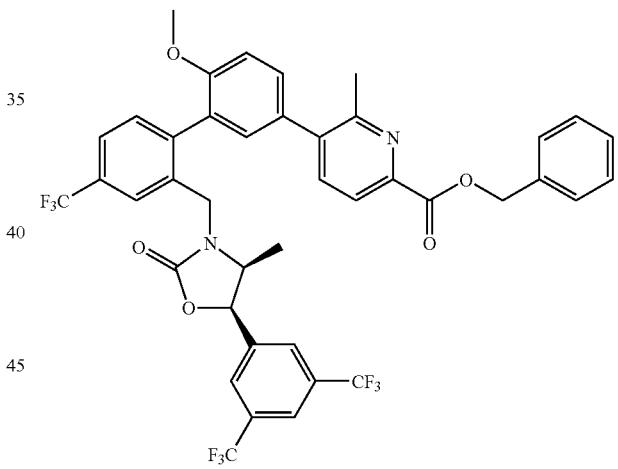

Benzyl 5-[2'-({(4S,5R)-5-[3,5-bis(trifluoromethyl)phenyl]-4-methyl-2-oxo-1,3-oxazolidin-3-yl}methyl)-6-methoxy-4'-(trifluoromethyl)biphenyl-3-yl]-6-methylpyridine-2-carboxylate (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one-methane (385 mg, 0.644 mmol) (INTERMEDIATE 9), benzyl 5-(3-iodo-4-methoxyphenyl)-6-methylpyridine-2-carboxylate (148 mg, 0.322 mmol), 1,1'-bis(diphenylphosphino)ferrocene-palladium dichloride (71 mg, 0.097 mmol), aqueous potassium hydroxide (215 μL, 3M, 0.645 mmol) and 1,4-dioxane (2 mL) were charged into a tube. The vessel was purged with nitrogen and then sealed. The reaction mixture was irradiated by microwave at 120° C. for 20 minutes then at 140° C. for 30 minutes. The reaction mixture was treated with water followed by extraction with ethyl acetate. The combined extracts were dried over Na$_2$SO$_4$ followed by filtration and concentration in vacuo to afford a dark oil. This oil was purified by preparative TLC on SiO$_2$ (eluted with 45% ethyl acetate in hexanes) to afford a dark oil. The resulting oil was further purified by reverse-phase preparative-HPLC (Kromasil 100-5C18, 100×21.1 mm) eluting with a MeCN (0.1% TFA, v/v)/H$_2$O (0.1% TFA, v/v) gradient mixture. The appropriate fractions were pooled and evaporated into a dark oil. This oil treated with sodium bicarbonate aqueous solution (sat.) followed by ethyl acetate extractions. The combined extracts were dried over Na$_2$SO$_4$ followed by filtration and concentration in vacuo to afford a dark oil. The oil still contained some baseline impurities. The resulting oil was again purified by preparative TLC on SiO$_2$ (eluted with 50% ethyl acetate in hexanes) to afford benzyl 5-[2'-({(4S,5R)-5-[3,5-bis(trifluoromethyl)phenyl]-4-methyl-2-oxo-1,3-oxazolidin-3-yl}methyl)-6-methoxy-4'-(trifluoromethyl)biphenyl-3-yl]-6-methylpyridine-2-carboxylate. LCMS calc.=802.21; found=803.21 (M+1)$^+$.

Step F 5-[2'-({(4S,5R)-5-[3,5-bis(trifluoromethyl)phenyl]-4-methyl-2-oxo-1,3-oxazolidin-3-yl}methyl)-6-methoxy-4-(trifluoromethyl)biphenyl-3-yl]-6-methylpyridine-2-carboxylic Acid Benzyl 5-[2'-({(4S,5R)-5-[3,5-bis(trifluoromethyl)phenyl]-4-methyl-2-oxo-1,3-oxazolidin-3-yl}methyl)-6-methoxy-4'-(trifluoromethyl)biphenyl-3-yl]-6-methylpyridine-2-carboxylate (52 mg, 0.065 mmol), palladium/active carbon (10%, w/w) (25 mg) were mixed in ethanol (10 mL). The resulting mixture was degassed and subject to H$_2$ under 45 psi at room temperature on a Parr shaker for 3 hours to complete the reaction. The reaction mixture was filtered through a pad of Celite (521). The filtrate was concentrated in vacuo to afford a light brown glass. The residue was purified by preparative reverse-phase HPLC (Kromasil 100-5C18, 100×21.1 mm) eluting with a MeCN/H$_2$O gradient mixture. The appropriate fractions were pooled and evaporated into an aqueous residue. The resulting residue was further lyophilized to afford 5-[2'-({(4S,5R)-5-[3,5-bis(trifluoromethyl)phenyl]-4-methyl-2-oxo-1,3-oxazolidin-3-yl}methyl)-6-methoxy-4'-(trifluoroethyl)biphenyl-3-yl]-6-methylpyridine-2-carboxylic acid. LCMS calc.=712.16; found=713.19 (M+1)$^+$. $^1$H NMR signals are doubled because of atropisomerism $^1$H NMR (CDCl$_3$, 500 MHz) δ 8.07 (s, 1H), 7.86 (s, 1H), 7.77 (s, 1H), 7.71-7.62 (m, 4H), 7.45-7.36 (m, 2H), 7.19-7.07 (m, 2H), 5.55 (d, J=7.0 Hz, 0.55H), 5.42 (d, J=7 Hz, 0.45H), 4.99 (d, J=13 Hz, 0.5H), 4.85 (d, J=12.5 Hz, 0.5H), 4.14 (d, J=13.5 Hz, 0.5H), 3.95 (d, J=13.5 Hz, 0.5H), 3.92-3.80 (m, 4H), 2.61, 2.58 (s, 3H), 0.58 (d, J=5.0 Hz, 1.35H), 0.49 (d, J=5.5 Hz, 1.65H).

Example 40

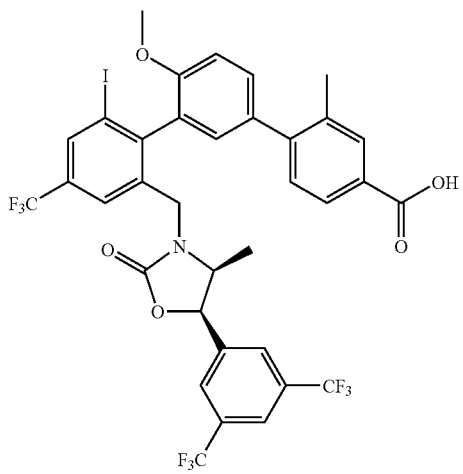

2"-({(4S,5R)-5-[3,5-bis(trifluoromethyl)phenyl]-4-methyl-2-oxo-1,3-oxazolidin-3-yl}methyl)-6"-iodo-4'-methoxy-2-methyl-4"-(trifluoromethyl)-1,1':3',1"-terphenyl-4-carboxylic Acid Step A

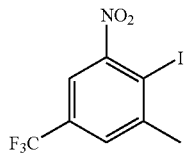

2-methyl-4-trifluoromethyl Aniline

A mixture of 2-iodo-4-trifluoromethyl aniline (5.0 g, 17.42 mmol), trimethylboroxine (3.64 ml, 26.1 mmol), tetrakis(triphenylphosphine) palladium (1.0 g, 0.87 mmol) and potassium carbonate (4.82 g, 34.8) in DMF (10 ml) was heated to 100° C. for 48 h. The reaction was quenched with water (50 ml) and extracted with EtOAc (3×50 ml). The combined EtOAc layers were washed with brine and dried over sodium sulfate. The title compound was obtained after flash column using EtOAc:hexane/1:9 as the eluant. $^1$H NMR (CDCl$_3$, 500 MHz): δ 7.13 (s, 1H), 7.30 (d, J=8 Hz, 1H), 6.71 (d, J=8 Hz, 1H), 3.98 (br s, 2H), 2.21 (s, 3H).

Step B 2-methyl-4-trifluoromethylphenyl Iodide

To a solution of 2-methyl-4-trifluoromethyl aniline (Step A) (2.2 g, 12.6 mmol) in chloroform (20 ml) at room temperature were added n-pentyl nitrite (2.2 g, 18.9 mmol) and iodine (6.38 g, 25.1 mmol). The mixture was heated to reflux for 1 h. The mixture was diluted with methylene chloride (50 ml). The solution was washed with saturated aqueous sodium thiosulfate, brine and dried over sodium sulfate. The title compound was obtained after flash column using hexane as the eluant.

Step C 2-methyl-4-trifluoromethyl-6-nitro-phenyl Iodide

A 1:1 mixture of H$_2$SO$_4$/HNO$_3$ (20 ml) was added to 2-methyl-4-trifluoromethylphenyl iodide at 0° C. The mixture was stirred at 0° C. and then warmed to room temperature overnight. LC/MS analysis indicated no remaining starting material. The mixture was diluted with water and extracted with EtOAc (3×50 ml). The combined EtOAc layers were washed with sodium bicarbonate and brine and dried over sodium sulfate. The title compound was obtained after removal of solvent. $^1$H NMR (CDCl$_3$, 500 MHz): δ 7.71 (s, 1H), 7.69 (s, 1H), 2.68 (s, 3H).

Step D

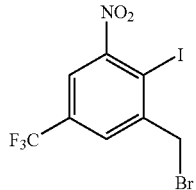

1-(bromomethyl)-2-iodo-3-nitro-5-(trifluoromethyl)benzene

A mixture of the title compound from Step C (0.38 g, 1.15 mmol), NBS (0.24 g, 1.38 mmol) and catalytic amount of AIBN in carbon tetrachloride (5 ml) was heated to reflux for 3 days. During the period more AIBN was added daily. The mixture was cooled and concentrated. The title compound was obtained after flash column using hexane as the eluant. $^1$H NMR (CDCl$_3$, 500 MHz): δ 7.91 (s, 1H), 7.80 (s, 1H), 4.75 (s, 2H).

Step E

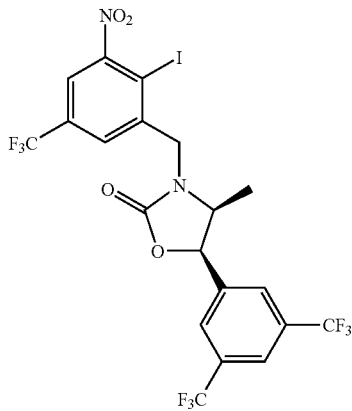

(4S,5R)-5-[3,5-bis(trifluoromethyl)phenyl]-3-[2-iodo-3-nitro-5-(trifluoromethyl)benzyl]-4-methyl-1,3-oxazolidin-2-one To a solution of (4S,5R)-5-[3,5-bis(trifluoromethyl)phenyl]-4-methyl-1,3-oxazolidin-2-one (0.14 g, 0.44 mmol) in THF (3 ml) at 0° C., NaH (21 mg, 0.53 mmol, 60%) was added. The mixture was stirred at 0° C. for 30 min A solution of the title compound from Step D (0.15 g, 0.37 mmol) in THF (1 ml) was added. The mixture was stirred room temperature overnight. The reaction was quenched with saturated aqueous ammonium chloride (5 ml) and extracted with EtOAc (3×15 ml). The combined EtOAc layers were washed with brine and dried over sodium sulfate. The title compound was obtained after flash column using EtOAc:hexane/15:85 as the eluant. $^1$H NMR (CDCl$_3$, 500 MHz) δ 7.95 (s, 1H), 7.87 (d, J=1.5 Hz, 1H), 7.83 (s, 2H), 7.79 (d, J=1.5 Hz, 1H), 5.83 (d, J=8 Hz, 1H), 4.95 (d, J=16.5 Hz, 1H), 4.53 (d, J=16.5 Hz, 1H), 4.19 (m, 1H), 0.87 (d, J=6.5 Hz, 3H).

Step F

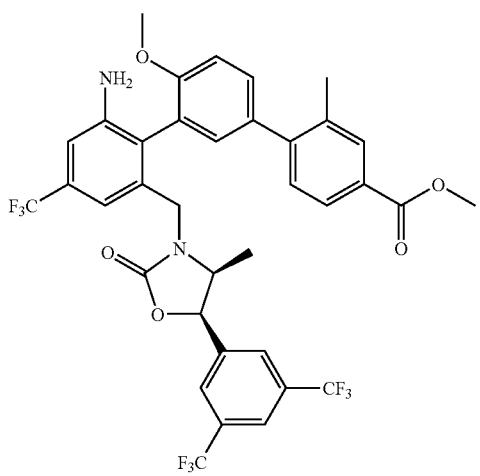

Methyl 2"-amino-6"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-carboxylate To a solution of the title compound from Step E (0.17 g, 0.26 mmol) in EtOH (5 ml), tin chloride dihydrate (0.30 g, 1.32 mmol) was added. The mixture was stirred at room temperature for 4 h. LC-MS analysis indicated complete consumption of starting material. EtOH was removed. EtOAc (20 ml) was added to the residue. The mixture was washed with water, brine and dried over sodium sulfate. Removal of the solvent afforded a white solid which was mixed with methyl 4'-methoxy-2-methyl-3'-(4,4,5,5-tetramethyl-1,3,2-dioxaborolan-2-yl)biphenyl-4-carboxylate (INTERMEDIATE 11, excess), tetrakis(triphenylphosphine) palladium (5% mol) and sodium carbonate (0.062 g, 0.58 mmol) in 7 ml of water/EtOH/toluene (1:2:4) and was heated to reflux for 2 h. TLC (EtOAc:hexane/1:3) showed that the reaction was over. The solvents were removed. Water (10 ml) was added. The organic was extracted with methylene chloride (3×20 ml). The combined methylene chloride layers were washed with brine, and dried over sodium sulfate. The title compound was obtained after purification with preparative TLC using 20% EtOAc in hexane as the eluant. $^1$H NMR (CDCl$_3$, 500 MHz) δ a 2:1 mixture of atropismers 7.96 (m, 1H), 7.88 (m, 2H), 7.73 (s, 0.66H), 7.66 (s, 0.33H), 7.44 (m, 1H), 7.28 (m, 2H), 7.16 (m, 2H), 7.02-7.07 (m, 2H), 5.59 (d, J=8 Hz, 0.66H), 5.42 (d, J=8 Hz, 0.33H), 4.80 (d, J=12 Hz, 0.33H), 4.77 (d, J=12 Hz, 0.66H), 3.95 (s, 3H), 3.94 (m, 1H), 3.90 (s, 2H), 3.87 (s, 1H), 3.82 (d, J=12 Hz, 1H), 2.38 (s, 1H), 2.37 (s, 2H), 0.59 (d, J=6.5 Hz, 1H), 0.54 (d, J=6.5 Hz, 2H).

Step G

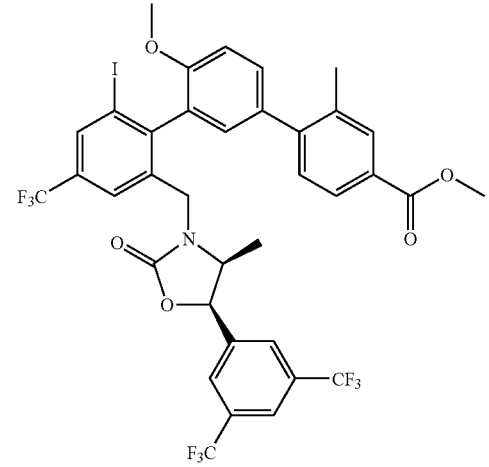

Methyl 2"-({(4S,5R)-5-[3,5-bis(trifluoromethyl)phenyl]-4-methyl-2-oxo-1,3-oxazolidin-3-yl}methyl)-6"-iodo-4'-methoxy-2-methyl-4"-(trifluoromethyl)-1,1':3',1"-terphenyl-4-carboxylate To a solution of the title compound from Step F (0.10 g, 0.135 mmol) in chloroform (5 ml) at room temperature, n-pentyl nitrite (0.024 g, 0.20 mmol) and iodine (0.044 g, 0.17 mmol) were added. The mixture was heated to reflux for 1 h. The mixture was diluted with methylene chloride (10 ml). The solution was washed with saturated aqueous sodium thiosulfate, brine and dried over sodium sulfate. The residue was purified by preparative reverse phase HPLC to afford the title compound. ¹H NMR (CDCl₃, 500 MHz): δ 2:1 mixture of atropisomers 8.21 (s, 1H), 7.97 (s, 1H), 7.88 (s, 2H), 7.72 (s, 1H), 7.76 (m, 1H), 7.44 (m, 1H), 7.29 (m, 1H), 7.20 (m, 1H), 7.12 (m, 1H), 7.00 (m, 1H), 5.59 (d, J=8 Hz, 0.66H), 5.53 (d, J=8 Hz, 0.33H), 4.80 (d, J=16 Hz, 1H), 3.96 (d, J=15.5 Hz, 1H), 3.95 (s, 3H), 3.90 (m, 1H), 3.89 (s, 2H), 3.86 (s, 1H), 2.04 (s, 1H), 2.38 (s, 2H), 0.60 (d, J=6.5 Hz, 1H), 0.54 (d, J=6.5 Hz, 2H). LC-MS (M+1): 852.1.

Step H 2"-({(4S,5R)-5-[3,5-bis(trifluoromethyl)phenyl]-4-methyl-2-oxo-1,3-oxazolidin-3-yl}methyl)-6"-iodo-4'-methoxy-2-methyl-4"-(trifluoromethyl-1,1':3',1"-terphenyl-4-carboxylic Acid To a solution of the title compound from Step G (0.016 g, 0.0188 mmol) in dioxane (2 ml) at room temperature, an aqueous solution of LiOH.H2O (0.007 g, 0.16 mmol) (1 ml) was added. The mixture was stirred at room temperature for 5 h. TLC (EtOAc:hexane/2:8) showed no starting material. The solvent was removed. 1N HCl (1 ml) was added. The mixture was extracted with EtOAc (3×15 ml). The combined EtOAc layers were dried over sodium sulfate. The title compound was obtained by preparative reverse phase HPLC. ¹H NMR (CDCl₃, 500 MHz): δ2:1 mixture of atropisomers 8.21 (s, 1H), 8.01 (s, 1H), 7.94 (d, J=7.5 Hz, 1H), 7.89 (s, 1H), 7.72 (s, 1H), 7.69 (s, 1H), 7.66 (d, J=7.5 Hz, 1H), 7.45 (m, 1H), 7.37 (m, 1H), 7.14 (m, 1H), 7.00 (m, 1H), 5.60 (d, J=8 Hz, 0.66H), 5.54 (d, J=8 Hz, 0.33H), 4.82 (d, J=7.5 Hz, 0.33H), 4.79 (d, J=8 Hz, 0.66H), 3.99 (d, J=10 Hz, 0.33H), 3.96 (d, J=9.5 Hz, 0.66H), 3.91 (m, 1H), 3.90 (s, 2H), 3.86 (s, 1H), 2.42 (s, 1H), 2.41 (s, 2H), 0.60 (d, J=7 Hz, 1H), 0.55 (d, J=6.5 Hz, 2H).

Example 41

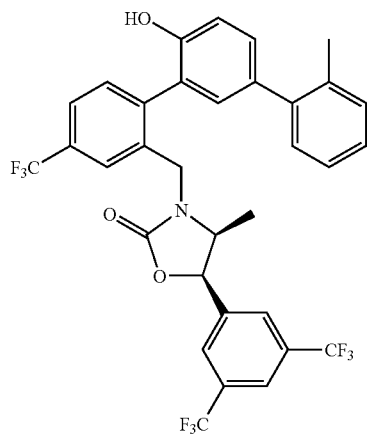

(4S,5R)-5-[3,5-bis(trifluoromethyl)phenyl]-3-{[6'-hydroxy-2"-methyl-4-(trifluoromethyl)-1,1':3,1"-terphenyl-2-yl]methyl}-4-methyl-1,1':3',1"-oxazolidin-2-one To a cold solution (−78° C. bath) of (4S,5R)-5-[3,5-bis(trifluoromethyl)phenyl]-3-{[6'-methoxy-2"-methyl-4-(trifluoromethyl)-1,1':3',1"-terphenyl-2-yl]methyl}-4-methyl-1,3-oxazolidin-2-one (75 mg, 0.11 mmol) in dichloromethane (1 mL) was added boron tribromide (106.6 mg, 0.426 mmol). The resulting mixture was aged cold (−78° C. bath) for 1 hour then allowed to warm to ambient temperature overnight. Reaction was quenched with ice followed by extraction with dichloromethane. The combined extracts were washed with brine and then over Na₂SO₄. The resulting mixture was filtered and concentrated. The residue was purified by preparative TLC on SiO₂ (eluted with 30% ethyl acetate in hexanes) to afford (4S,5R)-5-[3,5-bis(trifluoromethyl)phenyl]-3-{[6'-hydroxy-2"-methyl-4-(trifluoromethyl)-1,1':3',1"-terphenyl-2-yl]methyl}-4-methyl-1,3-oxazolidin-2-one. LCMS calc.=653.16; found=654.19 (M+1)⁺. ¹H NMR signals are doubled because of atropoisomerism ¹H NMR (CDCl₃, 500 MHz) δ 7.87-7.84 (m, 1H), 7.76 (s, 0.5H), 7.72-7.65 (m, 2.5H), 7.63 (s, 1H), 7.53-7.47 (m, 1H), 7.33-7.23 (m, 3H), 7.23-7.16 (m, 2H), 7.12 (dd, J=10.5, 2.5 Hz, 1H), 7.04 (d, J=8.0 Hz, 0.5H), 7.02 (d, J=8.5 Hz, 0.5H), 5.64 (d, J=8.0 Hz, 0.5H), 5.32 (d, J=7.5 Hz, 0.5H), 4.98, 4.92 (d, J=16 Hz, 1H), 4.23 (d, J=15.5 Hz, 0.5H), 4.07 (d, J=15.5 Hz, 0.5H), 3.89-3.82 (m, 0.5H), 3.74-3.67 (m, 0.5H), 2.32, 2.28 (s, 3H), 0.58 (d, J=7 Hz, 1.5H), 0.49 (d, J=6.5 Hz, 1.5H).

Example 42

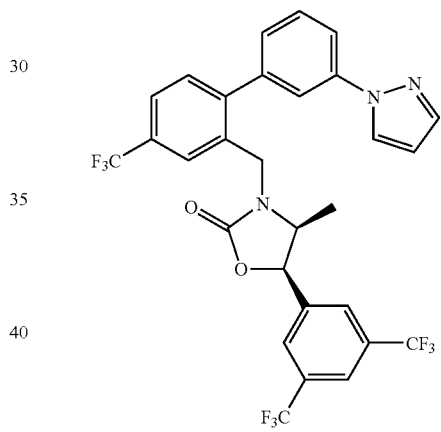

(4S,5R)-5-[3,5-bis(trifluoromethyl)phenyl]-4-methyl-3-{[3'-(1H-pyrazol-1-yl)-4-(trifluoromethyl)biphenyl-2-yl]methyl}-1,3-oxazolidin-2-one A mixture of (4S,5R)-5-[3,5-bis(trifluoromethyl)phenyl]-3-[2-iodo-5-(trifluoromethyl)-benzyl]-4-methyl-1,3-oxazolidin-2-one (0.05 g, 0.084 mmol), 3-(1H-pyrazol-1-yl)phenyl boronic acid (0.031 g, 0.167 mmol), tetrakis(triphenylphosphine) palladium (5% mol) and sodium carbonate (0.019 g, 0.18 mmol) in 7 ml of water/EtOH/toluene (1:2:4) was heated to reflux for 4 h. TLC (EtOAc:hexane/1:1) showed that the reaction was over. The solvents were removed. Water (10 ml) was added. The organic was extracted with methylene chloride (3×10 ml). The combined methylene chloride layers were washed with brine, and dried over sodium sulfate. The title compound was obtained after flash column using EtOAc:hexane/1:1 as the eluant. ¹H NMR (CDCl₃, 500 MHz): δ 8.02 (d, J=2.5 Hz, 1H), 7.88 (s, 1H), 7.84 (s, 1H), 7.77 (s, 1H), 7.76 (s, 1H), 7.75 (s, 2H), 7.73 (m, 1H), 7.71 (m, 1H), 7.61 (t, J=7.5 Hz, 1H), 7.53 (d, J=7.5 Hz, 1H), 7.26 (m, 1H), 6.54 (t, J=2 Hz, 1H), 5.55 (d, J=7.5 Hz, 1H), 5.02 (d, J=16 Hz, 1H), 4.21 (d, J=16 Hz, 1H), 3.82 (m, 1H), 0.54 (d, J=6.5 Hz, 3H). LC-MS (M+1): 614.3.

Example 43

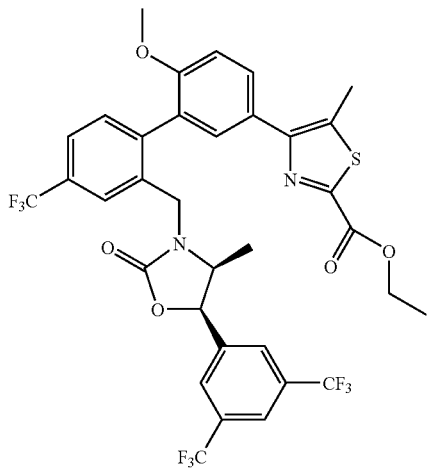

Ethyl 4-[2'-({(4S,5R)-5-[3,5-bis(trifluoromethyl) phenyl]-4-methyl-2-oxo-1,3-oxazolidin-3-yl}methyl)-6-methoxy-4'-(trifluoromethyl)biphenyl-3-yl]-5-methyl-1,3-thiazole-2-carboxylate Step A

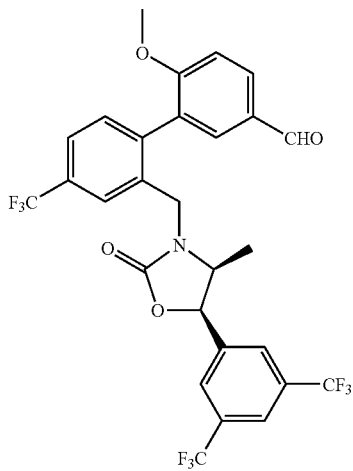

2'-({(4S,5R)-5-[3,5-bis(trifluoromethyl)phenyl]-4-methyl-2-oxo-1,3-oxazolidin-3-yl}methyl)-6-methoxy-4'-(trifluoromethyl)biphenyl-3-carbaldehyde A mixture of (4S,5R)-5-[3,5-bis(trifluoromethyl)phenyl]-3-[2-iodo-5-(trifluoromethyl)-benzyl]-4-methyl-1,3-oxazolidin-2-one (0.50 g, 0.84 mmol), 5-formyl 2-methoxy phenyl boronic acid (0.22 g, 1.25 mmol), tetrakis(triphenylphosphine) palladium (48 mg, 5% mol) and sodium carbonate (0.19 g, 1.84 mmol) in 20 ml of water/EtOH/toluene (1:2:4) was heated to reflux for 4 h. TLC (CH$_2$Cl$_2$:hexane/1:1) showed that the reaction was over. The solvents were removed. Water (30 ml) was added. The organic was extracted with methylene chloride (3×40 ml). The combined methylene chloride layers were washed with brine, and dried over sodium sulfate. The title compound was obtained after flash column using EtOAc:hexane/3:7 as the eluant. $^1$H NMR (CDCl$_3$, 500 MHz): δ 1:1 mixture of atropisomers 9.95 (s, 1H), 7.62-7.98 (m, 6H), 7.42 (m, 1H), 7.17 (m, 2H), 5.65 (d, J=8 Hz, 0.5H), 5.20 (d, J=8 Hz, 0.5H), 4.96 (d, J=15.5 Hz, 0.5H), 4.92 (d, J=16.5 Hz, 0.5H), 3.85-4.10 (m, 2H), 3.98 (s, 1.5H), 3.92 (s, 1.5H), 0.59 (d, J=6.5 Hz, 1.5H), 0.42 (d, J=6 Hz, 1.5H).

Step B

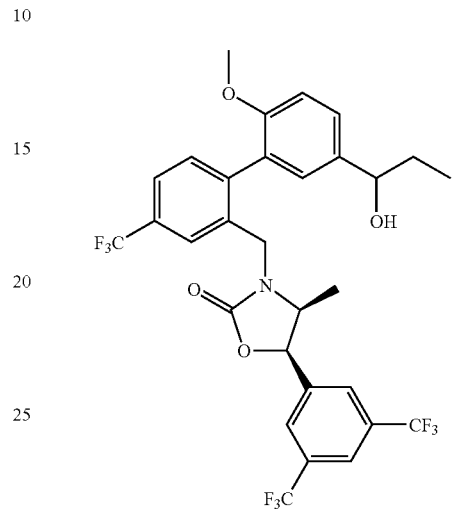

(4S,5R)-5-[3,5-bis(trifluoromethyl)phenyl]-3-{[5'-(1-hydroxypropyl)-2'-methoxy-4-(trifluoromethyl) biphenyl-2-yl]methyl}-4-methyl-1,3-oxazolidin-2-one To a solution of the title compound from Step A (0.44 g, 0.73 mmol) in THF at 0° C., EtMgBr (0.87 ml, 0.87 mmol, 1M in THF) was added. The solution was stirred at 0° C. for 2 h. The reaction was quenched with saturated solution ammonium chloride (10 ml). The organic was extracted with EtOAc (3×15 ml). The combined EtOAc layers were washed with brine and dried over sodium sulfate. The title compound was obtained after flash column using EtOAc:hexane/1:1 as the eluant. $^1$H NMR (CDCl$_3$, 500 MHz): δ mixture of atropisomers and diastereomers 7.86 (s, 1H), 7.61-7.71 (m, 4H), 7.18-7.47 (m, 4H), 6.99 (m, 1H), 5.28-5.49 (m, 1H), 4.92-5.07 (m, 1H), 4.61 (m, 1H), 3.92-4.14 (m, 1H), 3.97 (m, 3H), 3.66-3.79 (m, 1H), 1.80 (m, 2H), 0.98 (m, 3H), 0.50-0.60 (m, 3H).

Step C

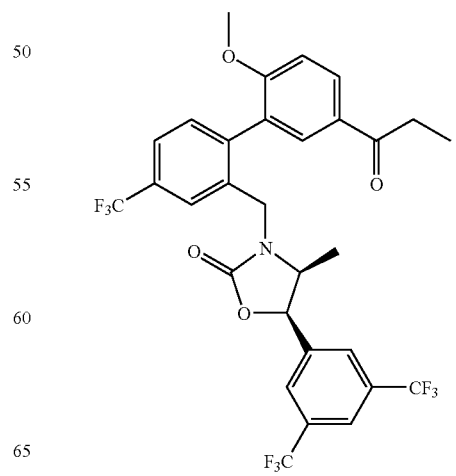

(4S,5R)-5-[3,5-bis(trifluoromethyl)phenyl]-3-{[2'-methoxy-5'-propionyl-4-(trifluoromethyl)biphenyl-2-yl]methyl}-4-methyl-1,3-oxazolidin-2-one To a solution of the title compound from Step B (0.32 g, 0.50 mmol) in methylene chloride (10 ml) at room temperature, Dess-Martin periodinane (0.28 g, 0.65 mmol) was added. The mixture was stirred at room temperature for 4 h. TLC showed that the reaction was over (EtOAc:hexane/2:8). The mixture was filtered and the filtrate was concentrated. The title compound was obtained after flash column using EtOAc:hexane/2:8 as the eluant. $^1$H NMR (CDCl$_3$, 500 MHz): δ 1:1 mixture of atropisomers 8.06 (m, 1H), 7.86 (m, 2H), 7.62-7.75 (m, 4H), 7.40 (m, 1H), 7.07 (m, 1H), 5.65 (d, J=8 Hz, 0.5H), 5.20 (d, J=8 Hz, 0.5H), 4.97 (d, J=15 Hz, 0.5H), 4.90 (d, J=15.5 Hz, 0.5H), 4.09 (d, J=15 Hz, 0.5H), 3.94 (s, 1.5H), 3.90 (s, 1.5H), 3.84 (d, J=15.5 Hz, 0.5H), 3.70-3.82 (m, 1H), 3.00 (m, 2H), 1.22 (m, 3H), 0.59 (d, J=7 Hz, 1.5H), 0.41 (d, J=6.5 Hz, 1.5H).
Step D

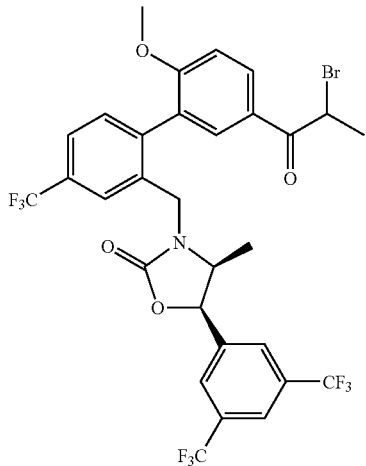

(4S,5R)-5-[3,5-bis(trifluoromethyl)phenyl]-3-{[5'-(2-bromopropanoyl)-2'-methoxy-4-(trifluoromethyl)biphenyl-2-yl]methyl}-4-methyl-1,3-oxazolidin-2-one To a solution of the title compound from Step C (0.28 g, 0.44 mmol) in 1:1 mixture of MeOH/CH$_2$Cl$_2$ (5 ml) at room temperature, tetrabutylammonium tribromide (0.28 g, 0.57 mmol) was added. The mixture was stirred at room temperature for 24 h. Water was added. The mixture was extracted with EtOAc (3×15 ml). The combined EtOAc layers were washed with brine and dried over sodium sulfate. The title compound was obtained after flash column using EtOAc:hexane/2:8 as the eluant. $^1$H NMR (CDCl$_3$, 500 MHz): δ mixture of atropisomers and diastereomers 8.10-8.18 (m, 1H), 7.85-7.98 (m, 2H), 7.62-7.77 (m, 4H), 7.39-7.46 (m, 1H), 7.08-7.12 (m, 1H), 4.88-5.65 (m, 3H), 4.06-4.12 (m, 1H), 3.90 (m, 3H), 3.65-3.86 (m, 2H), 1.90 (m, 3H), 0.37-0.59 (m, 3H).

Step E Ethyl 4-[2'-({(4S,5R)-5-[3,5-bis(trifluoromethyl)phenyl]-4-methyl-2-oxo-1,3-oxazolidin-3-yl}methyl)-6-methoxy-4'-(trifluoromethyl)biphenyl-3-yl]-5-methyl-1,3-thiazole-2-carboxylate A mixture of the title compound from Example 67, Step D (0.040 g, 0.056 mmol) and ethyl thiooxamate (11 mg, 0.084 mmol) in EtOH (2 ml) was heated to reflux overnight. The reaction mixture was concentrated. The title compound was obtained after preparative TLC plate using EtOAc:hexane/3:7 as the eluant. LC-MS (M+1): 747.2.

Example 44

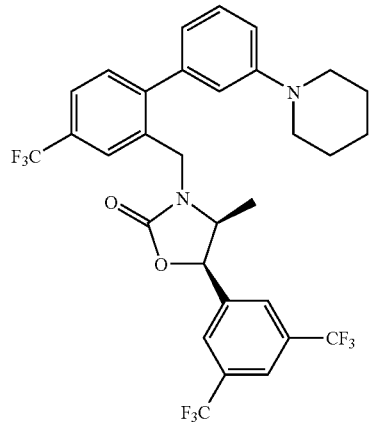

(4S,5R)-5-[3,5-bis(trifluoromethyl)phenyl]-3-{[2'-methoxy-5'-piperidin-1-yl-4-(trifluoromethyl)biphenyl-2-yl]methyl}-4-methyl-1,3-oxazolidin-2-one A mixture of (4S,5R)-5-[3,5-bis(trifluoromethyl)phenyl]-3-[2-iodo-5-(trifluoromethyl)-benzyl]-4-methyl-1,3-oxazolidin-2-one (0.05 g, 0.084 mmol), 3-(piperidino)phenyl boronic acid (0.040 g, 0.167 mmol), tetrakis(triphenylphosphine) palladium (5% mol) and sodium carbonate (0.019 g, 0.18 mmol) in 7 ml of water/EtOH/toluene (1:2:4) was heated to reflux for 4 h. TLC (EtOAc:hexane/1:1) showed that the reaction was over. The solvents were removed. Water (10 ml) was added. The organic was extracted with methylene chloride (3×10 ml). The combined methylene chloride layers were washed with brine, and dried over sodium sulfate. The title compound was obtained after flash column using EtOAc:hexane/6:4 as the eluant. LC-MS (M+1): 631.1.

Example 45

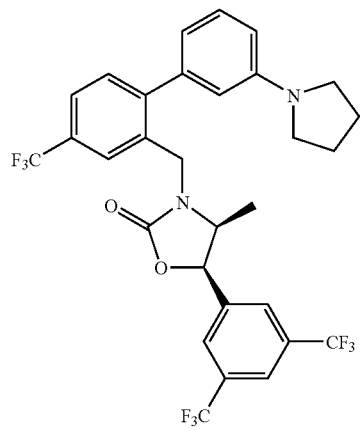

(4S,5R)-5-[3,5-bis(trifluoromethyl)phenyl]-4-methyl-3-{[3'-pyrrolidin-1-yl-4-(trifluoromethyl)biphenyl-2-yl]methyl}-1,3-oxazolidin-2-one A mixture of (4S,5R)-5-[3,5-bis(trifluoromethyl)phenyl]-3-[2-iodo-5-(trifluoromethyl)-benzyl]-4-methyl-1,3-oxazolidin-2-one (0.05 g, 0.084 mmol), 3-(pyrrolidino)phenyl boronic acid (0.032 g, 0.167 mmol), tetrakis(triphenylphosphine) palladium (5% mol) and sodium carbonate (0.019 g, 0.18 mmol) in 7 ml of water/EtOH/toluene (1:2:4) was heated to reflux for 4 h. TLC (EtOAc:hexane/1:1) showed that the reaction was over. The solvents were removed. Water (10 ml) was added. The organic was extracted with methylene chloride (3×10 ml). The combined methylene chloride layers were washed with brine, and dried over sodium sulfate. The title compound was obtained after flash column using EtOAc: hexane/6:4 as the eluant. LC-MS (M+1): 617.0.

Example 46

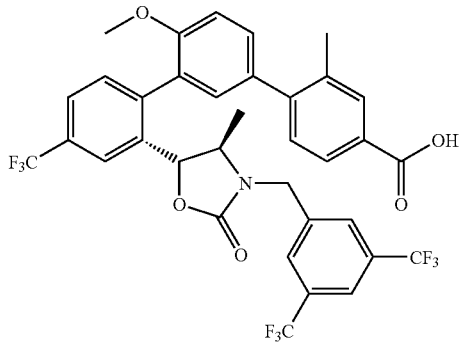

2"-{(4R,5R)-3-[3,5-bis(trifluoromethyl)benzyl]-4-methyl-2-oxo-1,3-oxazolidin-5-yl}-4'-methoxy-2-methyl-4"-(trifluoromethyl)-1,1':3',1"-terphenyl-4-carboxylic Acid Step A

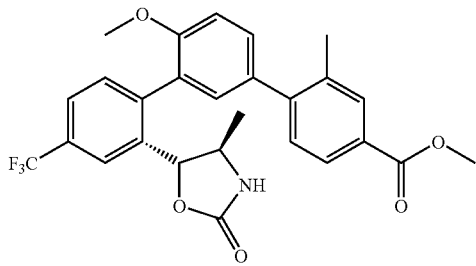

Methyl 4'-methoxy-2-methyl-2"-[(4R,5R)-4-methyl-2-oxo-1,3-oxazolidin-5-yl]-4"-(trifluoromethyl)-1,1': 3',1"-terphenyl-4-carboxylate (4R,5R)-5-[2-iodo-5-(trifluoromethyl)phenyl]-4-methyl-1,3-oxazolidin-2-one (INTERMEDIATE 12, 100 mg, 0.269 mmol), methyl 4'-methoxy-2-methyl-3'-(4,4,5,5-tetramethyl-1,3,2-dioxaborolan-2-yl)biphenyl-4-carboxylate (INTERMEDIATE 11, 124 mg, 0.323 mmol), 1,1'-bis(diphenylphosphino)ferrocene-palladium dichloride dichloromethane adduct (44 mg, 0.054 mmol), aqueous potassium carbonate (270 μL, 2M, 0.538 mmol) and 1,4-dioxane (2 mL) were sealed in a microwave vessel. The vessel was irradiated by microwave at 140° C. for 30 minutes. LCMS of the aliquot indicated complete consumption of starting iodide. The crude mixture was purified by SiO₂ (preparative TLC plates, 50% ethyl acetate in hexanes) to give a glassy residue. The residue was further purified by SiO₂ (preparative TLC plates, 10% ethyl acetate in dichloromethane) to afford methyl 4'-methoxy-2-methyl-2"-[(4R,5R)-4-methyl-2-oxo-1,3-oxazolidin-5-yl]-4"-(trifluoromethyl)-1,1':3', 1"-terphenyl-4-carboxylate. LCMS calc.=499.16; found=500.08 (M+1).

Step B

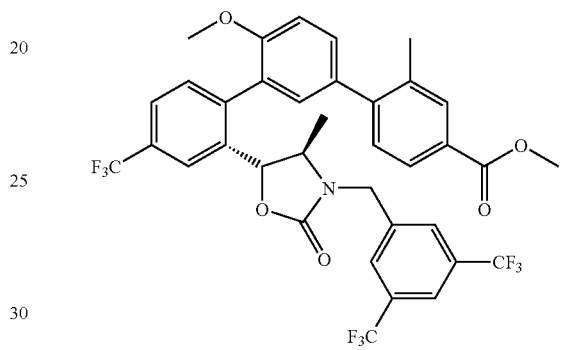

Methyl 2"-{(4R,5R)-3-[3,5-bis(trifluoromethyl)benzyl]-4-methyl-2-oxo-1,3-oxazolidin-5-yl}-4'-methoxy-2-methyl-4"-(trifluoromethyl)-1,1':3',1"-terphenyl-4-carboxylate The starting methyl 4'-methoxy-2-methyl-2"-[(4R,5R)-4-methyl-2-oxo-1,3-oxazolidin-5-yl]-4"-(trifluoromethyl)-1, 1':3',1"-terphenyl-4-carboxylate (40 mg, 0.080 mmol) was dissolved in anhydrous THF (1 mL) and cooled in an ice bath. Sodium hydride (60% w/w in mineral oil, 3.5 mg, 0.088 mmol) was added into the mixture. The reaction mixture was stirred cold (ice bath) for 10 min followed by addition of 1-(bromomethyl)-3,5-bis(trifluoromethyl)benzene (22 μL, 36.8 mg, 0.120 mmol). The resulting mixture was stirred cold for 20 min then the cold bath was removed. Aliquot at reaction time 2.5 hours indicated about 50% conversion. Reaction crude was cooled (ice bath) and quenched by NH₄Cl (aq., sat.). The resulting bi-phasic mixture was worked up with ethyl acetate. The combined organic extracts were dried over Na₂SO₄, filtered, and concentrated to afford an oil. This oil was purified by a preparative reverse-phase HPLC (Kromasil 100-5C18, 100×21.1 mm) eluted with a MeCN (0.1% TFA, v/v)/H₂O (0.1% TFA, v/v) gradient mixture. Related fractions were pooled and evaporated to afford methyl 2"-{(4R, 5R)-3-[3,5-bis(trifluoromethyl)benzyl]-4-methyl-2-oxo-1, 3-oxazolidin-5-yl}-4'-methoxy-2-methyl-4"-(trifluoromethyl)-1,1':3',1"-terphenyl-4-carboxylate.
Un-reacted starting material was also recovered. LCMS calc.=725.18; found 726.19 (M+1).

Step C

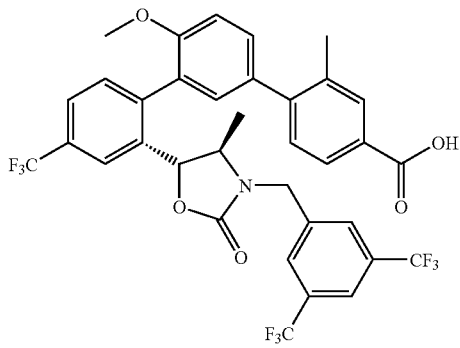

2"-{(4R,5R)-3-[3,5-bis(trifluoromethyl)benzyl]-4-methyl-2-oxo-1,3-oxazolidin-5-yl}-4'-methoxy-2-methyl-4"-(trifluoromethyl)-1,1':3',1"-terphenyl-4-carboxylic Acid methyl 2"-{(4R,5R)-3-[3,5-bis(trifluoromethyl)benzyl]-4-methyl-2-oxo-1,3-oxazolidin-5-yl}-4'-methoxy-2-methyl-4"-(trifluoromethyl)-1,1':3',1"-terphenyl-4-carboxylate (21 mg, 0.029 mmol), lithium hydroxide monohydrate (9 mg, 0.21 mmol), water (0.4 mL) and 1,4-dioxane (1 mL) were stirred at 20° C. for 2 hours to complete the hydrolysis. The reaction mixture was acidified by HCl (aq., 1 mL). The resulting crude mixture was worked up with ethyl acetate. The combined organic extracts were dried over $Na_2SO_4$, filtered, and concentrated to a clear oil. This oil was purified by a preparative reverse-phase HPLC (Kromasil 100-5C18, 100× 21.1 mm) eluted with a MeCN (0.1% TFA, v/v)/$H_2O$ (0.1% TFA, v/v) gradient mixture. Related fractions were pooled and evaporated to afford 2"-{(4R,5R)-3-[3,5-bis(trifluoromethyl)benzyl]-4-methyl-2-oxo-1,3-oxazolidin-5-yl}-4'-methoxy-2-methyl-4"-(trifluoromethyl)-1,1':3',1"-terphenyl-4-carboxylic acid. LCMS calc.=711.17; found=712.28 (M+1)$^+$. $^1$H NMR signals are doubled because of atropoisomerism. $^1$H NMR (CDCl$_3$, 500 MHz) δ 8.01 (s, 0.4H), 7.97 (s, 0.6H), 7.95 (d, J=7.0 Hz, 0.4H), 7.93 (d, J=6.5 Hz, 0.6H), 7.81 (s, 0.4H), 7.77 (s, 0.6H), 7.75 (s, 0.4H), 7.71 (s, 0.6H), 7.68 (d, J=6.5 Hz, 0.6H), 7.66 (d, J=6.5 Hz, 0.4H), 7.62 (s, 1H), 7.55 (s, 1H), 7.41-7.35 (m, 2H), 7.32 (d, J=6.5 Hz, 0.4H), 7.23 (d, J=6.5 Hz, 0.6H), 7.16 (d, J=2 Hz, 0.4H), 7.08 (d, J=7.5 Hz, 0.6H), 7.02 (d, J=7.5 Hz, 0.4H), 6.98 (d, J=2.0 Hz, 0.6H), 5.22 (d, J=4 Hz, 0.6H), 5.13 (d, J=4.5 Hz, 0.4H), 4.82, 4.75 (d, J=13.5 Hz, 1H), 4.29, 4.26 (d, J=15.5 Hz, 1H), 3.86 (s, 1.8H), 3.59 (s, 1.2H), 3.53-3.48 (m, 0.4H), 3.30-3.24 (m, 0.6H), 2.36, 2.22 (s, 3H), 0.89, 0.75 (d, J=5.5 Hz, 3H).

Example 47

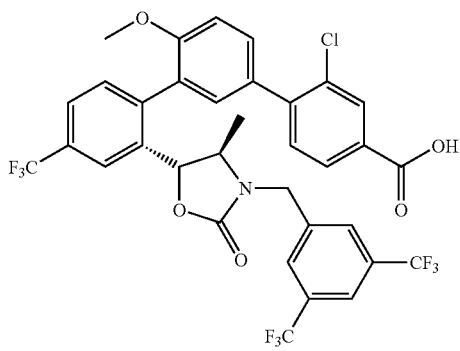

Step A

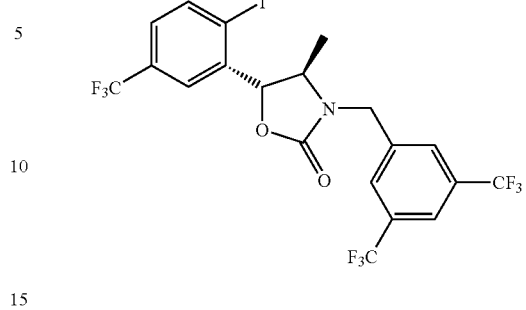

(4R,5R)-3-[3,5-bis(trifluoromethyl)benzyl]-5-[2-iodo-5-(trifluoromethyl)phenyl]-4-methyl-1,3-oxazolidin-2-one (4R,5R)-5-[2-iodo-5-(trifluoromethyl)phenyl]-4-methyl-1,3-oxazolidin-2-one (INTERMEDIATE 12, 1.451 g, 3.910 mmol) was dissolved in anhydrous THF (30 mL) and cooled in an ice bath. Sodium hydride (60% w/w in mineral oil, 172 mg, 4.301 mmol) was added into the reaction mixture all in once. The reaction was stirred cold (ice bath) for 30 min followed by addition of 1-(bromomethyl)-3,5-bis(trifluoromethyl)benzene (1.078 mL, 1.80 mg, 5.865 mmol). The crude mixture was cooled (ice bath) and quenched adding by NH$_4$Cl (aq, sat.) when reaction time was 5 hours. Reaction crude was extracted with ethyl acetate. The combined organic extracts were dried over Na$_2$SO$_4$, filtered, and concentrated to an oil. The oil was purified by flash chromatography (SiO$_2$, Biotage 40+M cartridge, EtOAc/hexanes) to afford (4R,5R)-3-[3,5-bis(trifluoromethyl)benzyl]-5-[2-iodo-5-(trifluoromethyl)phenyl]-4-methyl-1,3-oxazolidin-2-one. LCMS calc.=596.98; found=598.05 (M+1)$^+$. 132.6 mg of unreacted starting material was also recovered.

Step B

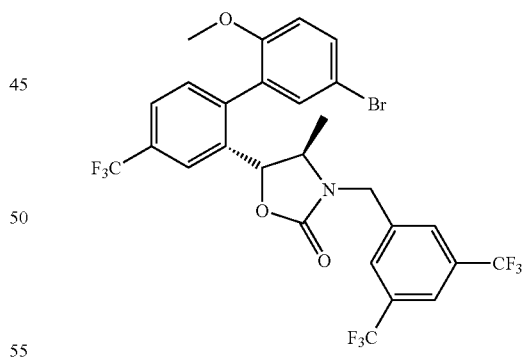

(4R,5R)-3-[3,5-bis trifluoromethyl)benzyl]-5-[5'-bromo-2'-methoxy-4-(trifluoromethyl)biphenyl-2-yl]-4-methyl-1,3-oxazolidin-2-one (4R,5R)-3-[3,5-bis(trifluoromethyl)benzyl]-5-[5'-bromo-2'-methoxy-4-(trifluoromethyl)biphenyl-2-yl]-4-methyl-1,3-oxazolidin-2-one (500 mg, 0.837 mmol), (5-bromo-2-methoxyphenyl)boronic acid (222 mg, 0.962 mmol), aqueous sodium carbonate (0.885 mL, 2M, 1.77 mmol), ethanol (300 μL) and toluene (2.5 mL) were stirred at room temperature for 0.5 hr followed by addition of tetrakis(triphenylphosphine) palladium(0) (44 mg, 4.5 mol %). The resulting mixture was heated in a 90° C. oil bath for 28.5 hours and then allowed to stir at ambient temperature overnight. The reaction crude was treated with water followed by ethyl acetate extraction. The combined extracts were dried over Na₂SO₄, filtrated and concentrated under reduced pressure to afford a yellow oil. This oil was purified by flash chromatography (SiO₂, Biotage 40+M cartridge, EtOAc/hexanes, gradient) to afford (4R,5R)-3-[3,5-bis(trifluoromethyl)benzyl]-5-[5'-bromo-2'-methoxy-4-(trifluoromethyl)biphenyl-2-yl]-4-methyl-1,3-oxazolidin-2-one. LCMS calc.=657.04; found=597.95 (M+1)⁺.

Step C

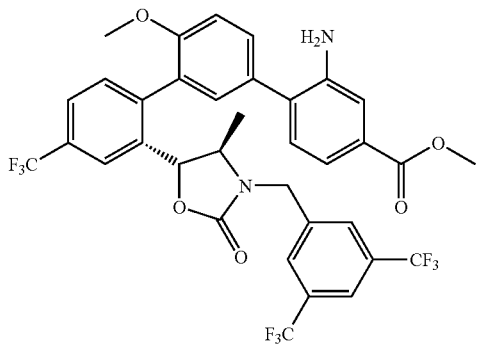

Methyl 2-amino-2"-{(4R,5R)-3-[3,5-bis(trifluoromethyl)benzyl]-4-methyl-2-oxo-1,3-oxazolidin-5-yl}-4'-methoxy-4"-(trifluoromethyl)-1,1':3',1"-terphenyl-4-carboxylate (4R,5R)-3-[3,5-bis(trifluoromethyl)benzyl]-5-[5'-bromo-2'-methoxy-4-(trifluoromethyl)biphenyl-2-yl]-4-methyl-1,3-oxazolidin-2-one (358 mg, 0.545 mmol), [2-amino-4-(methoxycarbonyl)phenyl]boronic acid (214 mg, 1.1 mmol), dichloro bis(triphenylphosphine)palladium(II) (76.5 mg, 0.109 mmol), aqueous potassium carbonate (545 µL, 2M, 1.09 mmol) and ethanol (5 mL) were mixed and heated in a 80° C. oil bath. Aliquot at reaction time 2 hours and 3.5 hours indicated about 6% of unreacted starting material. Added more [2-amino-4-(methoxycarbonyl)phenyl]boronic acid (50 mg, 0.256 mmol) when reaction time was 3 hours 45 minutes. Aliquot did not show any further progress. Crude mixture was cooled and mixed with brine. Volatiles were removed from the crude under reduced pressure. The resulting mixture was treated with water followed by ethyl acetate extraction. The combined extracts were dried over Na₂SO₄, filtrated and concentrated under reduced pressure to afford a dark oil. The resulting oil was purified by flash chromatography (SiO₂, Biotage 40+M cartridge, EtOAc/hexanes, gradient) followed by preparative TLC purification (SiO₂, 10% ethyl acetate in dichloromethane) to afford methyl 2-amino-2"-{(4R,5R)-3-[3,5-bis(trifluoromethyl)benzyl]-4-methyl-2-oxo-1,3-oxazolidin-5-yl}-4'-methoxy-4"-(trifluoromethyl)-1,1':3',1"-terphenyl-4-carboxylate. LCMS calc.=726.18; found=727.29 (M+1)⁺.

Step D

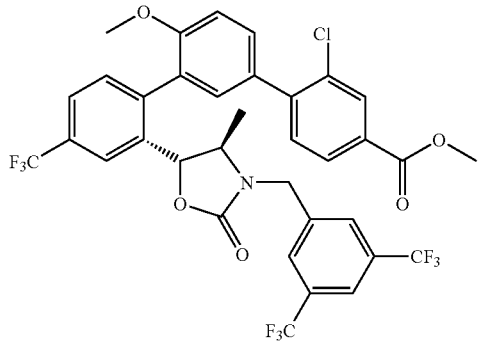

Methyl 2"-{(4R,5R)-3-[3,5-bis(trifluoromethyl)benzyl]4-methyl-2-oxo-1,3-oxazolidin-5-yl}-2-chloro-4'-methoxy-4"-(trifluoromethyl)-1,1':3',1"-terphenyl-4-carboxylate Amyl nitrite (33 µL, 29 mg, 0.248 mmol) and copper (II) chloride (27 mg, 0.198 mmol) were dissolved in anhydrous acetonitrile (1 mL) and sealed in a microwave vessel. The vessel was heated in a 65° C. oil bath. To this hot solution was added the starting methyl 2-amino-2"-{(4R,5R)-3-[3,5-bis(trifluoromethyl)benzyl]-4-methyl-2-oxo-1,3-oxazolidin-5-yl}-4'-methoxy-4"-(trifluoromethyl)-1,1':3',1"-terphenyl-4-carboxylate (120 mg, 0.165 mmol, in 1 mL MeCN) in about 1 minute. The sealed vessel was then heated in a 65° C. oil bath for 1 hour. Aliquot (LCMS) indicated completion of reaction. Crude solution was filtered and purified by a preparative reverse-phase HPLC (Kromasil 100-5C18, 100×21.1 mm) eluting with a MeCN (0.1% TFA, v/v)/H₂O (0.1% TFA, v/v) gradient mixture. The appropriate fractions were pooled & evaporated in vacuo to afford methyl 2"-{(4R,5R)-3-[3,5-bis(trifluoromethyl)benzyl]-4-methyl-2-oxo-1,3-oxazolidin-5-yl}-2-chloro-4'-methoxy-4"-(trifluoromethyl)-1,1':3',1"-terphenyl-4-carboxylate. LCMS calc.=745.13; found=746.12 (M+1)⁺.

Step E 2"-{(4R,5R)-3-[3,5-bis(trifluoromethyl)benzyl]-4-methyl-2-oxo-1,3-oxazolidin-5-yl}-2-chloro-4'-methoxy-4"-(trifluoromethyl)-1,1':3',1"-terphenyl-4-carboxylic Acid To a 1,4-dioxane solution (2 mL) of starting methyl 2"-{(4R,5R)-3-[3,5-bis(trifluoromethyl)benzyl]-4-methyl-2-oxo-1,3-oxazolidin-5-yl}-2-chloro-4'-methoxy-4"-(trifluoromethyl)-1,1':3',1"-terphenyl-4-carboxylate (65 mg, 0.087 mmol) was added a solution of lithium hydroxide monohydrate (36.5 mg, 0.87 mmol) in water (1 mL). The resulting mixture turned to a cloudy, slightly purple mixture (from a light yellow solution). Aliquot at reaction time=22 min indicated completion of reaction. Reaction crude was acidified (1N HCl, aq.). Volatiles were removed from the crude mixture. The resulting mixture was purified by a preparative reverse phase HIPLC (Kromasil 100-5C18, 100×21.1 mm) eluting w/a MeCN (0.1% TFA, v/v)/H₂O (0.1% TFA, v/v) gradient mixture. Related fractions were pooled & evaporated in vacuo to afford a colorless glass. The glass was dissolved in dichloromethane and washed with water. The organic layer was separated, dried over Na₂SO₄, filtered and concentrated in vacuo to afford 2"-{(4R,5R)-3-[3,5-bis(trifluoromethyl)benzyl]-4-methyl-2-oxo-1,3-oxazolidin-5-yl}-2-chloro-4'-methoxy-4"-(trifluoromethyl)-1,1':3',1"-terphenyl-4-carboxylic acid. LCMS calc.=731.11; found=732.08

(M+1)⁺. ¹H NMR signals are doubled because of atropoisomerism. ¹H NMR (CDCl₃, 500 MHz) 8.22, 8.13 (d, J=1.5 Hz, 1H), 8.05-7.99 (m, 1H), 7.79 (s, 1H), 7.74 (s, 1H), 7.70-7.64 (m, 1H), 7.60 (s, 0.6H), 7.54-7.51 (m, 1.8H), 7.50-7.44 (m, 1H), 7.42-7.30 (m, 2H), 7.13 (d, J=2.5 Hz, 0.6H), 7.10 (d, J=9.0 Hz, 0.6H), 7.17 (d, J=8.5 Hz, 0.4H), 5.22 (d, J=4.5 Hz, 1H), 4.82, 4.77 (d, J=16 Hz, 1H), 4.27, 4.22 (d, J=16 Hz, 1H), 3.87 (s, 1.8H), 3.59 (s, 1.2H), 3.49-3.43 (m, 0.4H), 3.32-3.25 (m, 0.6H), 0.86 (d, J=6.0 Hz, 1.2H), 0.73 (d, J=6.5 Hz, 1.8H).

Example 48

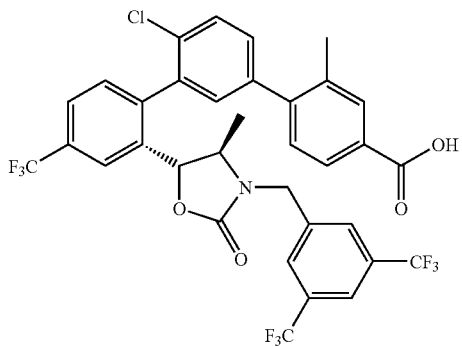

Step A

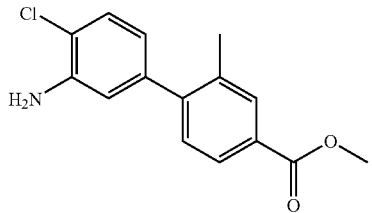

Methyl 3'-amino-4'-chloro-2-methylbiphenyl-4-carboxylate (3-amino-4-chlorophenyl)boronic acid (1.0 g, 5.834 mmol), methyl 4-bromo-3-methylbenzoate (1.337 g, 5.834 mmol), 1,1'-bis(diphenylphosphino)ferrocene-palladium dichloride dichloromethane adduct (476 mg, 0.583 mmol), aqueous potassium carbonate (11.57 mL, 1M, 11.57 mmol) and acetone (53 mL) were mixed and heated in a 70° C. oil bath for 1.5 hours to complete the coupling. Volatiles were removed from the crude mixture under reduced pressure. The resulting mixture was treated with water followed by ethyl acetate extraction. The combined extracts were dried over Na₂SO₄, filtrated and concentrated under reduced pressure to afford a dark oil. The resulting oil was purified by flash chromatography (SiO₂, Biotage 40+M cartridge, 0-40% EtOAc in hexanes) to afford methyl 3'-amino-4'-chloro-2-methylbiphenyl-4-carboxylate. LCMS calc.=275.07; found=276.23 (M+1)⁺.

Step B

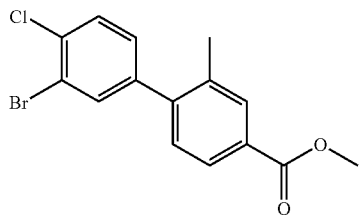

Methyl 3'-bromo-4'-chloro-2-methylbiphenyl-4-carboxylate methyl 3'-amino-4-chloro-2-methylbiphenyl-4-carboxylate (946 mg, 3.43 mmol) was dissolved in a mixture of CHBr₃ (5 mL) and dichloromethane (5 mL). To the above stirred mixture was added t-butyl nitrite (680 μL, 530.6 mg, 5.145 mmol). The reaction mixture was heated to 80° C. for 30 minutes. Aliquot (LCMS) indicated complete consumption of starting material. Crude mixture was purified by flash chromatography (SiO₂, Biotage 40+S cartridge) to afford methyl 3'-bromo-4'-chloro-2-methylbiphenyl-4-carboxylate. LCMS calc.=339.97; found=340.98 (M+1)⁺.

Step C

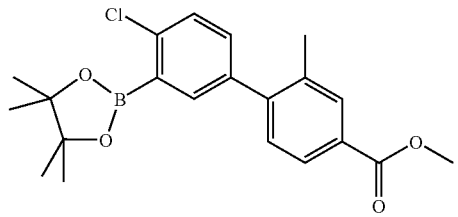

Methyl 4'-chloro-2-methyl-3'-(4,4,5,5-tetramethyl-1,3,2-dioxaborolan-2-yl)biphenyl-4-carboxylate methyl 3'-bromo-4'-chloro-2-methylbiphenyl-4-carboxylate (699 mg, 2.06 mmol), bis(pinacolato)diboron (556 mg, 2.47 mmol), 1,1'-bis(diphenylphosphino)ferrocene-palladium dichloride dichloromethane adduct (226 mg, 0.277 mmol), potassium acetate (404 mg, 4.12 mmol) and 1,4-dioxane (10 mL) were sealed in a microwave vessel. The reaction mixture was irradiated by microwave at 140° C. for 45 minutes. Aliquot (LCMS) indicated completion of reaction. The reaction crude was treated with water followed by ethyl acetate extractions. The combined extracts were dried over Na₂SO₄ followed by filtration and concentration to afford a dark oil as the crude mixture of methyl 4'-chloro-2-methyl-3'-(4,4,5,5-tetramethyl-1,3,2-dioxaborolan-2-yl)biphenyl-4-carboxylate which was used in the next step without further purification. LCMS calc.=386.15; found=387.13 (M+1)⁺.

Step D

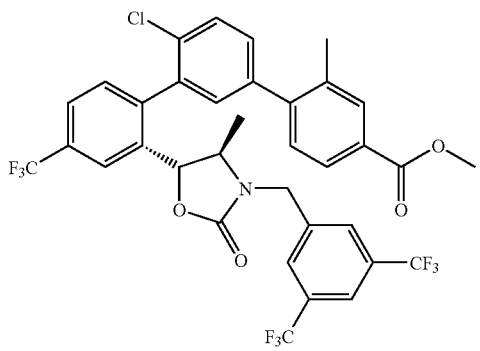

Methyl 2"-{(4R,5R)-3-[3,5-bis(trifluoromethyl)benzyl]-4-methyl-2-oxo-1,3-oxazolidin-5-yl}-4'-chloro-2-methyl-4"-(trifluoromethyl)-1,1':3',1"-terphenyl-4-carboxylate (4R,5R)-3-[3,5-bis(trifluoromethyl)benzyl]-5-[2-iodo-5-(trifluoromethyl)phenyl]-4-methyl-1,3-oxazolidin-2-one (103 mg, 0.172 mmol, in 515 µL toluene), methyl 4'-chloro-2-methyl-3'-(4,4,5,5-tetramethyl-1,3,2-dioxaborolan-2-yl)biphenyl-4-carboxylate (100 mg, 0.259 mmol), 1,1'-bis(diphenylphosphino)ferrocene-palladium dichloride dichloromethane adduct (14 mg, 10%), aqueous potassium carbonate (344 µL, 2M, 0.688 mmol), and ethanol (2 mL) were sealed in a microwave vessel. The reaction mixture was irradiated by microwave at 140° C. for 45 minutes. LC/MS analysis indicated complete consumption of starting material. Crude material was purified by SiO₂ (Prep-TLC 30% EtOAc/hex) to afford a yellow residue. The residue was further purified by a preparative reverse phase HPLC (Kromasil 100-5C18, 100×21.1 mm) eluting w/a MeCN (0.1% TFA, v/v)/H₂O (0-1% TFA, v/v) gradient mixture affording methyl 2"-{(4R,5R)-3-[3,5-bis(trifluoromethyl)benzyl]-4-methyl-2-oxo-1,3-oxazolidin-5-yl}-4'-chloro-2-methyl-4"-(trifluoromethyl)-1,1':3',1"-terphenyl-4-carboxylate. LCMS calc.=729.13; found=730.14 (M+1)⁺.

Step E

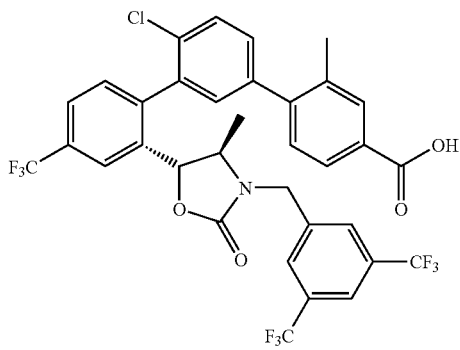

2"-{(4R,5R)-3-[3,5-bis(trifluoromethyl)benzyl]-4-methyl-2-oxo-1,3-oxazolidin-5-yl}-4'-chloro-2-methyl-4"-(trifluoromethyl)-1,1':3',1"-terphenyl-4-carboxylic acid To a 1,4-dioxane solution (3 mL) of methyl 2"-{(4R,5R)-3-[3,5-bis(trifluoromethyl)benzyl]-4-methyl-2-oxo-1,3-oxazolidin-5-yl}-4'-chloro-2-methyl-4"-(trifluoromethyl)-1,1':3',1"-terphenyl-4-carboxylate (65 mg, 0.089 mmol) was added a solution of lithium hydroxide monohydrate (26 mg, 0.623 mmol) in water (1.2 mL). Aliquot at reaction time 2 hours indicated completion of reaction (atropisomers present). Crude mixture was acidified by HCl (aq, 1N, 1 mL). The cloudy precipitation was dissolved by MeCN (2 mL). The resulting solution was purified by reverse-phase prep-HPLC (Kromasil 100-5C18, 100×21.1 mm) eluting w/a MeCN (0.1% TFA, v/v)/H₂O (0.1% TFA, v/v) gradient mixture affording 2"-{(4R,5R)-3-[3,5-bis(trifluoromethyl)benzyl]-4-methyl-2-oxo-1,3-oxazolidin-5-yl}-4'-chloro-2-methyl-4"-(trifluoromethyl)-1,1':3',1"-terphenyl-4-carboxylic acid. LCMS calc.=715.12; found=716.20 (M+1)⁺. ¹H NMR signals are doubled because of atropoisomerism. ¹H NMR ¹H NMR (CDCl₃, 500 MHz) 8.04 (s, 0.5H), 8.00 (s, 0.5H), 7.98-7.93 (m, 1H), 7.80-7.75 (m, 1.5H), 7.75 (s, 0.5H), 7.74-7.69 (m, 1H), 7.63-7.59 (m, 2H), 7.58, 7.56 (d, J=3.5 Hz, 1H), 7.42 (d, J=7.5 Hz, 0.5H), 7.40-7.34 (m, 1.5H), 7.31 (d, J=7.5 Hz, 0.4H), 7.28 (d, J=2 Hz, 0.6H), 7.24 (d, J=8.0 Hz, 0.6H), 7.09 (d, J=2.5 Hz, 0.4H), 5.14 (d, J=5.5 Hz, 0.4H), 5.10 (d, J=4.5 Hz, 0.6H), 4.83 (d, J=16 Hz, 0.6H), 4.73 (d, J=16 Hz, 0.4H), 4.28 (d, J=16 Hz, 1H), 3.57-3.51 (m, 0.4H), 3.42-3.35 (m, 0.6H), 2.35, 2.25 (s, 3H), 0.91 (d, J=6.5 Hz, 1.8H), 0.85 (d, J=6 Hz, 1.2H).

Example 49

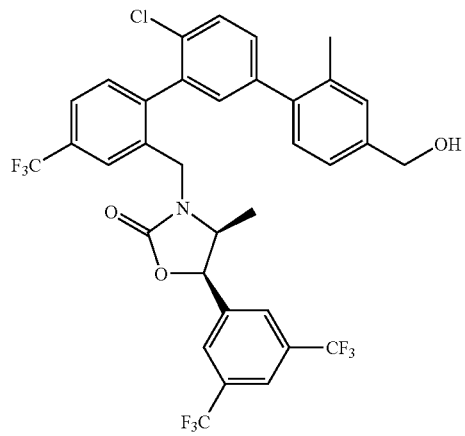

(4S,5R)-5-[3,5-bis(trifluoromethyl)phenyl]-3-{[6'-chloro-4"-(hydroxymethyl)-2"-methyl-4-(trifluoromethyl)-1,1':3',1"-terphenyl-2-yl]methyl}-4-methyl-1,3-oxazolidin-2-one To a solution of acid from Example 34 (1.0 g, 1.40 mmol) in THF (15 ml) at −78° C., Borane (2.79 ml, 2.79 mmol, 1M solution in THF) was added. The solution was stirred at −78° C. for 30 min and slowly warmed to room temperature for 2 h. TLC showed no more starting material (EtOAc/hexane 3:7). Water (10 ml) was added. The mixture was extracted with EtOAc (3×20 ml). The combined EtOAc layers were washed with saturated sodium bicarbonate, brine and dried over sodium sulfate. The solvent was removed and the residue was purified by flash column on silica gel, eluting with EtOAc/hexane (30:70) to give the title compound as a colorless solid. ¹H NMR (CDCl₃, 500 MHz): δ a mixture of 1:1 atropoisomers 7.89 (s, 1H), 7.73 (s, 1H), 7.72 (s, 2H), 7.70 (m, 1H), 7.59 (d, J=8.0 Hz, 1H), 7.49 (d, J=8.5 Hz, 0.5H), 7.47 (d, J=8.0 Hz, 0.5H), 7.39-7.36 (m, 2H), 7.32 (s, 1H), 7.25 (m 1.5H), 7.20 (d, J=2.0 Hz, 0.5H), 5.62 (d, J=8.0 Hz, 1H), 4.99 (d, J=15.0 Hz, 0.5H), 4.83 (d, J=16.0 Hz, 0.5H), 4.73 (s, 2H), 4.15 (s, 1H), 4.10 (d, J=16.0 Hz, 0.5H), 4.01 (d, J=15.5 Hz, 0.5H), 3.96 (m, 0.5H), 3.86 (m, 0.5H), 2.34 (s, 1.5H), 2.33 (s, 1.5H), 0.61 (d, J=6.5 Hz, 1.5H), 0.58 (d, J=6.5 Hz, 1.5H).

Example 50

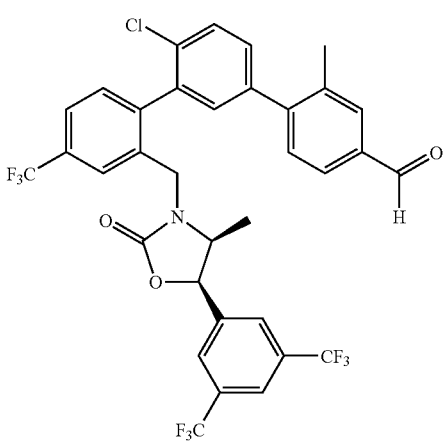

2"'-({(4S,5R)-5-[3,5-bis(trifluoromethyl)phenyl]-4-methyl-2-oxo-1,3-oxazolidin-3-yl}methyl)-4'-chloro-2-methyl-4"-(trifluoromethyl)-1,1':3',1"-terphenyl-4-carbaldehyde Dess-Martin Periodinane (145 mg, 0.34 mmol) was added to a solution of alcohol from Example 49 (200 mg, 0.285 mmol) in methylene chloride (5 ml) at room temperature. The resulting slurry was stirred at room temperature for 1 h. No starting material was seen by TLC (EtOAc/hexane 2:8). The solid was filtered. The filtrate was concentrated. The residue was purified by flash column on silica gel, eluting with EtOAc/hexane (30:70) to give the title compound as a colorless solid. $^1$H NMR (CDCl$_3$, 500 MHz): δ a mixture of 6:4 atopoisomers 10.03 (s, 1H), 7.90 (s, ⅖H), 7.89 (s, ⅗H), 7.83 (s, 1H), 7.78 (d, J=8.0 Hz, ⅗H), 7.75 (d, J=8.0 Hz, ⅖H), 7.74 (s, 1.2H), 7.73 (s, 0.8H), 7.72 (s, ⅖H), 7.70 (s, ⅗H), 7.64 (d, J=8.0 Hz, 1H), 7.52 (d, J=8.0 Hz, ⅗H), 7.47 (d, J=8.0 Hz, ⅖H), 7.46 (d, J=8.0 Hz, ⅗H), 7.43 (d, J=8.0 Hz, ⅖H), 7.40 (m, 1H), 7.28 (m, 1.5H), 7.23 (d, J=2.0 Hz, 0.5H), 5.64 (d, J=8.0 Hz, 1H), 5.04 (d, J=15.5 Hz, ⅗H), 4.83 (d, J=16 Hz, ⅖H), 4.09 (d, J=16 Hz, ⅖H), 4.01 (d, J=15.0 Hz, ⅗H), 4.00 (m, ⅖H), 3.91 (m, ⅗H), 2.43 (s, 1.8H), 2.41 (s, 1.2H), 0.65 (d, J=6.5 Hz, 1.8H), 0.61 (d, J=7.0 Hz, 1.2H).

Example 51

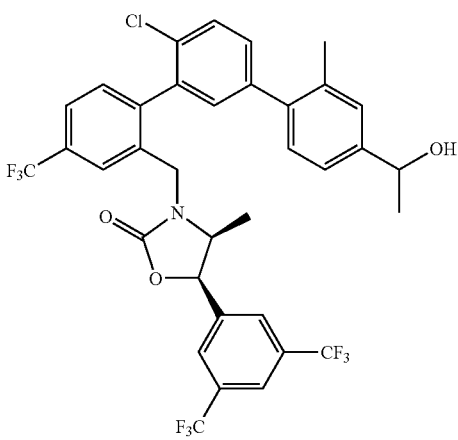

(4S,5R)-5-[3,5-bis(trifluoromethyl)phenyl]-3-{[6'-chloro-4"'-(1-hydroxyethyl)-2"-methyl-4-(trifluoromethyl)-1,1':3',1"-terphenyl-2-yl]methyl}-4-methyl-1,3-oxazolidin-2-one MeMgBr (0.274 ml, 0.274 mmol, 1 M solution) was added to a solution of aldehyde from Example 50 (160 mg, 0.229 mmol) in THF (3 ml) at −78° C. The solution was stirred at −78° C. for 2 h. Saturated ammonium chloride solution was added. The mixture was extracted with EtOAc (3×10 ml). The combined EtOAc layers were washed with brine, and dried over sodium sulfate. The residue was purified by flash column on silica gel, eluting with EtOAc/hexane (30:70) to give the title compound as a colorless solid. $^1$H NMR (CDCl$_3$, 500 MHz): δ a mixture of 1:1 atopoisomers 7.89 (s, 1H), 7.72 (m, 4H), 7.58 (d, J=8.5 Hz, 1H), 7.48 (m, 1H), 7.38 (m, 1H), 7.32-7.20 (m, 4H), 5.62 (d, J=8.0 Hz, 1H), 5.00 (d, J=15.5 Hz, 0.5H), 4.93 (m, 1H), 4.82 (d, J=16.0 Hz, 0.5H), 4.10 (d, J=15.5 Hz, 0.5H), 4.01 (d, J=15.5 Hz, 0.5H), 3.88 (m, 0.5H), 3.87 (m, 0.5H), 2.34 (s, 1.5H), 2.33 (s, 1.5H), 1.55 (m, 3H), 0.61 (d, J=6.5 Hz, 1.5H), 0.58 (d, J=6.5 Hz, 1.5H). LC/MS: M$^+$−18: 698.16.

Example 52

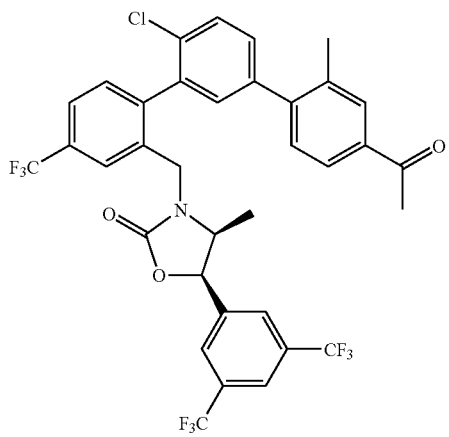

(4S,5R)-3-{[4"-acetyl-6'-chloro-2"-methyl-4-(trifluoromethyl)-1,1':3',1"-terphenyl-2-yl]methyl}-5-[3,5-bis(trifluoromethyl)phenyl]-4-methyl-1,3-oxazolidin-2-one Dess-Martin Periodinane (58.3 mg, 0.137 mmol) was added to a solution of alcohol from Example 51 (82 mg, 0.115 mmol) in methylene chloride (5 ml) at room temperature. The resulting slurry was stirred at room temperature for 1 h. No starting material was seen by TLC (EtOAc/hexane 2:8). The solid was filtered. The filtrate was concentrated. The residue was purified by flash column on silica gel, eluting with EtOAc/hexane (20:80) to give the title compound as a colorless solid. $^1$H NMR (CDCl$_3$, 500 MHz): δ a mixture of 1:1 atopoisomers 7.90 (s, 1H), 7.89 (s, 1H), 7.84 (d, J=8 Hz, 1H), 7.72 (m, 4H), 7.62 (d, J=8.5 Hz, 1H), 7.51 (d, J=8.0 Hz, 0.5H), 7.46 (d, J=8.0 Hz, 0.5H), 7.40-7.34 (m, 2H), 7.26 (d, J=2.5 Hz, 0.5H), 7.21 (d, J=2.5 Hz, 0.5H), 5.62 (d, J=8.0 Hz, 1H), 5.02 (d, J=15.5 Hz, 0.5H), 4.83 (d, J=16.0 Hz, 0.5H), 4.08 (d, J=16.0 Hz, 0.5H), 4.01 (d, J=15.5 Hz, 0.5H), 3.99 (m, 0.5H), 3.90 (m, 0.5H), 2.64 (s, 3H), 2.40 (s, 1.5M), 2.39 (s, 1.5H), 0.64 (d, J=6.5 Hz, 1.5H), 0.62 (d, J=6.5 Hz, 1.5H). LC/MS M+714.01.

Example 53

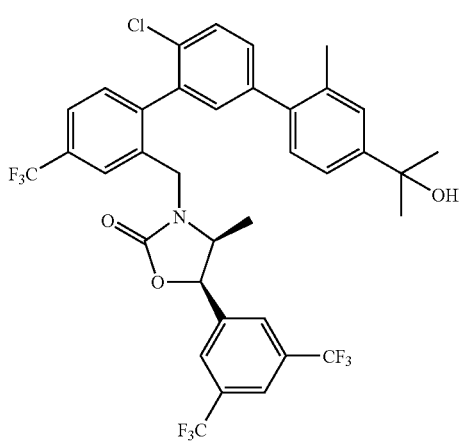

(4S,5R)-5-[3,5-bis(trifluoromethyl)phenyl]-3-{[6'-chloro-4"-(1-hydroxy-1-methylethyl)-2"-methyl-4-(trifluoromethyl)-1,1':3',1"-terphenyl-2-yl]methyl}-4-methyl-1,3-oxazolidin-2-one MeMgBr (0.168 ml, 0.168 mmol, 1 M solution) was added to a solution of ketone from Example 52 (80 mg, 0.112 mmol) in THF (3 ml) at −78° C. The solution was stirred at −78° C. for 2 h. Saturated ammonium chloride solution was added. The mixture was extracted with EtOAc (3×10 ml). The combined EtOAc layers were washed with brine, and dried over sodium sulfate. The residue was purified by flash column on silica gel, eluting with EtOAc/hexane (30:70) to give the title compound as a colorless solid. $^1$H NMR (CDCl$_3$, 500 MHz): δ a mixture of 1:1 atopoisomers 7.89 (s, 2H), 7.83 (d, J=8 Hz, 1H), 7.72 (m, 4H), 7.63 (d, J=8.5 Hz, 1H), 7.51 (d, J=8.0 Hz, 0.5H), 7.46 (d, J=8.0 Hz, 0.5H), 7.40-7.34 (m, 2H), 7.27 (d, J=2.0 Hz, 0.5H), 7.21 (d, J=2.5 Hz, 0.5H), 5.64 (d, J=8.0 Hz, 0.5H), 5.63 (d, J=8.0 Hz, 0.5H), 5.02 (d, J=16.0 Hz, 0.5H), 4.83 (d, J=16.0 Hz, 0.5H), 4.08 (d, J=16.0 Hz, 0.5H), 4.01 (d, J=15.5 Hz, 0.5H), 4.00 (m, 0.5H), 3.90 (m, 0.5H), 2.41 (s, 1.5H), 2.39 (s, 1.5H), 1.60 (m, 3H), 1.28 (m, 3H), 0.64 (d, J=6.5 Hz, 1.5H), 0.62 (d, J=6.5 Hz, 1.5H).

Example 54

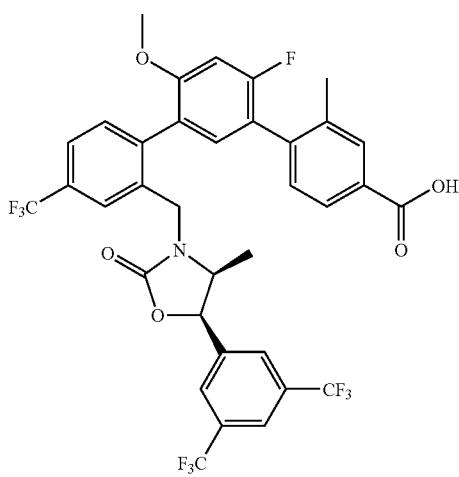

2'''-({(4S,5R)-5-[3,5-bis(trifluoromethyl)phenyl]-4-methyl-2-oxo-1,3-oxazolidin-3-yl}methyl)-6'-fluoro-4'-methoxy-2-methyl-4''-(trifluoromethyl)-1,1':3',1''-terphenyl-4-carboxylic Acid

Step A Methyl 2'-fluoro-4'-methoxy-2-methylbiphenyl-4-carboxylate

A mixture of 4-bromo-3-fluoro anisole (500 mg, 2.44 mmol), methyl 4'-methoxy-2-methyl-3'-(4,4,5,5-tetramethyl-1,3,2-dioxaborolan-2-yl)biphenyl-4-carboxylate (875 mg, 3.17 mmol), tetrakis(triphenylphosphine) palladium (282 mg, 5% mol) and sodium carbonate (569 mg, 5.37 mmol) in 20 ml of water/EtOH/toluene (1:2:4) was heated to reflux for 4 h. TLC (CH$_2$Cl$_2$:hexane/1:1) showed that the reaction was complete. The solvents were removed. Water (10 ml) was added. The organic was extracted with methylene chloride (3×10 ml). The combined methylene chloride layers were washed with brine, and dried over sodium sulfate. The title compound was obtained after flash column using CH$_2$Cl$_2$:hexane/6:4 as the elute.) $^1$H NMR (CDCl$_3$, 500 MHz): δ 7.98 (s, 1H), 7.92 (dd, J=8.0, 1.5 Hz, 1H), 7.29 (d, J=8.0 Hz, 1H), 7.16 (t, J=8.5 Hz, 1H), 6.80 (dd, J=8.5, 2.5 Hz, 1H), 6.77 (dd, J=11.5, 2.5 Hz, 1H), 3.95 (s, 3H), 3.88 (s, 3H), 2.28 (s, 3H).

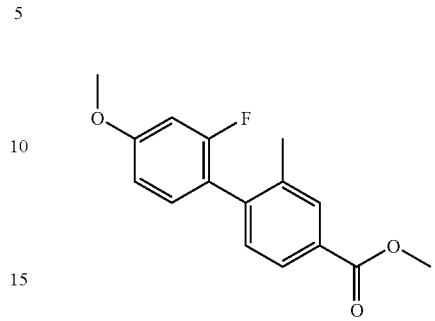

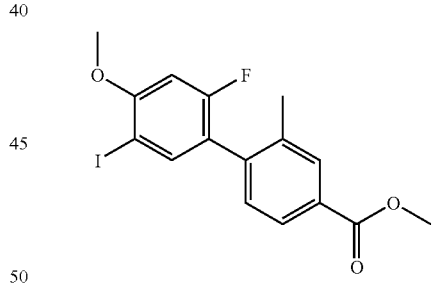

Step B Methyl 2'-fluoro-5'-iodo-4'-methoxy-2-methylbiphenyl-4-carboxylate

A solution of the title compound from Step A (1.30 g, 4.74 mmol) in MeOH/EtOAc(10:1) (10 ml) was added to a mixture of Ag$_2$SO$_4$ (1.47 g, 4.74 mmol) and I$_2$ (1.20 g, 4.74 mmol) in MeOH (20 ml) at room temperature. The mixture was stirred at room temperature for 4 h. The color of solution turned to light yellow from brown. The mixture was filtered. The filtrate was concentrated. The residue was purified by flash column, eluting with EtOAc/hexane (5:95) to give the title compound as a colorless solid.) $^1$H NMR (CDCl$_3$, 500 MHz): δ 7.98 (s, 1H), 7.92 (dd, J=8.0, 2.0 Hz, 1H), 7.67 (d, J=8.5 Hz, 1H), 7.28 (d, J=9.0 Hz, 1H), 6.69 (d, J=11.5 Hz, 1H), 3.96 (s, 3H), 3.95 (s, 3H), 2.27 (s, 3H).

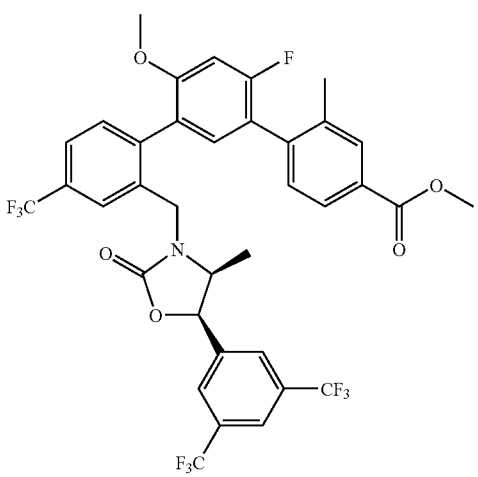

Step C Methyl 2"-({(4S,5R)-5-[3,5-bis(trifluoromethyl)phenyl]-4-methyl-2-oxo-1,3-oxazolidin-3-yl}methyl)-6'-fluoro-4'-methoxy-2-methyl-4"-(trifluoromethyl)-1,1':3',1"-terphenyl-4-carboxylate (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one-methane (1.30 g, 2.18 mmol) (INTERMEDIATE 9), the title compound from Step B (1.30 g, 3.25 mmol), tetrakis(triphenylphosphine) palladium (250 mg, 10% mol) and sodium carbonate (507 mg, 4.79 mmol) in 50 ml of water/EtOH/toluene (1:2:4) was heated to reflux for 4 h. TLC (CH$_2$Cl$_2$:hexane/1:1) showed that the reaction was complete. The solvents were removed. Water (20 ml) was added. The organic was extracted with methylene chloride (3×30 ml). The combined methylene chloride layers were washed with brine, and dried over sodium sulfate. The title compound was obtained after flash column using CH$_2$Cl$_2$:hexane/8:2 as the elute. $^1$H NMR (CDCl$_3$, 500 MHz): δ a mixture of 1:1 atopoisomers 7.98 (d, J=4.5 Hz, 1H), 7.89 (s, 2H), 7.68 (m, 4H), 7.42 (t, J=6.0 Hz, 1H), 7.30 (d, J=7.5 Hz, 0.5H), 7.26 (d, J=7.5 Hz, 0.5H), 7.07 (t, J=8.0 Hz, 1H), 6.87 (d, J=5.5 Hz, 0.5H), 6.85 (d, J=6.0 Hz, 0.5H), 5.63 (d, J=8.0 Hz, 0.5H), 5.41 (d, J=8.0 Hz, 0.5H), 5.00 (d, J=15.5 Hz, 0.5H), 4.92 (d, J=16.0 Hz, 0.5H), 4.17 (d, J=15.5 Hz, 0.5H), 3.95 (d, J=16.0 Hz, 0.5H), 3.95 (s, 3H), 3.88 (s, 3H), 3.84 (m, 1H), 2.32 (s, 1.5H), 2.28 (s, 1.5H), 0.64 (d, J=7.0 Hz, 1.5H), 0.62 (d, J=6.5 Hz, 1.5H). LC/MS M+744.2

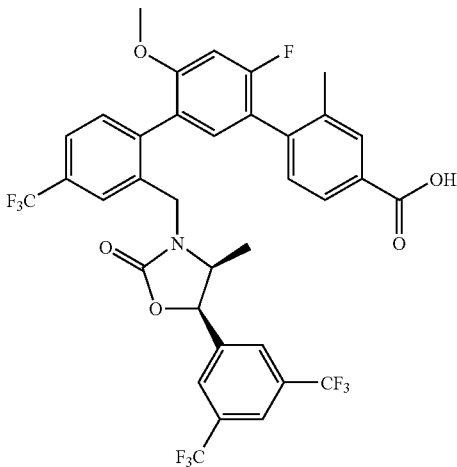

Step D 2"-({(4S,5R)-5-[3,5-bis(trifluoromethyl)phenyl]-4-methyl-2-oxo-1,3-oxazolidin-3-yl}methyl)-6'-fluoro-4'-methoxy-2-methyl-4"-(trifluoromethyl)-1,1':3',1"-terphenyl-4-carboxylic Acid The title compound from Step C (1.97 g, mmol) was stirred with LiOH (5 eq) in a 2:1 mixture of dioxane and water at room temperature overnight. The solvent was removed and the aqueous solution was acidified with 1N HCl to pH ~4. The organic was extracted with EtOAc (3×30 ml). The combined EtOAc layers were washed with brine and dried over sodium sulfate. The title compound was obtained after flash column eluting with EtOAc/hexane (1:1). $^1$H NMR (CDCl$_3$, 500 MHz): δ a mixture of 1:1 atopoisomers 8.03 (d, J=4.5 Hz, 1H), 7.95 (d, J=8.5 Hz, 1H), 7.89 (s, 1H), 7.73-7.65 (m, 4H), 7.43 (m, 1H), 7.34 (d, J=7.5 Hz, 0.5H), 7.29 (d, J=7.5 Hz, 0.5H), 7.08 (t, J=8.5 Hz, 1H), 6.88 (d, J$_1$=5.5 Hz, 0.5H), 6.86 (d, J=6.5 Hz, 0.5H), 5.63 (d, J=8.0 Hz, 0.5H), 5.42 (d, J=8.5 Hz, 0.5H), 5.01 (d, J=16.0 Hz, 0.5H), 4.93 (d, J=16.0 Hz, 0.5H), 4.17 (d, J=16.0 Hz, 0.5H), 3.95 (d, J=16.0 Hz, 0.5H), 3.89 (s, 3H), 3.84 (m, 1H), 2.34 (s, 1.5H), 2.30 (s, 1.5H), 0.61 (d, J=7.0 Hz, 1.5H), 0.50 (d, J=6.5 Hz, 1.5H).

Example 55

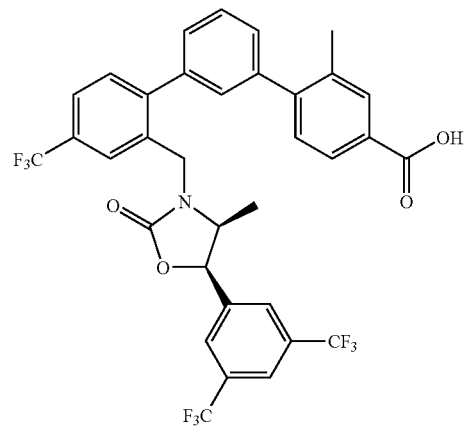

2"-({(4S,5R)-5-[3,5-bis(trifluoromethyl)phenyl]-4-methyl-2-oxo-1,3-oxazolidin-3-yl}methyl)-2-methyl-4"-(trifluoromethyl)-1,1':3',1"-terphenyl-4-carboxylic Acid

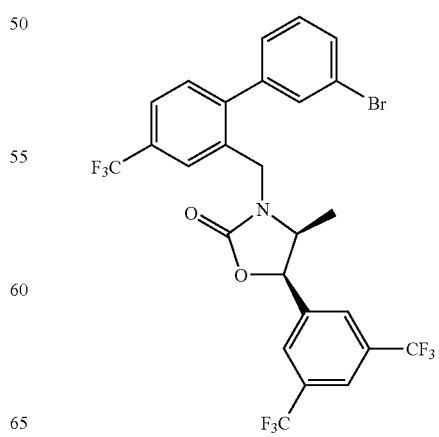

Step A (4S,5R)-5-[3,5-bis(trifluoromethyl)phenyl]-3-{[3'-bromo-4-(trifluoromethyl)biphenyl-2-yl]methyl}-4-methyl-1,3-oxazolidin-2-one A mixture of (4S,5R)-5-[3,5-bis(trifluoromethyl)phenyl]-3-[2-iodo-5-(trifluoromethyl)benzyl]-4-methyl-1,3-oxazolidin-2-one (2.0 g, 3.35 mmol), 3-bromo-phenyl boronic acid (0.74 g, 3.68 mmol), and sodium carbonate (0.71 g, 6.70 mmol) in 21 ml of 1:2:4 mixture of water:EtOH:toluene was stirred at room temperature for 30 min. Catalytic amount of tetrakis(triphenylphosphine) palladium (0.193 g, 5% mol) was added. The mixture was stirred under reflux for 3 h. The solvents were removed. Water (10 ml) was added. The mixture was extracted with methylene chloride (3×30 ml). The combined methylene chloride layers were washed with brine and dried over sodium sulfate. The title compound was obtained after flash column using $CH_2Cl_2$:hexane/1:1 as the elute.

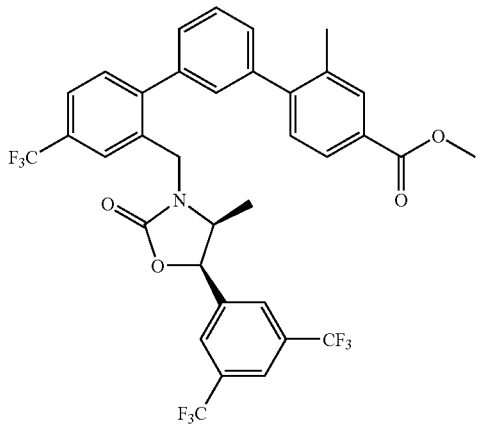

Step B Methyl 2"-({(4S,5R)-5-[3,5-bis(trifluoromethyl)phenyl]-4-methyl-2-oxo-1,3-oxazolidin-3-yl}methyl)-2-methyl-4"-(trifluoromethyl)-1,1':3',1"-terphenyl-4-carboxylate A mixture of methyl 4'-methoxy-2-methyl-3'-(4,4,5,5-tetramethyl-1,3,2-dioxaborolan-2-yl)biphenyl-4-carboxylate (150 mg, 0.542 mmol), the title compound from Step A (224 mg, 0.358 mmol), tetrakis(triphenylphosphine) palladium (20.66 mg, 5% mol) and sodium carbonate (76 mg, 0.715 mmol) in 14 ml of water/EtOH/toluene (1:2:4) was heated to reflux for 1 h. TLC ($CH_2Cl_2$:hexane/1:1) showed that the reaction was complete. The solvents were removed. Water (10 ml) was added. The organic was extracted with methylene chloride (3×10 ml). The combined methylene chloride layers were washed with brine, and dried over sodium sulfate. The title compound was obtained after flash column using $CH_2Cl_2$:hexane/8:2 as the elute. $^1H$ NMR (CDCl$_3$, 500 MHz): δ 7.99 (s, 1H), 7.92 (dd, J=7.5, 1.5 Hz, 1H), 7.88 (s, 1H), 7.75 (s, 1H), 7.71 (s, 2H), 7.67 (m, 1H), 7.57 (t, J=7.5 Hz, 1H), 7.50 (d, J=8.0 Hz, 1H), 7.42 (m, 1H), 7.35-7.28 (m, 3H), 5.53 (d, J=8.0 Hz, 1H), 4.97 (d, J=15.5 Hz, 1H), 4.25 (d, J=16.0 Hz, 1H), 3.95 (s, 3H), 3.80 (m, 1H), 2.36 (s, 3H), 0.48 (d, J=6.5 Hz, 3H).

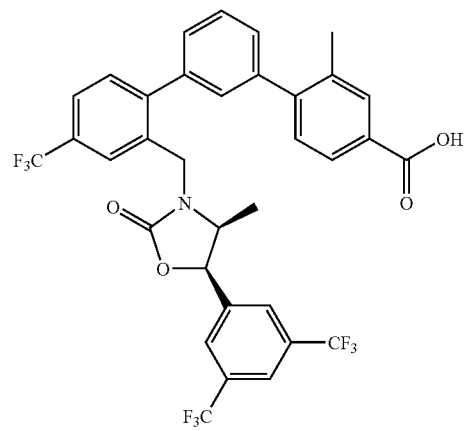

Step C 2"-({(4S,5R)-5-[3,5-bis(trifluoromethyl)phenyl]-4-methyl-2-oxo-1,3-oxazolidin-3-yl}methyl)-2-methyl-4"-(trifluoromethyl)-1,1':3',1"-terphenyl-4-carboxylic Acid The title compound from Step B (30 mg, 0.043 mmol) was stirred with LiOH (5 eq) in a 2:1 mixture of dioxane and water at room temperature overnight. The solvent was removed and the aqueous solution was acidified with 1N HCl to pH ~4. The organic was extracted with EtOAc (3×10 ml). The combined EtOAc layers were washed with brine and dried over sodium sulfate. The title compound was obtained after reverse phase HPLC as a colorless solid. $^1H$ NMR (CDCl$_3$, 500 MHz): δ 8.05 (s, 1H), 7.99 (d, J=8.0 Hz, 1H), 7.90 (s, 1H), 7.75 (s, 1H), 7.72 (s, 2H), 7.67 (m, 1H), 7.59 (t, J=7.5 Hz, 1H), 7.51 (d, J=8.0 Hz, 1H), 7.44 (m, 1H), 7.37 (m, 2H), 7.30 (m, 1H), 5.54 (d, J=8.0 Hz, 1H), 4.98 (d, J=15.5 Hz, 1H), 4.25 (d, J=16.0 Hz, 1H), 3.81 (m, 1H), 2.40 (s, 3H), 0.49 (d, J=6.5 Hz, 3H). LC/MS (M+1) 682.1.

Example 56

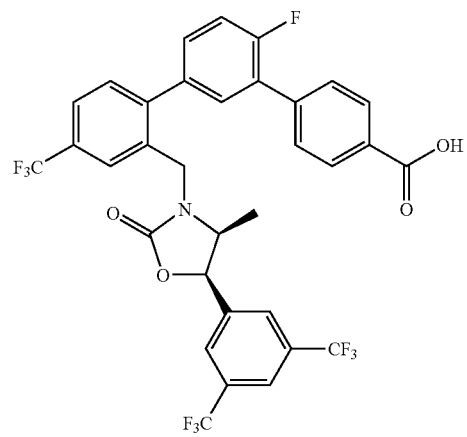

2''-({(4S,5R)-5-[3,5-bis(trifluoromethyl)phenyl]-4-methyl-2-oxo-1,3-oxazolidin-3-yl}methyl)-6'-fluoro-4''-(trifluoromethyl)-1,1':3',1''-terphenyl-4-carboxylic Acid

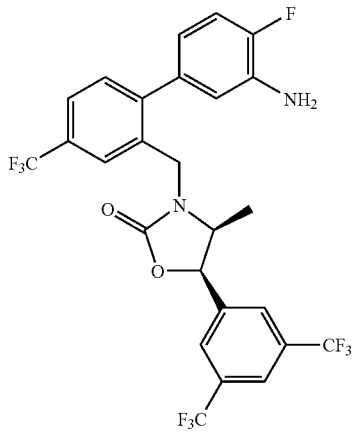

Step A (4S,5R)-3-{[3'-amino-4'-fluoro-4-(trifluoromethyl)biphenyl-2-yl]methyl}-5-[3,5-bis(trifluoromethyl)phenyl]-4-methyl-1,3-oxazolidin-2-one A mixture of (4S,5R)-5-[3,5-bis(trifluoromethyl)phenyl]-3-[2-iodo-5-(trifluoromethyl)benzyl]-4-methyl-1,3-oxazolidin-2-one (1.1 g, 1.84 mmol), 3-amino-4-fluorophenyl boronic acid (0.43 g, 2.76 mmol), sodium carbonate (0.39 g, 3.68 mmol), and catalytic amount of tetrakis(triphenylphosphine) palladium (0.213 g, 10% mol) in 14 ml of 1:2:4 mixture of water:EtOH:toluene was stirred under reflux for 2 h. The solvents were removed. Water (10 ml) was added. The mixture was extracted with methylene chloride (3×10 ml). The combined methylene chloride layers were washed with brine and dried over sodium sulfate. The title compound was obtained after flash column using $CH_2Cl_2$:hexane/7:3 as the elute. $^1$H NMR ($CDCl_3$, 500 MHz): δ 7.89 (s, 1H), 7.73 (s, 2H), 7.70 (s, 1H), 7.64 (d, J=8.5 Hz, 1H), 7.42 (d, J=8.0 Hz, 1H), 7.09 (dd, J=11, 8.5 Hz, 1H), 6.74 (dd, J=8.0, 2.5 Hz, 1H), 6.62 (m, 1H), 5.55 (d, J=8.5 Hz, 1H), 4.94 (d, J=15.5 Hz, 1H), 4.23 (d, J=16.0 Hz, 1H), 3.80 (m, 1H), 1.60 (br s, 2H), 0.51 (d, J=6.5 Hz, 3H).

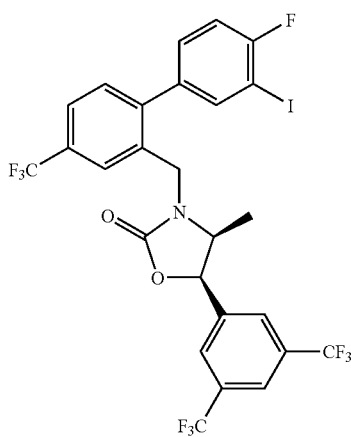

Step B (4S,5R)-5-[3,5-bis(trifluoromethyl)phenyl]-3-{[4'-fluoro-3'-iodo-4-(trifluoromethyl)biphenyl-2-yl]methyl}-4-methyl-1,3-oxazolidin-2-one n-Pentyl nitrite (0.42 g, 3.58 mmol) and iodine (0.68 g, 2.69 mmol) were added to a solution of the title compound from Step A (1.04 g, 1.79 mmol) in chloroform (10 ml). The mixture was stirred under refluxing for 1 h. The mixture was diluted with methylene chloride (10 ml). The purple solution was washed with saturated sodium thiosulfate solution, brine, and dried over sodium sulfate. The title compound was obtained after flash column using EtOAc:hexane/1:9 as the elute. $^1$H NMR ($CDCl_3$, 500 MHz): δ 7.90 (s, 1H), 7.75 (s, 2H), 7.74 (m, 1H), 7.67 (d, J=8.0 Hz, 1H), 7.42 (d, J=7.5 Hz, 1H), 7.30 (m, 2H), 7.20 (t, J=8.0, Hz, 1H), 5.55 (d, J=8.0 Hz, 1H), 4.89 (d, J=16.0 Hz, 1H), 4.15 (d, J=16.0 Hz, 1H), 3.84 (m, 1H), 0.51 (d, J=6.5 Hz, 3H).

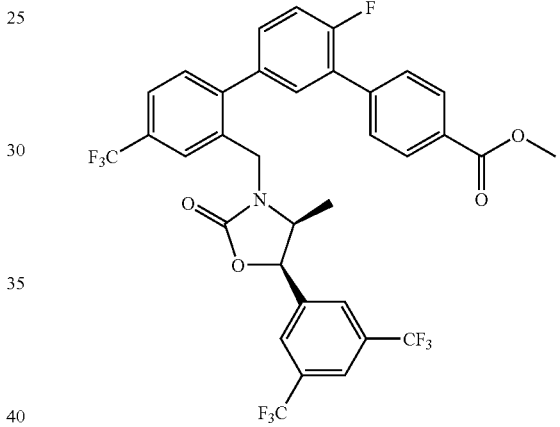

Step C Methyl 2''-({(4S,5R)-5-[3,5-bis(trifluoromethyl)phenyl]-4-methyl-2-oxo-1,3-oxazolidin-3-yl}methyl)-6'-fluoro-4''-(trifluoromethyl)-1,1':3',1''-terphenyl-4-carboxylate A mixture of the title compound from Step B (60 mg, 0.087 mmol), 4-methoxycarbonylphenyl boronic acid (31.2 mg, 0.174 mmol), sodium carbonate (18.4 mg, 0.174 mmol), and catalytic amount of tetrakis(triphenylphosphine) palladium (20 mg, 20% mol) in 7 ml of 1:2:4 mixture of water:EtOH:toluene was stirred under reflux for 2 h. The solvents were removed. Water (10 ml) was added. The mixture was extracted with methylene chloride (3×10 ml). The combined methylene chloride layers were washed with brine and dried over sodium sulfate. The title compound was obtained after flash column using $CH_2Cl_2$:hexane/7:3 as the elute. $^1$H NMR ($CDCl_3$, 500 MHz): δ 8.15 (d, J=8-5 Hz, 2H), 7.89 (s, 1H), 7.74 (s, 1H), 7.72 (s, 2H), 7.67 (m, 2H), 7.49 (d, J=8.0 Hz, 1H), 7.43 (d, J=7.5 Hz, 1H), 7.32 (d, J=8.0 Hz, 2H), 5.57 (d, J=8.0 Hz, 1H), 4.97 (d, J=16.0 Hz, 1H), 4.23 (d, J=16.0 Hz, 1H), 3.97 (s, 3H), 3.85 (m, 1H), 0.53 (d, J=6.5 Hz, 3H).

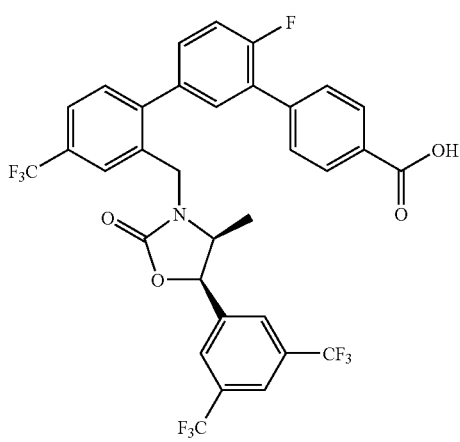

Step D 2"-({(4S,5R)-5-[3,5-bis(trifluoromethyl)phenyl]-4-methyl-2-oxo-1,3-oxazolidin-3-yl}methyl)-6'-fluoro-4"-(trifluoromethyl)-1,1':3',1"-terphenyl-4-carboxylic Acid The title compound from Step C (60 mg, 0.086 mmol) was stirred with LiOH (10 eq) in a 2:1 mixture of dioxane and water at room temperature overnight. The solvent was removed and the aqueous solution was acidified with 1N HCl to pH 4. The organic was extracted with EtOAc (3×10 ml). The combined EtOAc layers were washed with brine and dried over sodium sulfate. The title compound was obtained after reverse phase HPLC as a colorless solid. $^1$H NMR (CDCl$_3$, 500 MHz): δ 8.18 (d, J=7.0 Hz, 2H), 7.87 (s, 1H), 7.72 (s, 1H), 7.70 (s, 2H), 7.68 (m, 2H), 7.47 (d, J=6.5 Hz, 1H), 7.42 (d, J=5.5 Hz, 1H), 7.32 (d, J=6.5 Hz, 2H), 5.55 (d, J=6.5 Hz, 1H), 4.96 (d, J=13.0 Hz, 1H), 4.21 (d, J=13.0 Hz, 1H), 3.85 (m, 1H), 0.52 (d, J=5.0 Hz, 3H). LC/MS M+686.06.

The following examples were obtained following the general procedure described in Example 56.

| Example | R | LCMS (M + 1)$^+$ |
|---|---|---|
| 57 | Me | 700.09 |
| 58 | Cl | 720.07 |

The following examples were obtained using (4S,5R)-5-[3,5-bis(trifluoromethyl)phenyl]-3-{[2'-methoxy-5'-(4,4,5,5-tetramethyl-1,3,2-dioxaborolan-2-yl)-4-(trifluoromethyl)biphenyl-2-yl]methyl}-4-methyl-1,3-oxazolidin-2-one) (100 mg, 0.14 mmol) from Example 21, Step A and the corresponding bromides following the general procedure described in Example 56, Step C.

| Example | R | LCMS (M + Na)$^+$ |
|---|---|---|
| 59 | (3-CO$_2$H, 2-methylphenyl) | 734.20 |
| 60 | (3-methyl-4-HO$_2$C-phenyl) | 734.20 |

Example 61

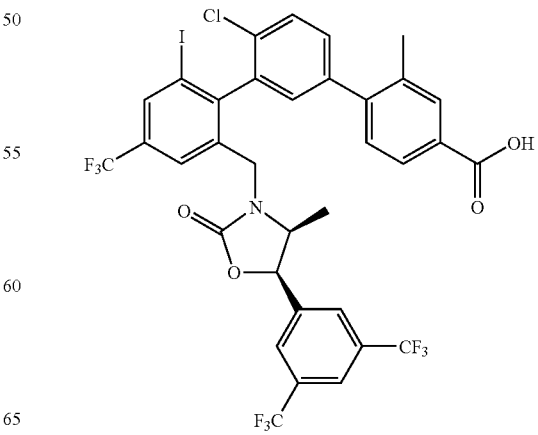

123

2"-({(4S,5-R)-5-[3,5-bis(trifluoromethyl)phenyl]-4-methyl-2-oxo-1,3-oxazolidin-3-yl}methyl)-4'-chloro-6"-iodo-2-methyl-4"-(trifluoromethyl)-1,1':3',1"-terphenyl-4-carboxylic Acid

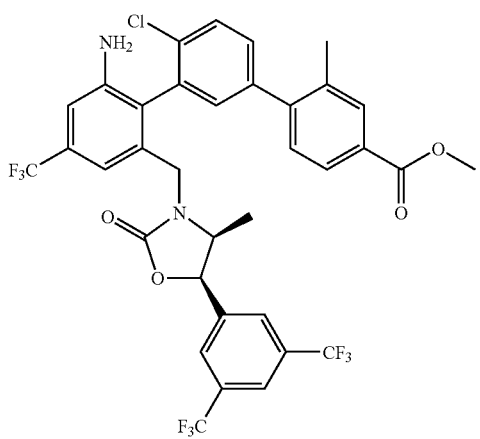

Step A Methyl 2"-amino-6"-({(4S,5R)-5-[3,5-bis(trifluoromethyl)phenyl]4-methyl-2-oxo-1,3-oxazolidin-3-yl}methyl)-4'-chloro-2-methyl-4"-(trifluoromethyl)-1,1':3',1"-terphenyl-4-carboxylate To a solution of the title compound from Example 40, Step E (500 mg, 0.779 mmol) in EtOH (10 ml), tin chloride dihydrate (1.64 g, 7.27 mmol) was added. The mixture was stirred at room temperature for 2 h. LC-MS analysis indicated complete consumption of starting material. EtOH was removed. EtOAc (200 ml) was added to the residue. The mixture was washed with water, brine and dried over sodium sulfate. Removal of the solvent afforded a white solid which was mixed with methyl 4'-chloro-2-methyl-3'-(4,4,5,5-tetramethyl-1,3,2-dioxaborolan-2-yl)biphenyl-4-carboxylate (Example 48, Step C, 281 mg, 0.727 mmol), tetrakis(triphenylphosphine) palladium (10% mol) and sodium carbonate (0.154 g, 1.45 mmol) in 32 ml of water/EtOH/toluene (1:2:4) and was heated to reflux for 48 h. TLC (EtOAc:hexane/2:8) showed that the reaction was over. The solvents were removed. Water (10 ml) was added. The organic was extracted with methylene chloride (3×30 ml). The combined methylene chloride layers were washed with brine, and dried over sodium sulfate. The title compound was obtained after purification with flash column using 20% EtOAc in hexane as the elute. $^1$H NMR (CDCl$_3$, 500 MHz): δ 7.99 (s, 1H), 7.91 (dd, J=8.0, 2.0 Hz, 1H), 7.88 (s, 1H), 7.74 (s, 2H), 7.67 (d, J=8.0 Hz, 1H), 7.42 (dd, J=8.5, 2.0 Hz, 1H), 7.36 (d, J=8.0 Hz, 1H), 7.30-7.24 (m, 1H), 7.07 (s, 1H), 7.01 (s, 1H), 5.70 (d, J=8.0 Hz, 1H), 4.83 (d, J=15.0 Hz, 1H), 4.01 (m, 1H), 3.96 (s, 3H), 3.83 (d, J=15.0 Hz, 1H), 3.81 (br s, 2H), 2.42 (s, 3H), 0.68 (d, J=6.0 Hz, 3H).

124

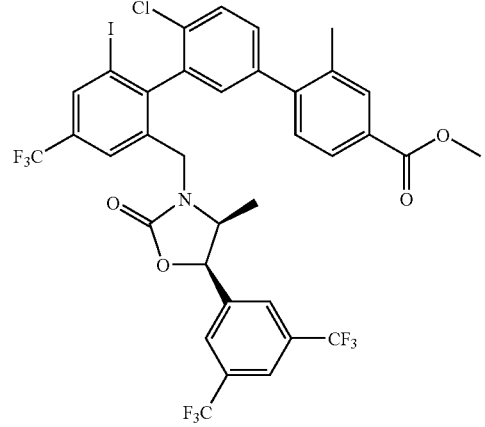

Step B Methyl 2"-({(4S,5R)-5-[3,5-bis(trifluoromethyl)phenyl]-4-methyl-2-oxo-1,3-oxazolidin-3-yl}methyl)-4'-chloro-6"-iodo-2-methyl-4"-(trifluoromethyl)-1,1':3',1"-terphenyl-4-carboxylate To a solution of the title compound from Step A (285 mg, 0.383 mmol) in chloroform (10 ml) at room temperature, n-pentyl nitrite (67.2 mg, 0.574 mmol) and iodine (126 mg, 0.497 mmol) were added. The mixture was heated to reflux for 1 h. The mixture was diluted with methylene chloride (10 ml). The solution was washed with saturated aqueous sodium thiosulfate, brine and dried over sodium sulfate. The residue was purified by preparative reverse phase HPLC to afford the title compound as a colorless solid. $^1$H NMR (CDCl$_3$, 500 MHz): δ 8.24 (s, 1H), 7.99 (s, 1H), 7.92 (d, J=8.0, Hz, 1H), 7.90 (s, 1H), 7.74 (s, 2H), 7.66 (s, 1H), 7.42 (dd, J=8.5, 2.5 Hz, 1H), 7.34 (d, J=8.0 Hz, 1H), 7.28 (m, 1H), 7.21-7.14 (m, 1H), 5.71 (d, J=8.0 Hz, 1H), 4.78 (d, J=15.5 Hz, 1H), 3.99 (m, 2H), 3.96 (s, 3H), 2.41 (s, 3H), 0.65 (d, J=6.5 Hz, 3H).

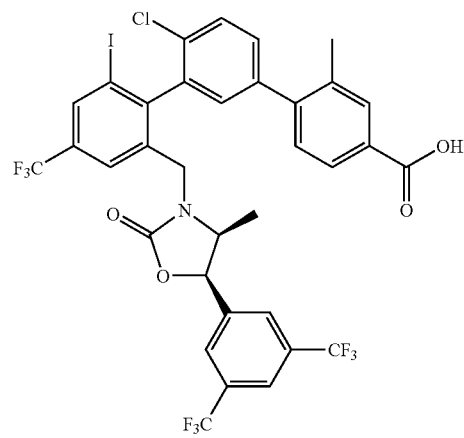

Step C 2"-({(4S,5R)-5-[3,5-bis(trifluoromethyl)phenyl]-4-methyl-2-oxo-1,3-oxazolidin-3-yl}methyl)-4'-chloro-6"-iodo-2-methyl-4'-(trifluoromethyl)-1,1':3',1"-terphenyl-4-carboxylic Acid To a solution of the title compound from Step B (30 mg, 0.035 mmol) in dioxane (2 ml) at room temperature, an aqueous solution of LiOH.H2O (7.36 mg, 0.175 mmol) was added. The mixture was stirred at room temperature for overnight. TLC (EtOAc:hexane/2:8) showed no starting material. The solvent was removed. 1N HCl (1 ml) was added. The mixture was extracted with methylene chloride (3×10 ml). The combined methylene chloride layers were dried over sodium sulfate. The title compound was obtained by preparative reverse phase HPLC as a colorless solid.

Example 62

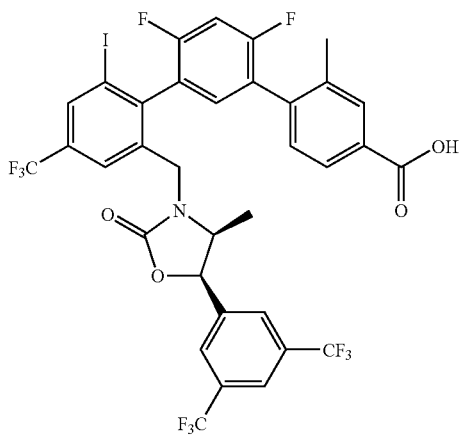

2"-({(4S,5R)-5-[3,5-bis(trifluoromethyl)phenyl]-4-methyl-2-oxo-1,3-oxazolidin-3-yl}methyl)-4',6'-difluoro-6"-iodo-2-methyl-4'-(trifluoromethyl)-1,1':3',1"-terphenyl-4-carboxylic Acid The title compound was obtained using the title compound from Example 40, Step E and methyl 4'-fluoro-2-methyl-3'-(4,4,5,5-tetramethyl-1,3,2-dioxaborolan-2-yl)biphenyl-4-carboxylate (INTERMEDIATE 22), following the procedure described in Example 61. $^1$H NMR (CDCl$_3$, 500 MHz): δ a mixture of 1:1 atopoisomers 8.26 (s, 0.5H), 8.24 (s, 0.5H), 8.06 (s, 1H), 7.98 (d, J=8.0 Hz, 1H), 7.91 (s, 1H), 7.75 (s, 2H), 7.69 (s, 0.5H), 7.65 (s, 0.5H), 7.39 (m, 1H), 7.16-7.04 (m, 2H), 5.66 (d, J=8.0 Hz, 0.5H), 5.64 (d, J=8.5 Hz, 0.5H), 4.88 (d, J=15.5 Hz, 0.5H), 4.81 (d, J=16.0 Hz, 0.5H), 4.02 (m, 1H), 3.91 (m, 1H), 2.39 (s, 1.5H), 2.36 (s, 1.5H), 0.70 (d, J=6.5 Hz, 1.5H), 0.69 (d, J=6.5 Hz, 1.5H). LC/MS M+1 844.04.

The following examples were obtained using the title compound from Example 56, Step B and the corresponding boronic acids, followed the general procedure described in Example 56, Step C.

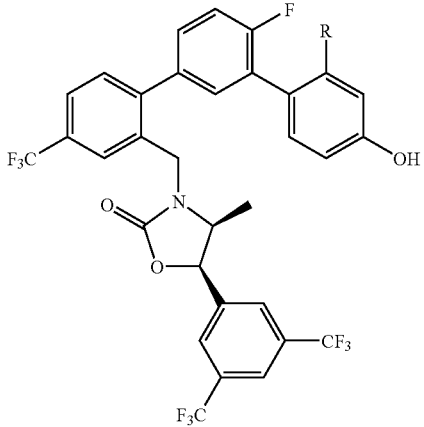

| Example | R | LC/MS |
|---------|-----|----------------|
| 63 | CF3 | 725.77 (M+) |
| 64 | Me | 672.17 (M + 1)$^+$ |

Example 65

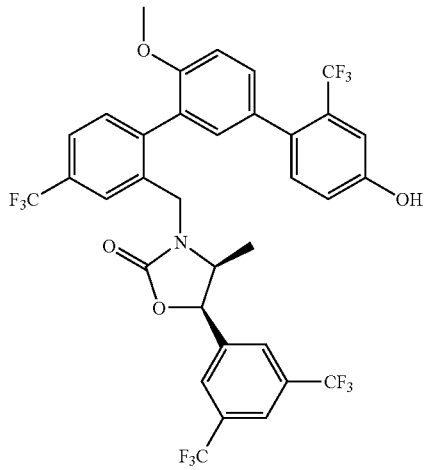

(4S,5R)-5-[3,5-bis(trifluoromethyl)phenyl]-3-{[4"-hydroxy-6'-methoxy-2,4-bis(trifluoromethyl)-1,1':3',1"-terphenyl-2'-yl]methyl}-4-methyl-1,3-oxazolidin-2-one The title compound was obtained using the intermediate from Example 1, Step A and 4-hydroxy-2-trifluoromethyl phenyl boronic acid, followed the procedure described in Example 56, Step C. LC/MS (M+1) 737.98.

Example 66

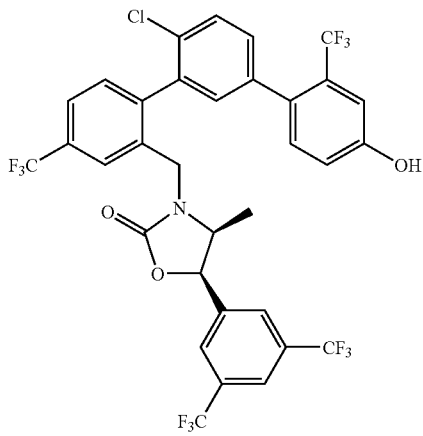

(4S,5R)-5-[3,5-bis(trifluoromethyl)phenyl]-3-{[6'-chloro-4"-hydroxy-2",4-bis(trifluoromethyl)-1,1':3',1"-terphenyl-2-yl]methyl}-4-methyl-1,3-oxazolidin-2-one The title compound was obtained using the intermediate from Example 22, Step B and 4-hydroxy-2-trifluoromethyl phenyl boronic acid, followed the procedure described in Example 56, Step C. LC/MS (M+) 741.70

Example 68

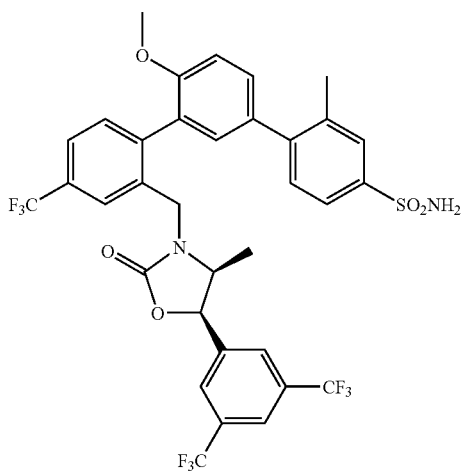

2"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-sulfonamide To a solution of 4-bromo-3-methyl-benzenesulfonyl chloride (120 mg, 0.37 mmol) in dioxane (5 ml) at room temperature, concentrated NH4OH (1 ml) was added. The mixture was stirred at room temperature for 4 h. A solution of the title compound from Example 21, Step A (100 mg, 0.14 mmol), sodium carbonate (30 mg, 0.28 mmol), and catalytic amount of tetrakis(triphenylphosphine) palladium (5% mol) in 14 ml of 1:2:4 mixture of water:EtOH:toluene was stirred under reflux for 6 h. The solvents were removed. Water (10 ml) was added. The mixture was extracted with methylene chloride (3×10 ml). The combined methylene chloride layers were washed with brine and dried over sodium sulfate. The title compound was obtained after reverse phase HPLC. $^1$H NMR (CDCl$_3$, 500 MHz): δ a mixture of 1:1 atopoisomers 7.89 (s, 1H), 7.86 (d, J=7.5 Hz, 1H), 7.79 (d, J=8.0 Hz, 1H), 7.72 (s, 2H), 7.68 (m, 2H), 7.45 (t, J=8.0 Hz, 1H), 7.39 (m, 2H), 7.13 (m, 2H), 5.60 (d, J=8.5 Hz, 0.5H), 5.38 (d, J=8.5 Hz, 0.5H), 5.00 (d, J=16.0 Hz, 0.5H), 4.94 (d, J=16.0 Hz, 0.5H), 4.17 (d, J=16.0 Hz, 0.5H), 3.99 (d, J=16.0 Hz, 0.5H), 3.90 (s, 1.5H), 3.89 (s, 1.5H), 3.84 (m, 1H), 2.42 (s, 1.5H), 2.37 (s, 1.5), 1.75 (br s, 2H), 0.59 (d, J=6.5 Hz, 1.5H), 0.48 (d, J=7.0 Hz, 1.5H). LC/MS (M+1) 747.20.

Example 69

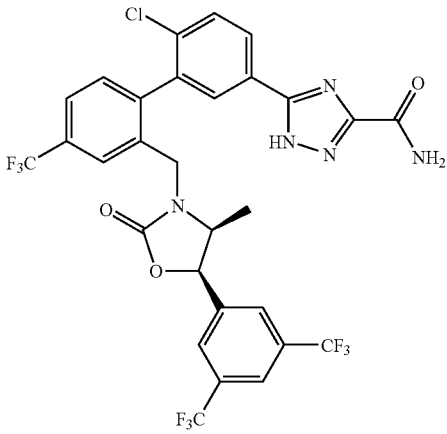

5-[2'-({(4S,5R)-5-[3,5-bis(trifluoromethyl)phenyl]-4-methyl-2-oxo-1,3-oxazolidin-3-yl}methyl)-6-chloro-4'-(trifluoromethyl)biphenyl-3-yl]-1H-1,2,4-triazole-3-carboxamide

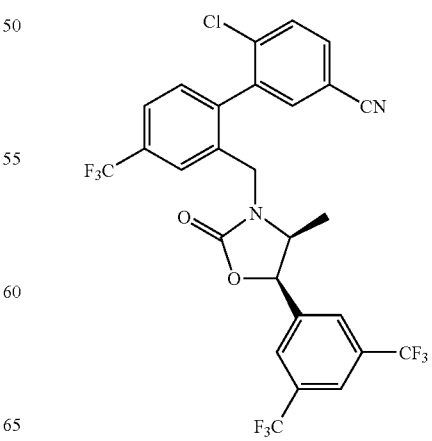

Step A 2'-({(4S,5R)-5-[3,5-bis(trifluoromethyl)phenyl]-4-methyl-2-oxo-1,3-oxazolidin-3-yl}methyl)-6-chloro-4'-(trifluoromethyl)biphenyl-3-carbonitrile A mixture of (4S,5R)-5-[3,5-bis(trifluoromethyl)phenyl]-3-[2-iodo-5-(trifluoromethyl)benzyl]-4-methyl-1,3-oxazolidin-2-one (0.5 g, 0.837 mmol), 2-chloro-5-cyanophenyl boronic acid (0.228 g, 1.26 mmol), sodium carbonate (0.18 g, 1.67 mmol), and catalytic amount of tetrakis(triphenylphosphine) palladium (0.097 g, 10% mol) in 14 ml of 1:2:4 mixture of water:EtOH:toluene was stirred under reflux for 2 h. The solvents were removed. Water (10 ml) was added. The mixture was extracted with methylene chloride (3×10 ml). The combined methylene chloride layers were washed with brine and dried over sodium sulfate. The title compound was obtained after flash column using $CH_2Cl_2$:hexane/8:2 as the elute. $^1$H NMR (CDCl$_3$, 500 MHz): δ a mixture of 1:1 atopoisomers 7.91 (s, 1H), 7.77-7.69 (m, 6H), 7.61 (d, J=2.0 Hz, 0.5H), 7.58 (d, J=2.0 Hz, 0.5H), 7.42 (d, J=8.0 Hz, 0.5H), 7.38 (d, J=8.0 Hz, 0.5H), 5.68 (d, J=8.0 Hz, 0.5H), 5.65 (d, J=8.0 Hz, 0.5H), 4.89 (d, J=15.5 Hz, 0.5H), 4.74 (d, J=16.0 Hz, 0.5H), 4.03 (d, J=16.0 Hz, 0.5H), 4.00 (m, 0.5H), 3.91 (d, J=16.0 Hz, 0.5H), 3.90 (m, 0.5H), 0.67 (d, J=6.5 Hz, 1.5H), 0.65 (d, J=6.5 Hz, 1.5H).

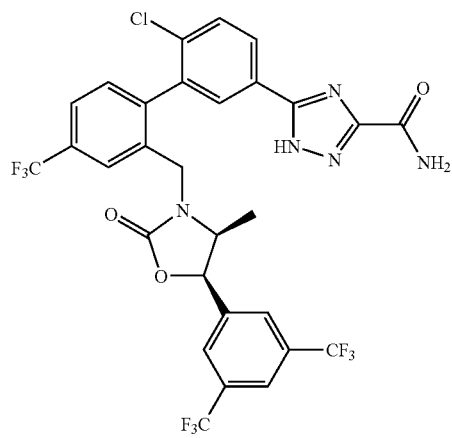

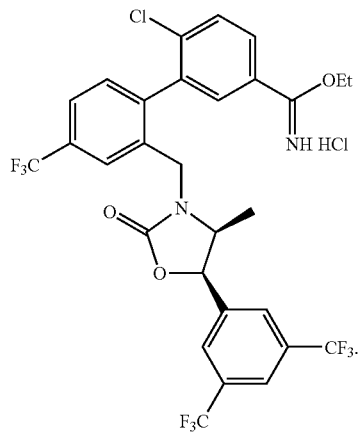

Step B Ethyl 2'-({(4S,5R)-5-[3,5-bis(trifluoromethyl)phenyl]-4-methyl-2-oxo-1,3-oxazolidin-3-yl}methyl)-6-chloro-4'-(trifluoromethyl)biphenyl-3-carboximidoate Hydrochloride The title compound from Step A (100 mg, 0.165 mmol) was mixed with a saturated solution of HCl in EtOH (10 ml). The solution was stirred at room temperature for 2 h. TLC (EtOAc/hexane 2:8) showed no starting material left. The solvent was removed to give a white solid. The material was used for next step without purification.

Step C 5-[2'-({(4S,5R)-5-[3,5-bis(trifluoromethyl)phenyl]-4-methyl-2-oxo-1,3-oxazolidin-3-yl}methyl)-6-chloro-4'-(trifluoromethyl)biphenyl-3-yl]-1H-1,2,4-triazole-3-carboxamide A mixture of the title compound from Step B (100 mg, 0.145 mmol), oxamic hydrazide (16.5 mg, 0.16 mmol) and KOAc (17.1 mg, 0.174 mmol) in EtOH (5 ml) was stirred under reflux for 2 h. LC/MS showed that the reaction was completed. The solvent was removed and the title compound was obtained after purification with reverse phase HPLC. LC/MS (M+1)$^+$ 692.38.

Example 70

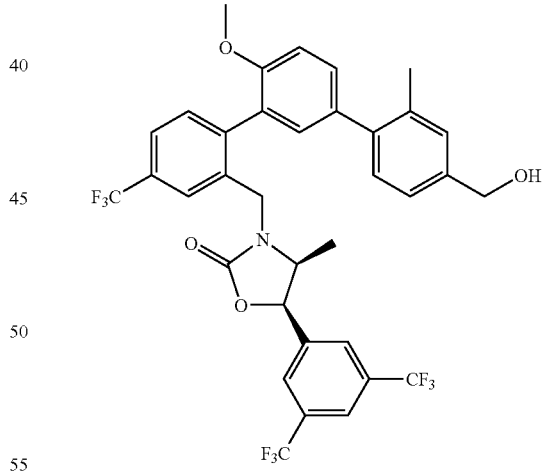

(4S,5R)-5-[3,5-bis(trifluoromethyl)phenyl]-3-{[4"-(hydroxymethyl)-6'-methoxy-2"-methyl-4-(trifluoromethyl)-1,1':3',1"-terphenyl-2-yl]methyl}-4-methyl-1,3-oxazolidin-2-one 2"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-carboxylic acid (2 g, 2.81 mmol) and THF (18.74 ml) were stirred at 0° C. (ice bath). To this mixture was added borane tetrahydrofuran complex (5.90 ml, 5.90 mmol) in 3 min. The resulting mixture was staged at 0° C. for 15 min. The ice bath was then removed. Reaction mixture was stirred at room temperature for additional 1 hr. TLC indicated completion of reaction. Reaction was quenched by water (ice bath). The crude mixture was worked up with aqueous sodium hydrogen carbonate, extracted with ethyl acetate, dried over $Na_2SO_4$, filtered and evaporated to afford a dark mixture. The resulting dark mixture was purified by flash chromatography ($SiO_2$, Biotage 40M cartridge). The column was eluted by a EtOAc/hexanes mixture (0% to 40%). Related fractions were pooled and evaporated affording the title compound. LCMS (ESI) calc.=697.19; found=680.29 $(M-OH^-)^+$. $^1H$ NMR ($CDCl_3$, 400 MHz, 1:1 mixture of atropisomers): δ 7.83 (d, J=4 Hz, 1H), 7.71 (s, 0.5H), 7.67 (s, 1H), 7.66-7.58 (m, 2.5H) 7.43 (d, J=8 Hz, 0.5H), 7.40 (d, J=8 Hz, 0.5H), 7.38-7.32 (m, 1H), 7.28-7.23 (m, 1H), 7.22-7.14 (m, 2H), 7.12 (s, 1H), 7.05 (d, J=5.6 Hz, 0.5H), 7.03 (d, J=5.6 Hz, 0.5H), 5.56 (d, J=8.4 Hz, 0.5H), 5.23 (d, J=8 Hz, 0.5H), 4.97 (d, J=10.8 Hz, 0.5H), 4.93 (d, J=10.8 Hz, 0.5H), 4.68 (s, 2H), 4.15 (d, J=15.6 Hz, 0.5H), 3.95 (d, J=15.6 Hz, 0.5H), 3.85 (s, 1.5H), 3.83 (s, 1.5H), 3.80-3.66 (m, 1H), 2.32 (s, 1.5H), 2.26 (s, 1.5H), 0.52 (d, J=6.8 Hz, 1.5H), 0.38 (d, J=6.8 Hz, 1.5H).

Example 71

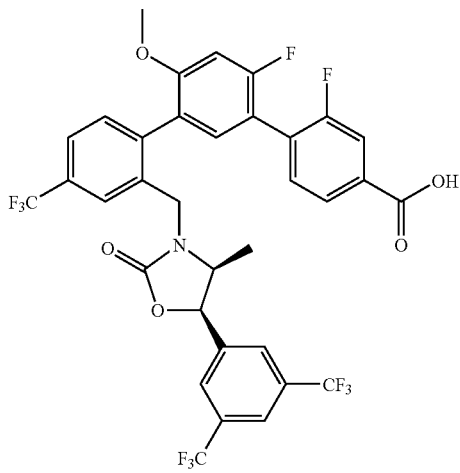

2'''-({(4S,5R)-5-[3,5-bis(trifluoromethyl)phenyl]-4-methyl-2-oxo-1,3-oxazolidin-3-yl}methyl)-2,6'-difluoro-4'-methoxy-4'''-(trifluoromethyl)-1,1':3',1'''-terphenyl-4-carboxylic Acid

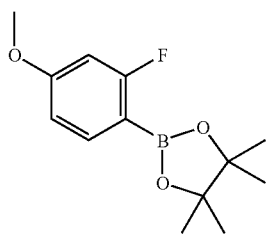

Step A 2-(2-fluoro-4-methoxyphenyl)-4,4,5,5-tetramethyl-1,3,2-dioxaborolane 1-bromo-2-fluoro-4-methoxybenzene (750 mg, 3.658 mmol), potassium acetate (718 mg, 7.32 mmol), 1,1'-bis(diphenylphosphino) ferrocene-palladium dichloride dichloromethane adduct (300 mg, 0.367 mmol), bis(pinacolato) diboron (984 mg, 4.39 mmol) and 1,4-dioxane (10 ml) were sealed and subject to microwave irradiation at 140° C. for a total of 50 minutes (40 min+10 min). LCMS of aliquot indicated complete consumption of starting material. The reaction crude was filtered through a pad of Celite (521). The filtrate was worked up with brine, extracted with ethyl acetate, dried over $Na_2SO_4$, filtered and evaporated to afford a dark oil as the crude mixture of the title compound. To be used as it was for next step. LCMS (ESI) calc.=252.13; found=253.09 $(M+1)^+$.

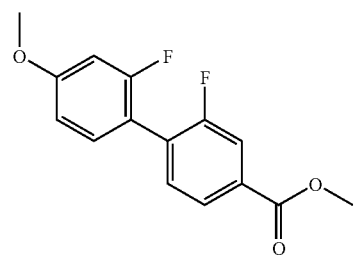

Step B Methyl 2,2'-difluoro-4'-methoxybiphenyl-4-carboxylate 2-(2-fluoro-4-methoxyphenyl)-4,4,5,5-tetramethyl-1,3,2-dioxaborolane (600 mg, 2.38 mmol), methyl 4-bromo-3-fluorobenzoate (665 mg, 2.856 mmol), 1,1'-bis(diphenylphosphino) ferrocene-palladium dichloride dichloromethane adduct (292 mg, 0.358 mmol), potassium carbonate (2.38 ml, aq., 2M, 4.76 mmol) and 1,4-dioxane (10 ml) were sealed and subject to microwave irradiation at 145° C. for 15 min. Aliquot indicated formation of the desired cpd. TLC (20% EtOAc/hex) indicated a bright purple spot @ Rf=0.4. Crude mixture was dried/$Na_2SO_4$ then purified by flash chromatography ($SiO_2$, Biotage 40+M cartridge). The column was eluted by a 0% to 20% EtOAc/hexanes mixture. Related fractions were pooled and concentrated in vacuo to afford the title compound. LCMS (ESI) calc.=278.08; found=279.09 $(M+1)^+$.

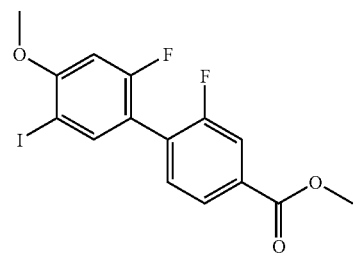

Step C Methyl 2,2'-difluoro-5'-iodo-4'-methoxybiphenyl-4-carboxylate methyl 2,2'-difluoro-4'-methoxybiphenyl-4-carboxylate (585 mg, 2.10 mmol), methanol (10 mL), iodide (534 mg, 2.10 mmol), silver sulfate (655 mg, 2.10 mmol) were stirred at room temperature. LCMS indicated formation of the desired compound. Reaction crude was worked up w/Na₂HSO₃ (aq., sat.). All volatiles were removed from the resulting mixture. The pot residue was worked up w/Na₂SO₄/EtOAc/filtration/concentration to afford a light brown solid. The crude solid was purified by flash chromatography (SiO₂, Biotage 40+M cartridge). The column was eluted by a 0% to 20% EtOAc/hexanes mixture. 5 major fractions were spilled by accident. The remaining related fractions were pooled and concentrated in vacuo to afford the title compound. LCMS (ESI) calc.=403.97; found=404.92 (M+1)⁺.

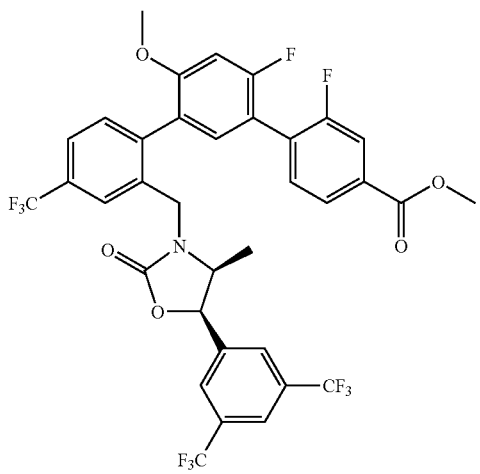

Step D Methyl 2"-({(4S,5R)-5-[3,5-bis(trifluoromethyl)phenyl]-4-methyl-2-oxo-1,3-oxazolidin-3-yl}methyl)-2,6'-difluoro-4'-ethoxy-4"-(trifluoromethyl)-1,1':3',1"-terphenyl-4-carboxylate methyl 2,2'-difluoro-5'-iodo-4'-methoxybiphenyl-4-carboxylate (100 mg, 0.247 mmol), (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (INTERMEDIATE 9, 179.2 mg, 0.30 mmol), sodium carbonate (247 µL, aq., 2M, 0.494 mmol), 1,1'-bis(diphenylphosphino) ferrocene-palladium dichloride dichloromethane adduct (40 mg, 0.049 mmol) and 1,4-dioxane (2.1 ml) were heated in a 80° C. oil bath for 8 hours. Aliquot indicated formation of the desired product. Crude mixture was concentrated under reduced pressure. The pot residue was worked up w/H₂O/EtOAc/Na₂SO₄/filtration followed by concentration to afford a dark oil. This oil was purified by a by reverse-phase prep-HPLC (Waters SunFire PrepC18 OBD 5µ, 30×100 mm) eluting w/a MeCN (0.05% TFA, v/v)/H₂O (0.05% TFA, v/v) gradient mixture (10 to 100% in 12 min, hold 100% for 3 min). Related fractions were pooled & evaporated in vacuo to afford a dark oil. The oil was further purified by SiO₂ (Prep-TLC 30% EtOAc/hex) to afford the title compound. LCMS (ESI) calc.=747.15; found=748.20 (M+1)⁺.

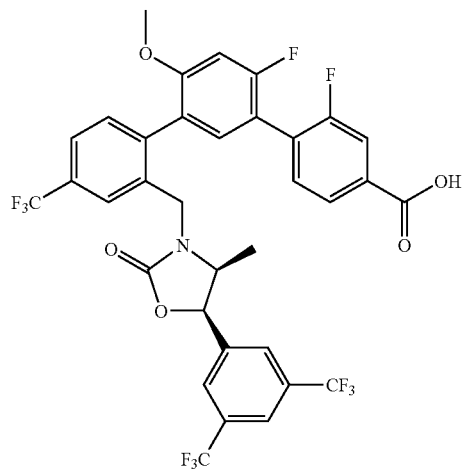

Step E 2"-({(4S,5R)-5-[3,5-bis(trifluoromethyl)phenyl]-4-methyl-2-oxo-1,3-oxazolidin-3-yl}methyl)-2,6'-difluoro-4'-methoxy-4"-(trifluoromethyl)-1,1':3',1"-terphenyl-4-carboxylic Acid methyl 2"-({(4S,5R)-5-[3,5-bis(trifluoromethyl)phenyl]-4-methyl-2-oxo-1,3-oxazolidin-3-yl}methyl)-2,6'-difluoro-4'-methoxy-4"-(trifluoromethyl)-1,1':3',1"-terphenyl-4-carboxylate (50 mg, 0.067 mmol), lithium hydroxide monohydrate (28 mg, 0.67 mmol), water (1 mL) and 1,4-dioxane (2 mL) were stirred at room temperature for 2.5 hours. LCMS of aliquot indicated formation of the desired product and complete consumption of starting material. Crude mixture was acidified (1N HCl, aq.). Volatiles were removed under reduced pressure. Pot residue was dissolved in MeCN and purified by a reverse-phase prep-HPLC (Kromasil 100-5C18, 100×21.1 mm) eluting w/MeCN (0.1% TFA, v/v)/H₂O (0.1% TFA, v/v). Corresponding fractions were pooled and evaporated in vacuo to afford a mixture. The resulting mixture was extracted with EtOAc. The separated organic phases were back washed w/water, separated, dried/Na₂SO₄, filtered and evaporated to afford the title compound. LCMS (ESI) calc.=733.13; found=734.14 (M+1)⁺. ¹H NMR (CDCl₃, 500 MHz, 1:1 mixture of atropisomers): δ 7.95 (t, J=6 Hz, 1H), 7.89-7.83 (m, 2H), 7.73 (s, 0.5H), 7.71 (s, 1H), 7.68-7.64 (m, 2H), 7.62 (s, 0.511) 7.58 (t, J=7 Hz, 0.5H), 7.53 (t, J=7.5 Hz, 0.5H), 7.42 (d, J=8 Hz, 0.5H), 7.39 (d, J=8 Hz, 0.5H), 7.31-7.23 (m, 1H), 6.89 (d, J=4 Hz, 0.5H), 6.87 (d, J=3.5 Hz, 0.5H), 5.61 (d, J=8 Hz, 0.5H), 5.29 (d, J=8 Hz, 0.5H), 5.05 (d, J=16 Hz, 0.5H), 4.93 (d, J=16 Hz, 0.5H), 4.16 (d, J=16.5 Hz, 0.5H), 3.94 (d, J=16 Hz, 0.5H), 3.89 (s, 1.5H), 3.87 (s, 1.5H), 3.85-3.72 (m, 1H), 0.59 (d, J=7 Hz, 1.5H), 0.43 (d, J=6 Hz, 1.5H).

Example 72

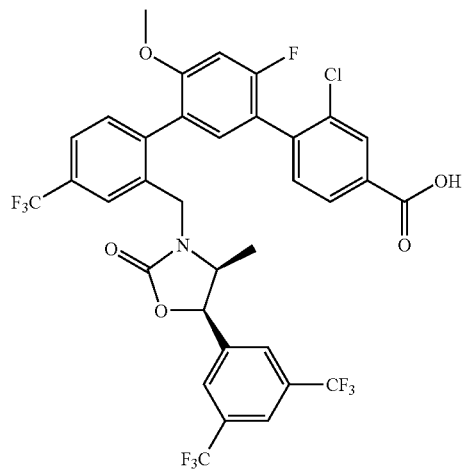

2"'-({(4S,5R)-5-[3,5-bis(trifluoromethyl)phenyl]-4-methyl-2-oxo-1,3-oxazolidin-3-yl}methyl)-2-chloro-6'-fluoro-4'-methoxy-4"-(trifluoromethyl)-1,1':3',1"-terphenyl-4-carboxylic Acid

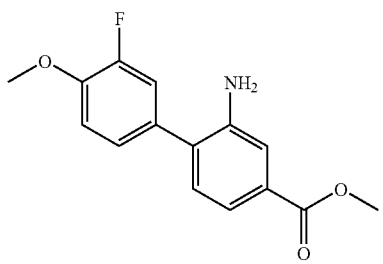

Step A Methyl 2-amino-2'-fluoro-4'-methoxybiphenyl-4-carboxylate 1-bromo-2-fluoro-4-methoxybenzene (750 mg, 3.66 mmol), [2-amino-4-(methoxycarbonyl)phenyl]boronic acid (856 mg, 4.39 mmol), potassium acetate (3.66 mL, 2M aq, 7.32 mmol), 1,1'-bis(diphenylphosphino) ferrocene-palladium dichloride dichloromethane adduct (299 mg, 10 mol. %) and ethanol (30 ml) were heated in a 80° C. oil bath for 3 hours. Reaction crude was worked up with brine, extracted with ethyl acetate, dried over Na$_2$SO$_4$, filtered and evaporated to afford a dark oil. This oil was purified by SiO$_2$ (Biotage Horizon Flash system, 40+M cartridge, 0-25% EtOAc/hexanes, v/v) to afford the title compound. LCMS (ESI) calc.=275.10; found=276.09 (M+1)$^+$.

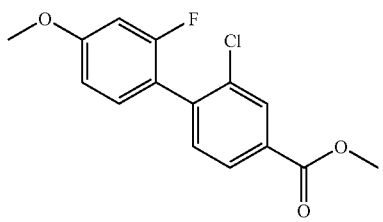

Step B Methyl 2-chloro-2'-fluoro-4'-methoxybiphenyl-4-carboxylate

Amyl nitrite (420 µL, 3.19 mmol) and copper (II) chloride (343 mg, 2.55 mmol) were suspended in acetonitrile (5 mL) and heated in a 65° C. oil bath with magnetic stirring. To this hot mixture was added methyl 2-amino-2'-fluoro-4'-methoxybiphenyl-4-carboxylate (585 mg, 2.13 mmol, in 5 mL MeCN) in about 1 minute. The resulting mixture was heated in a 65° C. oil bath for 2 hours. Reaction crude was purified by SiO$_2$ (Biotage Horizon Flash system, 40+M cartridge, 0-20% EtOAc/hexanes, v/v) to afford the title compound. LCMS (ESI) calc.=294.05; found=295.03 (M+1)$^+$.

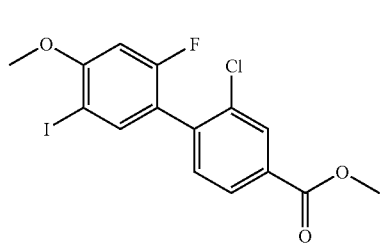

Step C Methyl 2-chloro-2'-fluoro-5'-iodo-4'-methoxybiphenyl-4-carboxylate methyl 2-chloro-2'-fluoro-4'-methoxybiphenyl-4-carboxylate (550 mg, 1.87 mmol), methanol (8 mL), iodide (474 mg, 1.87 mmol) and silver sulfate (583 mg, 1.87 mmol) were stirred at room temperature for 2 hours. Reaction crude was worked up with NaHSO$_3$ (aq). Volatiles were removed under reduced pressure. The pot residue was worked up with brine, extracted with ethyl acetate, dried over Na$_2$SO$_4$, filtered and evaporated to afford a light brown solid. This solid was purified by SiO$_2$ (Biotage Horizon Flash system, 40+M cartridge, 0-20% EtOAc/hexanes, v/v) to afford the title compound. LCMS (ESI) calc.=419.94; found=420.86 (M+1)$^+$.

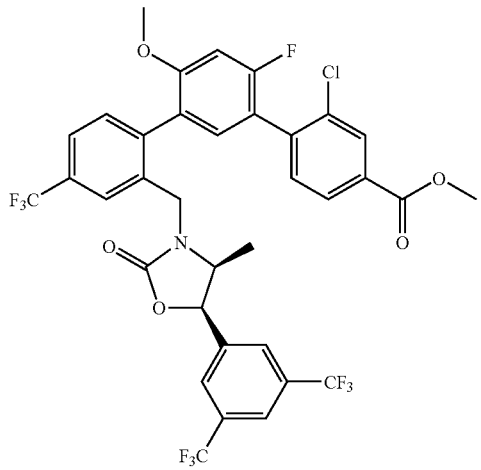

Step D Methyl 2"'-({(4S,5R)-5-[3,5-bis(trifluoromethyl)phenyl]-4-methyl-2-oxo-1,3-oxazolidin-3-yl}methyl)-2-chloro-6'-fluoro-4'-methoxy-4"-(trifluoromethyl)-1,1':3',1"-terphenyl-4-carboxylate methyl 2-chloro-2'-fluoro-5'-iodo-4'-methoxybiphenyl-4-carboxylate (177 mg, 0.42 mmol), (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (INTERMEDIATE 9, 250 mg, 0.42 mmol), potassium carbonate (0.42 mL, aq., 2M, 0.84 mmol), 1,1'-bis(diphenylphosphino) ferrocene-palladium dichloride dichloromethane adduct (51 mg, 0.06 mmol) and 1,4-dioxane (2 ml) were sealed and subject to microwave irradiation at 140° C. for 15 min. Aliquot indicated (LCMS) complete consumption of starting material and formation of the desired product. The crude was worked up w/H$_2$O/EtOAc/Na$_2$SO$_4$/filtration/concentration to afford a dark oil. This oil was purified by SiO$_2$ (Prep-TLC, 5% EtOAc/5% hex/90% DCM) to afford a dark oil as a mixture of product and impurities. The oil was further purified by reverse-phase prep-HPLC (Kromasil 100-5C18, 100×21.1 mm) eluting w/a MeCN (0.1% TFA, v/v)/H₂O (0.1% TFA, v/v) gradient mixture. Corresponding fractions were pooled & evaporated in vacuo to afford 205 mg of dark green glass. TLC (30% EtOAc/hex) indicated a dark baseline spot and traces of impurities above and below the compound spot. The green glass was further purified by SiO₂ (Prep-TLC, 100% DCM) to afford the title compound. LCMS (ESI) calc.=763.12; found=764.09 (M+1)⁺.

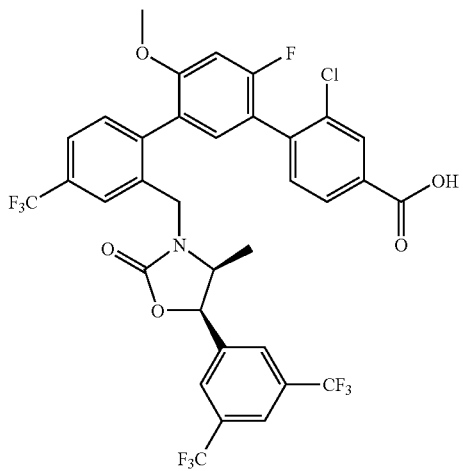

Step E 2"-({(4S,5R)-5-[3,5-bis(trifluoromethyl)phenyl]-4-methyl-2-oxo-1,3-oxazolidin-3-yl}methyl)-2-chloro-6'-fluoro-4'-methoxy-4"-(trifluoromethyl)-1,1':3',1"-terphenyl-4-carboxylic Acid methyl 2"-({(4S,5R)-5-[3,5-bis(trifluoromethyl)phenyl]-4-methyl-2-oxo-1,3-oxazolidin-3-yl}methyl)-2-chloro-6'-fluoro-4'-methoxy-4"-(trifluoromethyl)-1,1':3',1"-terphenyl-4-carboxylate (84.5 mg, 0.11 mmol), lithium hydroxide monohydrate (46.2 mg, 1.1 mmol), water (1 mL) and 1,4-dioxane (2 mL) were stirred at room temperature. LCMS of aliquot at reaction time was 2 hrs indicated completion of reaction. Volatiles were removed under reduced pressure. Crude mixture was dissolved in MeCN and acidified by HCl (1N, aq.) to afford a clear solution. This solution was purified by a reverse-phase prep-HPLC (Kromasil 100-5C18, 100×21.1 mm) eluting w/a MeCN (0.1% TFA, v/v)/H₂O (0.1% TFA, v/v) gradient mixture. Corresponding fractions were pooled & evaporated in vacuo to afford a colorless glass. This glass was dissolved in DCM and washed with water. Organic extracts were combined, dried/Na₂SO₄, filtered and evaporated to afford the title compound. LCMS (ESI) calc.=749.10; found-750.06 (M+1)⁺. ¹H NMR (CDCl₃, 500 MHz, 1:1 mixture of atropisomers): δ 8.21 (dd, J=10, 2 Hz, 1H), 8.03 (dd, J=8, 2 Hz, 1H), 7.86 (s, 1H), 7.73-7.68 (m, 1.5H), 7.68-7.62 (m, 2.5H), 7.48 (t, J=7.5 Hz, 1H), 7.41 (dd, J=11, 8 Hz, 1H), 7.17 (dd, J=8.5, 2 Hz, 1H), 6.86 (dd, J=11, 3.5 Hz, 1H), 6.60 (d, J=8 Hz, 0.5H), 5.40 (d, J=8 Hz, 0.5H), 4.94 (t, J=15 Hz, 1H), 4.18 (d, J=16 Hz, 0.5H), 3.95 (d, J=16 Hz, 0.5H), 3.87 (s, 3H), 3.85-3.74 (m, 1H), 0.56 (d, J=6.5 Hz, 1.5H), 0.46 (d, J=6.5 Hz, 1.5H).

Example 73

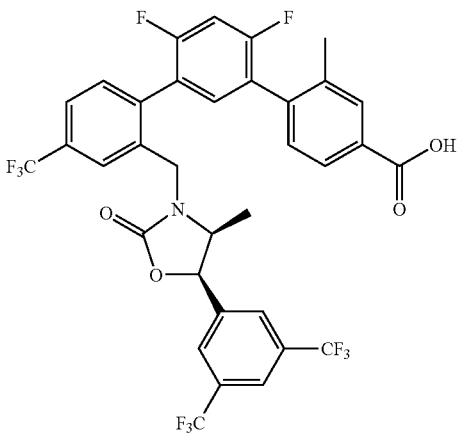

2"-({(4S,5R)-5-[3,5-bis(trifluoromethyl)phenyl]-4-methyl-2-oxo-1,3-oxazolidin-3-yl}methyl)-4',6'-difluoro-2-methyl-4'-(trifluoromethyl-1,1':3',1"-terphenyl-4-carboxylic Acid

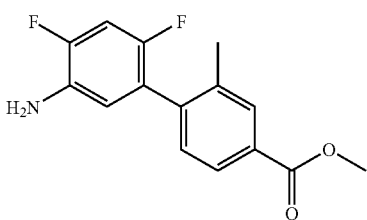

Step A Methyl 5'-amino-2',4'-difluoro-2-methylbiphenyl-4-carboxylate 5-bromo-2,4-difluoroaniline (500 mg, 2.40 mmol), methyl 3-methyl-4-(4,4,5,5-tetramethyl-1,3,2-dioxaborolan-2-yl)benzoate (INTERMEDIATE 16, 797 mg, 2.88 mmol), sodium carbonate (2.40 mL, aq., 2M, 2.88 mmol), 1,1'-bis(diphenylphosphino) ferrocene-palladium dichloride dichloromethane adduct (196 mg, 0.24 mmol) and ethanol (15 ml) were heated in an 80° C. oil bath for 3 hours then allowed to cool to ambient overnight. Volatiles were removed under reduced pressure. The pot residue was worked up w/DCM/brine/Na₂SO₄/filtration/concentration to afford a dark oil. The resulting oil was purified by flash chromatography (SiO₂, Biotage 40+M cartridge). The column was eluted by a 0% to 40% EtOAc/hexanes gradient mixture. Related fractions were pooled and concentrated in vacuo to afford the title compound. LCMS (ESI) calc.=277.09; found=278.03 (M+1)⁺.

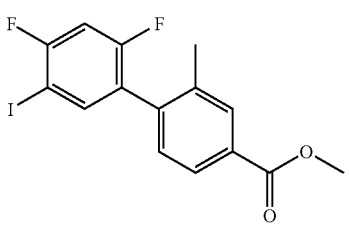

Step B Methyl 2',4'-difluoro-5'-iodo-2-methylbiphenyl-4-carboxylate methyl 5'-amino-2',4'-difluoro-2-methylbiphenyl-4-carboxylate (500 mg, 1.80 mmol), 3-methylbutyl nitrite (317 mg, 2.71 mmol), iodine (549 mg, 2.16 mmol) and chloroform (15 ml) were refluxed in an oil bath for 5 hours then allowed to cooled to ambient overnight. Reaction crude was purified by flash chromatography (SiO$_2$, Biotage 40+M cartridge) eluted with a EtOAc/hexanes gradient mixture. Related fractions were pooled and concentrated in vacuo to afford the title compound. LCMS (ESI) calc.=387.98; found=388.92 (M+1)$^+$.

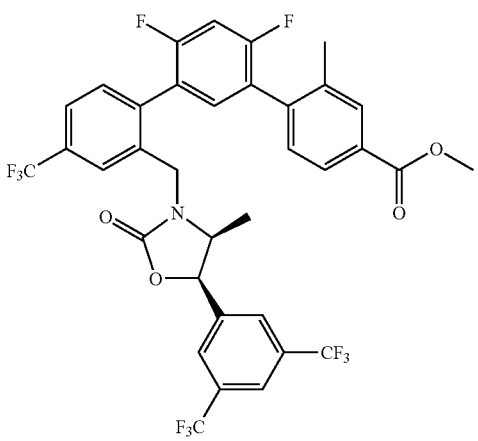

Step C Methyl 2"-({(4S,5R)-5-[3,5-bis(trifluoromethyl)-phenyl]-4-methyl-2-oxo-1,3-oxazolidin-3-yl}methyl)-4',6'-difluoro-2-methyl-4"-(trifluoromethyl)-1,1':3',1"-terphenyl-4-carboxylate methyl 2',4'-difluoro-5'-iodo-2-methylbiphenyl-4-carboxylate (100 mg, 0.26 mmol, dissolved in 1 mL ethanol), (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (INTERMEDIATE 9, 185 mg, 0.31 mmol, dissolved in 2.2 mL 1,4-dioxane), sodium carbonate (258 µL, aq., 2M, 0.516 mmol) and 1,1'-bis(diphenylphosphino) ferrocene-palladium dichloride dichloromethane adduct (42 mg, 0.05 mmol) were heated in an 80° C. oil bath for 2 hours. LCMS trace of reaction aliquot indicated completion of reaction. Reaction crude was dried/Na$_2$SO$_4$ and then deposited on 2 prep-TLC plates (SiO$_2$). The plates were developed by a 20% EtOAc/hexanes mixture to afford a clear glass. The glass was further purified by reverse-phase prep-HPLC (Kromasil 100-5C18, 100×21.1 mm) eluting w/a MeCN (0.1% TFA, v/v)/H$_2$O (0.1% TFA, v/v) gradient mixture. Corresponding fractions were pooled & evaporated in vacuo to afford a colorless glass. This glass was dissolved in DCM and washed with water. Organic extracts were combined, dried/Na$_2$SO$_4$, filtered and evaporated to afford the title compound. LCMS (ESI) calc.=731.15; found=732.06 (M+1)$^+$.

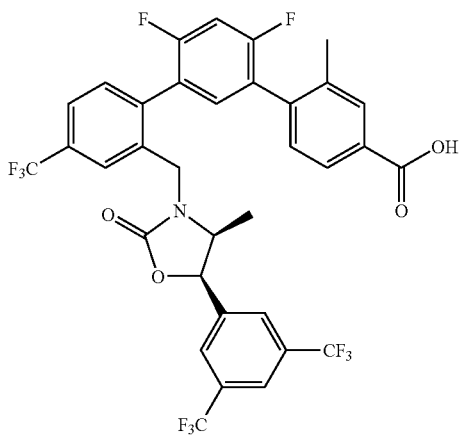

Step D 2"-({(4S,5R)-5-[3,5-bis(trifluoromethyl)phenyl]-4-methyl-2-oxo-1,3-oxazolidin-3-yl}methyl)-4',6'-difluoro-2-methyl-4"-(trifluoromethyl)-1,1':3',1"-terphenyl-4-carboxylic Acid methyl 2"-({(4S,5R)-5-[3,5-bis(trifluoromethyl)phenyl]-4-methyl-2-oxo-1,3-oxazolidin-3-yl}methyl)-4',6'-difluoro-2-methyl-4"-(trifluoromethyl)-1,1':3',1"-terphenyl-4-carboxylate (73.5 mg, 0.10 mmol), lithium hydroxide monohydrate (42 mg, 1 mmol), water (1 mL) and 1,4-dioxane (2 mL) were stirred at room temperature for 2 hrs. Volatiles were removed under reduced pressure. Pot residue was dissolved in a MeCN/1N HCl (aq) mixture and purified by reverse-phase prep-HPLC (Kromasil 100-5C18, 100×21.1 mm) eluting w/a MeCN (0.1% TFA, v/v)/H$_2$O (0.1% TFA, v/v) gradient mixture. Corresponding fractions were pooled & evaporated in vacuo to afford the title compound. LCMS (ESI) calc.=717.14; found=718.17 (M+1)$^+$. $^1$H NMR (CDCl$_3$, 500 MHz): δ 8.04 (s, 1H), 7.97 (d, J=8 Hz, 1H), 7.88 (s, 1H), 7.74-7.67 (m, 4H), 7.51-7.45 (m, 1H), 7.34 (d, J=8 Hz, 1H), 7.19 (br s, 1H), 7.09 (t, J=9 Hz, 1H), 5.59 (d, J=8 Hz, 1H), 5.08-4.80 (m, 1H), 4.20-3.78 (m, 2H), 2.32 (s, 3H), 0.62 (s, 3H).

Example 74

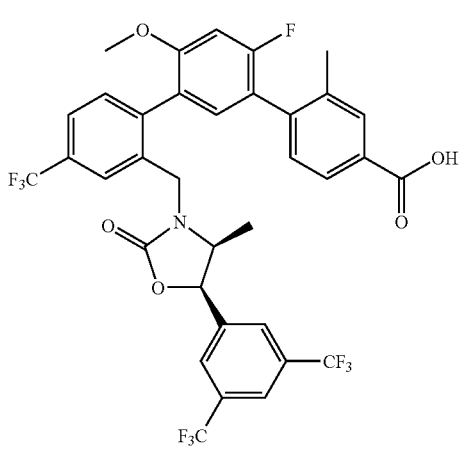

2'''-({(4S,5R)-5-[3,5-bis(trifluoromethyl)phenyl]-4-methyl-2-oxo-1,3-oxazolidin-3-yl}methyl)-6'-fluoro-4'-methoxy-3-methyl-4''-(trifluoromethyl)-1,1':3',1''-terphenyl-4-carboxylic Acid

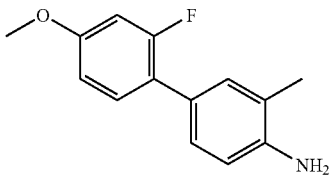

Step A 2'-fluoro-4'-methoxy-3-methylbiphenyl-4-amine (2-fluoro-4-methoxyphenyl)boronic acid (356.7 mg, 2.1 mmol), 4-bromo-2-methylaniline (391 mg, 2.1 mmol), potassium carbonate (3.15 mL, 2M aq, 6.3 mmol), 1,1'-bis(diphenylphosphino) ferrocene-palladium dichloride dichloromethane adduct (257 mg, 0.31 mol. %) and ethanol (12 ml) were heated in a 80° C. oil bath. Reaction was completed in 1 hour by TLC (40% EtOAc/hexanes) and LCMS. Volatiles were removed under reduced pressure. Crude residue was worked up with DCM/brine/Na$_2$SO$_4$/filtration/concentration to afford a dark oil. This oil was purified by flash chromatography (SiO$_2$, Biotage 40+M cartridge). The column was eluted by a 0% to 40% EtOAc/hexanes mixture. Related fractions were pooled and concentrated in vacuo to afford title compound. LCMS (ESI) calc.=231.11; found=232.09 (M+1)$^+$.

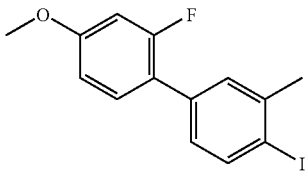

Step B 2-fluoro-4'-iodo-3'-methylbiphenyl-4-yl Methyl Ether

2'-fluoro-4'-methoxy-3-methylbiphenyl-4-amine (190 mg, 0.822 mmol), 3-methylbutyl nitrite (144.4 mg, 1.233 mmol), iodine (251 mg, 0.986 mmol) and chloroform (7 ml) were refluxed in an oil bath for 3.5 hours then allowed to cooled to ambient overnight. Reaction crude was purified by flash chromatography (SiO$_2$, Biotage 40+M cartridge) eluted with a EtOAc/hexanes gradient mixture. Related fractions were pooled and concentrated in vacuo to afford the title compound. LCMS was showing the solid to be about 70 A % pure. LCMS (ESI) calc.=LCMS (ESI) calc.=341.99; found=341.94 (M)$^+$.

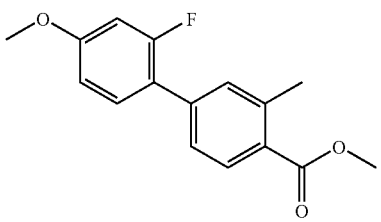

Step C Methyl 2'-fluoro-4'-methoxy-3-methylbiphenyl-4-carboxylate 2-fluoro-4'-iodo-3'-methylbiphenyl-4-yl methyl ether (289 mg, 0.845 mmol), trans-bis(triphenylphosphine)palladium (II) chloride (59.3 mg, 0.08 mmol), triethylamine (177 µL, 1.27 mmol) and methanol (5 mL) were shaked under carbon monoxide (50 psi) at 60° C. for 17 hours. Aliquot indicated complete consumption of starting material and a m/e 275 peak (major peak). Crude mixture was purified by SiO$_2$ (prep-TLC, 20% EtOAc/hexanes) to afford the title compound. LCMS (ESI) calc.=274.10; found=275.09 (M+1)$^+$.

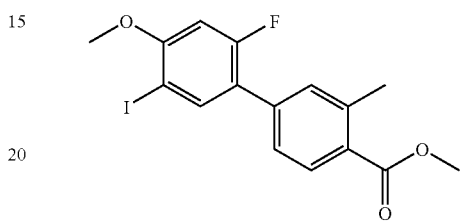

Step D Methyl 2'-fluoro-5'-iodo-4'-methoxy-3-methylbiphenyl-4-carboxylate methyl 2'-fluoro-4'-methoxy-3-methylbiphenyl-4-carboxylate (100 mg, 0.365 mmol), methanol (3 mL), iodide (93 mg, 0.366 mmol) and silver sulfate (114 mg, 0.366 mmol) were stirred at room temperature for 1.5 hours. Reaction crude was quenched by Na$_2$SO$_3$ (sat., aq.). Volatiles were removed from the grayish brown mixture. The pot residue was worked up with H$_2$O/EtOAc/Na$_2$SO$_4$/filtration/concentration to afford the title compound. LCMS (ESI) calc.=400.00; found=400.96 (M+1)$^+$.

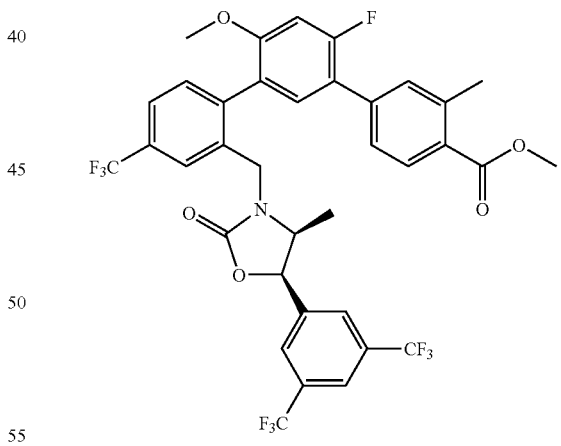

Step E Methyl 2'''-({(4S,5R)-5-[3,5-bis(trifluoromethyl)phenyl]-4-methyl-2-oxo-1,3-oxazolidin-3-yl}methyl)-6'-fluoro-4'-methoxy-3-methyl-4''-(trifluoromethyl)-1,1':3',1''-terphenyl-4-carboxylate methyl 2'-fluoro-5'-iodo-4'-methoxy-3-methylbiphenyl-4-carboxylate (135 mg, 0.337 mmol), (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (INTERMEDIATE 9, 403 mg, 0.675 mmol, dissolved in 4.75 mL 1,4-dioxane), sodium carbonate (337 μL, aq., 2M, 0.674 mmol) and 1,1'-bis(diphenylphosphino) ferrocene-palladium dichloride dichloromethane adduct (55 mg, 0.07 mmol) were heated in an 80° C. oil bath for 2 hours then allowed to cooled to ambient overnight. Added additional (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (INTERMEDIATE 9, 200 mg, 0.335 mmol, dissolved in 2.35 mL 1,4-dioxane) and resumed heating for 2 more hours. Reaction aliquot indicated the presence of M+23 (LCMS). Crude mixture was cooled, dried/$Na_2SO_4$ and deposited on prep-TLC plates ($SiO_2$). The plates were developed by a 30% DCM/hex mixture to afford a green oil of 350 mg. The green oil was further purified by prep-TLC ($SiO_2$, 30% DCM/hexanes) to afford a green glass. The green oil/glass was further purified by prep-TLC ($SiO_2$, 20% EtOAc/hexanes) to afford the title compound. LCMS (ESI) calc.=743.17; found=744 $(M+1)^+$.

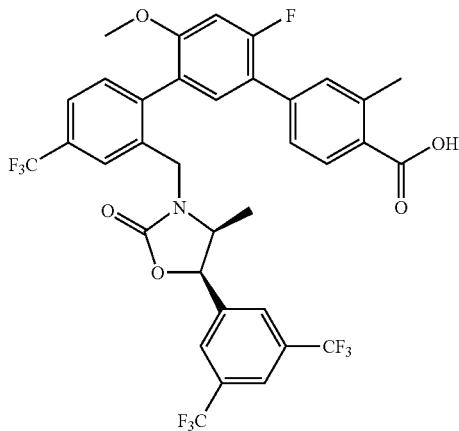

Step F 2"-({(4S,5R)-5-[3,5-bis(trifluoromethyl)phenyl]-4-methyl-2-oxo-1,3-oxazolidin-3-yl}methyl)-6'-fluoro-4'-methoxy-3-methyl-4"-(trifluoromethyl)-1,1':3',1"-terphenyl-4-carboxylic Acid methyl 2"-({(4S,5R)-5-[3,5-bis(trifluoromethyl)phenyl]-4-methyl-2-oxo-1,3-oxazolidin-3-yl}methyl)-6'-fluoro-4'-methoxy-3-methyl-4"-(trifluoromethyl)-1,1':3',1"-terphenyl-4-carboxylate (55 mg, 0.074 mmol), lithium hydroxide monohydrate (31 mg, 0.74 mmol), water (1 mL) and 1,4-dioxane (2 mL) were stirred at room temperature overnight. LCMS trace of reaction aliquot indicated completion of reaction. Crude mixture was acidified by HCl (1N aq.). Volatiles were removed under reduced pressure. Pot residue was dissolved in a water/MeCN mixture and purified by reverse-phase prep-HPLC (Kromasil 100-5C18, 100×21.1 mm) eluting w/a MeCN (0.1% TFA, v/v)/$H_2O$ (0.1% TFA, v/v) gradient mixture. Corresponding fractions were pooled & evaporated in vacuo to afford a light yellow glass. This residue was dissolved in EtOAc and washed w/water (10 mL×2), separated, dried/$Na_2SO_4$, filtered and concentrated to afford the title compound. LCMS (ESI) calc.=729.16; found=730.15 $(+1)^+$. $^1$H NMR (CDCl$_3$, 500 MHz, 1:1 mixture of atropisomers): δ 8.10 (t, J=7.8 Hz, 1H), 7.85 (d, J=5 Hz, 1H), 7.70 (s, 1.5H), 7.66 (d, J=8 Hz, 1H), 7.62 (s, 1.5H), 7.47-7.38 (m, 3H), 7.30-7.25 (m, 1H), 6.85 (dd, J=12.5, 3 Hz, 1H), 5.61 (d, J=8 Hz, 0.5H), 5.31 (d, J=8 Hz, 0.5H), 4.94 (d, J=4.5 Hz, 0.5H), 4.91 (d, J=4 Hz, 0.5H), 4.15 (d, J=16.5 Hz, 0.5H), 3.93 (d, J=16 Hz, 0.5H), 3.86 (s, 3H), 3.86-3.76 (m, 1H), 2.68 (s, 3H), 0.57 (d, J=6.5 Hz, 1.5H), 0.46 (d, J=6.5 Hz, 1.5H).

Example 75

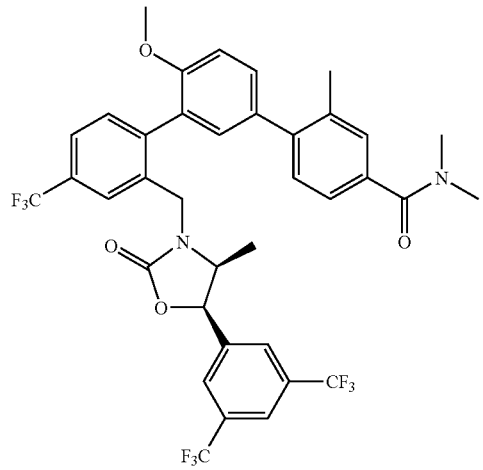

2"-({(4S,5R)-5-[3,5-bis(trifluoromethyl)phenyl]-4-methyl-2-oxo-1,3-oxazolidin-3-yl}methyl)-4'-methoxy-N,N,2-trimethyl-4"-(trifluoromethyl)-1,1':3',1"-terphenyl-4-carboxamide 2"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-carboxylic acid (EXAMPLE 30,300 mg, 0.42 mmol), N-methylmethanamine hydrochloride (41 mg, 0.50 mmol), N-[3-(dimethylamino)propyl]-N'-ethylcarbodiimide hydrochloride (121 mg, 0.63 mmol), 1H-1,2,3-benzotriazol-1-ol hydrate (86 mg, 0.56 mmol) and triethylamine (146 μL, 1.05 mmol) were stirred in DCM (5 mL) at room temperature for 1.5 hours. LCMS of aliquot at this time indicated formation of the desired product and complete consumption of starting material. Crude mixture was diluted with MeCN and purified by reversed phase preparative HPLC (Kromasil 100-5C18, 100× 21.1 mm) eluting with (acetonitrile+0.1% v/v TFA)/(water+ 0.1% v/v TFA) (10% to 100% organic in 10 min, hold 100% for 2 min, 20 mL/min) to give a solid foam. This solid foam was dissolved in EtOAc and washed with NaHCO$_3$ (sat., aq) and then with water. Aqueous layers were separated from the extracts. The combined aqueous phases were back extracted with EtOAc. The combined extracts were dried over $Na_2SO_4$, filtered and then concentrated in vacuo to afford the title compound. LCMS (ESI) calc.=738.21; found=739.41 $(M+1)^+$. $^1$H NMR (CDCl$_3$, 500 MHz, 1:1 mixture of atropisomers): δ 7.85 (s, 0.5H), 7.71 (s, 0.5H), 7.69 (s, 1H), 7.67-7.62 (m, 2.5H), 7.44 (d, J=8 Hz, 0.5H), 7.41 (d, J=8.5 Hz, 0.5H), 7.36 (t, J=7.5 Hz, 1H), 7.32 (d, J=8 Hz, 1H), 7.25 (s, 0.5H), 7.23 (s, 1H), 7.19 (d, J=8 Hz, 0.5H), 7.12 (t, J=2 Hz, 1H), 7.07 (d, J=7 Hz, 0.5H), 7.05 (d, J=7 Hz, 0.5H), 5.58 (d, J=8 Hz, 0.5H), 5.30 (d, J=8 Hz, 0.5H), 4.96 (d, J=16 Hz, 1H), 4.16 (d, J=16 Hz, 0.5H), 3.97 (d, J=15.5 Hz, 0.5H), 3.86 (s, 3H), 3.81-3.73 (m, 1H), 3.11 (s, 3H), 3.02 (s, 3H), 2.33 (s, 1.5H), 2.27 (s, 1.5H), 0.54 (d, J=6.5 Hz, 1.5H), 0.41 (d, J=6.5 Hz, 1.5H).

145

The following compounds were prepared following the general procedure outlined in Example 21.

146

The following compounds were prepared following the general procedure outlined in Example 1.

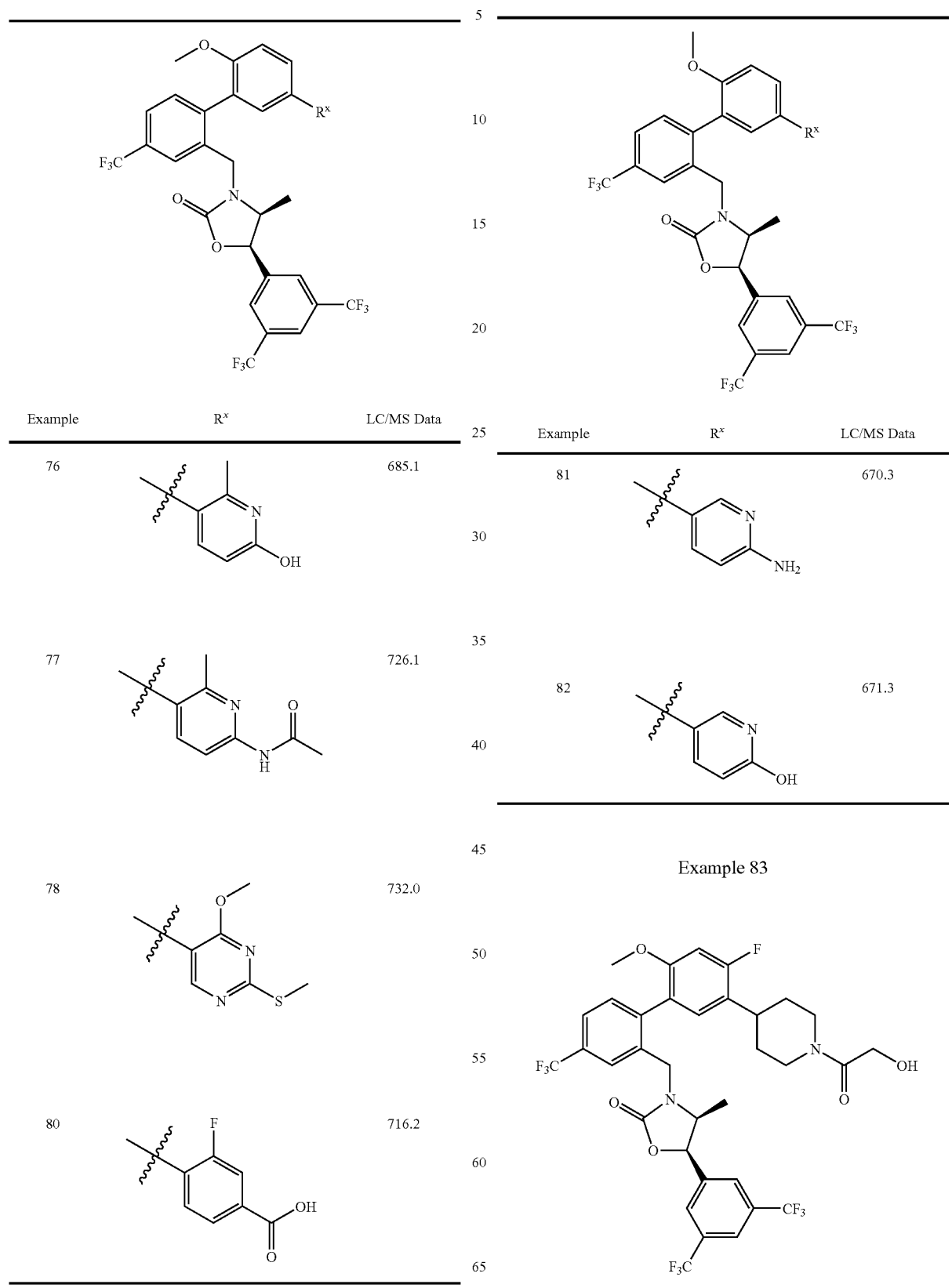

| Example | R$^x$ | LC/MS Data |
|---|---|---|
| 76 | 2-methyl-6-hydroxypyridin-3-yl | 685.1 |
| 77 | 6-acetamido-2-methylpyridin-3-yl | 726.1 |
| 78 | 4-methoxy-2-(methylthio)pyrimidin-5-yl | 732.0 |
| 80 | 3-fluoro-4-carboxyphenyl | 716.2 |

| Example | R$^x$ | LC/MS Data |
|---|---|---|
| 81 | 6-aminopyridin-3-yl | 670.3 |
| 82 | 6-hydroxypyridin-3-yl | 671.3 |

Example 83

(4S,5R)-5-[3,5-bis(trifluoromethyl)phenyl]-3-{[4-fluoro-5'-(1-glycoloylpiperidin-4-yl)-2'-methoxy-4-(trifluoromethyl)biphenyl-2-yl]methyl}-4-methyl-1,3-oxazolidin-2-one Step A: 2-[4-(2-fluoro-5-iodo-4-methoxyphenyl)piperidin-1-yl]-2-oxoethyl Acetate A stirred solution of 4-(2-fluoro-5-iodo-4-methoxyphenyl)piperidine (50 mg; 0.149 mmol) in DMF (1.2 mL) under $N_2$ was treated with N,N-diisopropylethylamine (26 µL; 0.149 mmol), followed by acetoxyacetyl chloride (16 µL, 0.149 mmol). The resultant solution was stirred at room temperature for 5 h. The reaction was partitioned between EtOAc (25 mL) and saturated NaHCO₃ (25 mL). The aqueous layer was extracted with EtOAc (3×25 mL) and the combined organic fractions were washed with water and brine (25 mL each), dried ($Na_2SO_4$), filtered and concentrated in vacuo. The residue was purified by flash silica gel chromatography, eluting with EtOAC/hexanes, to afford 2-[4-(2-fluoro-5-iodo-4-methoxyphenyl)piperidin-1-yl]-2-oxoethyl acetate as a colorless oil. LCMS=435.8 (M+1)⁺. ¹H NMR (CDCl₃, 500 MHz) δ 7.52 (d, J=8.2 Hz, 1H), 6.56 (d, J=12.2 Hz, 1H), 4.76 (s, 2H), 4.76-4.70 (m, 1H), 3.85 (s, 3H), 3.76 (br d, J=13 Hz, 1H), 3.17 (t, J=12.6 Hz, 1H), 2.98 (tt, J=12.1, 3.4 Hz, 1H), 2.68 (t, J=12.4 Hz, 1H), 2.20 (s, 3H), 1.90-1.82 (m, 2H), 1.70-1.62 (m, 2H).

Step B: 2-{4-[2'-({(4S,5R)-5-[3,5-bis(trifluoromethyl)phenyl]-4-methyl-2-oxo-1,3-oxazolidin-3-yl}methyl)-4-fluoro-6-methoxy-4'-(trifluoromethyl)biphenyl-3-yl]piperidin-1-yl}-oxoethyl Acetate A mixture of 2-[4-(2-fluoro-5-iodo-4-methoxyphenyl)piperidin-1-yl]-2-oxoethyl acetate (Step A; 33 mg; 0.076 mmol) and (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (Intermediate 9; 68 mg, 0.114 mmol) was treated with 1,1'-bis(di-1-butylphosphino)ferrocene palladium dichloride (~5 mg) as described earlier. The product was purified by chiral HPLC (ChiralPak IA column, 15% IPA/heptane) to afford 2-{4-[2'-({(4S,5R)-5-[3,5-bis(trifluoromethyl)phenyl]-4-methyl-2-oxo-1,3-oxazolidin-3-yl}methyl)-4-fluoro-6-methoxy-4'-(trifluoromethyl)biphenyl-3-yl]piperidin-1-yl}-2-oxoethyl acetate as a colorless glass. LCMS=779.0 (M+1)⁺. ¹H NMR (CDCl₃, 500 MHz, mixture of atropisomers) δ 7.86 (s, 1H), 7.69 (s, 2H), 7.68-7.60 (m, 2H), 7.32 (d, J=7.8 Hz, 1H), 6.96-6.91 (m, 1H), 6.72 (dd, J=11.9, 2.1 Hz, 1H), 5.59-5.54 (m, 1H), 4.90 (d, J=15.6 Hz, 1H), 4.80-4.65 (m, 3H), 4.13-4.04 (m, 1H), 3.88-3.72 (m, 2H), 3.78 (s, 3H), 3.21-3.04 (m, 2H), 2.72-2.67 (m, 1H), 2.17 (s, 3H), 1.96-1.83 (m, 2H), 1.70-1.59 (m, 2H), 0.42-0.39 (m, 3H)

Step C (4S,5R)-5-[3,5-bis(trifluoromethyl)phenyl]-3-{[4'-fluoro-5'-(1-glycoloylpiperidin-4-yl)-2'-methoxy-4-(trifluoromethyl)biphenyl-2-yl]methyl}-4-methyl-1,3-oxazolidin-2-one To a stirred solution of 2-{4-[2'-({(4S,5R)-5-[3,5-bis(trifluoromethyl)phenyl]-4-methyl-2-oxo-1,3-oxazolidin-3-yl}methyl)-4-fluoro-6-methoxy-4'-(trifluoromethyl)biphenyl-3-yl]piperidin-1-yl}-2-oxoethyl acetate (24 mg, 0.031 mmol) in MeOH (1 mL) under $N_2$ was added sodium methoxide (6.66 mg, 0.031 mmol). The resultant mixture was stirred at room temperature for 15 min. Water (10 mL) was added and the mixture was extracted with EtOAc (3×10 mL). The combined organic fractions were washed with brine (10 mL), dried (MgSO₄), filtered and concentrated in vacuo. The residue was purified by flash silica gel chromatography (0-100% EtOAC/hexanes) to afford (4S,5R)-5-[3,5-bis(trifluoromethyl)phenyl]-3-{[4'-fluoro-5'-(1-glycoloylpiperidin-4-yl)-2'-methoxy-4-(trifluoromethyl)biphenyl-2-yl]methyl}-4-methyl-1,3-oxazolidin-2-one as a yellow gum. LCMS=737.1 (M+1)⁺. ¹H NMR (CDCl₃, 500 MHz, mixture of atropisomers) δ 7.87 (s, 1H), 7.69 (s, 2H), 7.68-7.60 (m, 2H), 7.34-7.30 (m, 1H), 6.96-6.91 (m, 1H), 6.72 (d, J=11.9 Hz, 1H), 5.44 (d, J=7.8 Hz, 1H), 4.90 (d, J=15.8 Hz, 1H), 4.78-4.70 (m, 1H), 4.18-4.13 (m, 2H), 3.78 (s, 3H), 3.62-3.54 (m, 1H), 3.15-3.05 (m, 2H), 2.82-2.73 (m, 1H), 1.96-1.84 (m, 2H), 1.70-1.52 (m, 4H), 0.43-0.39 (m, 3H).

The compounds below were prepared by methods analogous to those described in Example 83.

| Example | R | LCMS (M+1)⁺ |
|---|---|---|
| 84 | (4-methoxy-2-fluorophenyl)-piperidine-N-acetyl | 721.0 |
| 85 | (4-methoxy-2-fluorophenyl)-3-methylpiperidine-N-acetyl, isomer A | 735.2 |
| 86 | (4-methoxy-2-fluorophenyl)-3-methylpiperidine-N-acetyl, isomer B | 735.2 |

149
-continued

| Example | R | LCMS (M + 1)+ |
|---|---|---|
| 87 | (4-methoxy-2-fluoro-5-yl)-3-methyl-1-acetylpiperidin-4-yl, isomer C | 735.2 |
| 88 | (4-methoxy-2-fluoro-5-yl)-3-methyl-1-acetylpiperidin-4-yl, isomer D | 735.2 |
| 89 | (4-methoxyphenyl-3-yl)-1-acetylpiperidin-4-yl | 703.0 |
| 90 | (4-methoxyphenyl-3-yl)-1-(hydroxyacetyl)piperidin-4-yl | 719.2 |

150
-continued

| Example | R | LCMS (M + 1)+ |
|---|---|---|
| 91 | (4-methoxy-2-fluoro-5-yl)-1-(hydroxyacetyl)piperidin-3-yl, racemic | 737.5 |
| 92 | (4-methoxy-2-fluoro-5-yl)-1-((S)-2-hydroxypropanoyl)piperidin-4-yl | 751.2 |
| 93 | (4-methoxy-2-fluoro-5-yl)-1-(2-hydroxy-2-methylpropanoyl)piperidin-4-yl | 765.5 |

Example 94

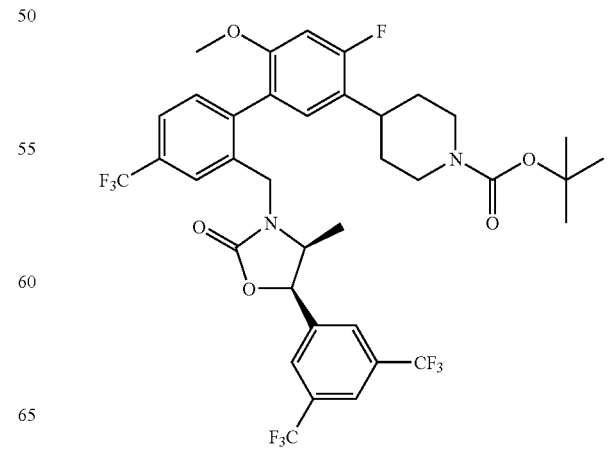

Tert-Butyl 4-[2'-({(4S,5R)-5-[3,5-bis(trifluoromethyl)phenyl]-4-methyl-2-oxo-1,3-oxazolidin-3-yl}methyl)-4-fluoro-6-methoxy-4'-(trifluoromethyl)biphenyl-3-yl]piperidine-1-carboxylate A mixture of tert-butyl 4-(2-fluoro-5-iodo-4-methoxyphenyl)piperidine-1-carboxylate (58 mg; 0.133 mmol) and (4S,1R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (111 mg, 0.187 mmol) was treated with 1,1'-bis(di-1-butylphosphino)ferrocene palladium dichloride (~10 mg) as described earlier. The product was purified by chiral HPLC (ChiralPak OD column, 10% IPA/heptane) to afford tert-butyl 4-[2'-({(4S,5R)-5-[3,5-bis(trifluoromethyl)phenyl]-4-methyl-2-oxo-1,3-oxazolidin-3-yl}methyl)-4-fluoro-6-methoxy-4'-(trifluoromethyl)biphenyl-3-yl]piperidine-1-carboxylate as a colorless glass. LCMS=678.8 (M+1−100)$^+$. $^1$H NMR (CDCl$_3$, 500 MHz, mixture of atropisomers) δ 7.86 (s, 1H), 7.69 (s, 2H), 7.64-7.61 (m, 2H), 7.32 (d, J=8 Hz, 1H), 6.96 (d, J=8.4 Hz, 1H), 6.70 (d, J=11.9 Hz, 1H), 5.57 (d, J=8 Hz, 1H), 4.88 (d, J=15.8 Hz, 1H), 4.26-4.17 (m, 2H), 3.86 (d, J=15.8 Hz, 1H), 3.83-3.78 (m, 1H), 3.77 (s, 3H), 3.01-2.93 (m, 1H), 2.84-2.75 (m, 2H), 1.84-1.69 (m, 2H), 1.64-1.50 (m, 2H), 1.45 (s, 9H), 0.38 (d, J=6.7 Hz, 3H).

Example 95

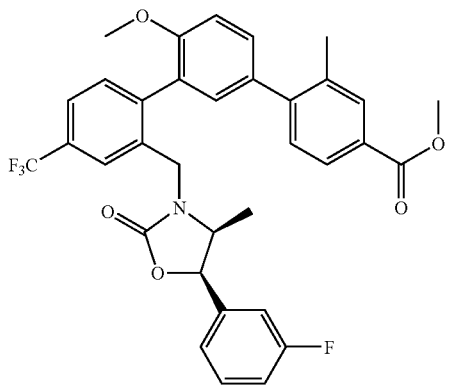

Methyl 2"-{[(4S,5R)-5-(3-fluorophenyl)-4-methyl-2-oxo-1,3-oxazolidin-3-yl]methyl}-4'-methoxy-2-methyl-4"-(trifluoromethyl)-1,1':3',1"-terphenyl-4-carboxylate To a 0° C. solution of (4S,5R)-5-(3-fluorophenyl)-4-methyl-1,3-oxazolidin-2-one (16.2 mg, 0.0830 mmol) in DMA (1 mL) was added NaHMDS (83 µL, 0.083 mmol). Next, a solution of methyl 2"-(bromomethyl)-4'-methoxy-2-methyl-4"-(trifluoromethyl)-1,1':3',1"-terphenyl-4-carboxylate (49 mg, 0.0996 mmol) in DMA (1 mL) was added via cannula. After 5 minutes, the reaction was quenched with saturated NH$_4$Cl solution (10 mL) and diluted with EtOAc (20 ml). The aqueous layer was extracted with EtOAc (20 mL), and the combined organic extracts were washed with brine (10 mL), dried over Na$_2$SO$_4$, filtered, and concentrated. Purification of the residue by flash chromatography on silica gel (5 to 25% EtOAc/hexanes) afforded methyl 2"-{[(4S,5R)-5-(3-fluorophenyl)-4-methyl-2-oxo-1,3-oxazolidin-3-yl]methyl}-4'-methoxy-2-methyl-4"-(trifluoromethyl)-1,1':3',1"-terphenyl-4-carboxylate. LCMS=608.2 (M+1)$^+$. $^1$H NMR (CDCl$_3$, 500 MHz, rotamers present) a 7.94 (d, J=5.9 Hz, 1H), 7.87 (d, J=7.8 Hz, 1H), 7.71-7.61 (m, 2H), 7.41-7.36 (m, 2H), 7.33-7.24 (m, 2H), 7.14-7.12 (m, 1H), 7.07-7.05 (m, 1H), 7.02-6.90 (m, 3H), 5.46 (d, J=8.2 Hz), 5.24 (d, J=8.2 Hz), 4.90 (d, J=15.8 Hz), 4.82 (d, J=15.8 Hz), 4.20 (d, J=15.8 Hz), 3.97 (d, J=15.8 Hz), 3.92 (s, 3H), 3.95 (s, 3H), 3.75-3.69 (m, 1H), 2.36 (s), 2.31 (s), 0.53 (d, J=6.6 Hz), 0.43 (d, J=6.6 Hz).

Example 96

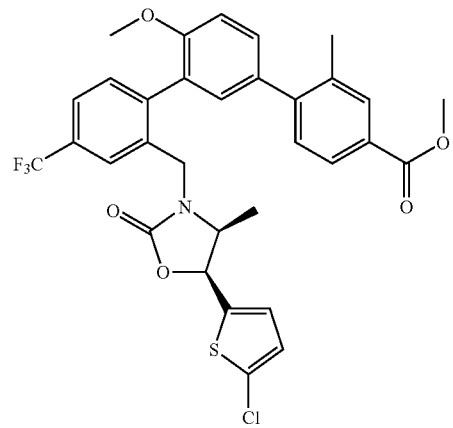

Methyl 2"-{[(4S,5S)-5-(5-chloro-2-thienyl)-4-methyl-2-oxo-1,3-oxazolidin-3-yl]methyl}-4'-methoxy-2-methyl-4"-(trifluoromethyl)-1,1':3',1"-terphenyl-1-4-carboxylate To a solution of (4S,5S)-5-(5-chloro-2-thienyl)-4-methyl-1,3-oxazolidin-2-one (39.9 mg, 0.184 mmol) in DMF (1.8 mL) was added t-BuOK (21.1 mg, 0.183 mmol). The reaction was stirred for 15 minutes, then a solution of methyl 2"-(bromomethyl)-4'-methoxy-2-methyl-4"-(trifluoromethyl)-1,1':3',1"-terphenyl-4-carboxylate (90 mg, 0.184 mmol) in DMF (2 mL) was added via cannula. The reaction was stirred at room temperature for 1 hour, and then quenched with saturated NH$_4$Cl solution (10 mL), diluted with EtOAc (20 mL), washed with brine (10 mL), dried over Na$_2$SO$_4$, filtered, and concentrated. The residue was purified by reverse-phase chromatography (C-18, 10 to 95% MeCN/water with 0.1% TFA) to afford methyl 2"-{[(4S,5S)-5-(5-chloro-2-thienyl)-4-methyl-2-oxo-1,3-oxazolidin-3-yl]methyl}-4'-methoxy-2-methyl-4'-(trifluoromethyl)-1,1':3',1"-terphenyl-1-4-carboxylate. R$_f$=0.43 (50% EtOAc/hexanes). LCMS=629.7 (M+1)$^+$. $^1$H NMR (CDCl$_3$, 500 MHz, rotamers present) δ 7.88-7.71 (m, 3H), 7.67-7.48 (m, 2H), 7.28-7.12 (m, 2H), 7.00-6.92 (m, 2H), 6.66-6.55 (m, 2H), 5.42 (d, J=8.0 Hz), 5.21 (d, J=8.0 Hz), 4.70 (d, J=16.0 Hz), 4.58 (d, J=16.0 Hz), 4.14 (d, J=16.0 Hz), 3.88 (d, J=16.0 Hz), 3.79 (m, 3H), 3.72-3.71 (m, 3H), 3.58-3.55 (m, 1H), 2.23 (s), 2.20 (s), 0.59 (d, J=6.4 Hz), 0.51 (d, J=6.4 Hz).

In a similar manner, the following compound was synthesized:

| Compound | Molecular structure | LCMS (M + 1)+ |
|---|---|---|
| 97 | 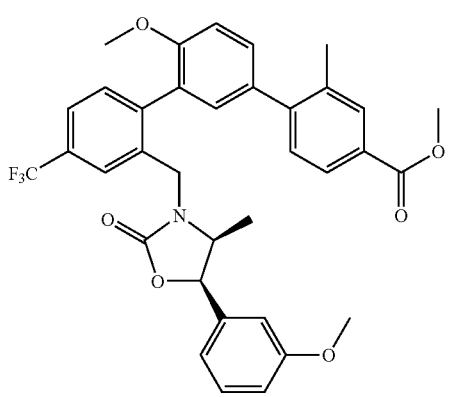 | 591.1 |

Example 98

Methyl 4'-methoxy-2"-{[(4S,5R)-5-(3-methoxyphenyl)-4-methyl-2-oxo-1,3-oxazolidin-3-yl]methyl}-2-methyl-4"-(trifluoromethyl)-1,1':3',1"-terphenyl-4-carboxylate

To a 0° C. solution of benzyl [(1S,2R)-2-hydroxy-2-(3-methoxyphenyl)-1-methylethyl]carbamate (40 mg, 0.126 mmol) in DMA (1.5 mL) was added NaHMDS (0.246 mL of a 1M solution in THF, 0.246 mmol). After 5 minutes, a solution of methyl 2"-(bromomethyl)-4'-methoxy-2-methyl-4"-(trifluoromethyl)-1,1':3',1"-terphenyl-4-carboxylate (68 mg, 0.138 mmol) in DMA (2.5 mL) was added via cannula. After 5 minutes, the reaction was quenched with saturated NH₄Cl solution (10 mL), diluted with EtOAc (20 mL), washed with brine (10 mL), dried over Na₂SO₄, filtered, and concentrated. Purification of the residue by flash chromatography on silica gel (0 to 25% acetone/hexanes), followed by reverse-phase chromatography (C-18, 10 to 95% MeCN/water with 0.1% TFA) afforded methyl 4'-methoxy-2"-{[(4S,5R)-5-(3-methoxyphenyl)-4-methyl-2-oxo-1,3-oxazolidin-3-yl]methyl}-2-methyl-4"-(trifluoromethyl)-1,1':3',1"-terphenyl-4-carboxylate. LCMS=644.0 (M+1)+. ¹H NMR (CDCl₃, 500 MHz, rotamers present) δ 7.94-7.86 (m, 2H), 7.71-7.62 (m, 2H), 7.43-7.36 (m, 2H), 7.31-7.22 (m, 2H), 7.3 (m, 1H), 7.08-7.05 (m, 1H), 6.85-6.83 (m, 1H), 6.75-6.68 (m, 2H), 5.45 (d, J=8.0 Hz), 5.23 (d, J=8.0 Hz), 4.89 (d, J=16.0 Hz), 4.82 (d, J=16.0 Hz), 4.20 (d, J=15.8 Hz), 3.96 (d, J=15.8 Hz), 3.91 (s, 3H), 3.85 (s, 3H), 3.77-3.75 (m, 3H), 3.72-3.69 (m, 1H), 2.31 (s), 2.08 (s), 0.54 (d, J=6.4 Hz), 0.44 (d, J=6.4 Hz).

In a similar manner, the following compound was synthesized:

| Compound | Molecular structure | LCMS (M + 1)+ |
|---|---|---|
| 99 | 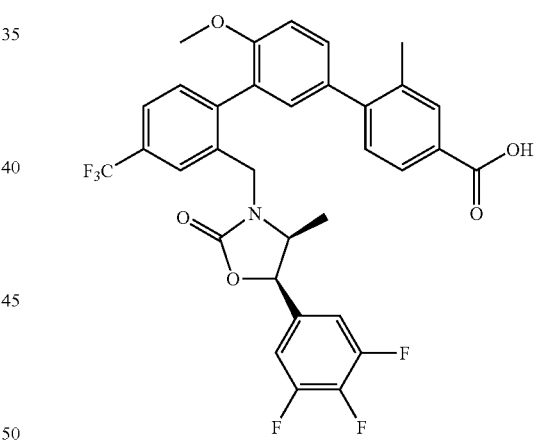 | 620.0 |

Example 100

4'-methoxy-2-methyl-2"-{[(4S,5R)-4-methyl-2-oxo-5-(3,4,5-trifluorophenyl)-1,3-oxazolidin-3-yl]methyl}-4"-(trifluoromethyl)-1,1':3',1"-terphenyl-4-carboxylic Acid

To a solution of methyl 4'-methoxy-2-methyl-2"-{[(4S,5R)-4-methyl-2-oxo-5-(3,4,5-trifluorophenyl)-1,3-oxazolidin-3-yl]methyl}-4"-(trifluoromethyl)-1,1':3',1"-terphenyl-4-carboxylate (23 mg, 0.0358 mmol) in MeOH (1 mL) was added 4 M KOH solution (0.5 mL). The reaction was stirred at room temperature for 3 hours, then quenched with 1 N HCl (5 mL) and diluted with EtOAc (15 mL). The aqueous layer was extracted with EtOAc (10 mL), and the combined organic extracts were washed with brine (10 mL), dried over Na₂SO₄, filtered, and concentrated. The residue was purified by reverse-phase chromatography (C-18, 10 to 95% MeCN/water with 0.1% TFA) to afford 4'-methoxy-2-methyl-2"-{[(4S,5R)-4-methyl-2-oxo-5-(3,4,5-trifluorophenyl)-1,3-oxazolidin-3-yl]methyl}-4"-(trifluoromethyl)-1,1':3',1"-terphenyl-4-carboxylic acid. LCMS=629.9 (M+1)+. $^1$H NMR (CDCl$_3$, 500 MHz, rotamers present) a 8.01-7.93 (m, 2H), 7.70-7.62 (m, 2H), 7.43-7.38 (m, 2H), 7.33-7.30 (m, 1H), 7.14-7.12 (m, 1H), 7.09-7.06 (m, 1H), 6.88-6.80 (m, 2H), 5.39 (d, J=8.0 Hz), 5.15 (d, J=8.0 Hz), 4.92 (d, J=15.6 Hz), 4.86 (d, J=15.6 Hz), 4.16 (d, J=15.8 Hz), 3.95 (d, J=15.8 Hz), 3.86 (m, 3H), 3.72-3.69 (m, 1H), 2.38 (s), 2.34 (s), 0.57 (d, J=6.6 Hz), 0.46 (d, J=6.6 Hz).

In a similar manner, the following compounds were synthesized:

| Compound | Molecular structure | LCMS (M + 1)+ |
|---|---|---|
| 101 | 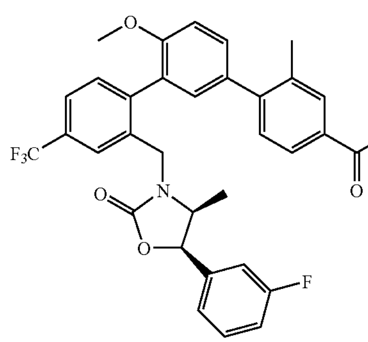 | 593.9 |
| 102 | 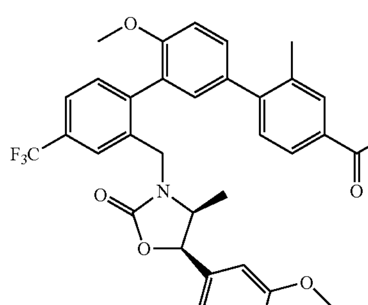 | 606.4 |
| 103 | 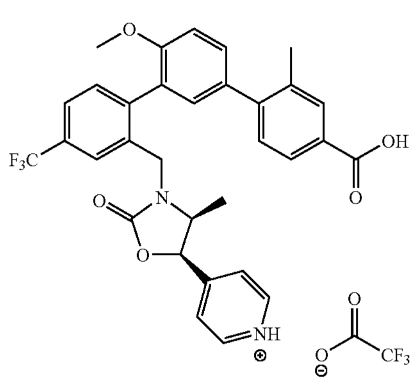 | 576.9 |
| 104 | | 616.0 |

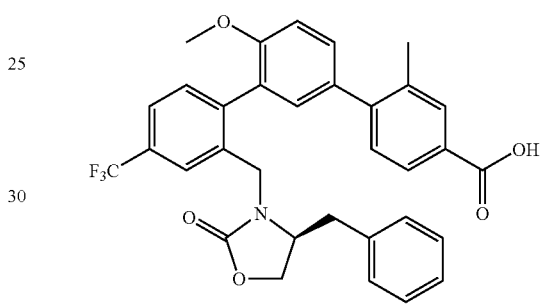

Example 105

2"-{[(4S)-4-benzyl-2-oxo-1,3-oxazolidin-3-yl]methyl}-4'-methoxy-2-methyl-4"-(trifluoromethyl)-1,1':3',1"-terphenyl-4-carboxylic Acid To a solution of (4S)-4-benzyl-1,3-oxazolidin-2-one (29.8 mg, 0.168 mmol) in DMF (1.5 mL) was added t-BuOK (17.5 mg, 0.152 mmol). After 10 minutes, a solution of methyl 2"-(bromomethyl)-4'-methoxy-2-methyl-4"-(trifluoromethyl)-1,1':3',1"-terphenyl-4-carboxylate (75 mg, 0.152 mmol) in DMF (1.5 mL) was added by cannula. The reaction was stirred for 30 minutes, and then quenched with saturated NH$_4$Cl solution (10 mL), diluted with EtOAc (15 mL), washed with brine (10 mL), dried over Na$_2$SO$_4$, filtered, and concentrated. The residue was dissolved with MeOH (2 mL) and 4M KOH solution (0.5 mL) was added. The reaction was stirred at room temperature for 2 hours, then stored in the freezer for 16 hours. The reaction was warmed to room temperature, and stirred for 2 hours. The reaction was quenched with 1 N HCl solution (5 mL), diluted with EtOAc (15 mL), washed with brine (5 mL), dried over Na$_2$SO$_4$, filtered, and concentrated. The residue was purified by reverse-phase chromatography (C-18, 10 to 95% MeCN/water with 0.1% TFA), followed by lyophilization to afford 2"-f{[(4S)-4-benzyl-2-oxo-1,3-oxazolidin-3-yl]methyl}-4'-methoxy-2-methyl-4"-(trifluoromethyl)-1,1':3',1"-terphenyl-4-carboxylic acid. LCMS=576.0 (M+1)+. $^1$H NMR (CDCl$_3$, 500 MHz, rotamers present) δ 8.01-7.86 (m, 2H), 7.67-7.50 (m, 2H), 7.44-7.32 (m, 3H), 7.23-7.07 (m, 5H), 6.91-6.85 (m, 2H), 4.92-4.58 (m, 2H), 4.27 (d, J=15.6 Hz), 4.11 (d, J=15.6 Hz), 4.06-3.82 (m, 5H), 3.64-3.51 (m, 1H), 2.86-2.71 (m, 1H), 2.47-2.28 (m, 4H). In a similar manner, the following compound was synthesized:

| Compound | Molecular structure | LCMS (M + 1)+ |
|---|---|---|
| 106 | 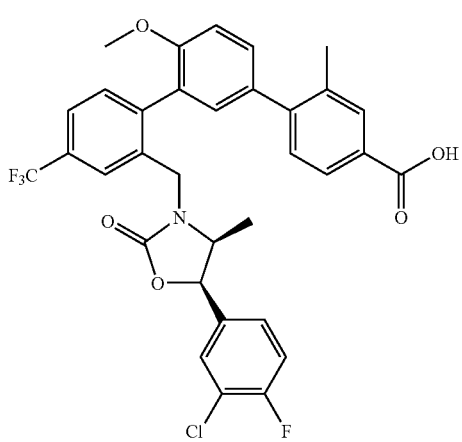 | 610.1 |

Example 107

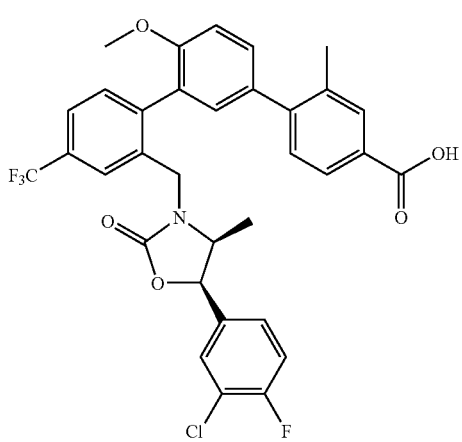

2"-{[(4S,5R)-5-(3-chloro-4-fluorophenyl)-4-methyl-2-oxo-1,3-oxazolidin-3-yl]methyl}-4'-methoxy-2-methyl-4"-(trifluoromethyl)-1,1':3',1"-terphenyl-4-carboxylic Acid To a 0° C. solution of benzyl [(1S,2R)-2-(3-chloro-4-fluorophenyl)-2-hydroxy-1-methylethyl]carbamate (51.4 mg, 0.152 mmol) in DMA (1.5 mL) was added NaHMDS (0.296 mL of a 1M solution in THF, 0.296 mmol). After 5 minutes, a solution of methyl 2"-(bromomethyl)-4'-methoxy-2-methyl-4"-(trifluoromethyl)-1,1':3',1"-terphenyl-4-carboxylate (75 mg, 0.152 mmol) in DMA (2.5 mL) was added via cannula. After 5 minutes, saturated aqueous NaOH solution (3 mL) was added, and the mixture was allowed to warm to room temperature. After 3 hours, the mixture was acidified with 6 N HCl and concentrated. The residue was purified by reverse-phase chromatography (C-18, 10 to 95% MeCN/water with 0.1% TFA) to afford 2"-{[(4S,5R)-5-(3-chloro-4-fluorophenyl)-4-methyl-2-oxo-1,3-oxazolidin-3-yl]methyl}-4'-methoxy-2-methyl-4"-(trifluoromethyl)-1,1':3',1"-terphenyl-4-carboxylic acid. LCMS=627.9 (M+1)+. $^1$H NMR (CDCl$_3$, 500 MHz, rotamers present) δ 7.95-7.62 (m, 2H), 7.69-7.52 (m, 2H), 7.43-7.37 (m, 2H), 7.30-7.24 (m, 1H), 7.18-7.11 (m, 2H), 7.08-6.86 (m, 3H), 5.44 (d, J=8.0 Hz), 5.18 (d, J=8.0 Hz), 4.92-4.85 (m, 1H), 4.18 (d, J=15.5), 3.96 (d, J=15.5), 3.93-3.85 (m, 3H), 3.73-3.66 (m, 1H), 2.36 (s), 2.32 (s), 0.55 (d, J=6.6 Hz), 0.44 (d, J=6.6 Hz).

Example 108

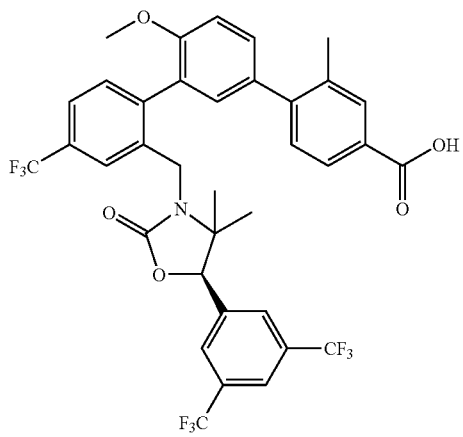

2"-({5-[3,5-bis(trifluoromethyl)phenyl]-4,4-dimethyl-2-oxo-1,3-oxazolidin-3-yl}methyl)-4'-methoxy-2-methyl-4"-(trifluoromethyl)-1,1':3',1"-terphenyl-4-carboxylic Acid To a solution of benzyl {2-[3,5-bis(trifluoromethyl)phenyl]-2-hydroxy-1,1-dimethylethyl}carbamate (65 mg, 0.149 mmol) in THF (1.5 mL) was added NaH (13 mg, 0.542 mmol) and methyl 2"-(bromomethyl)-4'-methoxy-2-methyl-4"-(trifluoromethyl)-1,1':3',1"-terphenyl-4-carboxylate (91.1 mg, 0.185 mmol). The reaction was stirred for 72 hours, and then additional NaH (36.2 mg, 1.51 mmol) was added. After 6 more hours at room temperature, the reaction was quenched with saturated NH$_4$Cl solution (10 mL) and diluted with EtOAc (20 mL). The aqueous layer was extracted with EtOAc (20 mL), and the combined organic extracts were washed with brine (10 mL), dried over Na$_2$SO$_4$, filtered, and concentrated. Purification of the residue by reverse-phase chromatography (C-18, 10 to 95% MeCN/water with 0.1% TFA) afforded 2"-({5-[3,5-bis(trifluoromethyl)phenyl]-4,4-dimethyl-2-oxo-1,3-oxazolidin-3-yl}methyl)-4'-methoxy-2-methyl-4"-(trifluoromethyl)-1,1':3',1"-terphenyl-4-carboxylic acid. LCMS=726.0 (M+1)+. $^1$H NMR (CDCl$_3$, 500 MHz, rotamers present) δ 8.03-8.02 (m, 1H), 7.80-7.96 (m, 1H), 7.89 (s, 1H), 7.79-7.76 (m, 2H), 7.62-7.59 (m, 1H), 7.42-7.31 (m, 3H), 7.22-7.08 (m, 3H), 5.26-5.28 (m, 1H), 4.81 (d, J=16.6 Hz), 4.44-4.42 (m, 1H), 4.02 (d, J=16.6 Hz), 3.85 (s, 3H), 2.37-2.35 (m, 3H), 1.24 (s), 1.06 (s), 0.56-0.54 (m, 3H).

Example 109

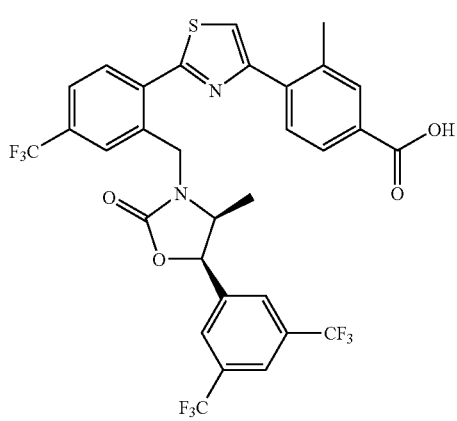

4-{2-[2[({(4S,5R)-5-[3,5-bis(trifluoromethyl)phenyl]-4-methyl-2-oxo-1,3-oxazolidin-3-yl}methyl)-4-(trifluoromethyl)phenyl]-1,3-thiazol-4-yl}-3-methylbenzoic Acid Step 1: (4S,5R)-5-[3,5-bis(trifluoromethyl)phenyl]-3-[2-(4-bromo-1,3-thiazol-2-yl)-5-(trifluoromethyl)benzyl]-4-methyl-1,3-oxazolidin-2-one In a tube were placed (4S,5R)-5-[3,5-bis(trifluoromethyl)phenyl]-4-methyl-3-[2-(4,4,5,5-tetramethyl-1,3,2-dioxaborolan-2-yl)-5-(trifluoromethyl)benzyl]-1,3-oxazolidin-2-one (59 mg, 0.099 mmol), 2,4-dibromothiazole (60 mg, 0.247 mmol), DME (420 µL), EtOH (140 µL), and 1M Na$_2$CO$_3$ (296 µL, 0.296 mmol). The mixture was degassed with N$_2$ and then Pd(PPh$_3$)$_4$ (5.7 mg, 4.94×10$^{-3}$ mmol) was added. The mixture was degassed with N$_2$ again, and then the tube was sealed, and the reaction was heated at 100° C. for 90 minutes. The reaction was cooled to room temperature and diluted with EtOAc (30 mL). The organic layer was washed with water and brine (10 mL) each, dried over Na$_2$SO$_4$, filtered and concentrated. Purification of the residue by flash chromatography on silica gel (5 to 25% EtOAc/hexanes) afforded (4S,5R)-5-[3,5-bis(trifluoromethyl)phenyl]-3-[2-(4-bromo-1,3-thiazol-2-yl)-5-(trifluoromethyl)benzyl]-4-methyl-1,3-oxazolidin-2-one. R$_f$=0.33 (25% EtOAc/hexanes). LCMS=635.0 (M+1)$^+$. $^1$H NMR (CDCl$_3$, 500 MHz) δ 7.89 (bs, 2H), 7.78 (s, 2H), 7.75 (d, J=8.3 Hz, 1H), 7.68 (dd, J=8.1, 1.0 Hz, 1H), 7.41 (s, 1H), 5.66 (d, J=8.0 Hz, 1H), 5.02 (d, J=15.8 Hz, 1H), 4.84 (d, J=15.8 Hz, 1H), 4.20 (m, 1H), 0.78 (d, J=6.7 Hz, 3H).

Step 2: Methyl 4-{2-[2-({(4S,5R)-5-[3,5-bis(trifluoromethyl)phenyl]-4-methyl-2-oxo-1,3-oxazolidin-3-yl}methyl)-4-(trifluoromethyl)phenyl]-1,3-thiazol-4-yl}-3-methylbenzoate In a tube were placed (4S,5R)-5-[3,5-bis(trifluoromethyl)phenyl]-3-[2-(4-bromo-1,3-thiazol-2-yl)-5-(trifluoromethyl)benzyl]-4-methyl-1,3-oxazolidin-2-one (46.0 mg, 0.073 mmol), methyl 3-methyl-4-(4,4,5,5-tetramethyl-1,3,2-dioxaborolan-2-yl)benzoate (30 mg, 0.11 mmol), 1,1'-bis(di-t-butylphosphino)ferrocene palladium dichloride (5 mg, 7.3×10$^{-3}$ mmol), THF (1 mL) and 1M K$_2$CO$_3$ (1 mL, 1 mmol). The mixture was degassed with N$_2$, the tube was sealed, and the reaction was heated to 90° C. for 90 minutes. The reaction was cooled to room temperature and diluted with EtOAc (30 mL). The organic layer was washed with water and brine (10 mL) each, dried over Na$_2$SO$_4$, filtered and concentrated. Purification of the residue by flash chromatography on silica gel (5 to 40% EtOAc/hexanes) afforded methyl 4-{2-[2-({(4S,5R)-5-[3,5-bis(trifluoromethyl)phenyl]-4-methyl-2-oxo-1,3-oxazolidin-3-yl}methyl)-4-(trifluoromethyl)phenyl]-1,3-thiazol-4-yl}-3-methylbenzoate. R$_f$=0.29 (25% EtOAc/hexanes). LCMS=702.9 (M+1)$^+$. $^1$H NMR (CDCl$_3$, 600 MHz) δ 7.97 (s, 1H), 7.92 (dd, J=8.0, 1.4 Hz, 1H), 7.85-7.86 (m, 3H), 7.69-7.72 (m, 4H), 7.53 (s, 1H), 5.66 (d, J=8.0 Hz, 1H), 5.11 (d, J=16.2 Hz, 1H), 4.95 (d, J=16.2 Hz, 1H), 4.11 (m, 1H), 3.93 (s, 3H), 2.54 (s, 3H), 0.60 (d, J=6.6 Hz, 3H).

Step 3: 4-{2-[2[({(4S,5R)-5-[3,5-bis(trifluoromethyl)phenyl]-4-methyl-2-oxo-1,3-oxazolidin-3-yl}methyl)-4-(trifluoromethyl)phenyl]-1,3-thiazol-4-yl}-3-methylbenzoic Acid To a solution of methyl 4-{2-[2-({(4S,5R)-5-[3,5-bis(trifluoromethyl)phenyl]-4-methyl-2-oxo-1,3-oxazolidin-3-yl}methyl)-4-(trifluoromethyl)phenyl]-1,3-thiazol-4-yl}-3-methylbenzoate (35.2 mg, 0.05 mmol) in THF (2 mL) was added water (800 µL), 4N KOH (75 µL, 0.3 mmol), and EtOH (200 µL). The reaction was stirred at room temperature for 24 hours and then acidified with 1N HCl and extracted with EtOAc (30 mL). The organic layer was washed with water and brine (10 mL each), dried over Na$_2$SO$_4$, filtered and concentrated. Purification of the residue by flash chromatography on silica gel (10 to 100% EtOAc/hexanes) afforded 4-{2-[2-[({(4S,5R)-5-[3,5-bis(trifluoromethyl)phenyl]-4-methyl-2-oxo-1,3-oxazolidin-3-yl}methyl)-4-(trifluoromethyl)phenyl]-1,3-thiazol-4-yl}-3-methylbenzoic acid. LCMS=688.8 (M+1)$^+$. $^1$H NMR (CDCl$_3$, 500 MHz) δ 8.04 (s, 1H), 7.99 (d, J=8.0 Hz, 1H), 7.84-7.87 (m, 3H), 7.70-7.75 (m, 4H), 7.56 (s, 1H), 5.67 (d, J=8.1 Hz, 1H), 5.14 (d, J=16.2 Hz, 1H), 4.96 (d, J=16.2 Hz, 1H), 4.10 (m, 1H), 2.56 (s, 3H), 0.62 (d, J=6.6 Hz, 3H).

Example 110

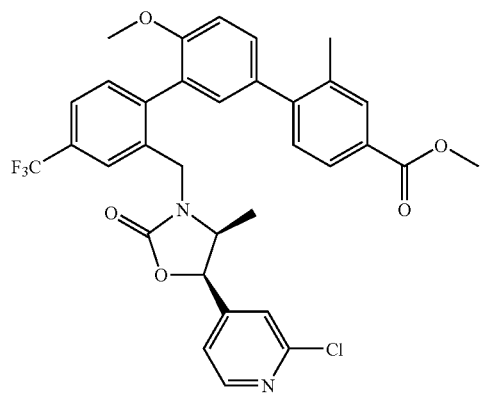

Methyl 2"-{[(4S,5R)-5-(2-chloropyridin-4-yl)-4-methyl-2-oxo-1,3-oxazolidin-3-yl]methyl}-4'-methoxy-2-methyl-4"-(trifluoromethyl)-1,1':3',1"-terphenyl-4-carboxylate To a solution of methyl 4'-methoxy-2-methyl-2"-{[(4S,5R)-4-methyl-2-oxo-5-pyridin-4-yl-1,3-oxazolidin-3-yl]methyl}-4"-(trifluoromethyl)-1,1':3',1"-terphenyl-4-carboxylate (175 mg, 0.296 mmol) in CH$_2$Cl$_2$ (15 mL) at 0° C. under N$_2$, was added 3-chloroperbenzoic acid (146 mg, 0.593 mmol) as a powder. The mixture was stirred at 0° C. for 15 min. Then it was allowed to warm up to room temperature and stirred for 2 h. The reaction mixture was diluted with CH$_2$Cl$_2$ and washed with satd Na$_2$SO$_3$ (1×) followed by satd K$_2$CO$_3$ (2×). The organic layer was dried (Na$_2$SO$_4$), filtered and the solvent was evaporated in vacuo. The residue obtained was dissolved in POCl$_3$ (10 mL). The resulting solution was heated at 110° C. under N$_2$ for 2 h. Then it was allowed to warm to room temperature and stirred for 2 h. The reaction was concentrated in vacuo. The residue was diluted with EtOAc (50 mL) and water (10 mL) and washed with satd NaHCO$_3$ (20 mL). The aqueous layer was extracted with EtOAc (2×40 mL). The combined organic layers were dried (Na$_2$SO$_4$), filtered and the solvent was evaporated in vacuo. The residue was purified by flash chromatography on silica gel to give methyl 2"-{[(4S,5R)-5-(2-chloropyridin-4-yl)-4-methyl-2-oxo-1,3-oxazolidin-3-yl]methyl}-4'-methoxy-2-methyl-4"-(trifluoromethyl)-1,1':3',1"-terphenyl-4-carboxylate. LCMS calc.=625.2; found=625.0 (M+1)$^+$. $^1$H NMR (500 MHz, CDCl$_3$, 1:1 mixture of atropisomers) δ 8.40 (s, 0.5H); 8.39 (s, 0.5H); 7.97 (s, 1H); 7.90 (t, J=5.8 Hz, 1H); 7.72 (s, 0.5H); 7.69-7.63 (m, 1.5H); 7.48 (d, J=11.8 Hz, 0.5H); 7.44 (s, 0.5H); 7.43-7.37 (m, 1H); 7.32-7.26 (m, 1H); 7.24 (s, 0.5H); 7.20 (s, 0.5H); 7.16 (d, J=2.2 Hz, 0.5H); 7.14 (d, J=2.2 Hz, 0.5H); 7.12-7.06 (m, 1.5H); 7.05 (d, J=5.1 Hz, 0.5H); 5.42 (d, J=8.1 Hz, 0.5H); 5.18 (d, J=8.1 Hz, 0.5H); 4.92 (dd, J=15.9, 18.5 Hz, 1H); 4.19 (d, J=15.8 Hz, 0.5H); 3.99 (d, J=15.8 Hz, 0.5H); 3.95 (s, 3H); 3.88 (s, 3H); 3.81-3.75 (m, 1H); 2.39 (s, 1.5H); 2.35 (s, 1.5H); 0.60 (d, J=6.5 Hz, 1.5H); 0.49 (d, J=6.5 Hz, 1.5H).

Example 111

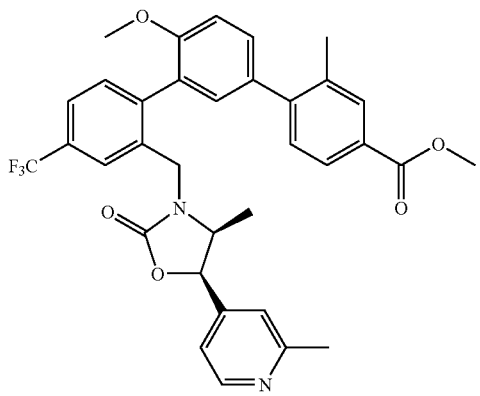

Methyl 4'-methoxy-2-methyl-2"-{[(4S,5R)-4-methyl-5-(2-methylpyridin-4-yl)-2-oxo-1,3-oxazolidin-3-yl]methyl}-4"-(trifluoromethyl)-1,1':3',1"-terphenyl-4-carboxylate To a solution of methyl 2"-{[(4S,5R)-5-(2-chloropyridin-4-yl)-4-methyl-2-oxo-1,3-oxazolidin-3-yl]methyl}-4'-methoxy-2-methyl-4"-(trifluoromethyl)-1,1':3',1"-terphenyl-4-carboxylate (48 mg, 0.077 mmol) in THF (1 mL) and K$_2$CO$_3$ (1N) (1 mL) was added trimethylboroxine (0.107 mL, 0.768 mmol) and 1,1-bis(di-tert-butylphosphino)ferrocene palladium dichloride (7.1 mg, 0.011 mmol). The mixture was sealed and heated at 80° C. overnight. The mixture was diluted with water and EtOAc and filtered through Celite. The organic layer was separated and the aqueous layer was extracted with EtOAc (2×). The combined organic layers were washed with brine (1×), dried (Na$_2$SO$_4$), filtered and the solvent was evaporated in vacuo. The residue was purified by flash chromatography on silica gel to give methyl 4'-methoxy-2-methyl-2"-{[(4S,5R)-4-methyl-5-(2-methylpyridin-4-yl)-2-oxo-1,3-oxazolidin-3-yl]methyl}-4"-(trifluoromethyl)-1,1':3',1"-terphenyl-4-carboxylate. LCMS calc.=605.2; found=605.0 (M+1)$^+$. $^1$H NMR (500 MHz, CDCl$_3$, 1:1 mixture of atropisomers) δ 8.49 (t, J=4.3 Hz, 1H); 7.98 (t, J=6.6 Hz, 1H); 7.91 (t, J=10.0 Hz, 1H); 7.73 (s, 0.5H); 7.67 (s, 0.5H); 7.65 (s, 1H); 7.47-7.39 (m, 2H); 7.33-7.26 (m, 1H); 7.15 (dd, J=2.2, 5.7 Hz, 1H); 7.09 (dd, J=6.8, 8.4 Hz, 1H); 7.06 (s, 0.5H); 7.00 (s, 0.5H); 6-95 (d, J=4.8 Hz, 0.5H); 6.90 (d, J=4.7 Hz, 0.5H); 5.43 (d, J=8.2 Hz, 0.5H); 5.18 (d, J=8.1 Hz, 0.5H); 4.92 (d, J=15.8 Hz, 0.5H); 4.87 (d, J=15.8 Hz, 0.5H); 4.22 (d, J=15.8 Hz, 0.5H); 4.00 (d, J=15.8 Hz, 0.5H); 3.95 (s, 3H); 3.89 (s, 1.5H); 3.88 (s, 1.5H); 3.81-3.73 (m, 1H); 2.57 (s, 1.5H); 2.56 (s, 1.5H); 2.39 (s, 1.5H); 2.34 (s, 1.5H); 0.57 (d, J=6.6 Hz, 1.5H); 0.47 (d, J=6.6 Hz, 1.5H).

Example 112

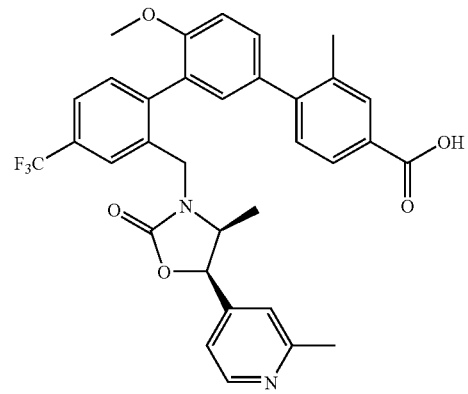

4'-Methoxy-2-methyl-2"-{[(4S,5R)-4-methyl-5-(2-methylpyridin-4-yl)-2-oxo-1,3-oxazolidin-3-yl]methyl}-4"-(trifluoromethyl)-1,1':3',1"-terphenyl-4-carboxylic Acid To a solution of methyl 4'-methoxy-2-methyl-2"-{[(4S,5R)-4-methyl-5-(2-methylpyridin-4-yl)-2-oxo-1,3-oxazolidin-3-yl]methyl}-4"-(trifluoromethyl)-1,1':3',1"-terphenyl-4-carboxylate (30.1 mg, 0.050 mmol) in 1,4-dioxane (1.5 mL) and water (1.5 mL) was added 1M aqueous LiOH (0.498 mL, 0.498 mmol). The mixture was stirred at room temperature for 4 h. The mixture was acidified with 1N HCl. The aqueous layer was extracted with EtOAc (3×). The combined organic layers were dried (Na$_2$SO$_4$), filtered and the solvent was evaporated in vacuo. The crude material was purified by preparative HPLC reverse phase (C-18), eluting with MeCN/water. The fractions were collected and lyophilized to give 4'-methoxy-2-methyl-2"-{[(4S,5R)-4-methyl-5-(2-methylpyridin-4-yl)-2-oxo-1,3-oxazolidin-3-yl]methyl}-4"-(trifluoromethyl)-1,1':3',1"-terphenyl-4-carboxylic acid. LCMS calc.=591.2; found=591.1 (M+1)$^+$. $^1$H NMR (500 MHz, CDCl$_3$, 1:1 mixture of atropisomers) δ 8.83 (s, 1H); 8.02 (s, 1H); 7.94 (t, J=10.0 Hz, 1H); 7.72 (s, 0.5H); 7.69 (t, J=6.0 Hz, 1H); 7.64 (s, 0.5H); 7.49-7.43 (m, 3H); 7.40 (d, J=5.2 Hz, 0.5H); 7.35 (d, J=5.4 Hz, 0.5H); 7.31 (m, 1H); 7.16 (dd, J=2.1, 6.0 Hz, 1H); 7.12 (t, J=8.8 Hz, 1H); 5.56 (d, J=8.1 Hz, 0.5H); 5.26 (d, J=8.2 Hz, 0.5H); 4.94 (dd, J=8.7, 15.7 Hz, 1H); 4.77 (br s, 1H); 4.20 (d, J=15.8 Hz, 0.5H); 4.00 (d, J=15.7 Hz, 0.5H); 3.90 (s, 1.5H); 3.89 (s, 1.5H); 3.89-3.81 (m, 1H); 2.82 (s, 1.5H); 2.81 (s, 1.5H); 2.41 (s, 1.5H); 2.36 (s, 1.5H); 0.62 (d, J=6.5 Hz, 1.5H); 0.49 (d, J=6.5 Hz, 1.5H).

Example 113

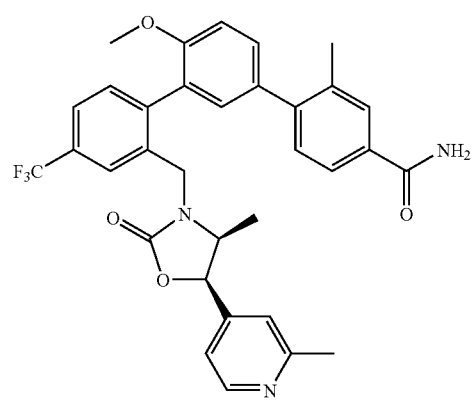

4'-Methoxy-2-methyl-2"-{[(4S,5R)-4-methyl-5-(2-methylpyridin-4-yl)-2-oxo-1,3-oxazolidin-3-yl]methyl}-4"-(trifluoromethyl)-1,1':3',1"-terphenyl-4-carboxamide To a solution of 4'-methoxy-2-methyl-2"-{[(4S,5R)-4-methyl-5-(2-methylpyridin-4-yl)-2-oxo-1,3-oxazolidin-3-yl]methyl}-4"-(trifluoromethyl)-1,1':3',1"-terphenyl-4-carboxylic acid (15 mg, 0.025 mmol) in $CH_2Cl_2$ (2 mL), was added 2M oxalyl chloride in $CH_2Cl_2$ (0.038 mL, 0.076 mmol) and 2 drops of DMF. The mixture was stirred at room temperature under $N_2$ for 30 min. The reaction mixture was concentrated in vacuo. The residue was re-dissolved in THF (2 mL), then ammonium hydroxide (0.035 mL, 0.254 mmol) and diisopropylethylamine (0.013 mL, 0.076 mmol) were added. The resulting mixture was stirred at room temperature for 3 h. The reaction mixture was concentrated in vacuo and the residue was purified by preparative HPLC reverse phase (C-18), eluting with MeCN/water. The fractions were collected and lyophilized to give 4'-methoxy-2-methyl-2"-{[(4S,5R)-4-methyl-5-(2-methylpyridin-4-yl)-2-oxo-1,3-oxazolidin-3-yl]methyl}-4"-(trifluoromethyl)-1,1':3',1"-terphenyl-4-carboxamide as a white powder. LCMS calc.=590.2; found=590.0 $(M+1)^+$. $^1H$ NMR (500 MHz, $CDCl_3$, 1:1 mixture of atropisomers) δ 8.49 (t, J=4.3 Hz, 1H); 7.77 (br s, 1H); 7.72 (s, 0.5H); 7.66 (br s, 1.5H); 7.46-7.38 (m, 3H); 7.33-7.29 (m, 1H); 7.14 (dd, J=2.2, 7.7 Hz, 1H); 7.09 (dd, J=6.2, 8.5 Hz, 1H); 7.06 (s, 0.5H); 7.01 (s, 0.5H); 6.95 (d, J=4.3 Hz, 0.5H); 6.90 (d, J=4.4 Hz, 0.5H); 6.17 (br s, 1H); 5.79 (br s, 1H); 5.43 (d, J=8.1 Hz, 0.5H); 5.20 (d, J=8.0 Hz, 0.5H); 4.92 (d, J=15.9 Hz, 0.5H); 4.86 (d, J=15.8 Hz, 0.5H); 4.22 (d, J=15.8 Hz, 0.5H); 4.00 (d, J=15.8 Hz, 0.5H); 3.88 (s, 1.5H); 3.87 (s, 1.5H); 3.80-3.75 (m, 1H); 2.57 (s, 1.5H); 2.56 (s, 1.5H); 2.39 (s, 1.5H); 2.35 (s, 1.5H); 0.58 (d, J=6.5 Hz, 1.5H); 0.47 (d, J=6.5 Hz, 1.5H).

EXAMPLES 114-123 below were prepared according to the procedures described above.

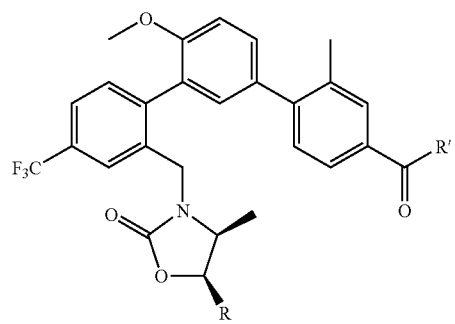

| Example | R | R' | LCMS $(M + 1)^+$ |
|---|---|---|---|
| 114 | (1,4-dimethyl-1H-imidazol-2-yl) | $OCH_3$ | 608.1 |

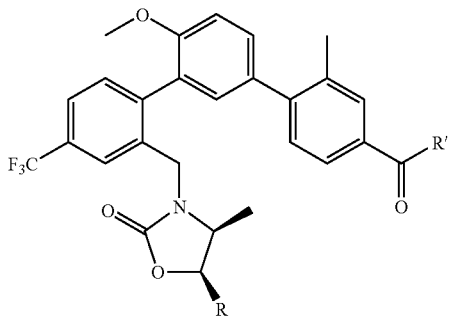

| Example | R | R' | LCMS $(M + 1)^+$ |
|---|---|---|---|
| 115 | (1-methyl-1H-pyrazol-5-yl) | $OCH_3$ | 594.1 |
| 116 | (1,3-dimethyl-1H-pyrazol-5-yl) | $OCH_3$ | 608.1 |
| 117 | (1-methyl-1H-1,2,4-triazol-5-yl) | $OCH_3$ | 595.1 |
| 118 | (1,4-dimethyl-1H-imidazol-2-yl) | OH | 594.1 |
| 119 | (1-methyl-1H-pyrazol-5-yl) | OH | 580.1 |
| 120 | (1,3-dimethyl-1H-pyrazol-5-yl) | OH | 594.1 |
| 121 | (1-methyl-1H-1,2,4-triazol-5-yl) | OH | 581.1 |
| 122 | (1-methyl-1H-pyrazol-5-yl) | $NH_2$ | 579.0 |

-continued

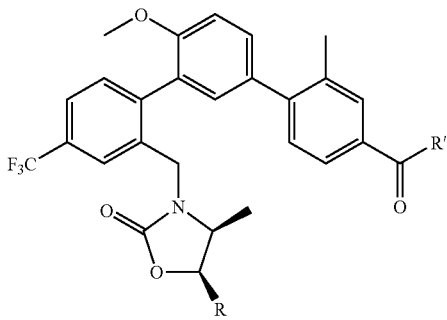

| Example | R | R' | LCMS (M + 1)+ |
|---|---|---|---|
| 123 | ![1,3-dimethylpyrazol-5-yl] | NH₂ | 593.0 |

Example 124

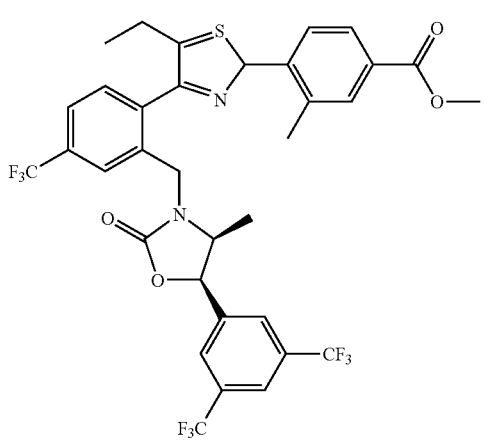

Methyl 4-{-4-[2-({(4S,5R)-5-[3,5-bis(trifluoromethyl)phenyl]-4-methyl-2-oxo-1,3-oxazolidin-3-yl}methyl)-4-(trifluoromethyl)phenyl]-5-ethyl-1,3-thiazol-2-yl}-3-methylbenzoate A solution of (4S,5R)-5-[3,5-bis(trifluoromethyl)phenyl]-3-[2-(2-bromobutanoyl)-5-(trifluoromethyl)benzyl]-4-methyl-1,3-oxazolidin-2-one (25 mg, 0.040 mmol) and methyl 4-(aminocarbonothioyl)-3-methylbenzoate (16.87 mg, 0.081 mmol) in EtOH (450 μL) was heated at 70° C. overnight. The reaction was concentrated in vacuo and the residue was purified by preparative TLC (Si, 1000 microns, Hex/EtOAc (80:20)) to afford methyl 4-{4-[2-({(4S,5R)-5-[3,5-bis(trifluoromethyl)phenyl]-4-methyl-2-oxo-1,3-oxazolidin-3-yl}methyl)-4-(trifluoromethyl)phenyl]-5-ethyl-1,3-thiazol-2-yl}-3-methylbenzoate, as colorless oil. LCMS calc.=731.2; found=731.0 (M+1)+. ¹H NMR (500 MHz, CDCl₃) δ 7.99 (s, 1H); 7.92 (d, J=8.1 Hz, 1H); 7.86 (d, J=8.0 Hz, 2H); 7.79 (s, 1H); 7.72 (d, J=7.9 Hz, 1H); 7.69 (s, 1H); 7.55 (d, J=7.9 Hz, 1H); 7.29 (s, 1H); 5.59 (d, J=8.0 Hz, 1H); 4.91 (d, J=15.7 Hz, 1H); 4.27 (d, J=15.7 Hz, 1H); 4.04-3.99 (m, 1H); 3.95 (s, 3H); 2.88-2.76 (m, 2H); 2.68 (s, 3H); 1.36 (t, J=7.5 Hz, 3H); 0.57 (d, J=6.5 Hz, 3H).

Example 125

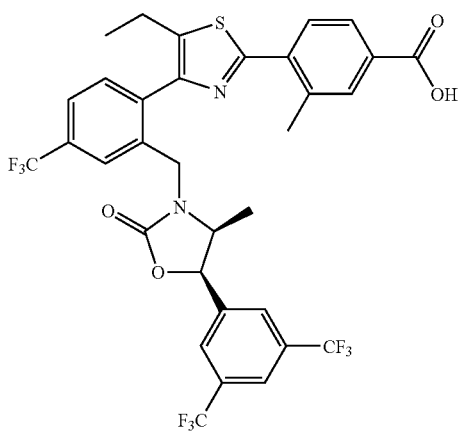

4-{4-[2-({(4S,5R)-5-[3,5-Bis(trifluoromethyl)phenyl]-4-methyl-2-oxo-1,3-oxazolidin-3-yl}methyl)-4-(trifluoromethyl)phenyl]-5-ethyl-1,3-thiazol-2-yl}-3-methylbenzoic Acid To a solution of methyl 4-{4-[2-({(4S,5R)-5-[3,5-bis(trifluoromethyl)phenyl]-4-methyl-2-oxo-1,3-oxazolidin-3-yl}methyl)-4-(trifluoromethyl)phenyl]-5-ethyl-1,3-thiazol-2-yl}-3-methylbenzoate (11 mg, 0.015 mmol) in 1,4-dioxane (0.4 mL) and water (0.4 mL), was added 1N LiOH (0.151 mL, 0.151 mmol). The mixture was stirred at room temperature for 2 h. The mixture was acidified with 1N HCl. The aqueous layer was extracted with EtOAc (3×). The combined organic layers were dried (Na₂SO₄), filtered and the solvent was evaporated in vacuo. The residue was purified by preparative HPLC reverse phase (C-18), eluting with MeCN/water containing 0.1% TFA. The fractions were collected and lyophilized to give 4-{4-[2-({(4S,5R)-5-[3,5-bis(trifluoromethyl)phenyl]-4-methyl-2-oxo-1,3-oxazolidin-3-yl}methyl)-4-(trifluoromethyl)phenyl]-5-ethyl-1,3-thiazol-2-yl}-3-methylbenzoic acid. LCMS calc.=717.1; found=717.0 (M+1)+. ¹H NMR (500 MHz, CDCl₃) δ 8.05 (s, 1H); 7.99 (d, J=8.1 Hz, 1H); 7.89 (d, J=8.1 Hz, 1H); 7.87 (s, 1H); 7.78 (s, 1H); 7.74 (d, J=8.0 Hz, 1H); 7.71 (s, 2H); 7.57 (d, J=7.9 Hz, 1H); 5.61 (d, J=8.0 Hz, 1H); 4.94 (d, J=15.7 Hz, 1H); 4.25 (d, J=15.7 Hz, 1H); 4.04-3.98 (m, 1H); 2.89-2.76 (m, 2H); 2.69 (s, 3H); 1.37 (t, J=7.5 Hz, 3H); 0.60 (d, J=6.5 Hz, 3H).

The compounds below were synthesized according to the procedure described in EXAMPLE 124 from INTERMEDIATE 20 and the corresponding thioamides.

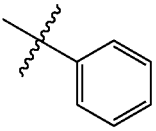
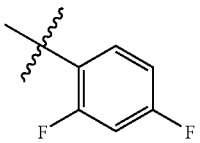
| Example | R | LCMS (M + 1)+ |
|---|---|---|
| 126 | 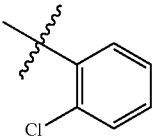 | 658.9 |
| 127 | 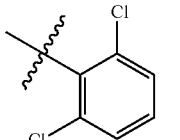 | 693.0 |
| 128 | 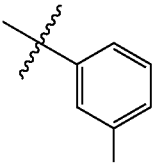 | 692.9 |
| 129 | 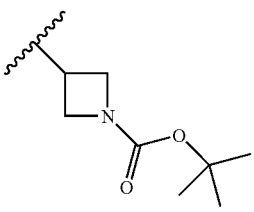 | 692.9 |
| 130 | 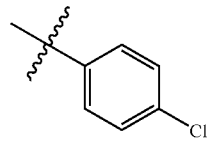 | 672.9 |
| 131 | 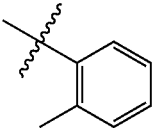 | 689.0 |
| 132 | 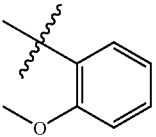 | 676.9 |
| 133 | 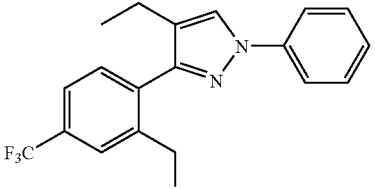 | 694.9 |
| 134 | 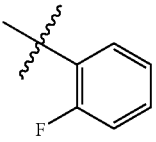 | 726.9 |
| 135 | 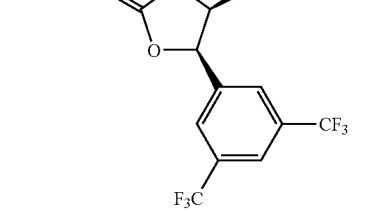 | 738.0 |
Example 136
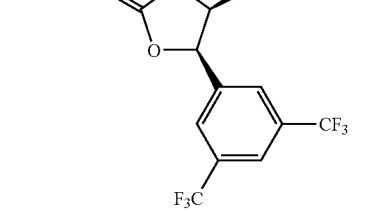

(4S,5R)-5-[3,5-Bis(trifluoromethyl)phenyl]-3-[2-(4-ethyl-1-phenyl-1H-pyrazol-3-yl)-5-(trifluoromethyl)benzyl]-4-methyl-1,3-oxazolidin-2-one A solution of (4S,5R)-5-[3,5-bis(trifluoromethyl)phenyl]-3-[2-butyryl-5-(trifluoromethyl)benzyl]-4-methyl-1,3-oxazolidin-2-one (300 mg, 0.554 mmol) (46.3 mg, 0.086 mmol)) in N,N-dimethylformamide dimethyl acetal (0.5 mL, 3.78 mmol) was heated at 110° C. overnight. The reaction was concentrated in vacuo to give the crude enaminone. The enaminone obtained was dissolved in EtOH (200 μL) and phenylhydrazine (16.97 μL, 0.171 mmol) was added. The mixture was heated at 80° C. for 3 h. The reaction mixture was concentrated in vacuo and the residue was purified by preparative HPLC reverse phase (C-18), eluting with MeCN/water. The fractions of the second peak to elute were collected and lyophilized to give a mixture of diastereoisomers of the title compound. The diastereoisomers were separated by preparative TLC (Si, 1000 microns, Hex/EtOAc (70:30)), to afford (4S,5R)-5-[3,5-bis(trifluoromethyl)phenyl]-3-[2-(4-ethyl-1-phenyl-1H-pyrazol-3-yl)-5-(trifluoromethyl)benzyl]-4-methyl-1,3-oxazolidin-2-one. LCMS calc.=642.2; found=641.9 (M+1). $^1$H NMR (500 MHz, CDCl$_3$) δ 7.89 (s, 1H); 7.87 (s, 1H); 7.84 (s, 1H); 7.74-7.65 (m, 5H); 7.57 (d, J=7.9 Hz, 1H); 7.46 (t, J=7.9 Hz, 2H); 7.31 (d, J=7.9 Hz, 1H); 5.59 (d, J=8.0 Hz, 1H); 4.97 (d, J=15.5 Hz, 1H); 4.36 (d, J=15.5 Hz, 1H); 4.05-4.00 (m, 1H); 2.50 (q, J=7.5 Hz, 2H); 1.22 (t, J=7.5 Hz, 3H); 0.53 (d, J=6.5 Hz, 3H).

Example 137

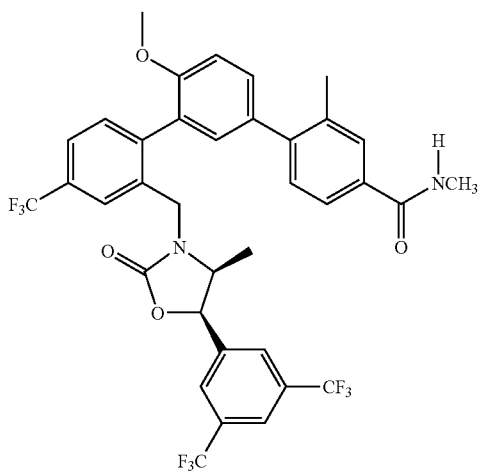

This was made by the method of Example 75.
LC/MS 725.2

Example 138

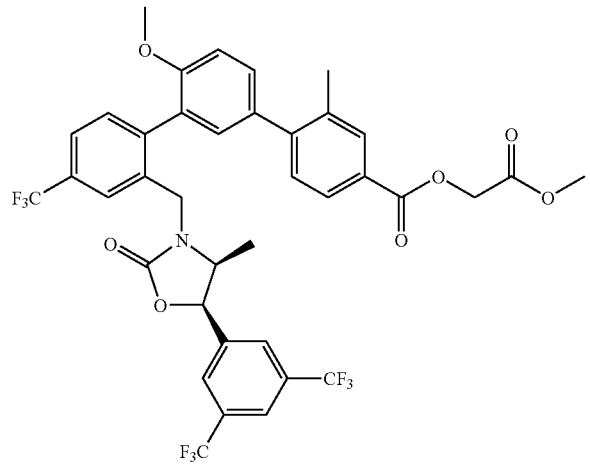

2-methoxy-2-oxoethyl 2"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-carboxylate 2"-({(4S,5R)-5-[3,5-bis(trifluoromethyl)phenyl]-4-methyl-2-oxo-1,3-oxazolidin-3-yl}methyl)-4'-methoxy-2-methyl-4"-(trifluoromethyl)-1,1':3',1"-terphenyl-4-carboxylic acid (EXAMPLE 30, 200 mg, 0.281 mmol), methyl hydroxyacetate (0.022 mL, 0.281 mmol), N-[3-(dimethylamino)propyl]-N'-ethylcarbodiimide hydrochloride (81 mg, 0.422 mmol) and triethylamine (0.059 ml; 0.422 mmol) were stirred in DCM (2.811 mL) at room temperature overnight. LCMS of aliquot indicated formation of the desired product and complete consumption of starting material. Volatiles were evaporated from the reaction crude. The pot residue was purified by prep HPLC to afford a light yellow solid as the titled compound. LCMS (ESI) calc.=783.19; found=784.0 (M+1)$^+$. $^1$H NMR (CDCl$_3$, 400 MHz, 1:1 mixture of atropisomers): δ 7.99 (d, J=6.8 Hz, 1H), 7.92 (d, J=8 Hz, 1H), 7.85 (s, 1H), 7.72-7.68 (m, 1.5H), 7.67-7.61 (m, 2.5H), 7.45-7.36 (m, 2H), 7.32-7.26 (m, 1H), 7.13 (s, 1H), 7.08 (d, J=5.6 Hz, 0.5H), 7.06 (d, J=5.6 Hz, 0.5H), 5.59 (d, J=8 Hz, 0.5H), 5.30 (d, J=8 Hz, 0.5H), 4.97 (d, J=14 Hz, 0.5H), 4.93 (d, J=14 Hz, 0.5H), 4.87 (s, 2H), 4.16 (d, J=15.6 Hz, 0.5H), 3.95 (d, J=16 Hz, 0.5H), 3.86 (s, 3H), 3.80 (s, 3H), 3.80-3.75 (m, 1H), 2.37 (s, 1.5H), 2.32 (s, 1.5H), 0.54 (d, J=6.8 Hz, 1.5H), 0.42 (d, J=6.8 Hz, 1.5H).

The following compounds were made using the method of EXAMPLE 138.

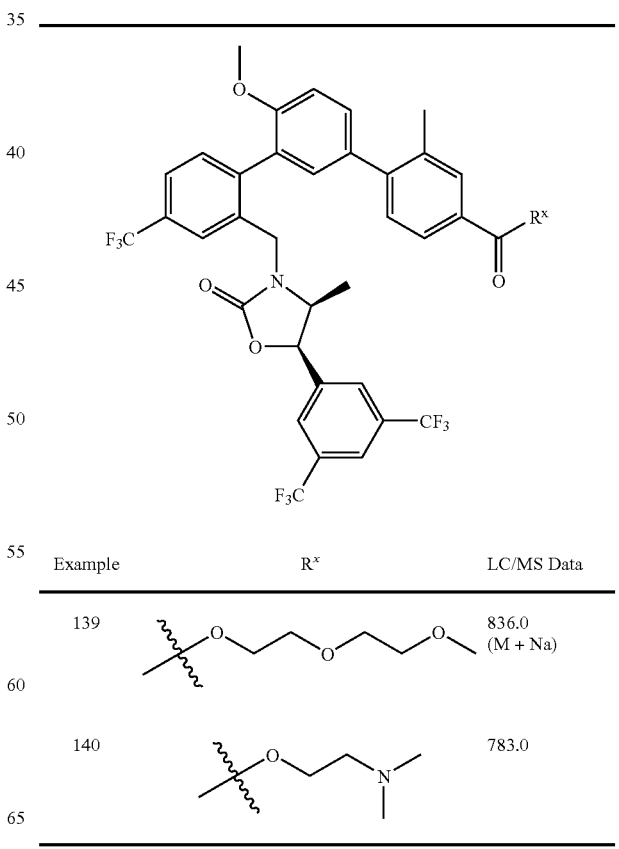

| Example | R$^x$ | LC/MS Data |
|---|---|---|
| 139 | | 836.0 (M + Na) |
| 140 | | 783.0 |

What is claimed is:

1. A compound having Formula I, or a pharmaceutically acceptable salt thereof, wherein

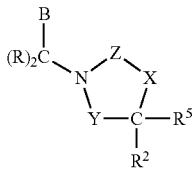

Y is —(CRR$^1$)—;
X is —O—;
Z is —C(=O)—;
Each R is independently selected from the group consisting of H, —C$_1$-C$_5$ alkyl, and halogen, wherein —C$_1$-C$_5$ alkyl is optionally substituted with 1-11 halogens;
B is, A$^1$; wherein A$^1$ has the structure:

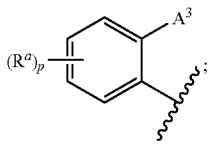

R$^1$ is selected from the group consisting of H, —C$_1$-C$_5$ alkyl, and halogen, wherein —C$_1$-C$_5$ alkyl is optionally substituted with 1-11 halogens;
R$^2$ is —(C(R)$_2$)$_n$A$^2$, wherein n is 0;
A$^3$ is selected from the group consisting of:
 (a) an aromatic ring selected from phenyl and naphthyl;
 (b) a phenyl ring fused to a 5-7 membered non-aromatic cycloalkyl ring, which optionally comprises 1-2 double bonds;
 (c) a 5-6-membered heterocyclic ring having 1-4 heteroatoms independently selected from N, S, O, and —N(O)—, and optionally also comprising 1-3 double bonds and a carbonyl group, wherein the point of attachment of A$^3$ to the phenyl ring to which A$^3$ is attached is a carbon atom; and
 (d) a benzoheterocyclic ring comprising a phenyl ring fused to a 5-6-membered heterocyclic ring having 1-2 heteroatoms independently selected from O, N, and —S(O)$_x$— and optionally 1-2 double bonds, wherein the point of attachment of A$^3$ to the phenyl ring to which A$^3$ is attached is a carbon atom;
wherein A$^3$ is substituted with one group A$^4$ and is optionally substituted with 1-4 groups R$^a$;
A$^2$ is phenyl,
wherein A$^2$ is optionally substituted with 1-5 substituent groups independently selected from R$^a$;
A$^4$ is selected from the group consisting of:
 (a) an aromatic ring selected from phenyl and naphthyl;
 (b) a phenyl ring fused to a 5-7 membered non-aromatic cycloalkyl ring, which optionally comprises 1-2 double bonds;
 (c) a 5-6-membered heterocyclic ring having 1-4 heteroatoms independently selected from N, S, O, and —N(O)—, and optionally also comprising 1-3 double bonds and a carbonyl group; and
 (d) a benzoheterocyclic ring comprising a phenyl ring fused to a 5-6-membered heterocyclic ring having 1-2 heteroatoms independently selected from O, N, and —S(O)$_x$— and optionally 1-2 double bonds;
wherein when A$^4$ is (a) an aromatic ring selected from phenyl and naphthyl; (b) a phenyl ring fused to a 5-7 membered non-aromatic cycloalkyl ring, which optionally comprises 1-2 double bonds; (c) a 5-6-membered heterocyclic ring having 1-4 heteroatoms independently selected from N, S, O, and —N(O)—, and optionally also comprising 1-3 double bonds and a carbonyl group, wherein the point of attachment of the heterocyclic ring to A$^3$ is a N atom of A$^4$; or (d) a benzoheterocyclic ring comprising a phenyl ring fused to a 5-6-membered heterocyclic ring having 1-2 heteroatoms independently selected from O, N, and —S(O)$_x$— and optionally 1-2 double bonds; then A$^4$ is optionally substituted with 1-5 groups R$^a$;
and when A$^4$ is a 5-6-membered heterocyclic ring having 1-4 heteroatoms independently selected from N, S, O, and —N(O)—, and optionally also comprising 1-3 double bonds and a carbonyl group, wherein the point of attachment of the heterocyclic ring to A$^3$ is a carbon atom of A$^4$, then A$^4$ is substituted with one group R$^e$ and is optionally also substituted with 1-4 groups independently selected from R$^a$;
Each R$^a$ is independently selected from the group consisting of —C$_1$-C$_6$ alkyl, —C$_2$-C$_6$ alkenyl, —C$_2$-C$_6$ alkynyl, —C$_3$-C$_8$ cycloalkyl optionally having 1-3 double bonds, —OC$_1$-C$_6$alkyl, —OC$_2$-C$_6$ alkenyl, —OC$_2$-C$_6$ alkynyl, —OC$_3$-C$_8$ cycloalkyl optionally having 1-3 doublebonds, —C(=O)C$_1$-C$_6$alkyl, —C(=O)C$_3$-C$_8$ cycloalkyl, —C(=O)H, —CO$_2$H, —CO$_2$C$_1$-C$_6$alkyl, —C(=O)SC$_1$-C$_6$alkyl, —OH, —NR$^3$R$^4$, —C(=O)NR$^3$R$^4$, —NR$^3$C(=O)OC$_1$-C$_6$ alkyl, —NR$^3$C(=O)NR$^3$R$^4$, —S(O)$_x$C$_1$-C$_6$ alkyl, —S(O)$_y$NR$^3$R$^4$, —NR$^3$S(O)$_y$NR$^3$R$^4$, halogen, —CN, —NO$_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which R$^a$ is attached is a carbon atom, wherein said heterocyclic ring is optionally substituted with 1-5 substituent groups independently selected from halogen, —C$_1$-C$_3$ alkyl, and —OC$_1$-C$_3$ alkyl, wherein —C$_1$-C$_3$ alkyl and —OC$_1$-C$_3$ alkyl are optionally substituted with 1-7 halogens;
wherein for compounds in which R$^a$ is selected from the group consisting of —C$_1$-C$_6$ alkyl, —C$_2$-C$_6$ alkenyl, —C$_2$-C$_6$ alkynyl, —C$_3$-C$_8$ cycloalkyl optionally having 1-3 double bonds, —OC$_1$-C$_6$alkyl, —OC$_2$-C$_6$ alkenyl, —OC$_2$-C$_6$ alkynyl, —OC$_3$-C$_8$ cycloalkyl optionally having 1-3 double bonds, —C(=O)C$_1$-C$_6$alkyl, —C(=O)C$_3$-C$_8$ cycloalkyl, —CO$_2$C$_1$-C$_6$alkyl, —C(=O)SC$_1$-C$_6$alkyl, —NR$^3$C(=O)OC$_1$-C$_6$alkyl, and —S(O)$_x$C$_1$-C$_6$ alkyl, R$^a$ is optionally substituted with 1-15 halogens and is optionally substituted with 1-3 substituent groups independently selected from (a) —OH, (b) —CN, (c) —NR$^3$R$^4$, (d) —C$_3$-C$_8$ cycloalkyl optionally having 1-3 double bonds and optionally substituted with 1-15 halogens, (e) —OC$_1$-C$_4$alkyl optionally substituted with 1-9 halogens and optionally substituted with 1-2 substituent groups independently selected from —OC$_1$-C$_2$ alkyl and phenyl, (f) —OC$_3$-C$_8$ cycloalkyl optionally having 1-3 double bonds and optionally substituted with 1-15 halogens, (g) —CO$_2$H, (h) —C(=O)CH$_3$, (i) —CO$_2$C$_1$-C$_4$alkyl which is optionally substituted with 1-9 halogens, and (j) phenyl which is optionally substituted with 1-3 groups independently selected from halogen, —CH$_3$, —CF$_3$, —OCH$_3$, and —OCF$_3$;

Each $R^e$ is independently selected from the group consisting of —$C_2$-$C_6$ alkenyl, —$C_2$-$C_6$ alkynyl, —$C_3$-$C_8$ cycloalkyl optionally having 1-3 double bonds, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)S$C_1$-$C_6$alkyl, —OH, —$NR^3R^4$, —C(=O)$NR^3R^4$, —$NR^3$C(=O)$OC_1$-$C_6$ alkyl, —$NR^3$C(=O)$NR^3R^4$, —S(O)$_x C_1$-$C_6$ alkyl, —S(O)$_y NR^3R^4$, —$NR^3$S(O)$_y NR^3R^4$, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^e$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^e$ is selected from the group consisting of —$C_2$-$C_6$ alkenyl, —$C_2$-$C_6$ alkynyl, —$C_3$-$C_8$ cycloalkyl optionally having 1-3 double bonds, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —$CO_2C_1$-$C_6$alkyl, —C(=O)S$C_1$-$C_6$alkyl, —$NR^3$C(=O)O$C_1$-$C_6$ alkyl, and —S(O)$_x C_1$-$C_6$ alkyl, $R^e$ is optionally substituted with 1-15 halogens and is optionally substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$OC_1$-$C_2$ alkyl and phenyl, (f) —$OC_3$-$C_8$ cycloalkyl optionally having 1-3 double bonds and optionally substituted with 1-15 halogens, (g) —$CO_2$H, (h) —C(=O)$CH_3$, (i) —$CO_2C_1$-$C_4$alkyl which is optionally substituted with 1-9 halogens, and (j) phenyl which is optionally substituted with 1-3 groups independently selected from halogen, —$CH_3$, —$CF_3$, —$OCH_3$, and —$OCF_3$;

p is an integer from 0-4;

x is 0, 1, or 2;

y is 1 or 2;

$R^3$ and $R^4$ are each independently selected from H, —$C_1$-$C_5$ alkyl, —C(=O)$C_1$-$C_5$ alkyl and —S(O)$_y C_1$-$C_5$ alkyl, wherein —$C_1$-$C_5$ alkyl in all instances is optionally substituted with 1-11 halogens; and $R^5$ is selected from the group consisting of H, —OH, —$C_1$-$C_5$ alkyl, and halogen, wherein —$C_1$-$C_5$ alkyl is optionally substituted with 1-11 halogens.

2. The compound of claim 1 of Formula Ia, or a pharmaceutically acceptable salt thereof:

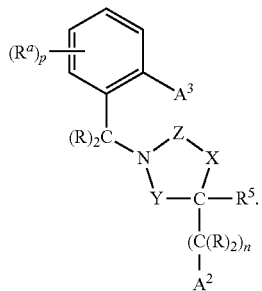

Ia

3. The compound of claim 1, or a pharmaceutically acceptable salt thereof, wherein:

R is selected from the group consisting of H and —$C_1$-$C_5$ alkyl, wherein —$C_1$-$C_5$ alkyl is optionally substituted with 1-11 halogens;

$R^1$ is selected from the group consisting of H and —$C_1$-$C_5$ alkyl, wherein —$C_1$-$C_5$ alkyl is optionally substituted with 1-11 halogens;

$A^3$ is selected from the group consisting of:
(a) an aromatic ring selected from phenyl and naphthyl;
(b) a 5-6-membered heterocyclic ring having 1-4 heteroatoms independently selected from N, S, O, and —N(O)—, and optionally also comprising 1-3 double bonds and a carbonyl group, wherein the point of attachment of $A^3$ to the phenyl ring to which $A^3$ is attached is a carbon atom; and
(c) a benzoheterocyclic ring comprising a phenyl ring fused to a 5-6-membered heterocyclic ring having 1-2 heteroatoms independently selected from O, N, and —S(O)$_x$— and optionally 1-2 double bonds, wherein the point of attachment of $A^3$ to the phenyl ring to which $A^3$ is attached is a carbon atom;

wherein $A^3$ is substituted with one group $A^4$ and is optionally substituted with 1-4 groups $R^a$;

$A^2$ is phenyl,
wherein $A^2$ is optionally substituted with 1-5 substituent groups independently selected from $R^a$;

Each $R^a$ is independently selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —C(=O)H, —$CO_2$H, —$CO_2C_1$-$C_6$alkyl, —OH, —$NR^3R^4$, —$NR^3$C(=O)$OC_1$-$C_6$ alkyl, —S(O)$_x C_1$-$C_6$ alkyl, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —$CO_2C_1$-$C_6$alkyl, —$NR^3$C(=O)O$C_1$-$C_6$ alkyl, and —S(O)$_x C_1$-$C_6$ alkyl, $R^a$ is optionally substituted with 1-15 halogens and is optionally substituted with one substituent group selected from (a) —OH, (b) —$NR^3R^4$, (c) —$OC_1$-$C_4$alkyl optionally substituted with 1-9 halogens and optionally substituted with 1-2 substituent groups independently selected from —$OC_1$-$C_2$ alkyl and phenyl, and (d) phenyl which is optionally substituted with 1-3 groups independently selected from halogen, —$CH_3$, —$CF_3$, —$OCH_3$, and —$OCF_3$;

Each $R^e$ is independently selected from the group consisting of —$C_2$-$C_6$ alkenyl, —$C_3$-$C_8$ cycloalkyl optionally having 1-3 double bonds, —C(=O)$C_1$-$C_6$alkyl, —C(=O)H, —$CO_2$H, —$CO_2C_1$-$C_6$alkyl, —OH, —$NR^3R^4$, —$NR^3$C(=O)$OC_1$-$C_6$ alkyl, —S(O)$_x C_1$-$C_6$ alkyl, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^e$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^e$ is selected from the group consisting of —$C_2$-$C_6$ alkenyl, —$C_3$-$C_8$ cycloalkyl optionally having 1-3 double bonds, —C(=O)$C_1$-$C_6$alkyl, —$CO_2C_1$-$C_6$alkyl, —$NR^3$C(=O)$OC_1$-$C_6$ alkyl, and —S(O)$_x$$C_1$-$C_6$ alkyl, $R^e$ is optionally substituted with 1-15 halogens and is optionally substituted with one substituent group selected from (a) —OH, (b) —$NR^3R^4$, (c) —$OC_1$-$C_4$alkyl optionally substituted with 1-9 halogens and optionally also substituted with 1-2 substituent groups independently selected from —$OC_1$-$C_2$ alkyl and phenyl, and (d) phenyl which is optionally substituted with 1-3 groups independently selected from halogen, —$CH_3$, —$CF_3$, —$OCH_3$, and —$OCF_3$;

p is an integer from 0-2;

$R^3$ and $R^4$ are each independently selected from H and —$C_1$-$C_5$ alkyl, wherein —$C_1$-$C_5$ alkyl in all instances is optionally substituted with 1-11 halogens; and $R^5$ is selected from the group consisting of H, —OH, and —$C_1$-$C_5$ alkyl, wherein —$C_1$-$C_5$ alkyl is optionally substituted with 1-11 halogens.

4. The compound of claim 1, or a pharmaceutically acceptable salt thereof, wherein:

Each R is independently selected from the group consisting of H and $C_1$-$C_2$ alkyl;

$R^1$ is selected from the group consisting of H and —$C_1$-$C_3$ alkyl, and wherein —$C_1$-$C_3$ alkyl is optionally substituted with 1-5 halogens;

$A^3$ is selected from the group consisting of:
(a) phenyl;
(b) a 5-6-membered aromatic heterocyclic ring having 1-2 heteroatoms independently selected from N, S, O, and —N(O)—, wherein the point of attachment of $A^3$ to the phenyl ring to which $A^3$ is attached is a carbon atom; and
(c) a benzoheterocyclic ring comprising a phenyl ring fused to a 5-membered aromatic heterocyclic ring having 1-2 heteroatoms independently selected from O, N, and —S(O)$_x$, wherein the point of attachment of $A^3$ to the phenyl ring to which $A^3$ is attached is a carbon atom;

wherein $A^3$ is substituted with one group $A^4$ and is optionally substituted with 1-4 groups $R^a$;

Each $R^a$ is independently selected from the group consisting of —$C_1$-$C_4$ alkyl, —$C_2$-$C_4$ alkenyl, cyclopropyl, —$OC_1$-$C_2$alkyl, —C(=O)$C_1$-$C_2$alkyl, —C(=O)H, —$CO_2$H, —$CO_2C_1$-$C_4$alkyl, —OH, —$NR^3R^4$, —$NR^3$C(=O)$OC_1$-$C_4$ alkyl, —S(O)$_x$$C_1$-$C_2$ alkyl, halogen, —CN, —$NO_2$, and a 5-6-membered heterocyclic ring having 1-2 heteroatoms independently selected from N, S, and O, wherein the point of attachment of said heterocyclic ring to the ring to which $R^a$ is attached ring is a carbon atom, wherein said heterocyclic ring is optionally substituted with 1-5 substituent groups independently selected from halogen;

wherein for compounds in which $R^a$ is selected from the group consisting of —$C_1$-$C_4$ alkyl, —$C_2$-$C_4$ alkenyl, —$OC_1$-$C_2$alkyl, —C(=O)$C_1$-$C_2$alkyl, —$CO_2C_1$-$C_4$alkyl, —$NR^3$C(=O)$OC_1$-$C_4$ alkyl, and —S(O)$_x$$C_1$-$C_2$ alkyl, the alkyl group of $R^a$ is optionally substituted with 1-5 halogens and is optionally substituted with one substituent group selected from (a) —OH, (b) —$NR^3R^4$, (c) —$OCH_3$ optionally substituted with 1-3 fluorine atoms and optionally also substituted with one phenyl group, and (d) phenyl which is optionally substituted with 1-3 groups independently selected from halogen, —$CH_3$, —$CF_3$, —$OCH_3$, and —$OCF_3$;

Each $R^e$ is independently selected from the group consisting of —$C_2$-$C_4$ alkenyl, cyclopropyl, —C(=O)$C_1$-$C_2$alkyl, —C(=O)H, —$CO_2$H, —$CO_2C_1$-$C_4$alkyl, —OH, —$NR^3R^4$, —$NR^3$C(=O)$OC_1$-$C_4$alkyl, —S(O)$_x$$C_1$-$C_2$ alkyl, —CN, —$NO_2$, and a 5-6-membered heterocyclic ring having 1-2 heteroatoms independently selected from N, S, and O, wherein the point of attachment of said heterocyclic ring to the ring to which $R^e$ is attached is a carbon atom, wherein said heterocyclic ring is optionally substituted with 1-5 substituent groups independently selected from halogen;

wherein for compounds in which $R^e$ is selected from the group consisting of —$C_2$-$C_4$ alkenyl, —C(=O)$C_1$-$C_2$alkyl, —$CO_2C_1$-$C_4$alkyl, —$NR^3$C(=O)$OC_1$-$C_4$ alkyl, and —S(O)$_x$$C_1$-$C_2$ alkyl, the alkyl group of $R^e$ is optionally substituted with 1-5 halogens and is optionally also substituted with one substituent group selected from (a) —OH, (b) —$NR^3R^4$, (c) —$OCH_3$ optionally substituted with 1-3 fluorine atoms and optionally substituted with one phenyl group, and (d) phenyl which is optionally substituted with 1-3 groups independently selected from halogen, —$CH_3$, —$CF_3$, —$OCH_3$, and —$OCF_3$;

p is an integer from 0-2; and $R^3$, $R^4$, and $R^5$ are each independently selected from H and —$C_1$-$C_3$ alkyl.

5. The compound of claim 1, or a pharmaceutically acceptable salt thereof, wherein X is —O—;

Z is —C(=O)—;

Y is —$CHR^1$, where $R^1$ is selected from H and $C_1$-$C_2$alkyl;

R and $R^5$ are H;

$A^3$ is selected from the group consisting of phenyl, thiazolyl, and pyrazolyl;

$A^4$ is selected from the group consisting of phenyl, pyridyl, thiazolyl, pyrazolyl, 1,2,4-triazolyl, pyrimidinyl, piperidinyl, pyrrolidinyl, and azetidinyl;

$A^2$ is optionally substituted with 1-3 substituents independently selected from halogen, —$OCH_3$, —$OCF_3$, and $C_1$-$C_3$alkyl optionally substituted with 1-3 halogens;

$A^3$ is substituted with one group $A^4$ and is optionally substituted with 1-2 substituents independently selected from halogen, —OH, —$OCH_3$, —$OCF_3$, and $C_1$-$C_3$alkyl optionally substituted with 1-3 halogens;

$A^4$ is optionally substituted with 1-3 substituents independently selected from the group consisting of (a) —$C_1$-$C_5$ alkyl optionally substituted with 1-3 halogens and optionally substituted with —OH, (b) —$C_2$-$C_4$ alkenyl optionally substituted with 1-3 halogens, (c) —C(=O)$C_1$-$C_2$alkyl optionally substituted with 1-3 halogens and optionally substituted with one group selected from —OH, —$CO_2CH_3$, —C(=O)$CH_3$, —$NR^3R^4$, and —$OC_1$-$C_2$alkyleneO$C_1$-$C_2$alkyl, (d) —C(=O)H, (e) —$CO_2$H, (f) —$CO_2C_1$-$C_4$alkyl optionally substituted with one group selected from —C(=O)$C_1$-$C_2$alkyl, —OH, —$CO_2CH_3$, —$CO_2$H, —$NR^3R^4$, and —$OC_1$-$C_2$alkyleneO$C_1$-$C_2$alkyl, (g) —OH, (h) —S(O)$_x$$C_1$-$C_2$ alkyl, (i) halogen, (j) —CN, (k) —$NO_2$, (l) —C(=O)$NR^3R^4$, (m) —$OC_1$-$C_2$alkyleneO$C_1$-$C_2$alkyl, (n)

—OC$_1$-C$_3$ alkyl optionally substituted with 1-3 halogens, (o) —C(=O)OC$_1$-C$_2$alkyl optionally substituted with 1-3 halogens and optionally substituted with one group selected from —OH, —CO$_2$CH$_3$, —NR$^3$R$^4$, and —OC$_1$-C$_2$alkyleneOC$_1$-C$_2$alkyl, (p) —NR$^3$C(=O)C$_1$-C$_2$alkyl, (q) —NR$^3$R$^4$, and (r) —S(O)$_x$NR$^3$R$^4$, provided that if A$^4$ is a heterocyclic group connected to A$^3$ through a ring carbon atom of A$^4$, then at least one substituent on A$^4$ must be selected from R$^e$, where R$^e$ is selected from the group consisting of (a) —C$_1$-C$_5$ alkyl substituted with —OH and optionally substituted with 1-3 halogens, (b) —C$_2$-C$_4$ alkenyl optionally substituted with 1-3 halogens, (c) —C(=O)C$_1$-C$_2$alkyl optionally substituted with 1-3 halogens and optionally substituted with one group selected from —OH, —CO$_2$CH$_3$, —C(=O)CH$_3$, —NR$^3$R$^4$, and —OC$_1$-C$_2$alkyleneOC$_1$-C$_2$alkyl, (d) —C(=O)H, (e) —CO$_2$H, (f) —CO$_2$C$_1$-C$_4$alkyl optionally substituted with one group selected from —C(=O)C$_1$-C$_2$alkyl, —OH, —CO$_2$CH$_3$, —CO$^2$H, —NR$^3$R$^4$, and —OC$_1$-C$_2$alkyleneOC$_1$-C$_2$alkyl, (g) —OH, (h) —S(O)$_x$C$_1$-C$_2$ alkyl, (i) —CN, (j) —NO$_2$, (k) —C(=O)NR$^3$R$^4$, (l) —OC$_1$-C$_2$alkyleneOC$_1$-C$_2$alkyl, (m) —C(=O)OC$_1$-C$_2$alkyl optionally substituted with 1-3 halogens and optionally substituted with one group selected from —OH, —CO$_2$CH$_3$, —NR$^3$R$^4$, and —OC$_1$-C$_2$alkyleneOC$_1$-C$_2$alkyl, (n) —NR$^3$C(=O)C$_1$-C$_2$alkyl, (o) —NR$^3$R$^4$; and (p) —S(O)$_x$NR$^3$R$^4$;

p is 0, 1, or 2; and

R$^a$ is selected from halogen, —CH$_3$, —CF$_3$, —OCH$_3$, and —OCF$_3$;

R$^3$ and R$^4$ are each independently selected from H and CH$_3$; and x is 0, 1 or 2.

6. The compound of claim 4, or a pharmaceutically acceptable salt thereof, wherein A$^2$, A$^3$, and A$^4$ are phenyl; and Each R$^a$ is selected from the group consisting of (a) —C$_1$-C$_4$ alkyl which is optionally substituted with 1-5 fluorine atoms and is optionally substituted with one group selected from —OH, —OCH$_3$, and —NR$^3$R$^4$; (b) —OC$_1$-C$_2$alkyl, which is optionally substituted with 1-3 fluorine atoms; (c) —C$_2$-C$_4$ alkenyl; (d) —C$_1$-C$_2$ alkyl-O—C$_1$-C$_2$ alkyl-phenyl; (e) cyclopropyl; (f) —C(=O)H; (g) —CO$_2$H; (h) —CO$_2$C$_1$-C$_4$alkyl; (i) —OH; (j) —NR$^3$R$^4$; (k) —S(O)$_x$C$_1$-C$_2$ alkyl; (l) halogen; (m) —CN; (n) —NO$_2$; and (o) a 5-6-membered heterocyclic ring comprising 1-2 oxygen atoms which is optionally substituted with C$_1$-C$_2$alkyl.

7. The compound of claim 1 of Formula Ic, or a pharmaceutically acceptable salt thereof,

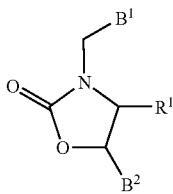

Ic wherein B$^1$ is:

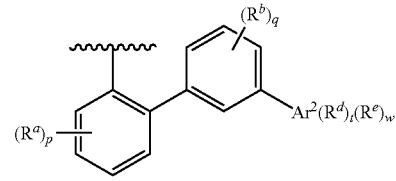

and B$^2$ is Ar$^1$(R$^c$)$_u$;

Ar$^1$ is phenyl;

Ar$^2$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a benzoheterocyclic ring comprising a phenyl ring fused to a 5-6-membered heterocyclic ring having 1-2 heteroatoms independently selected from O, N, and S and optionally 1-2 double bonds; and
(d) a 5-6-membered heterocyclic ring having 1-4 heteroatoms independently selected from N, S, O, and —N(O)—, and optionally also comprising 1-3 double bonds and a carbonyl group;

R$^1$ is selected from the group consisting of H, —C$_1$-C$_5$ alkyl, and halogen, wherein —C$_1$-C$_5$ alkyl is optionally substituted with 1-11 halogens;

R$^3$ and R$^4$ are each independently selected from H, —C$_1$-C$_5$ alkyl, —C(=O)C$_1$-C$_5$ alkyl and —S(O)$_y$C$_1$-C$_5$ alkyl, wherein —C$_1$-C$_5$ alkyl in all instances is optionally substituted with 1-11 halogens;

Each R$^a$, R$^b$, R$^c$, and R$^d$ is independently selected from the group consisting of —C$_1$-C$_6$ alkyl, —C$_2$-C$_6$ alkenyl, —C$_2$-C$_6$ alkynyl, —C$_3$-C$_8$ cycloalkyl optionally having 1-3 double bonds, —OC$_1$-C$_6$alkyl, —OC$_2$-C$_6$ alkenyl, —OC$_2$-C$_6$ alkynyl, —OC$_3$-C$_8$ cycloalkyl optionally having 1-3 double bonds, —C(=O)C$_1$-C$_6$alkyl, —C(=O)C$_3$-C$_8$ cycloalkyl, —C(=O)H, —CO$_2$H, —CO$_2$C$_1$-C$_6$alkyl, —C(=O)SC$_1$-C$_6$alkyl, —OH, —NR$^3$R$^4$, —C(=O)NR$^3$R$^4$, —NR$^3$C(=O)OC$_1$-C$_6$ alkyl, —NR$^3$C(=O)NR$^3$R$^4$, —S(O)$_x$C$_1$-C$_6$ alkyl, —S(O)$_y$NR$^3$R$^4$, —NR$^3$S(O)$_y$NR$^3$R$^4$, halogen, —CN, —NO$_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which R$^a$, R$^b$, R$^c$, or R$^d$ is attached is a carbon atom, wherein said heterocyclic ring is optionally substituted with 1-5 substituent groups independently selected from halogen, —C$_1$-C$_3$ alkyl, and —OC$_1$-C$_3$ alkyl, wherein —C$_1$-C$_3$ alkyl and —OC$_1$-C$_3$ alkyl are optionally substituted with 1-7 halogens;

wherein when R$^a$, R$^b$, R$^c$, and R$^d$ are selected from the group consisting of —C$_1$-C$_6$ alkyl, —C$_2$-C$_6$ alkenyl, —C$_2$-C$_6$ alkynyl, —C$_3$-C$_8$ cycloalkyl optionally having 1-3 double bonds, —OC$_1$-C$_6$alkyl, —OC$_2$-C$_6$ alkenyl, —OC$_2$-C$_6$ alkynyl, —OC$_3$-C$_8$ cycloalkyl optionally having 1-3 double bonds, —C(=O)C$_1$-C$_6$alkyl, —C(=O)C$_3$-C$_8$ cycloalkyl, —CO$_2$C$_1$-C$_6$alkyl, —C(=O)SC$_1$-C$_6$alkyl, —NR$^3$C(=O)OC$_1$-C$_6$alkyl, and —S(O)$_x$C$_1$-C$_6$ alkyl, then R$^a$, R$^b$, R$^c$, and R$^d$ are optionally substituted with 1-15 halogens and are optionally substituted with 1-3 substituent groups independently selected from (a) —OH, (b) —CN, (c)

—NR³R⁴, (d) —C₃-C₈ cycloalkyl optionally having 1-3 double bonds and optionally substituted with 1-15 halogens, (e) —OC₁-C₄alkyl optionally substituted with 1-9 halogens and optionally substituted with 1-2 substituent groups independently selected from —OC₁-C₂ alkyl and phenyl, (f) —OC₃-C₈ cycloalkyl optionally having 1-3 double bonds and optionally substituted with 1-15 halogens, (g) —CO₂H, (h) —C(=O)CH₃, (i) —CO₂C₁-C₄alkyl which is optionally substituted with 1-9 halogens, and (j) phenyl which is optionally substituted with 1-3 groups independently selected from halogen, —CH₃, —CF₃, —OCH₃, and —OCF₃;

R$^e$ is selected from the group consisting of —C₂-C₆ alkenyl, —C₂-C₆ alkynyl, —C₃-C₈ cycloalkyl optionally having 1-3 double bonds, —OC₂-C₆ alkenyl, —OC₂-C₆ alkynyl, —OC₃-C₈ cycloalkyl optionally having 1-3 double bonds, —C(=O)C₁-C₆alkyl, —C(=O)C₃-C₈ cycloalkyl, —C(=O)H, —CO₂H, —CO₂C₁-C₆alkyl, —C(=O)SC₁-C₆alkyl, —OH, —NR³R⁴, —C(=O)NR³R⁴, —NR³C(=O)OC₁-C₆ alkyl, —NR³C(=O)NR³R⁴, —S(O)$_x$C₁-C₆ alkyl, —S(O)$_y$NR³R⁴, —NR³S(O)$_y$NR³R⁴, —CN, —NO₂, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which R$^e$ is attached is a carbon atom, wherein said heterocyclic ring is optionally substituted with 1-5 substituent groups independently selected from halogen, —C₁-C₃ alkyl, and —OC₁-C₃ alkyl, wherein —C₁-C₃ alkyl and —OC₁-C₃ alkyl are optionally substituted with 1-7 halogens;

wherein when R$^e$ is selected from the group consisting of —C₂-C₆ alkenyl, —C₂-C₆ alkynyl, —C₃-C₈ cycloalkyl optionally having 1-3 double bonds, —OC₂-C₆ alkenyl, —OC₂-C₆ alkynyl, —OC₃-C₈ cycloalkyl optionally having 1-3 double bonds, —C(=O)C₁-C₆alkyl, —C(=O)C₃-C₈ cycloalkyl, —CO₂C₁-C₆alkyl, —C(=O)SC₁-C₆alkyl, —NR³C(=O)OC₁-C₆ alkyl, and —S(O)$_x$C₁-C₆ alkyl, then R$^e$ is optionally substituted with 1-15 halogens and is optionally substituted with 1-3 substituent groups independently selected from (a) —OH, (b) —CN, (c) —NR³R⁴, (d) —C₃-C₈ cycloalkyl optionally having 1-3 double bonds and optionally substituted with 1-15 halogens, (e) —OC₁-C₄alkyl optionally substituted with 1-9 halogens and optionally substituted with 1-2 substituent groups independently selected from —OC₁-C₂ alkyl and phenyl, (f) —OC₃-C₈ cycloalkyl optionally having 1-3 double bonds and optionally substituted with 1-15 halogens, (g) —CO₂H, (h) —C(=O)CH₃, (i) —CO₂C₁-C₄alkyl which is optionally substituted with 1-9 halogens, and (j) phenyl which is optionally substituted with 1-3 groups independently selected from halogen, —CH₃, —CF₃, —OCH₃, and —OCF₃;

p is an integer from 0-4;
q is an integer from 0-4;
u is an integer from 0-5;
x is 0, 1 or 2; and
y is 1 or 2;

wherein when Ar² is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a benzoheterocyclic ring comprising a phenyl ring fused to a 5-6-membered heterocyclic ring having 1-2 heteroatoms independently selected from O, N, and S and optionally 1-2 double bonds; and
(d) a 5-6-membered heterocyclic ring having 1-4 heteroatoms independently selected from N, S, O, and —N(O)—, and optionally also comprising 1-3 double bonds and a carbonyl group, wherein the point of attachment of the heterocyclic ring to the phenyl group to which the heterocyclic ring is attached is a heteroatom of the heterocyclic ring;

then t is an integer from 0-5, and w is 0;

and when Ar² is a 5-6-membered heterocyclic ring having 1-4 heteroatoms independently selected from N, S, O, and —N(O)—, and optionally also comprising 1-3 double bonds and a carbonyl group, wherein the point of attachment of the heterocyclic ring to the phenyl group to which the heterocyclic ring is attached is a carbon atom of the heterocyclic ring, then t is an integer from 0-4, and w is 1.

8. The compound of claim 7 of Formula Ie, or a pharmaceutically acceptable salt thereof:

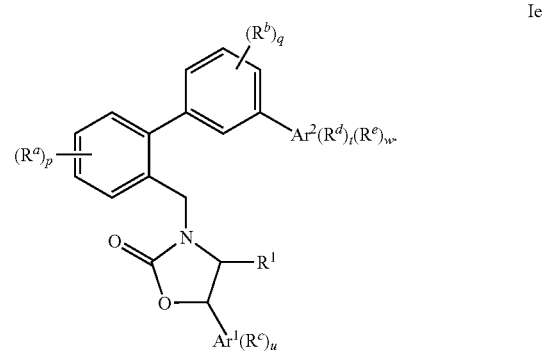

Ie

9. The compound of claim 8 of Formula Ig, or a pharmaceutically acceptable salt thereof, wherein

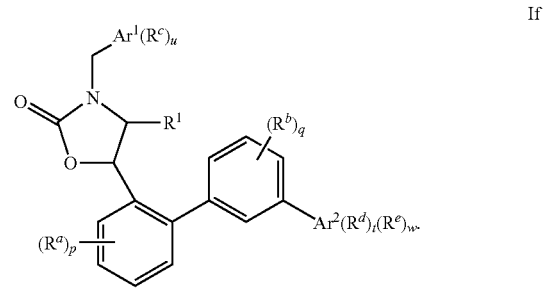

If

Each R$^d$ is independently selected from the group consisting of —C₁-C₄ alkyl, —C₂-C₄ alkenyl, cyclopropyl, —OC₁-C₄alkyl, —C(=O)C₁-C₄alkyl, —C(=O)H, —CO₂H, —CO₂C₁-C₄alkyl, —OH, —NR³R⁴, —NR³C(=O)OC₁-C₄ alkyl, —S(O)$_x$C₁-C₂ alkyl, halogen, —CN, —NO₂, and a 5-6-membered heterocyclic ring having 1-2 heteroatoms independently selected from N, S, and O, wherein the point of attachment of said heterocyclic ring to the ring to which R$^d$ is attached is a carbon atom, wherein said heterocyclic ring is optionally substituted with 1-5 substituent groups independently selected from halogen;

wherein when $R^d$ is selected from the group consisting of —$C_1$-$C_4$ alkyl, —$C_2$-$C_4$ alkenyl, cyclopropyl, —$OC_1$-$C_4$alkyl, —C(=O)$C_1$-$C_4$alkyl, —$CO_2C_1$-$C_4$alkyl, —$NR^3$C(=O)$OC_1$-$C_4$ alkyl, and —S(O)$_x$$C_1$-$C_2$ alkyl, then the alkyl, alkenyl and cyclopropyl group of $R^d$ is optionally substituted with 1-5 halogens and is optionally substituted with one substituent group selected from (a) —OH, (b) —$NR^3R^4$, (c) —$OCH_3$ optionally substituted with 1-3 fluorine atoms and optionally substituted with one phenyl group, and (d) phenyl which is optionally substituted with 1-3 groups independently selected from halogen, —$CH_3$, —$CF_3$, —$OCH_3$, and —$OCF_3$; and t is an integer from 0-5.

10. The compound of claim 9 of Formula Ih, or a pharmaceutically acceptable salt thereof:

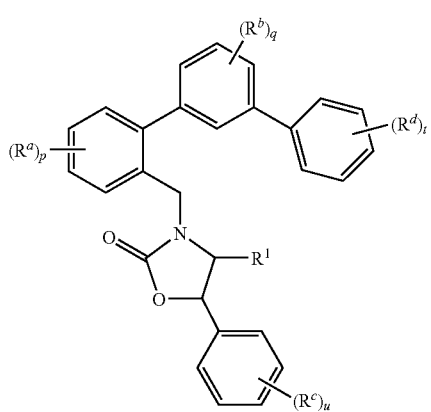

Ih

11. The compound of claim 7, or a pharmaceutically acceptable salt thereof:
wherein $R^1$ is selected from the group consisting of H, and —$C_1$-$C_5$ alkyl, wherein —$C_1$-$C_5$ alkyl is optionally substituted with 1-11 halogens;
$R^3$ and $R^4$ are each independently selected from H and —$C_1$-$C_5$ alkyl, wherein —$C_1$-$C_5$ alkyl in all instances is optionally substituted with 1-11 halogens;
Each $R^a$, $R^b$, and $R^c$ is independently selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —C(=O)H, —$CO_2$H, —$CO_2C_1$-$C_6$alkyl, —OH, —$NR^3R^4$, —$NR^3$C(=O)$OC_1$-$C_6$ alkyl, —S(O)$_x$$C_1$-$C_6$ alkyl, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;
wherein when $R^a$, $R^b$, and $R^c$ are selected from the group consisting of —$C_1$-$C_6$ alkyl, —$C_2$-$C_6$ alkenyl, —$C_3$-$C_8$ cycloalkyl optionally having 1-3 double bonds, —$OC_1$-$C_6$alkyl, —C(=O)$C_1$-$C_6$alkyl, —$CO_2C_1$-$C_6$alkyl, —$NR^3$C(=O)$OC_1$-$C_6$ alkyl, and —S(O)$_x$$C_1$-$C_6$ alkyl, then $R^a$, $R^b$ and $R^d$ are optionally substituted with 1-15 halogens and are optionally substituted with one substituent group selected from (a) —OH, (b) —$NR^3R^4$, (c) —$OC_1$-$C_4$alkyl optionally substituted with 1-9 halogens and optionally substituted with 1-2 groups independently selected from —$OC_1$-$C_2$ alkyl and phenyl, and (d) phenyl which is optionally substituted with 1-3 groups independently selected from halogen, —$CH_3$, —$CF_3$, —$OCH_3$, and —$OCF_3$;

Each $R^d$ is independently selected from the group consisting of —$C_1$-$C_4$ alkyl, —$C_2$-$C_4$ alkenyl, —$OC_1$-$C_2$alkyl, —C(=O)$C_1$-$C_2$alkyl, —C(=O)H, —$CO_2$H, —$CO_2C_1$-$C_4$alkyl, —OH, —$NR^3R^4$, —$NR^3$C(=O)$OC_1$-$C_4$ alkyl, —S(O)$_x$$C_1$-$C_2$ alkyl, halogen, —CN, —$NO_2$, and a 5-6-membered heterocyclic ring having 1-2 heteroatoms independently selected from N, S, and O, wherein the point of attachment of said heterocyclic ring to the ring to which $R^a$ is attached is a carbon atom, wherein said heterocyclic ring is optionally substituted with 1-5 substituent groups independently selected from halogen;

wherein when $R^d$ is selected from the group consisting of —$C_1$-$C_4$ alkyl, —$C_2$-$C_4$ alkenyl, —$OC_1$-$C_2$alkyl, —C(=O)$C_1$-$C_2$alkyl, —$CO_2C_1$-$C_4$alkyl, —$NR^3$C(=O)$OC_1$-$C_4$ alkyl, and —S(O)$_x$$C_1$-$C_2$ alkyl, then the alkyl or alkenyl group of $R^d$ is optionally substituted with 1-5 halogens and is optionally substituted with one group selected from (a) —OH, (b) —$NR^3R^4$, (c) —$OCH_3$ optionally substituted with 1-3 fluorine atoms and optionally substituted with one phenyl group, and (d) phenyl which is optionally substituted with 1-3 groups independently selected from halogen, —$CH_3$, —$CF_3$, —$OCH_3$, and —$OCF_3$;

p is an integer from 0-2;
q is an integer from 0-2;
t is an integer from 0-3;
u is an integer from 0-2;
x is 0, 1 or 2; and
y is 1 or 2.

12. The compound of claim 7, or a pharmaceutically acceptable salt thereof, wherein:
$R^1$ is selected from H and —$C_1$-$C_2$ alkyl;
$R^3$ and $R^4$ are each independently selected from H and —$C_1$-$C_3$ alkyl;
Each $R^a$, $R^b$, and $R^c$ is independently selected from the group consisting of —$C_1$-$C_4$ alkyl, —$C_2$-$C_4$ alkenyl, —$OC_1$-$C_2$alkyl, —C(=O)$C_1$-$C_2$alkyl, —C(=O)H, —$CO_2$H, —$CO_2C_1$-$C_4$alkyl, —OH, —$NR^3R^4$, —$NR^3$C(=O)$OC_1$-$C_4$ alkyl, —S(O)$_x$$C_1$-$C_2$ alkyl, halogen, —CN, and —$NO_2$;
wherein when $R^a$, $R^b$, and $R^c$ are selected from —$C_1$-$C_4$ alkyl, —$C_2$-$C_4$ alkenyl, —$OC_1$-$C_2$alkyl, —C(=O)$C_1$-$C_2$alkyl, —$CO_2C_1$-$C_4$alkyl, —$NR^3$C(=O)$OC_1$-$C_4$ alkyl, and —S(O)$_x$$C_1$-$C_2$ alkyl, then the alkyl and alkenyl groups of $R^a$, $R^b$, and $R^c$ are optionally substituted with 1-5 halogens and are optionally substituted with one group selected from (a) —OH, (b) —$NR^3R^4$, (c) —$OCH_3$ optionally substituted with 1-3 fluorine atoms and optionally substituted with one phenyl group, and (d) phenyl which is optionally substituted with 1-3 groups independently selected from halogen, —$CH_3$, —$CF_3$, —$OCH_3$, and —$OCF_3$;
$R^d$ is selected from the group consisting of —$C_1$-$C_4$ alkyl, —$C_2$-$C_4$ alkenyl, —$NR^3R^4$, —C(=O)H, —$CO_2$H, —$CO_2C_1$-$C_4$alkyl, —OH, halogen, —CN, and —$NO_2$, wherein —$C_1$-$C_4$ alkyl and —$C_2$-$C_4$ alkenyl in all uses are optionally substituted with 1-5 fluorine atoms
p is an integer from 1-2;
q is an integer from 1-2;
t is an integer from 0-3;
u is an integer from 1-2; and
x is 0, 1 or 2.

13. The compound of claim 7, or a pharmaceutically acceptable salt thereof, wherein $R^1$, $R^3$ and $R^4$ are each independently selected from H and $CH_3$;

$R^a$, $R^b$, and $R^c$ are each independently selected from the group consisting of $-C_1-C_3$ alkyl, $-OC_1-C_2$alkyl, halogen and $-OH$, wherein $-C_1-C_3$ alkyl and $-OC_1-C_2$alkyl are optionally substituted with 1-3 F;

$R^d$ is selected from the group consisting of $-C_1-C_3$ alkyl, $-NR^3R^4$, $-CO_2H$, $-CO_2C_1-C_3$alkyl, halogen, and $-CN$, wherein $-C_1-C_3$ alkyl and $-CO_2C_1-C_3$alkyl are optionally substituted with 1-3 F;

p is an integer from 1-2;
q is an integer from 1-2;
t is an integer from 0-3; and
u is an integer from 1-2.

14. The compound of claim 7, or a pharmaceutically acceptable salt thereof, wherein $Ar^2$ is selected from the group consisting of phenyl, pyridyl, pyrimidyl, pyrazinyl, pyrazolyl, pyrrolyl, oxazolyl, isoxazolyl, thiazolyl, isothiazolyl, thienyl, furyl, benzothiophenyl, benzoxazolyl, benzisoxazolyl, and benzofuryl.

15. A pharmaceutical composition comprising the compound of claim 1, or a pharmaceutically acceptable salt thereof, and a pharmaceutically acceptable carrier.

16. The compound of claim 1, which is selected from the group consisting of the following compounds, or a pharmaceutically acceptable salt thereof:

Ex. 1
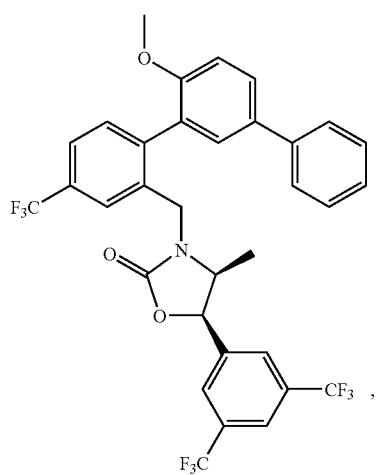

Ex. 21
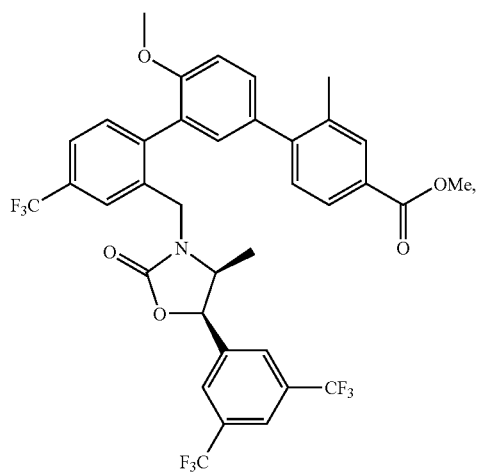

Ex. 22
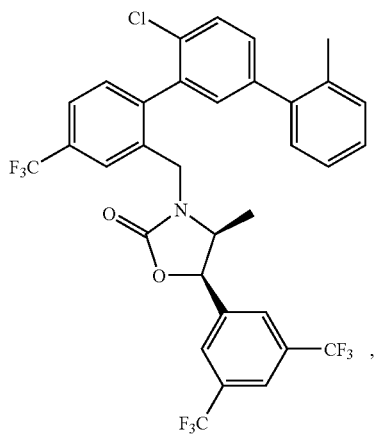

Ex. 23
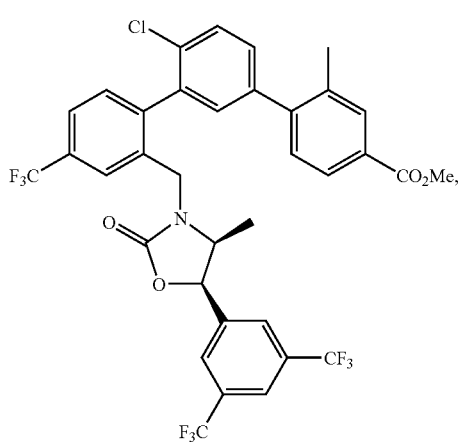

Ex. 24

Ex. 25
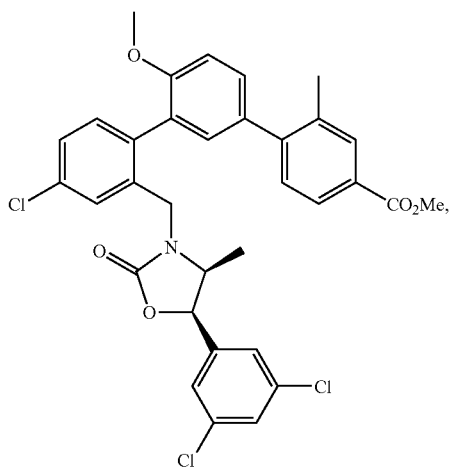
Ex. 26
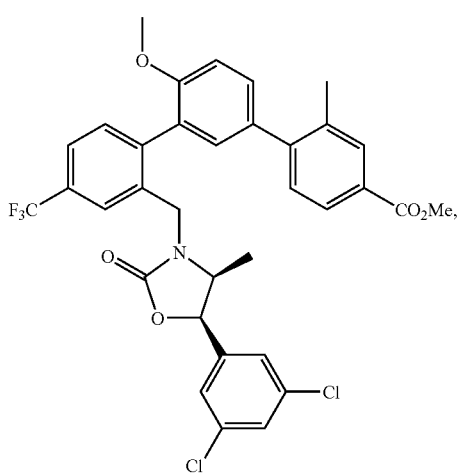
Ex. 27
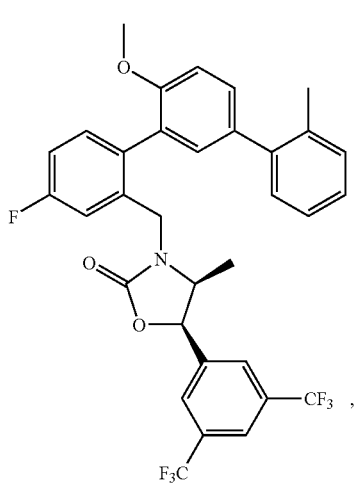
Ex. 28
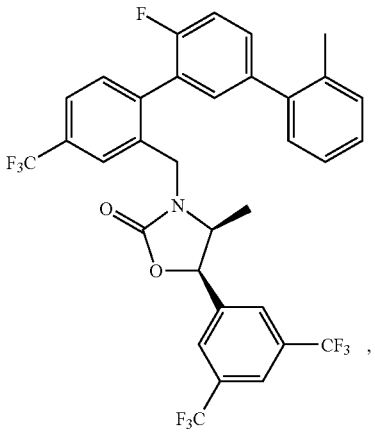
Ex. 29
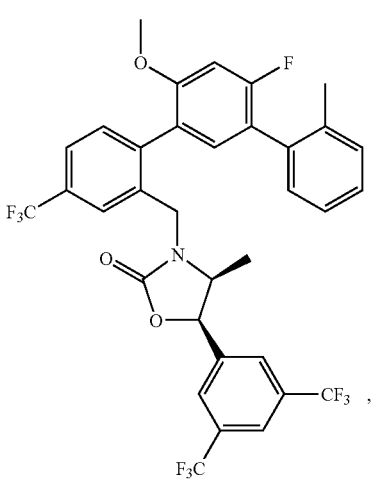
Ex. 30
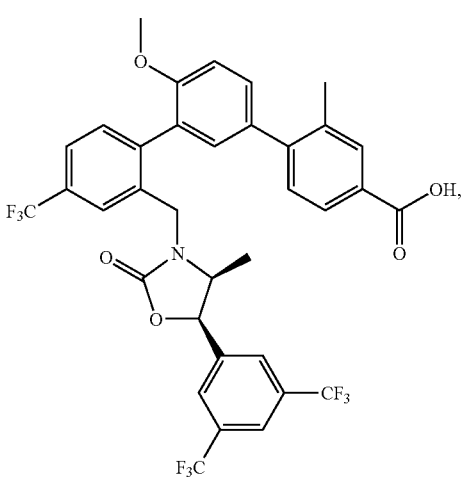

Ex. 31
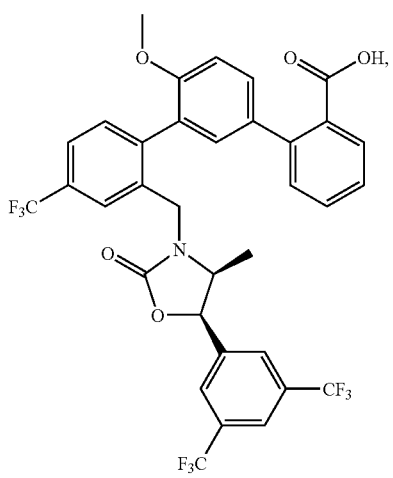
Ex. 32
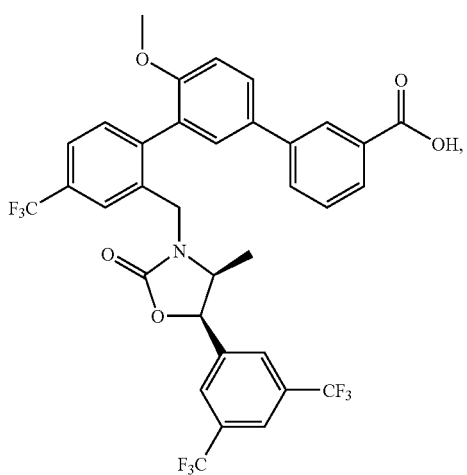
Ex. 33
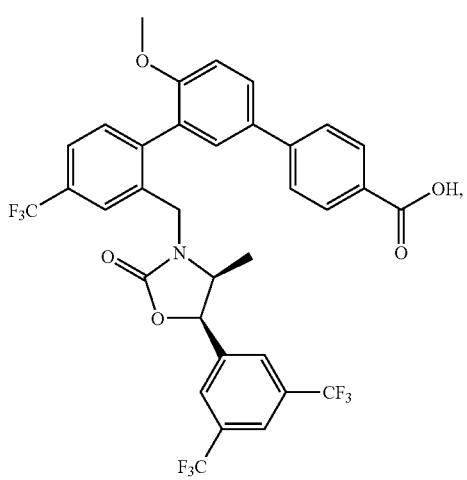
Ex. 34
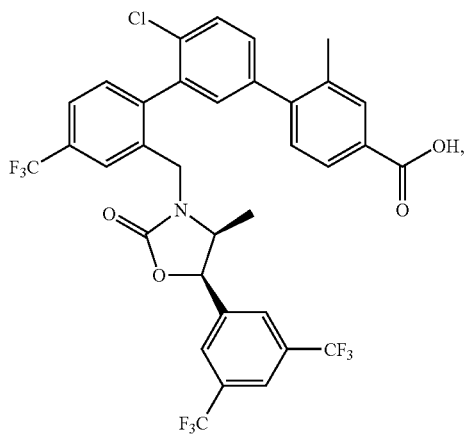
Ex. 35
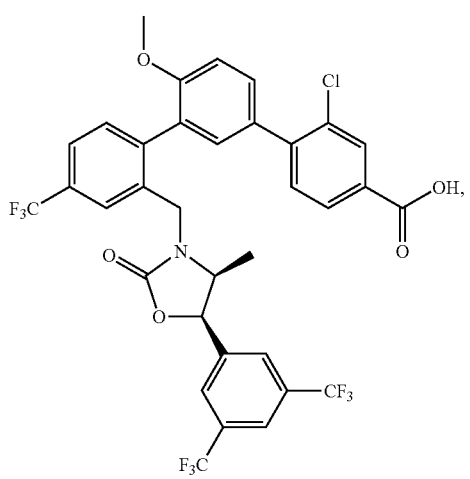
Ex. 36
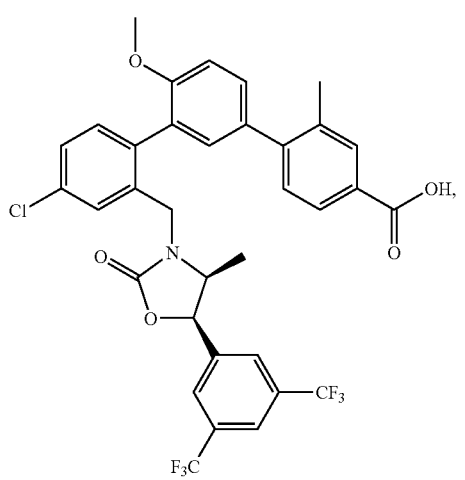

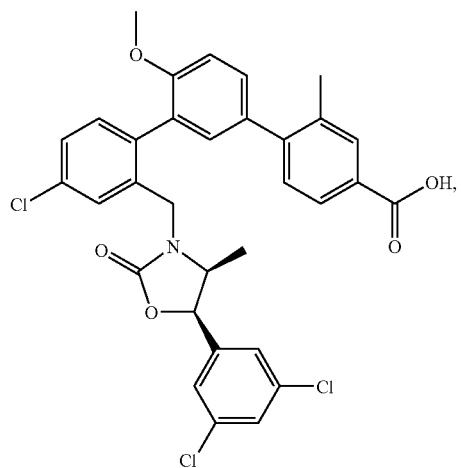
Ex. 37
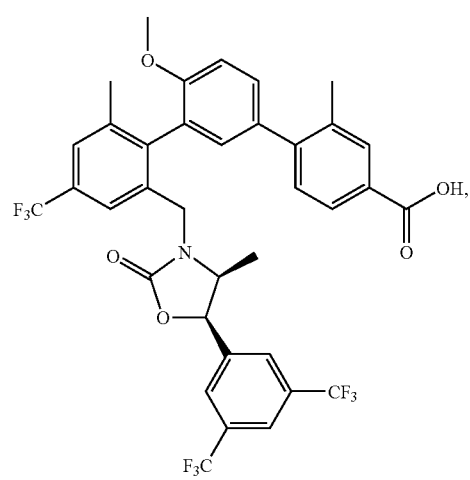
Ex. 40
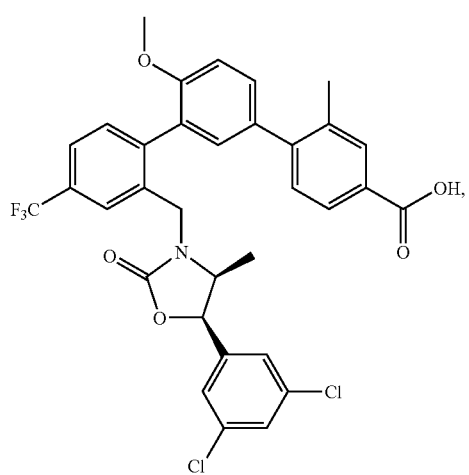
Ex. 38
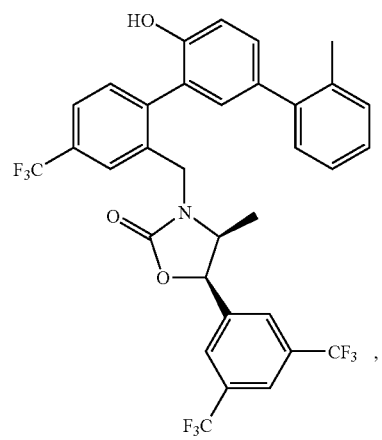
Ex. 41
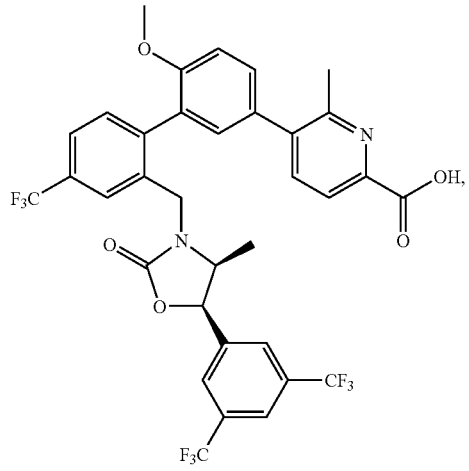
Ex. 39
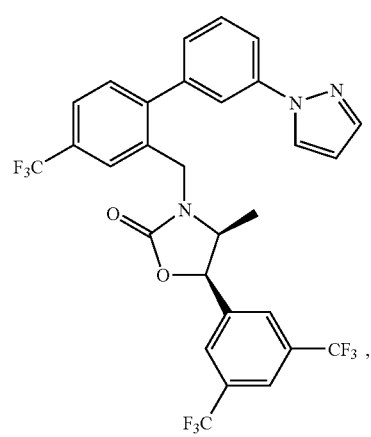
Ex. 42

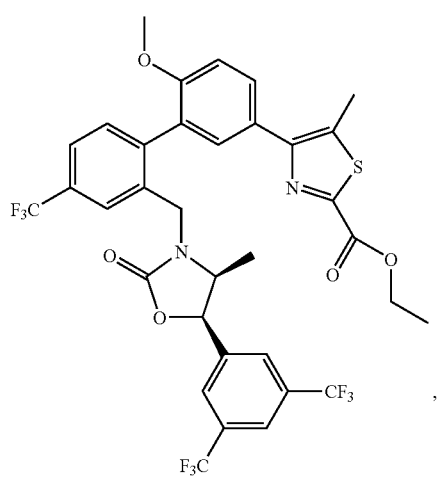
Ex. 43
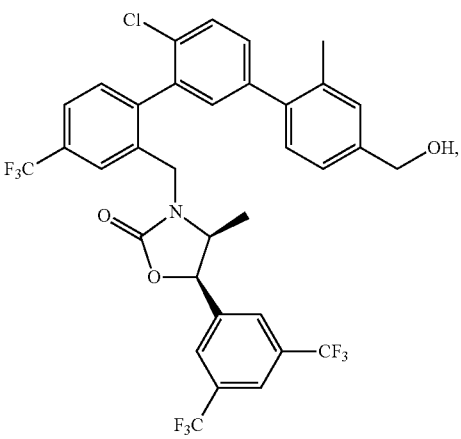
Ex. 49
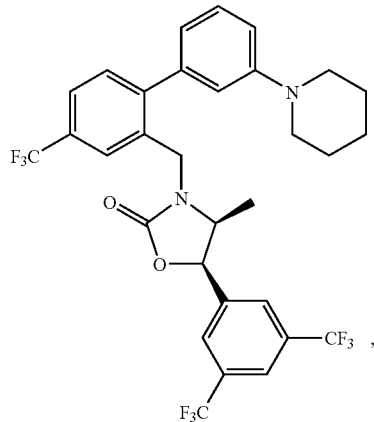
Ex. 44
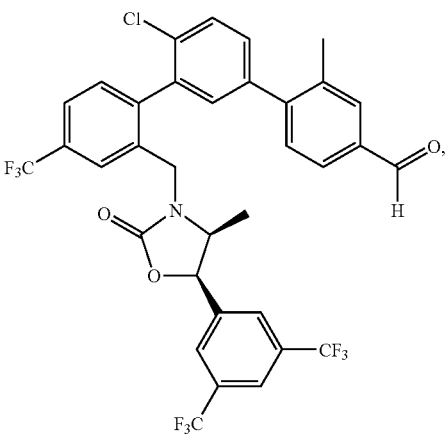
Ex. 50
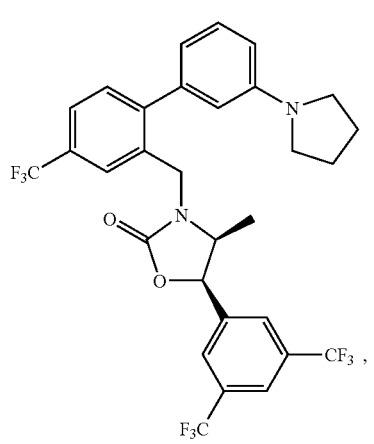
Ex. 45
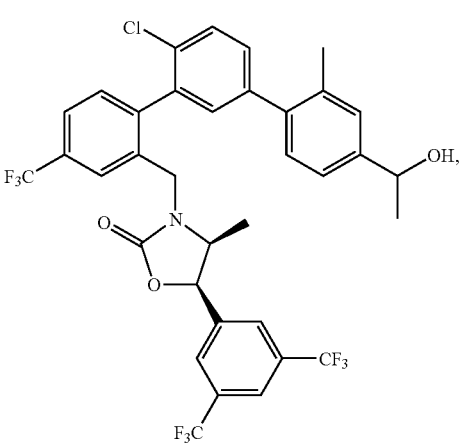
Ex. 51

-continued
Ex. 52
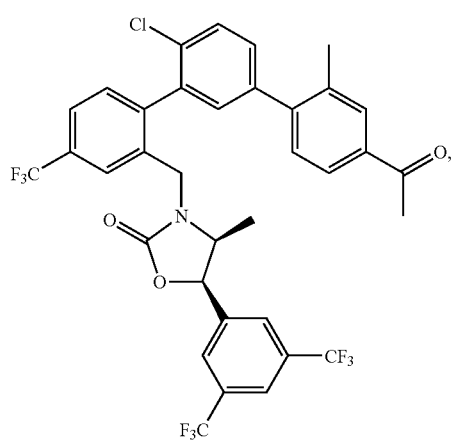
Ex. 55
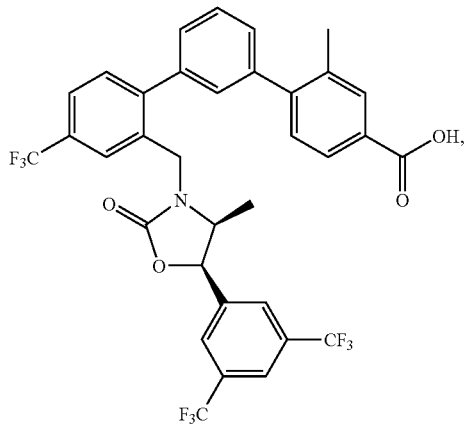
Ex. 53
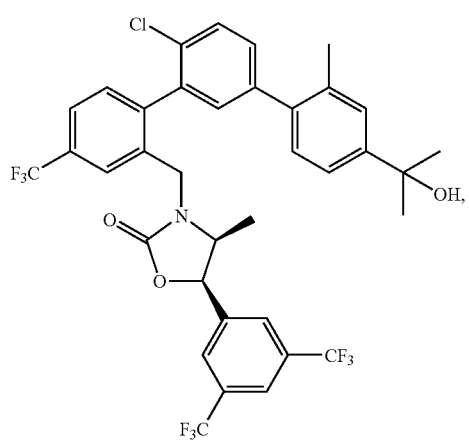
Ex. 56
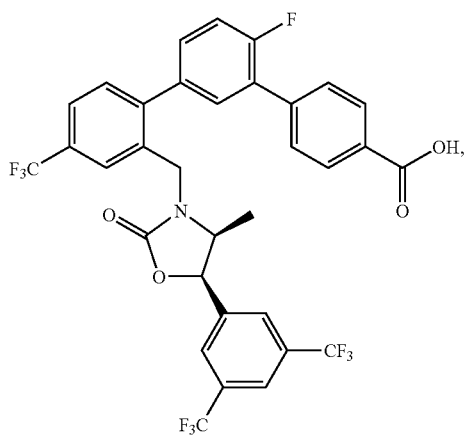
Ex. 54
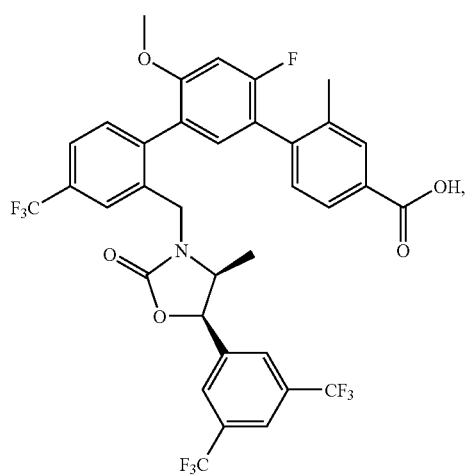
Ex. 138
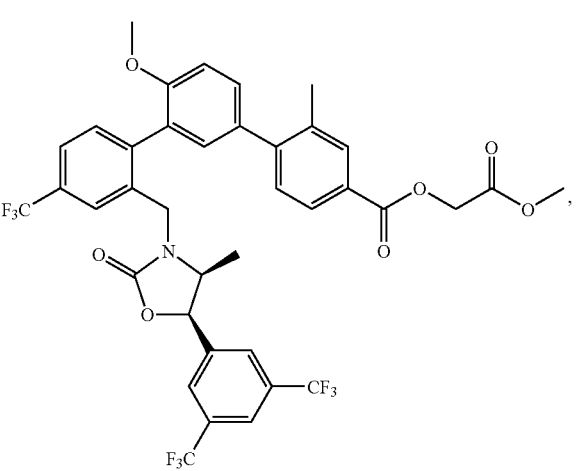

-continued
Ex. 62
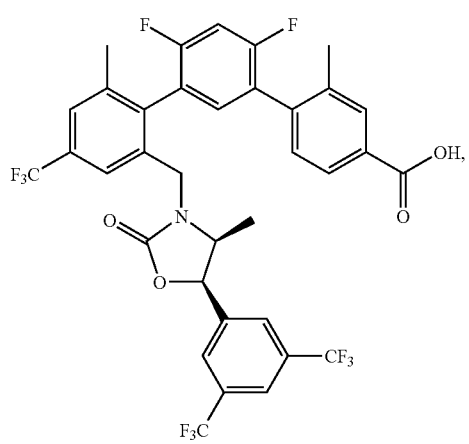
Ex. 68
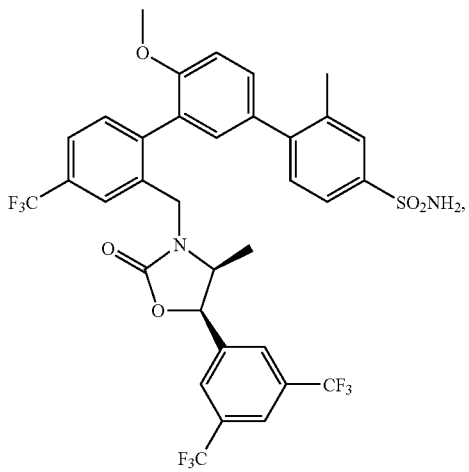
Ex. 65
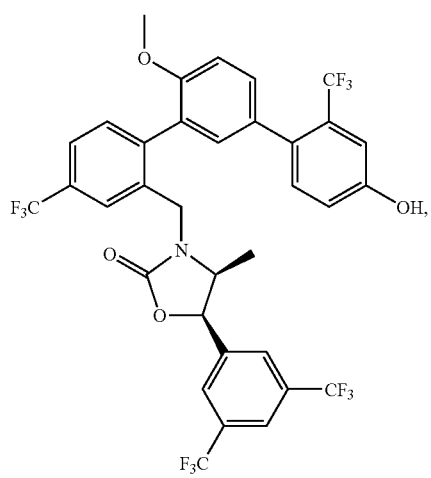
Ex. 69
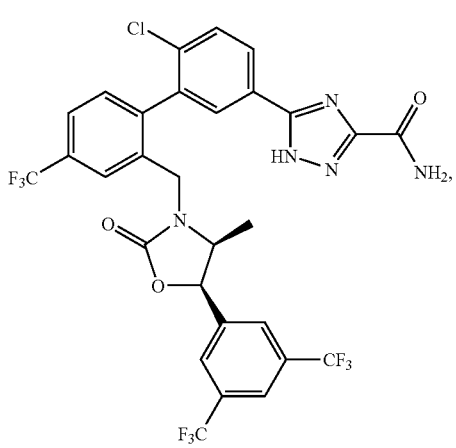
Ex. 66
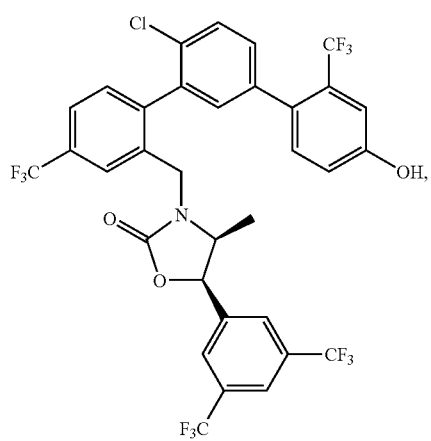
Ex. 70
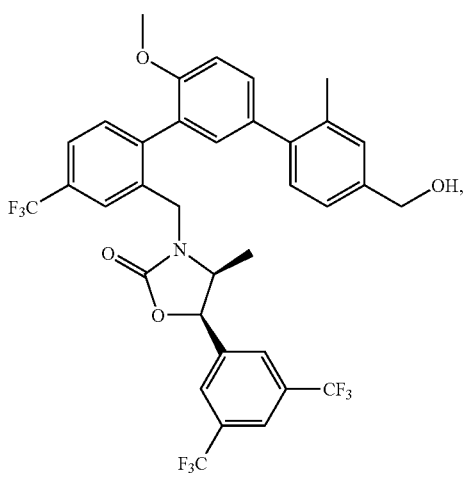

-continued
Ex. 71
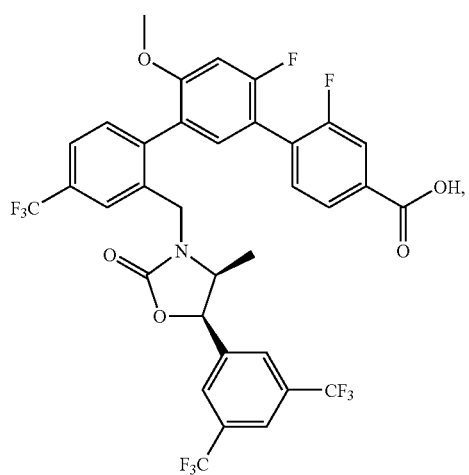
Ex. 72
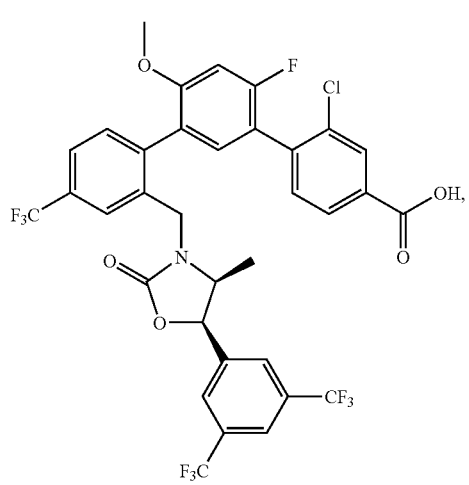
Ex. 73
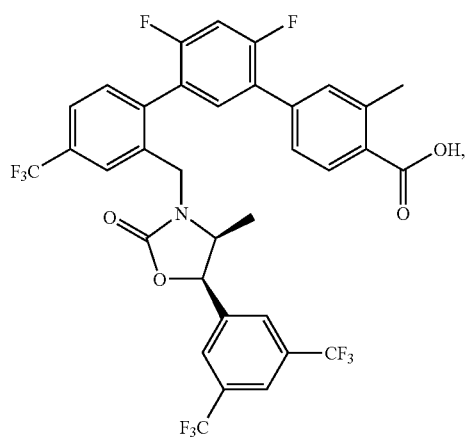
-continued
Ex. 74
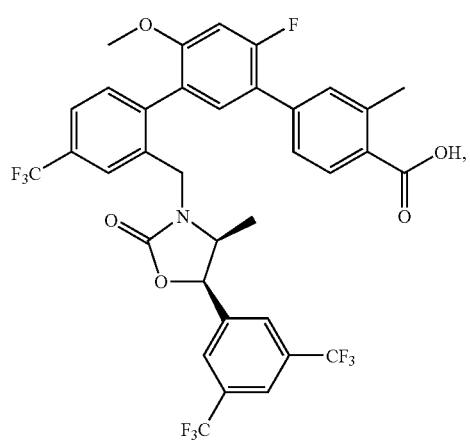
Ex. 75
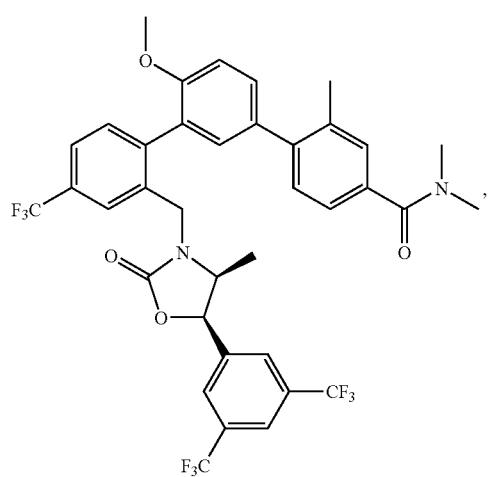
Ex. 83
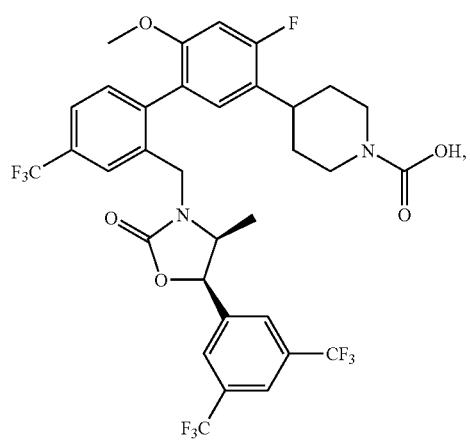

Ex. 94
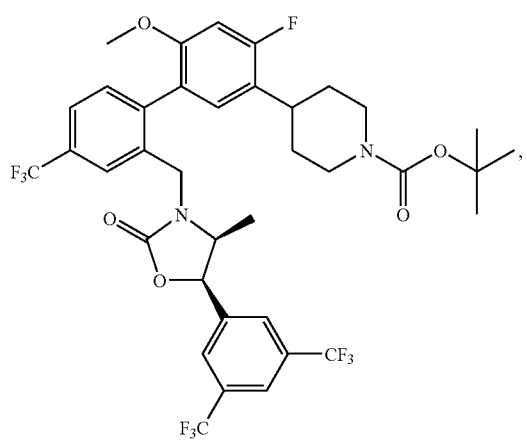
Ex. 95
Ex. 98
Ex. 99
Ex. 100
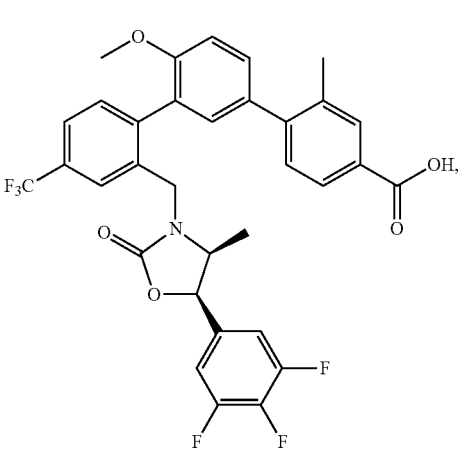
Ex. 101
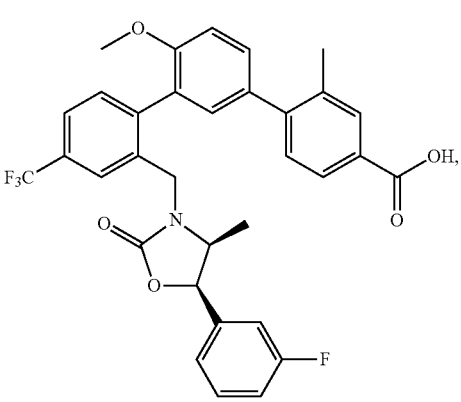
Ex. 102
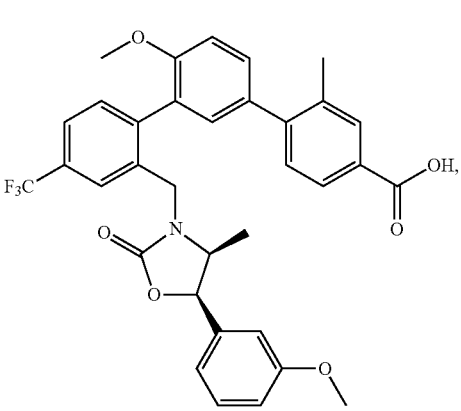

-continued
Ex. 106
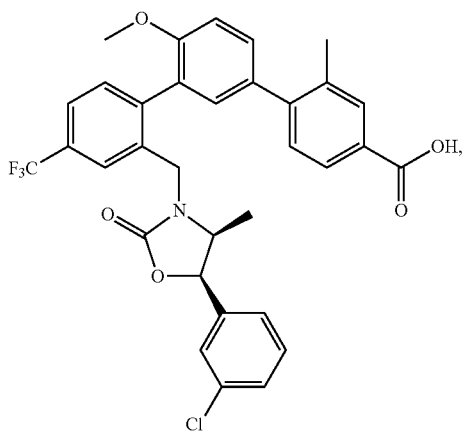
Ex. 107
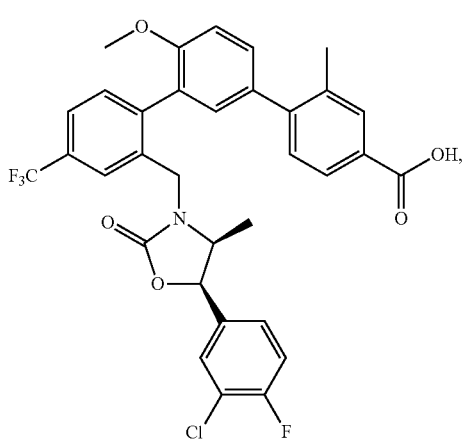
Ex. 108
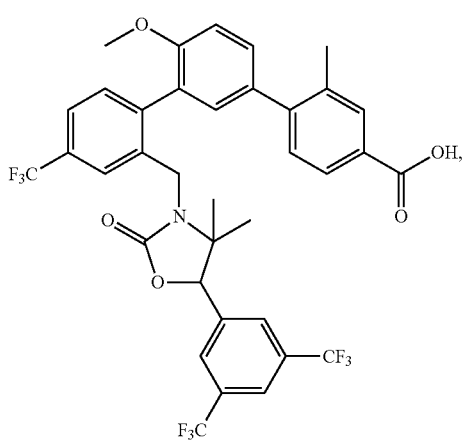
-continued
Ex. 109
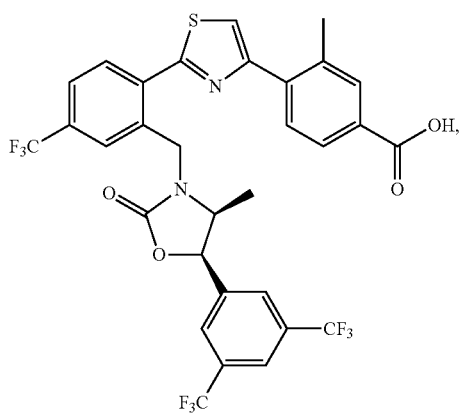
Ex. 124
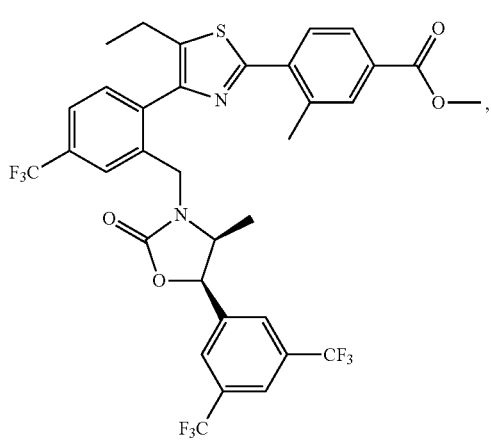
Ex. 125
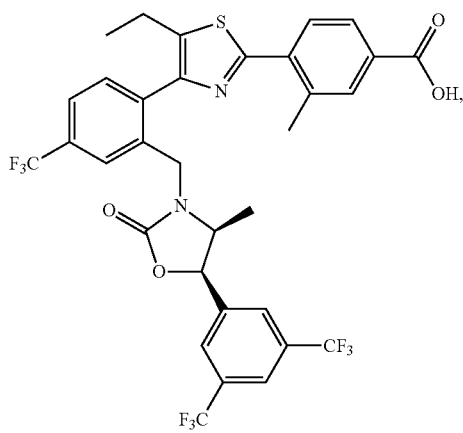

-continued
Ex. 136
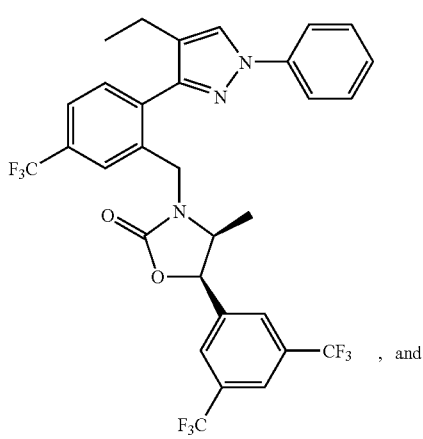
, and
Ex. 137
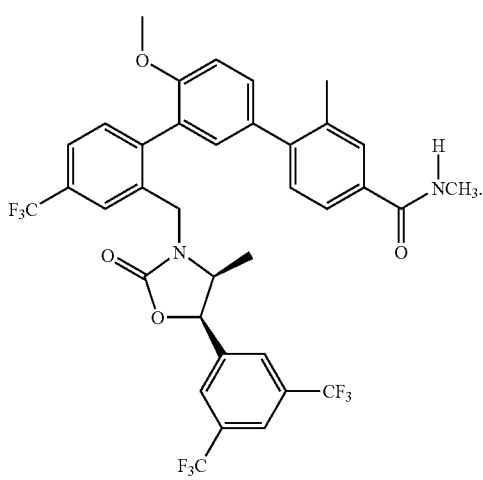
17. The compound of claim 1, which is selected from the group consisting of the following compounds, or a pharmaceutically acceptable salt thereof:
(a)
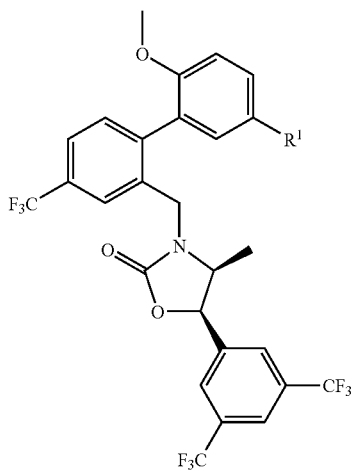
wherein R¹ is selected from the group consisting of:
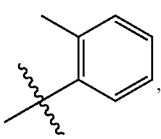
Ex. 2
,
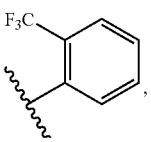
Ex. 3
,
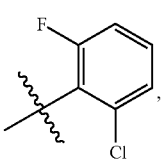
Ex. 4
,
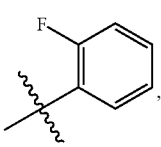
Ex. 5
,
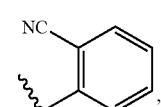
Ex. 6
,
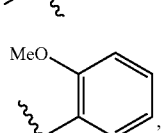
Ex. 7
,
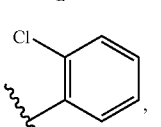
Ex. 8
,
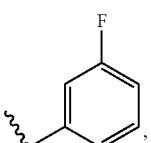
Ex. 9
,
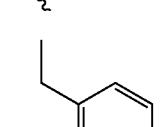
Ex. 10
,
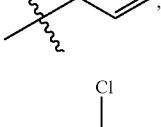
Ex. 11
, -continued
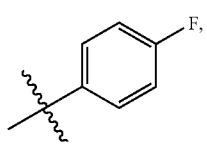
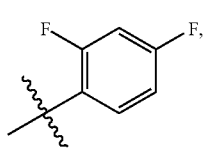
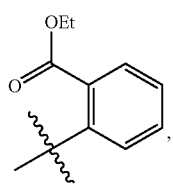
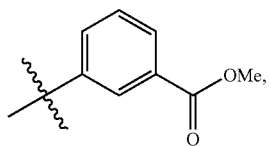
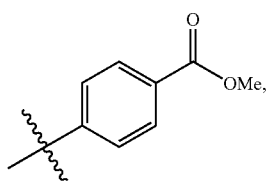
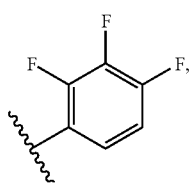
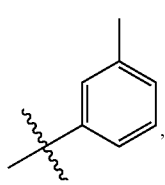
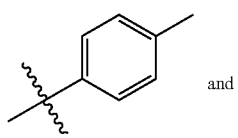 and
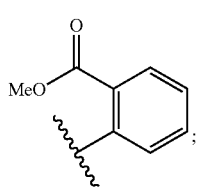
Ex. 12 (b)
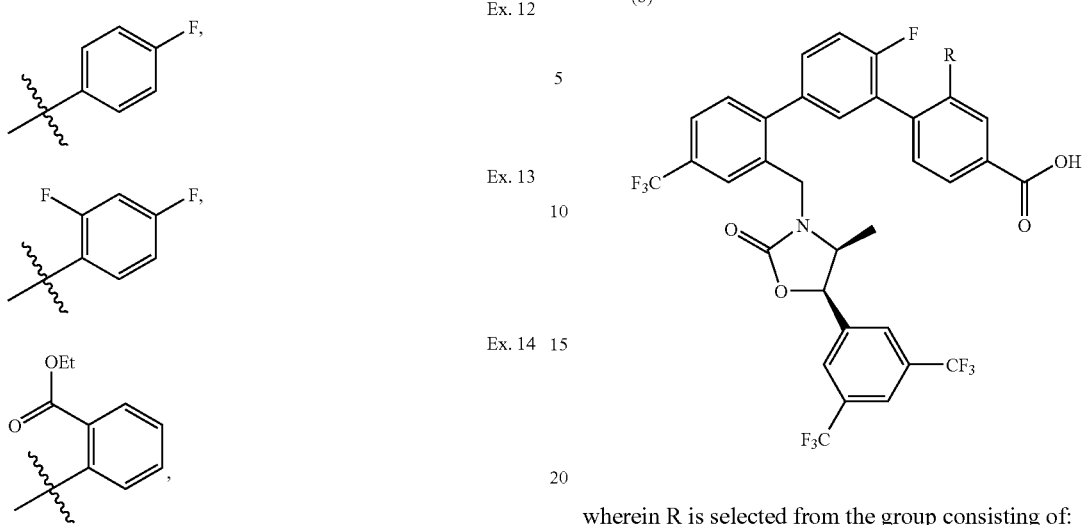
wherein R is selected from the group consisting of:
| | | |
|---|---|---|
| 57 | Me, and | |
| 58 | Cl; | |
Ex. 16
(c)
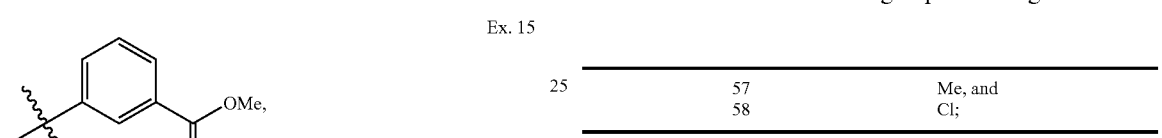
wherein R is selected from the group consisting of:
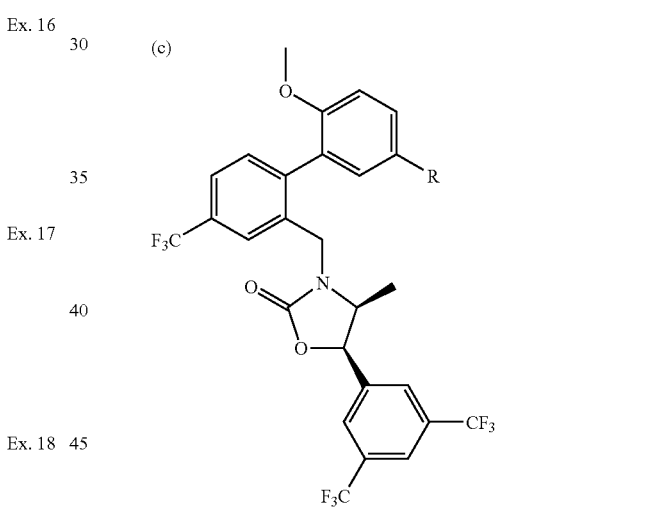
59
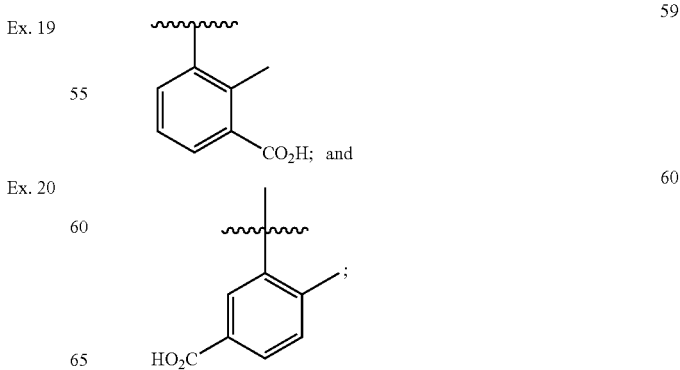
60

(d)
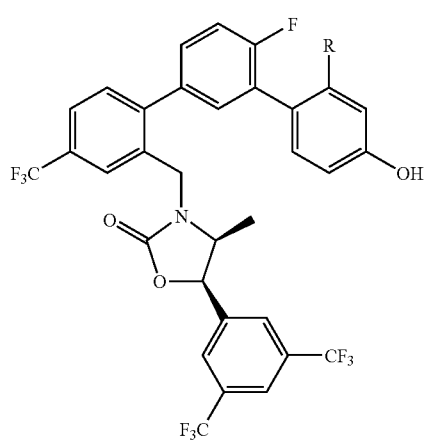
wherein R is selected from the group consisting of:
| 63 | CF3 and |
| 64 | Me; |
(e)
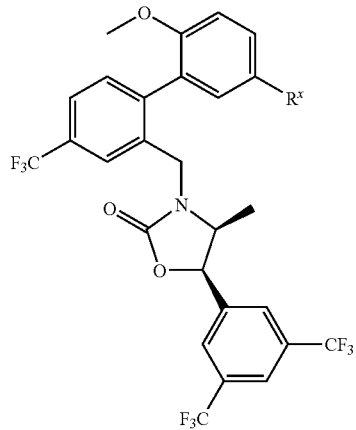
wherein $R^x$ is selected from the group consisting of:
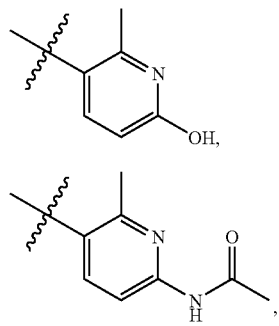
76
77
-continued
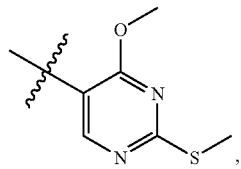
78
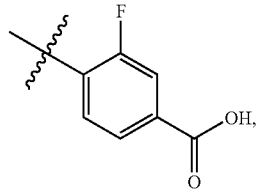
80
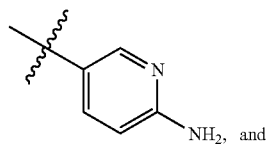
81
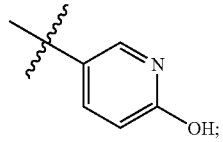
82
(f)
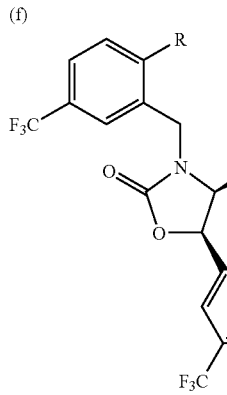
wherein R is selected from the group consisting of:
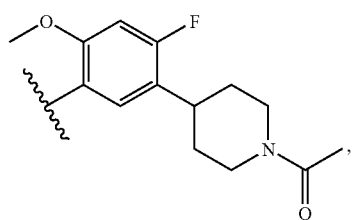
84
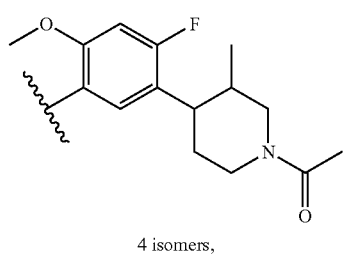
85, 86, 87, 88
4 isomers, -continued
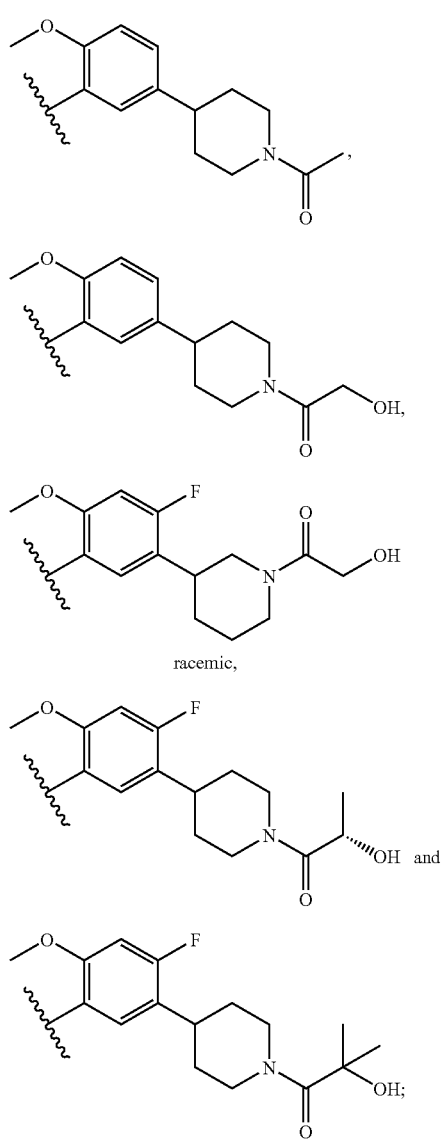
(h)
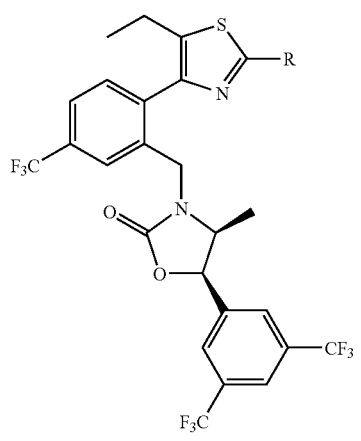
wherein R is selected from the group consisting of:
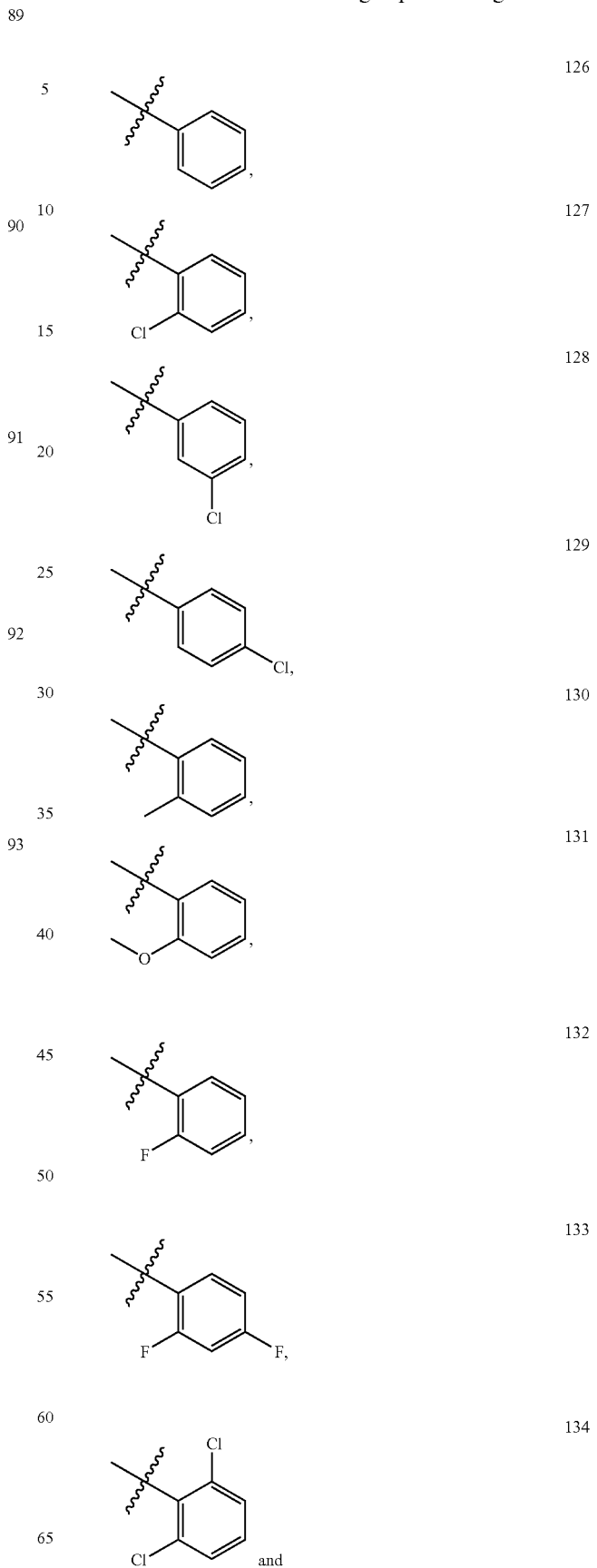

-continued

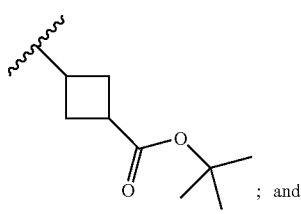
; and (i)

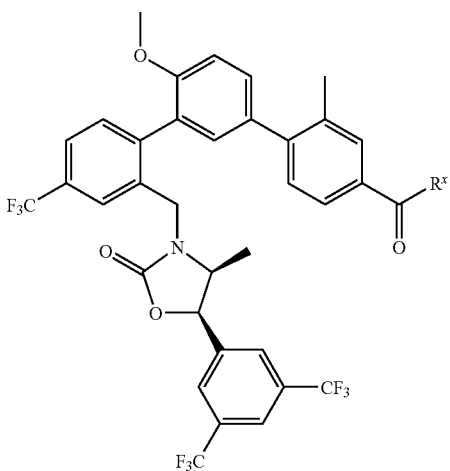

wherein $R^x$ is selected from the group consisting of:

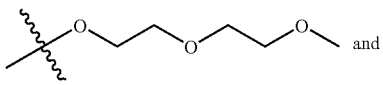
and

-continued

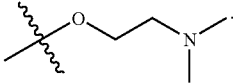

18. A method of treating atherosclerosis in a patient in need of treatment comprising the administration of a therapeutically effective amount of the compound of claim 1 to said patient, or a pharmaceutically acceptable salt thereof.

19. A method of raising HDL-C in a patient in need of treatment comprising the administration of a therapeutically effective amount of the compound of claim 1 to said patient, or a pharmaceutically acceptable salt thereof.

20. A method of lowering LDL-C in a patient in need of treatment comprising the administration of a therapeutically effective amount of the compound of claim 1 to said patient, or a pharmaceutically acceptable salt thereof.

21. A pharmaceutical composition comprising the compound of claim 1 or a pharmaceutically acceptable salt thereof, a pharmaceutically acceptable carrier, and one or more active ingredients selected from the group consisting of:
  (i) HMG-CoA reductase inhibitors;
  (ii) bile acid sequestrants;
  (iii) niacin and related compounds;
  (iv) PPARα agonists;
  (v) cholesterol absorption inhibitors;
  (vi) acyl CoA:cholesterol acyltransferase (ACAT) inhibitors;
  (vii) phenolic anti-oxidants;
  (viii) microsomal triglyceride transfer protein (MTP)/ApoB secretion inhibitors;
  (ix) anti-oxidant vitamins;
  (x) thyromimetics;
  (xi) LDL (low density lipoprotein) receptor inducers;
  (xii) platelet aggregation inhibitors;
  (xiii) vitamin B12 (also known as cyanocobalamin);
  (xiv) folic acid or a pharmaceutically acceptable salt or ester thereof;
  (xv) FXR and LXR ligands;
  (xvi) agents that enhance ABCA1 gene expression; and
  (xvii) ileal bile acid transporters.

* * * * *